(12) United States Patent
Turnbull

(10) Patent No.: US 6,657,052 B1
(45) Date of Patent: Dec. 2, 2003

(54) BIOMOLECULAR LABELING

(75) Inventor: Kenneth D. Turnbull, Fayetteville, AR (US)

(73) Assignee: University of Arkansas, Little Rock, AK (US)

(*) Notice: Subject to any disclaimer, the term of this patent is extended or adjusted under 35 U.S.C. 154(b) by 0 days.

(21) Appl. No.: 09/516,700

(22) Filed: Mar. 1, 2000

Related U.S. Application Data

(63) Continuation-in-part of application No. 09/057,957, filed on Apr. 9, 1998, now abandoned.
(60) Provisional application No. 60/041,883, filed on Apr. 11, 1997.

(51) Int. Cl.[7] .................. C07H 19/00; C07H 21/00; C07H 21/02; C07H 21/04; C12Q 1/68
(52) U.S. Cl. .................. 536/23.1; 536/22.1; 536/24.3; 536/25.3; 536/25.32; 435/6
(58) Field of Search ................. 435/6; 536/22.1, 536/23.1, 24.3, 25.3, 25.32

(56) References Cited

U.S. PATENT DOCUMENTS

| | | | |
|---|---|---|---|
| 2,393,999 A | 2/1946 | McCrone | 260/326 |
| 2,405,559 A | 8/1946 | Bousquet | 260/326 |
| 2,524,145 A | 10/1950 | Tawney | 260/313 |

Primary Examiner—Jezia Riley
(74) Attorney, Agent, or Firm—Head, Johnson & Kachigian

(57) ABSTRACT

A method for using an organic compound to label polynucleotides is described. The method utilizes an organic compound including an oligonucleotide, and electrophilic active site, an active complex, and a phosphate binding site. The oligonucleotide has a sequence that is complimentary to a specific region of a polynucleotide. This facilitates labeling of DNA or RNA at a specific site in its sequence. The active site consists of a stable precursor, and only becomes reactive upon activation. Leaving and protecting functional groups may be attached to the active site in order to facilitate the formation of a stable precursor and subsequent activation. The active complex may be a drug, polypeptide or a reporter molecule such as an isotope or fluorescing compound. The phosphate binding sites may be any functional group capable of forming ionic bonds with phosphate oxygens. Nucleotide labeling using this compound does not interfere with a polynucleotide sequence. The described method for utilizing this compound may be performed in situ. Latent reactivity is utilized to make the reaction chemically specific, alkylating only phosphodiester groups on the polynucleotide. A lactonization reaction traps the trialkylphosphate in a stable form.

10 Claims, 87 Drawing Sheets

FIG. 1D

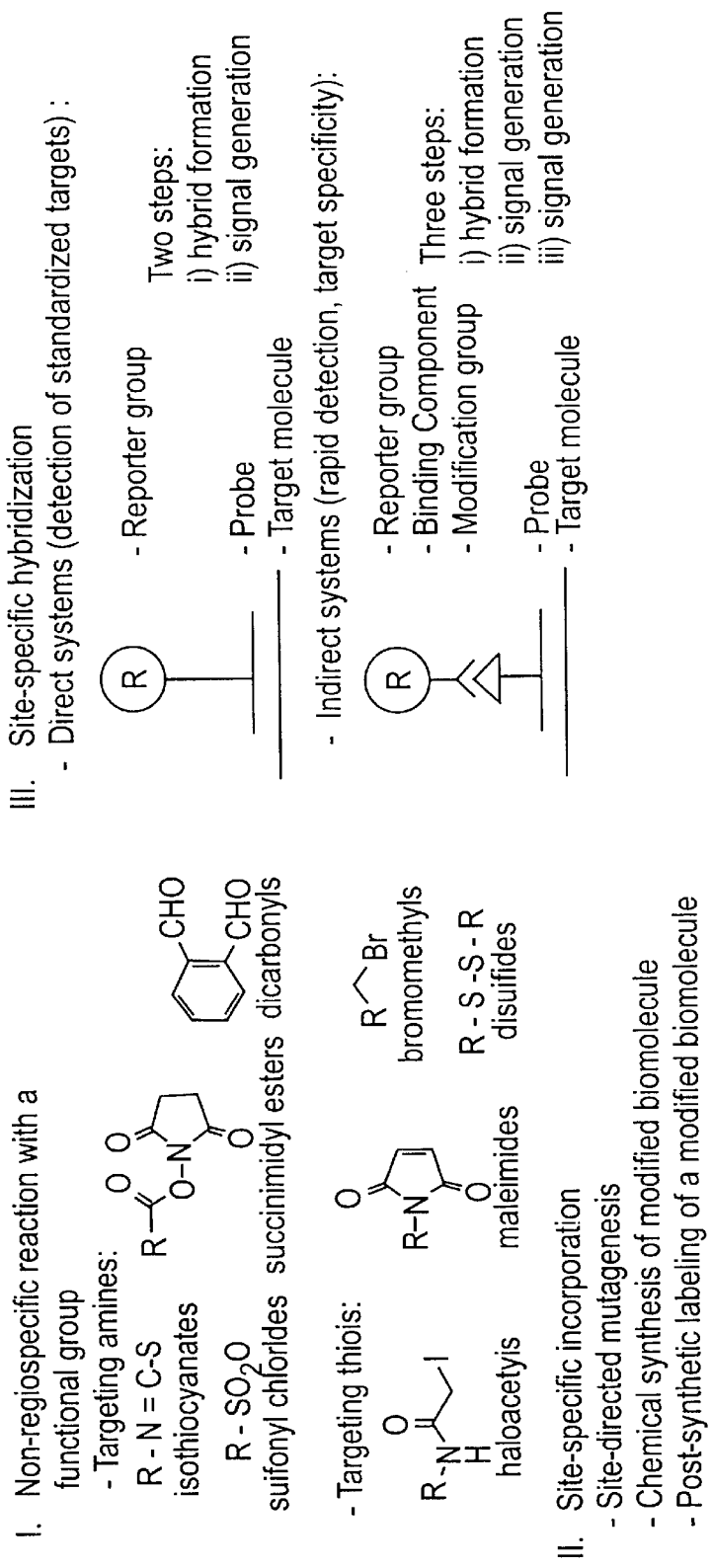

I. Non-regiospecific reaction with a functional group
 - Targeting amines:
   R-N=C=S isothiocyanates
   R-SO₂O sulfonyl chlorides
   succinimidyl esters
   dicarbonyls
 - Targeting thiols:
   haloacetyls
   maleimides
   R-S-S-R disulfides II. Site-specific incorporation
 - Site-directed mutagenesis
 - Chemical synthesis of modified biomolecule
 - Post-synthetic labeling of a modified biomolecule III. Site-specific hybridization
 - Direct systems (detection of standardized targets):
   - Reporter group
   - Probe
   - Target molecule
   Two steps:
   i) hybrid formation
   ii) signal generation

- Indirect systems (rapid detection, target specificity):
   - Reporter group
   - Binding Component
   - Modification group
   - Probe
   - Target molecule
   Three steps:
   i) hybrid formation
   ii) signal generation
   iii) signal generation

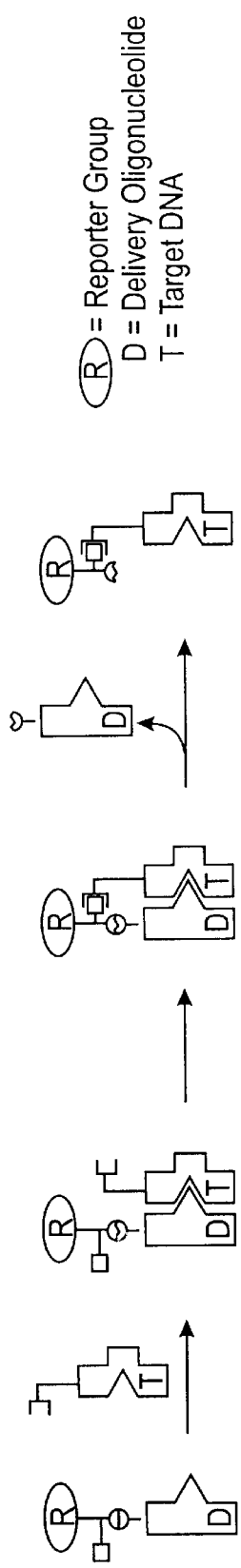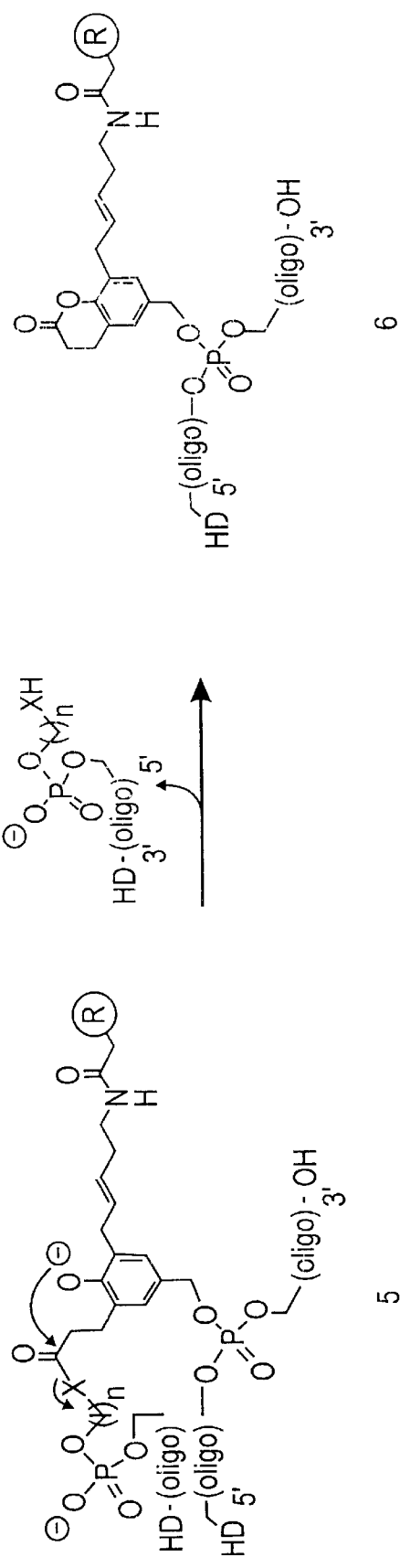
FIG. 1E
FIG. 3E

9

10a (Y = O)
10b (Y = CR$_2$)

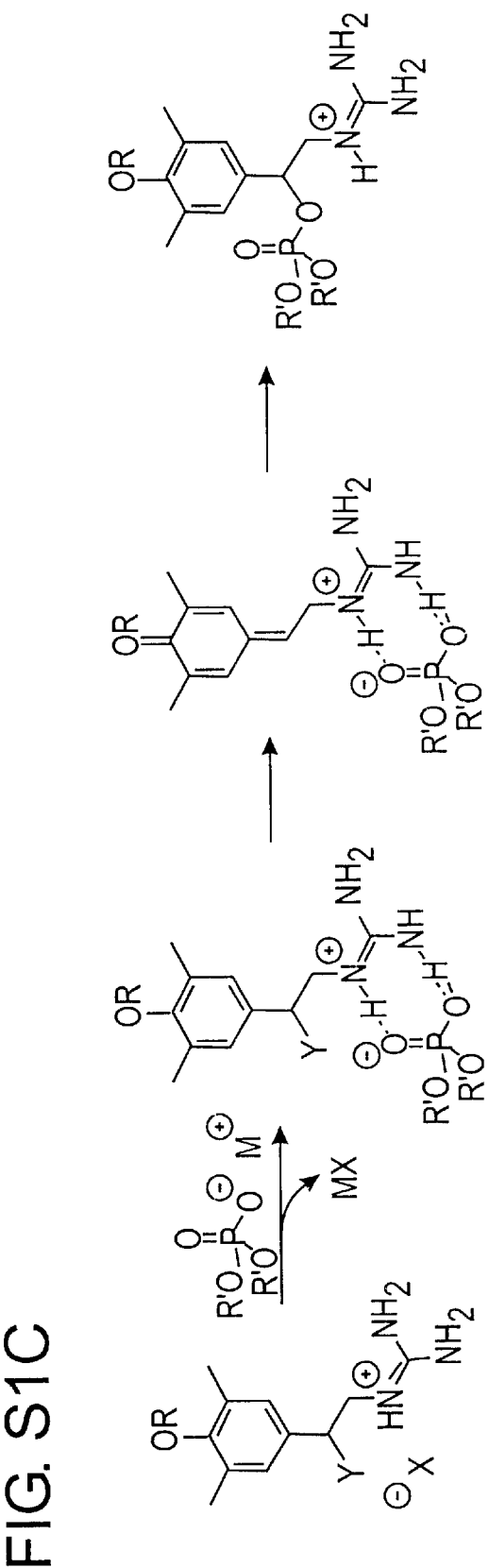
FIG. S1C

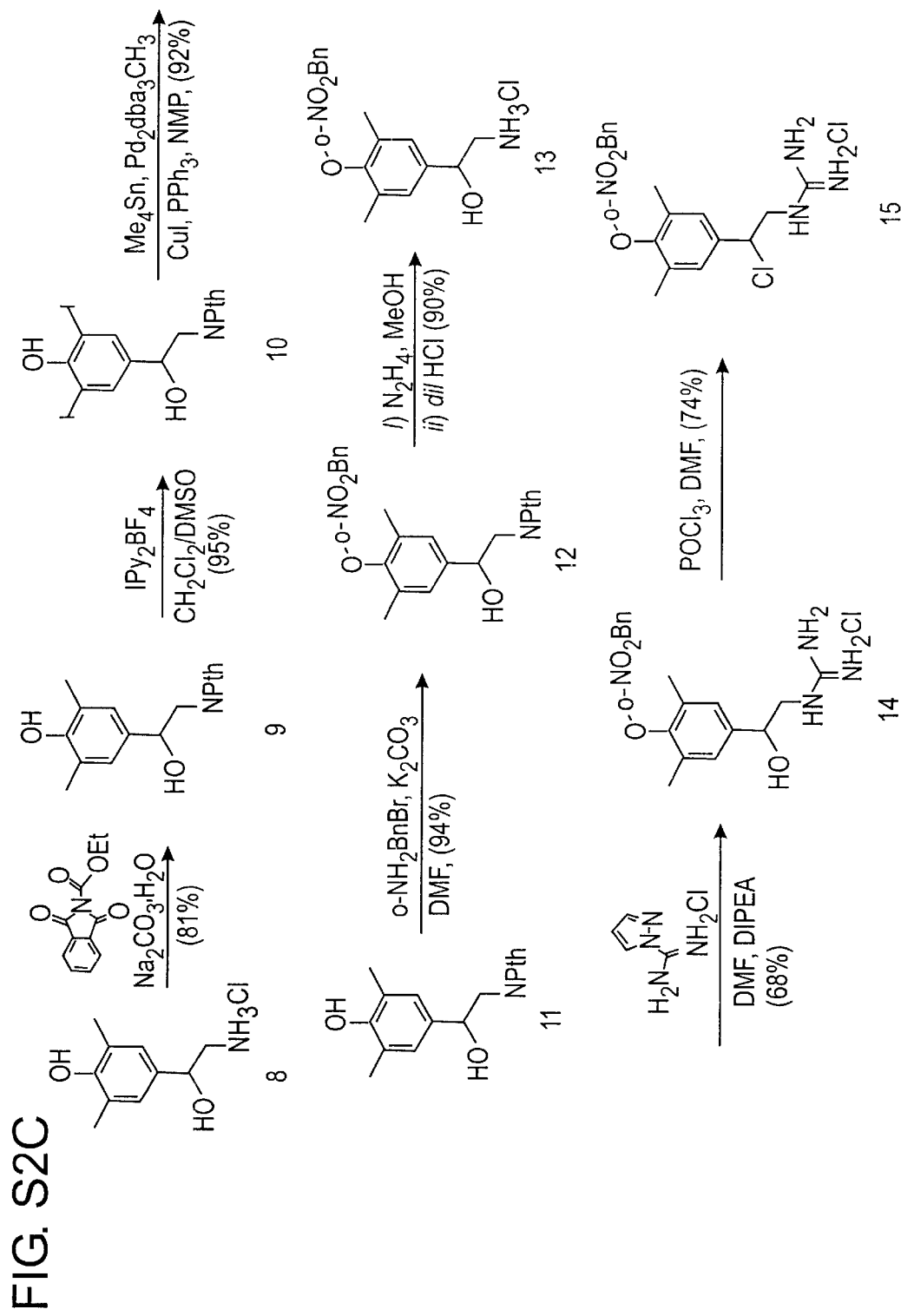
FIG. S2C

FIG. 9D
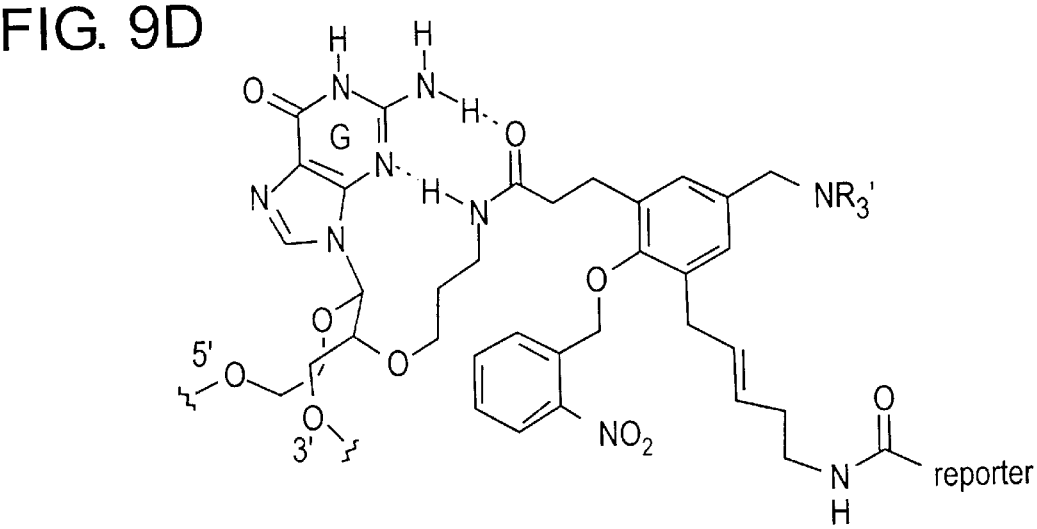
FIG. S16D
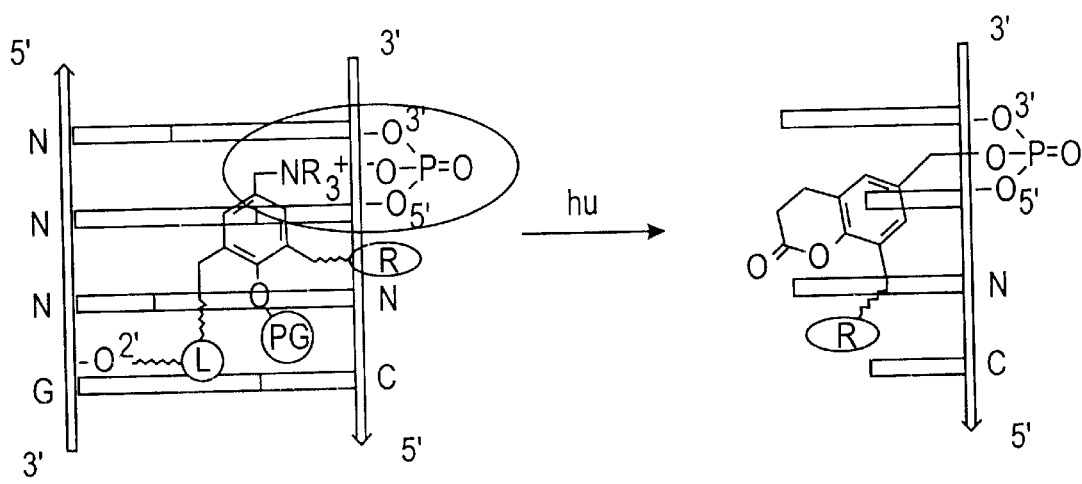

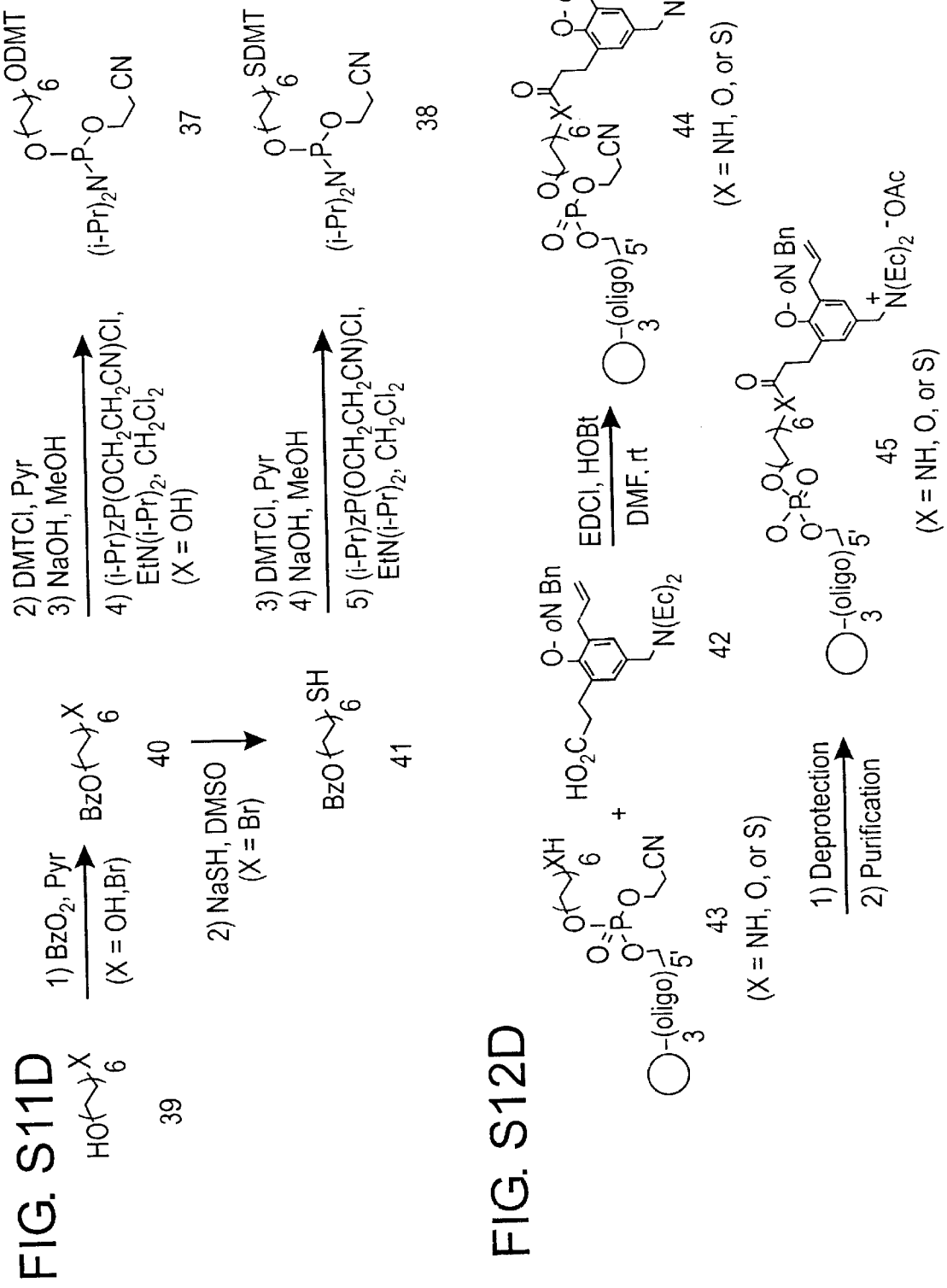
FIG. S11D
FIG. S12D

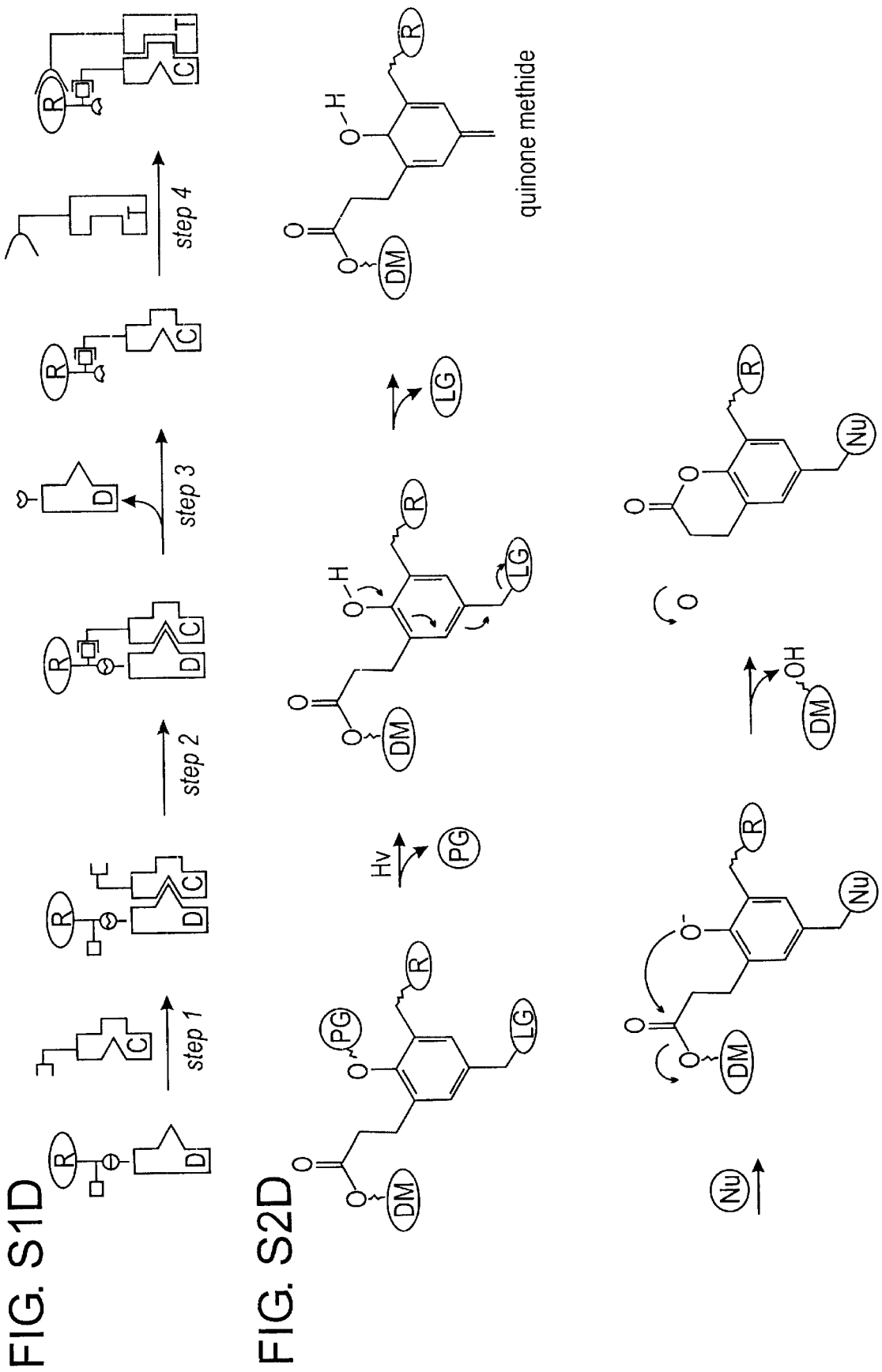
FIG. S1D
FIG. S2D

Fig. T1

*Table 1.* Effect of Acid/Base on Equilibrium of 7:8

| Acid/Base | pK$_a$ | Effect on 7:8 Equilibrium |
|---|---|---|
| F$_3$CCO$_2$H | 0.3 | favors quinone methide 7 |
| Cl$_2$HCCO$_2$H | 1.26 | favors quinone methide 7 |
| ClH$_2$CCO$_2$H | 2.87 | favors quinone methide 7 |
| (BnO)$_2$PO$_2$H | (3.0)* | favors trialkylphosphate 8 |
| p-O$_2$NC$_6$H$_4$CO$_2$H | 3.44 | favors trialkylphosphate 8 |
| H$_3$CCO$_2$H | 4.76 | favors trialkylphosphate 8 |
| imidazole | 6.92 | favors trialkylphosphate 8 |
| lutidine | 7.71 | favors quinone methide 7 |

*pK$_a$ in relevant solvent has not been found

Fig. S2

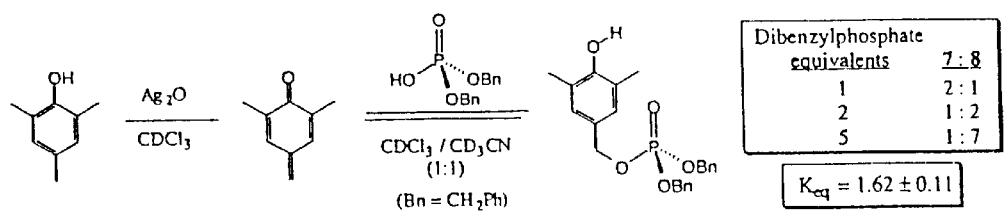

Fig. S3
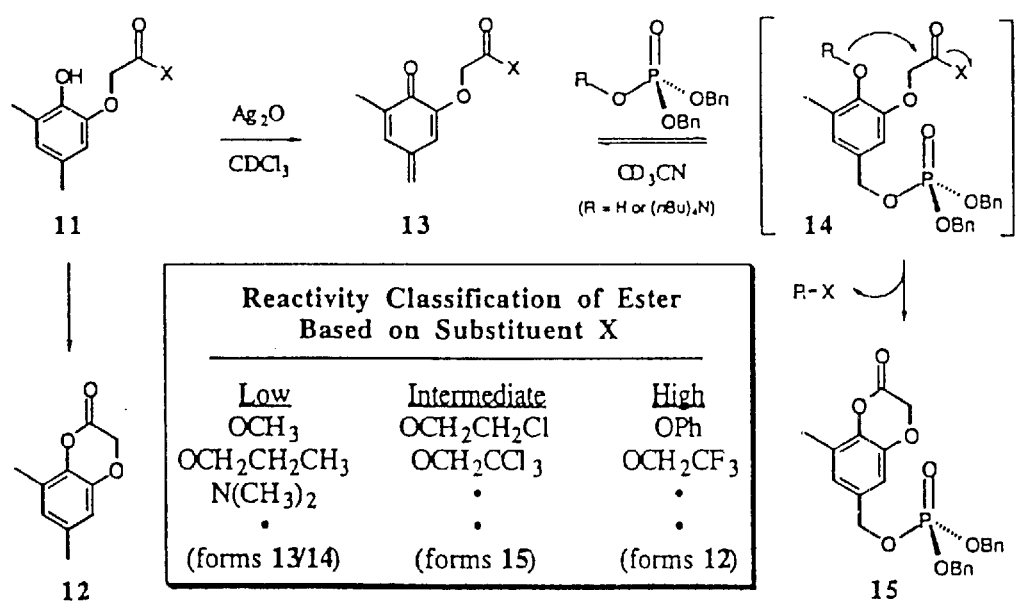

Fig. T2
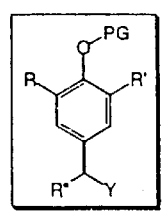
PG = photolabile protecting group
Y = leaving group
NB = 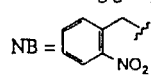
MDNBC = 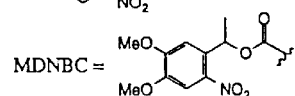
DMBC = 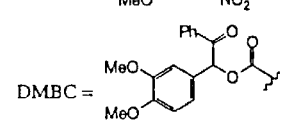
| Entry | PG | R | R' | R* | Y |
|---|---|---|---|---|---|
| 1 | NB | Me | Me | Me | Br |
| 2 | NB | Me | Me | Me | Cl |
| 3 | NB | Me | Me | Me | $O_2CCH_3$ |
| 4 | NB | Me | Me | Me | $O_2CCF_3$ |
| 5 | NB | Me | Me | H | $MeEt_2N^+$ |
| 6 | NB | H | OMe | H | Cl |
| 7 | MDNBC | H | OMe | H | Cl |
| 8 | MDNBC | Me | Me | H | Cl |
| 9 | MDNBC | Me | Me | H | $O_2CCH_3$ |
| 10 | DMBC | Me | Me | H | Cl |
| 11 | DMBC | Me | Me | H | $O_2CCH_3$ |
Fig. S5
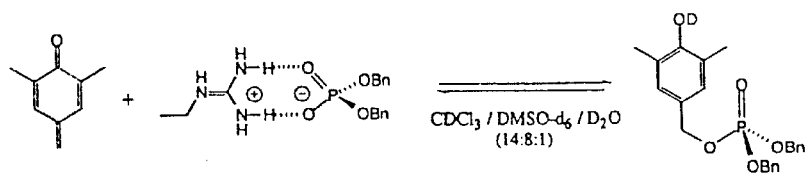

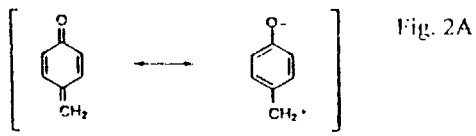

Fig. 2A

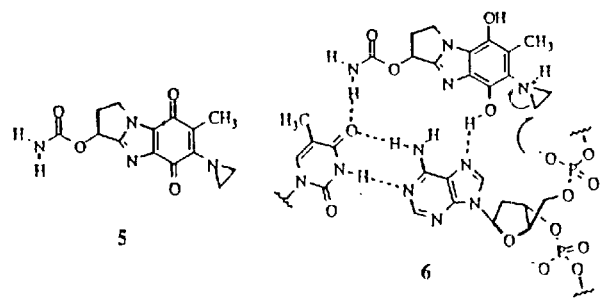

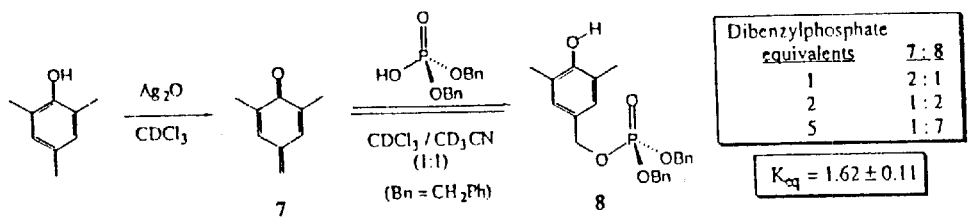

| Effect of Acid/Base on Equilibrium of 7:8 | | |
|---|---|---|
| Acid/Base | pK$_a$ | Effect on 7:8 Equilibrium |
| F$_3$CCO$_2$H | 0.3 | favors quinone methide 7 |
| Cl$_2$HCCO$_2$H | 1.26 | favors quinone methide 7 |
| ClH$_2$CCO$_2$H | 2.87 | favors quinone methide 7 |
| (BnO)$_2$PO$_2$H | (3.0)* | favors trialkylphosphate 8 |
| p-O$_2$NC$_6$H$_4$CO$_2$H | 3.44 | favors trialkylphosphate 8 |
| H$_3$CCO$_2$H | 4.76 | favors trialkylphosphate 8 |
| imidazole | 6.92 | favors trialkylphosphate 8 |
| lutidine | 7.71 | favors quinone methide 7 |

*pK$_a$ in relevant solvent has not been found

Fig. T1A

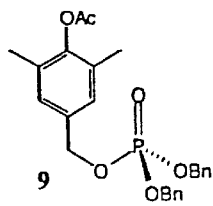
Fig. 4A
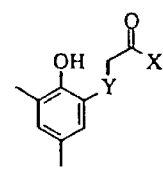
10a (Y = O)
10b (Y = CR₂)
Fig. 5A
Fig. S3A
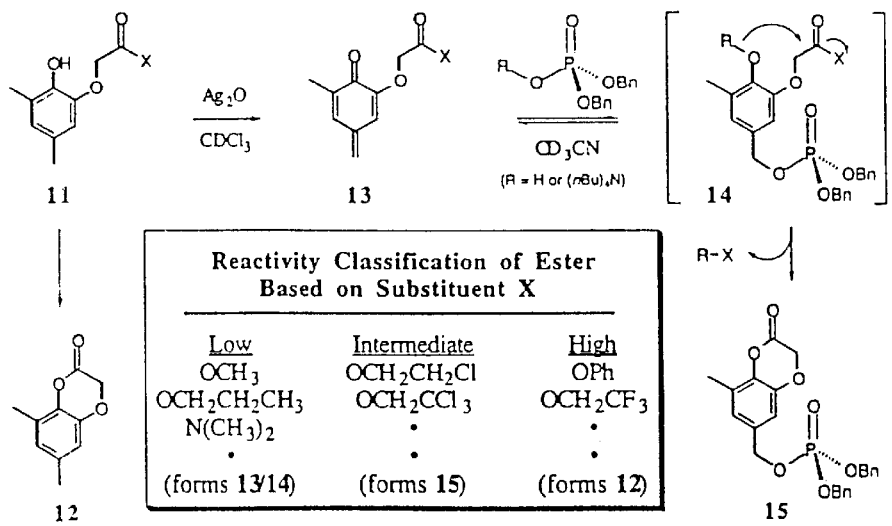

Fig. S4A
Fig. T2A
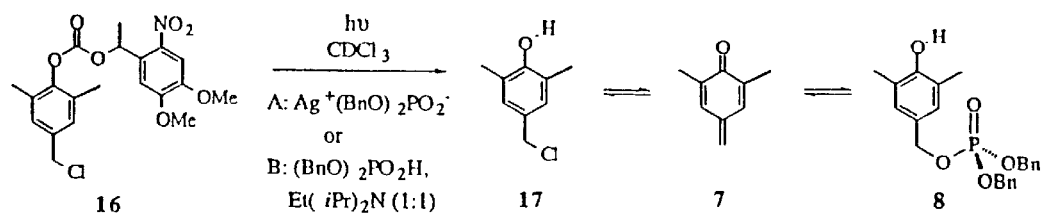
Fig. S5A
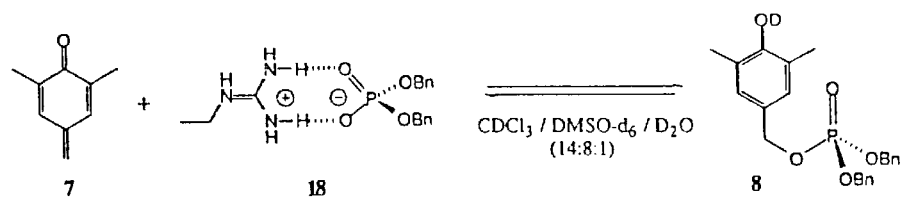

Fig. S6A
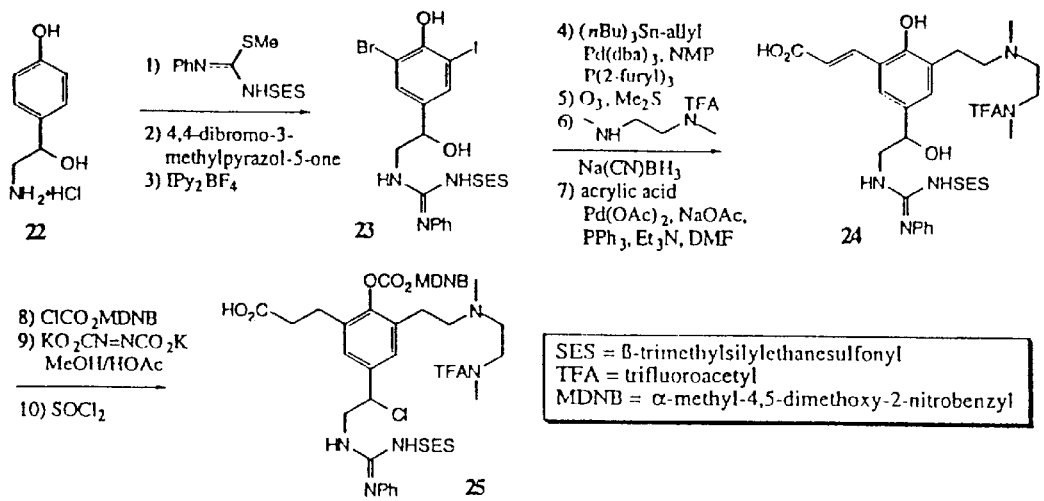
Fig. S7A
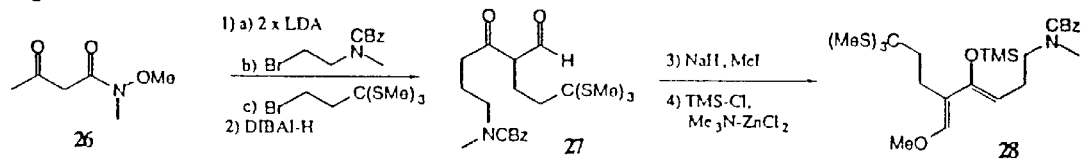
Fig. S8A
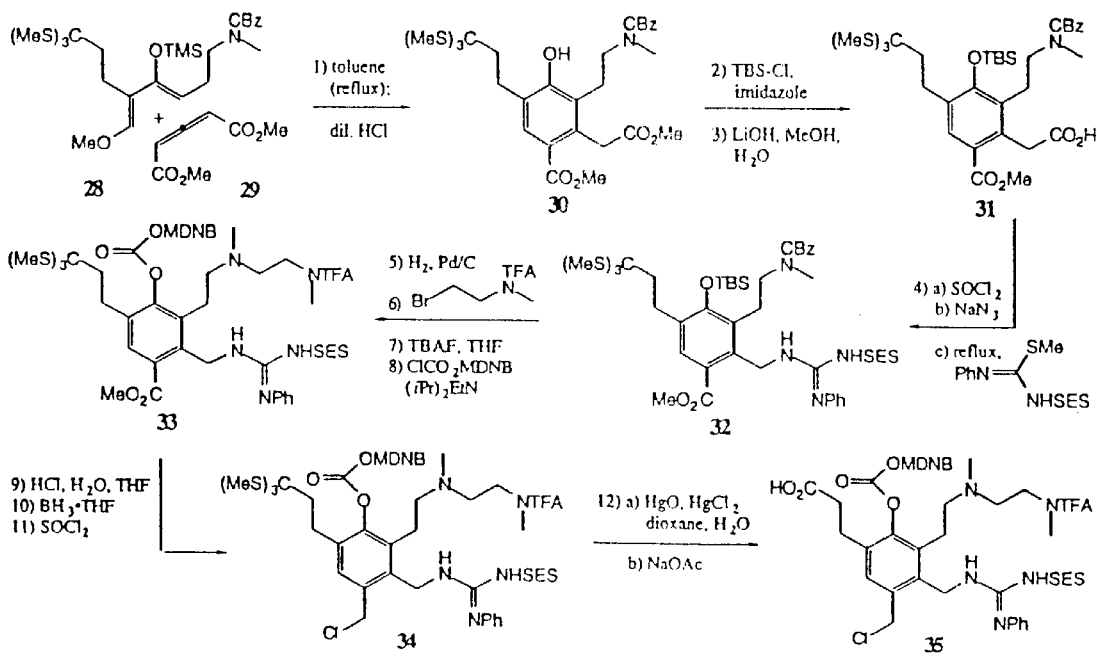

Fig. S13D
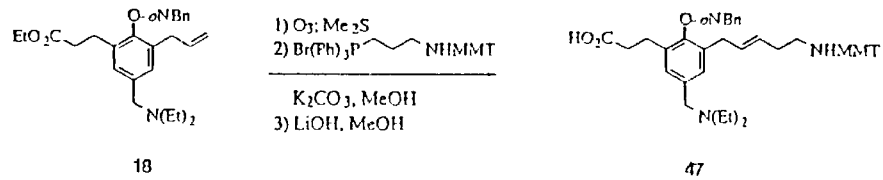
Fig. S14D
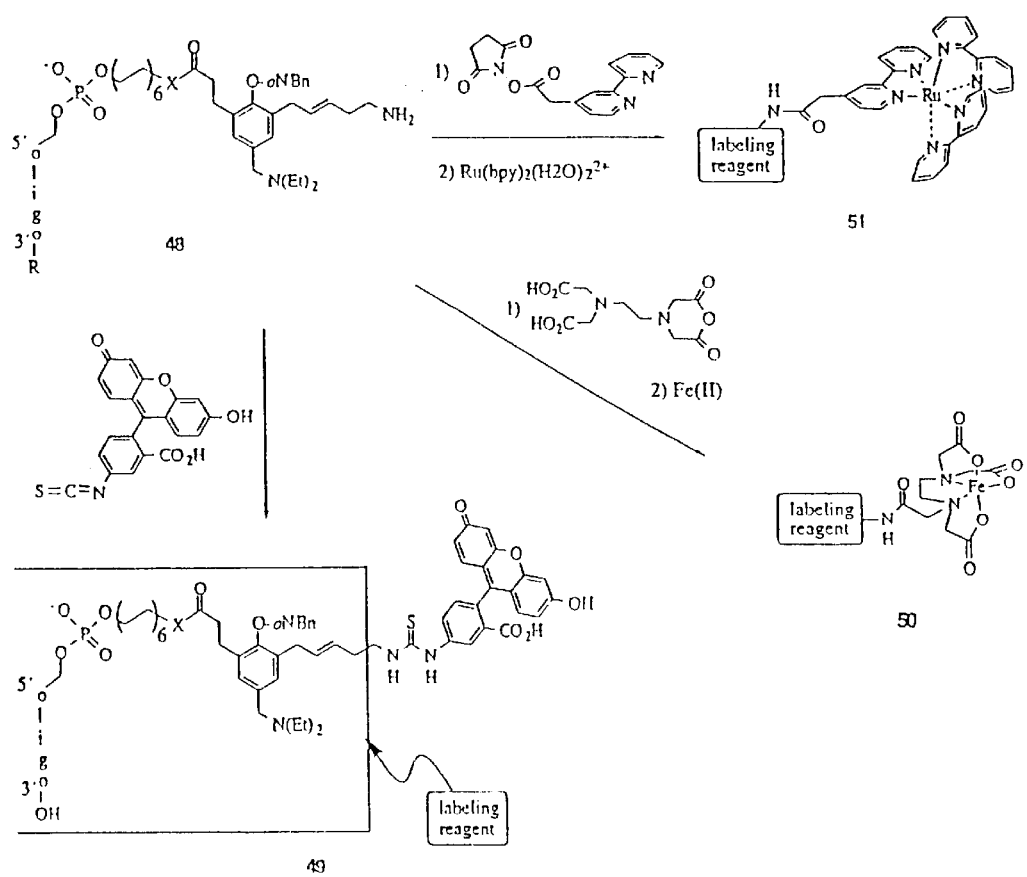

Fig. S15D
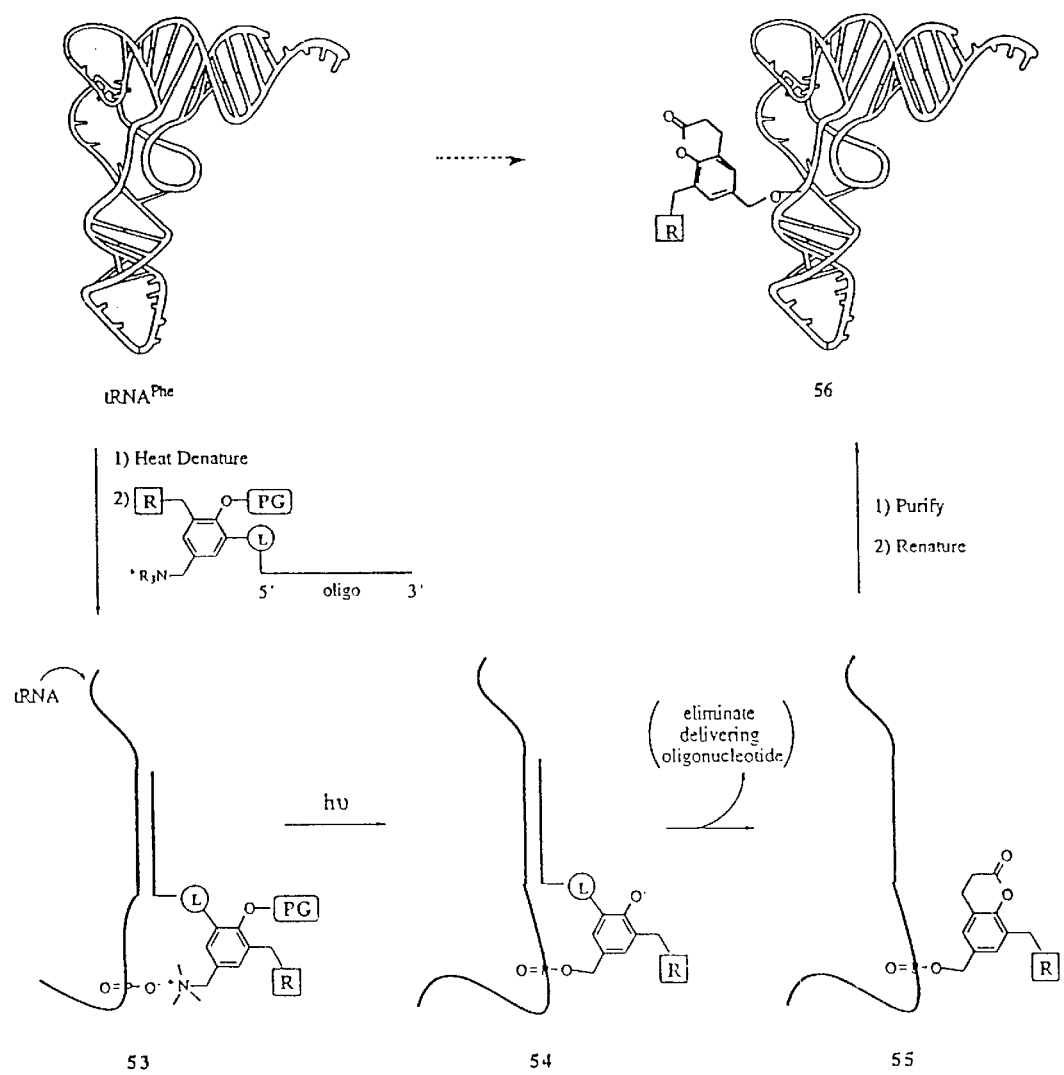

Fig. S8D
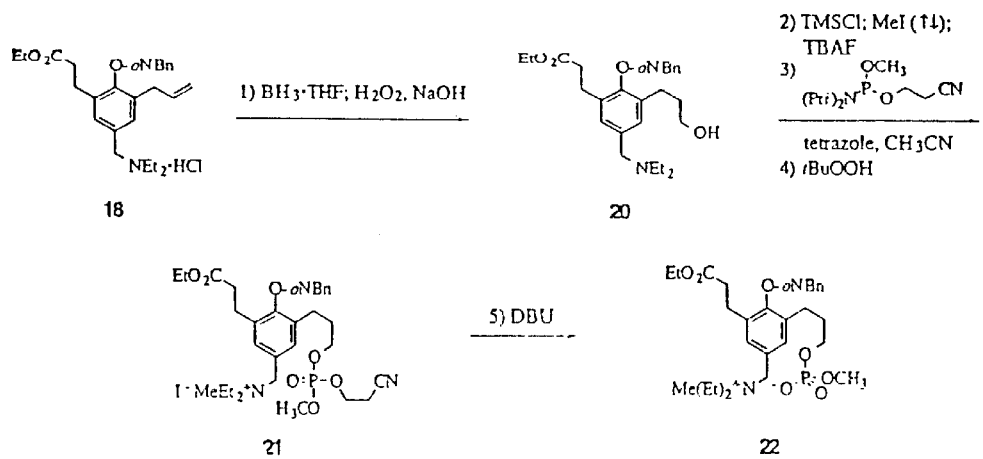
Fig. S9D
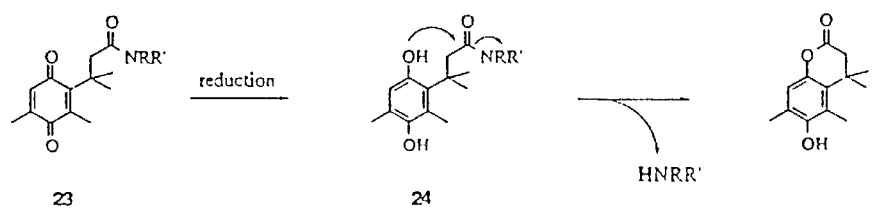
Fig. S10D
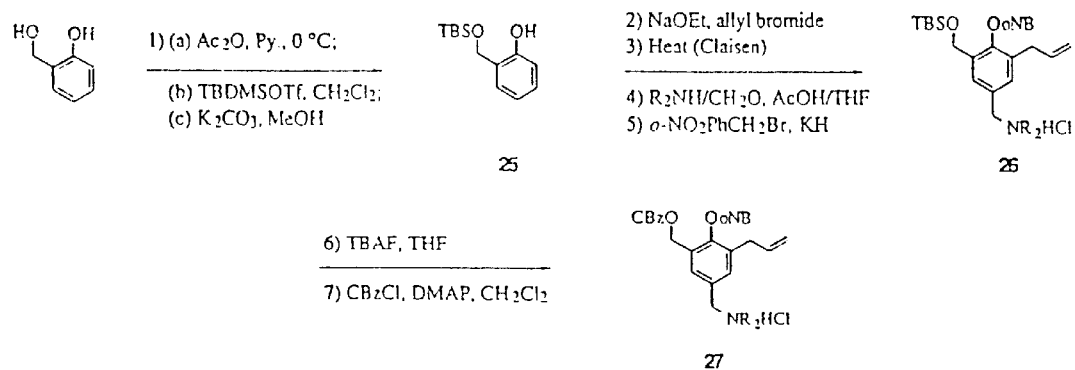

Fig. T3A
Teaching Experience and Purdue Student Evaluation Scores.
| Semester | Course Number | Course Title | Enrollment | Purdue Mean Score (of 5.0) |
|---|---|---|---|---|
| Fall, 1994 | CHEM 5633 | Organic Reactions | 6 | 4.1 |
| Fall, 1995 | 3603 / 3603H / 3703 | Organic Chemistry I | 79 / 2 / 5 | 3.9 / 4.3 / 3.7 |
| Spring, 1996 | CHEM 5633 | Organic Reactions | 5 | 4.8 |
| Fall, 1996 | CHEM 4723 / 5753 | Phys. Meth. Org. Chem. | 14 / 7 | 4.2 / 4.5 |
| Spring, 1996 | CHEM 5633 | Organic Reactions | 6 | 4.0 |
Fig. S9A
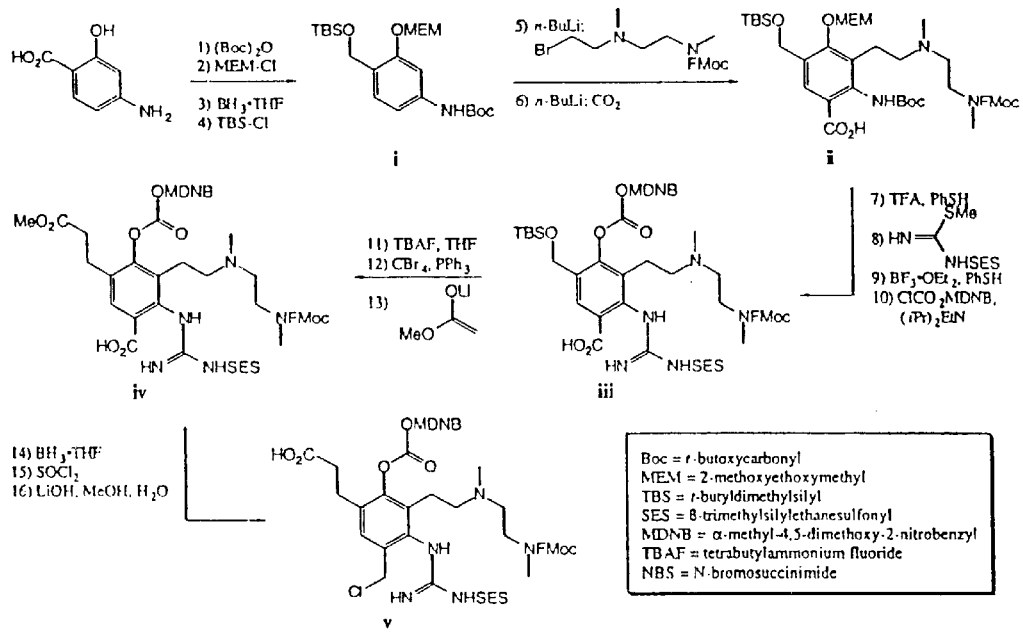

Fig. S1B
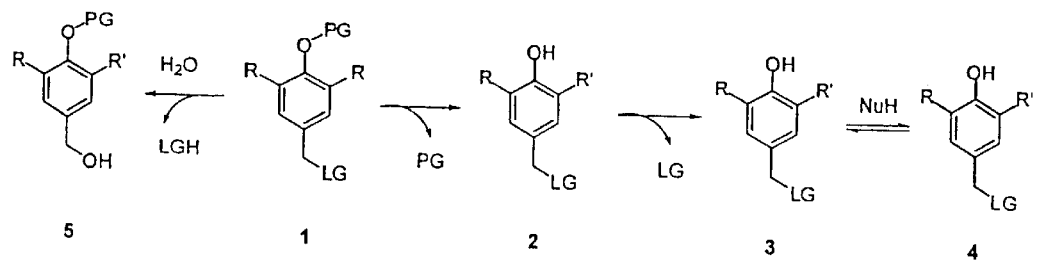
Fig. T1B
Synthesis of Quinone Methide Precursors.
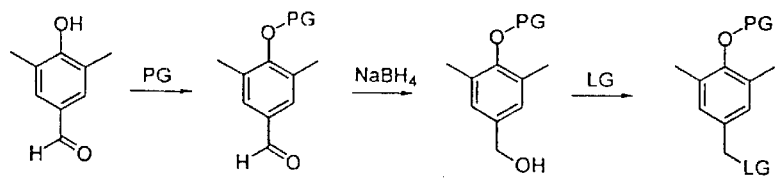
| Entry | Compound | Protection Conditions[a] | 7 (% yield) | PG[b] | 8 (% yield)[c] | LG | Halogenation Conditions[d] | 9 (% yield) |
|---|---|---|---|---|---|---|---|---|
| 1 | a | | | NBE | | F | | |
| 2 | b | i | 88 | NBE | 99 | Cl | i | 68 |
| 3 | c | | | NBE | | Br | | |
| 4 | d | | | MNVE | | F | | |
| 5 | e | ii | 60 | MNVE | 54 | Cl | i | 86 |
| 6 | f | | | MNVE | | Br | | |
| 7 | g | | | NBC | | F | | |
| 8 | h | iii | 75 | NBC | 56 | Cl | i | 90 |
| 9 | i | | | NBC | | Br | | |
| 10 | j | | | MNVC | | F | | |
| 11 | k | iv | 49 | MNVC | 75 | Cl | i | 76 |
| 12 | l | | | MNVC | | Br | | |

Fig. T2B

| Entry | Compound | t₁/₂ of hydrolysis (hrs) | | | | | | |
|---|---|---|---|---|---|---|---|---|
| | | % water in acetonitrile[a] | | | | temperature (° C)[b] | | |
| | | 5 | 10 | 33 | 50 | 25 | 37 | 50 |
| 1 | 9a | | | | | | | |
| 2 | 9b | | | 64.0 | | | | |
| 3 | 9c | | | | | | | |
| 4 | 9d | | | | | | | |
| 5 | 9e | | | 24.9[c] | | | | |
| 6 | 9f | | | | | | | |
| 7 | 9g | | | | | | | |
| 8 | 9h | | | d | d | | 752.6 | |
| 9 | 9i | | | | | | | |
| 10 | 9j | | | | | | | |
| 11 | 9k | | | d | d | | 1003.4 | |
| 12 | 9l | | | | | | | |

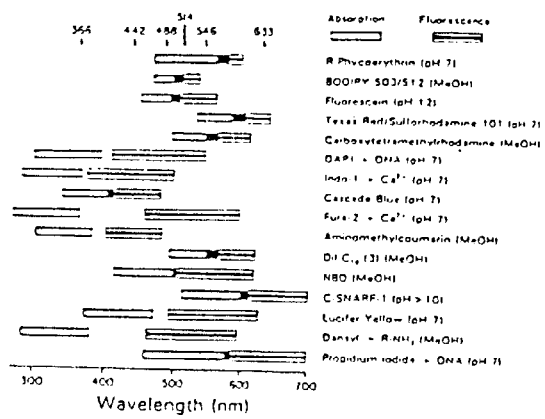
Vitamin: binding protein (biotin: avidin/streptavidin)
Hapten: hapten specific antibody (digoxigenin: anti-digoxigenin)
Bioluminescence (D-luciferin-$O$-phosphate with alkaline phosphatase (AP))
Chemiluminescence (1,2-dioxetane substrates with AP)
Chemically reactive, redox reactive and nuclear reporter groups:
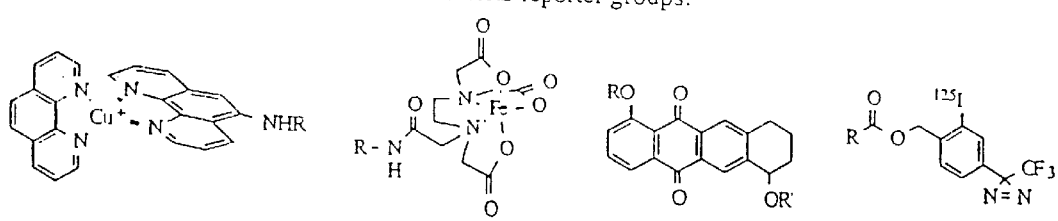
Fig. 2D Fig. S3 D
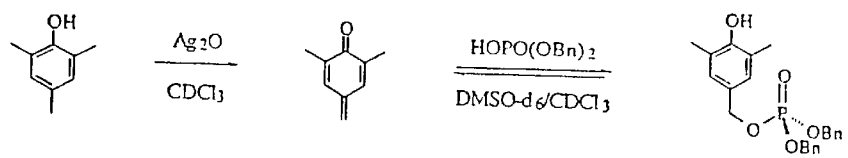
Fig. S4 D
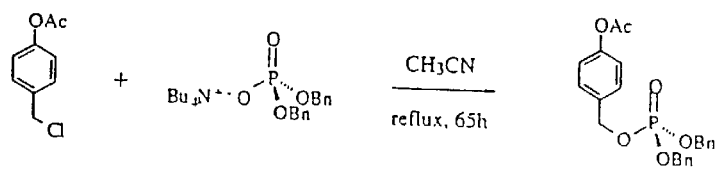
Fig. S5 D
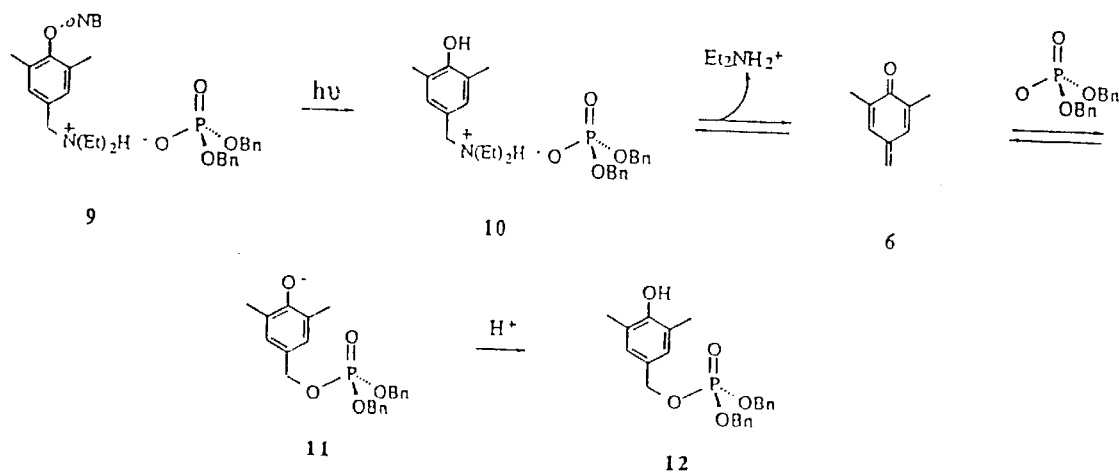

Fig. S6 D
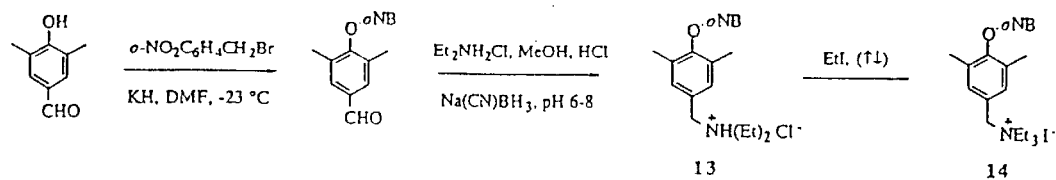
Fig. 3D
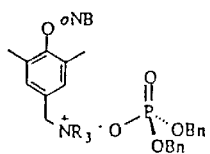
Fig. 4D
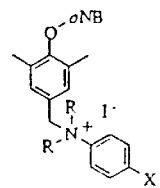
Fig. S7 D
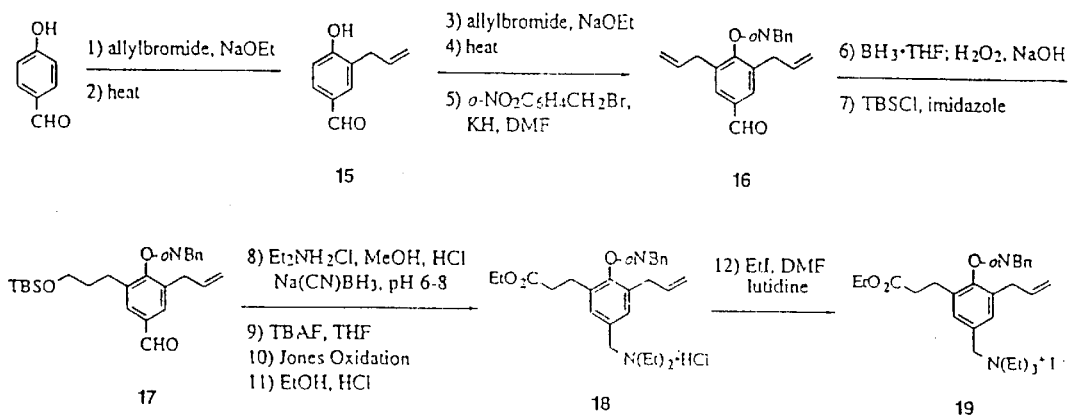

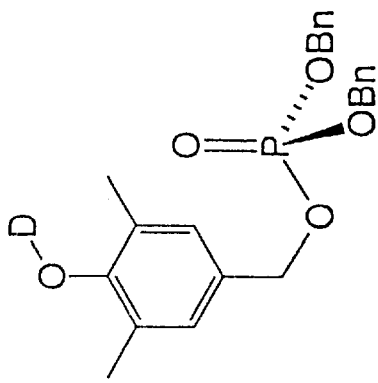
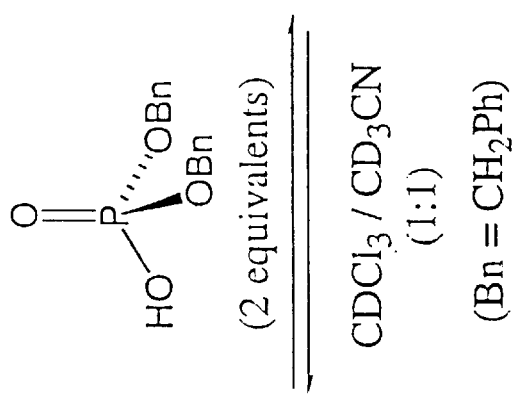
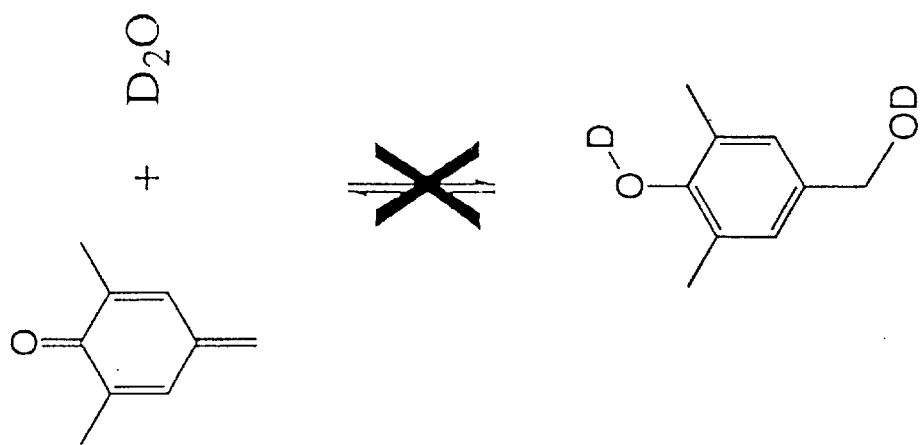
Fig. 9E (R = CH₃ or H)

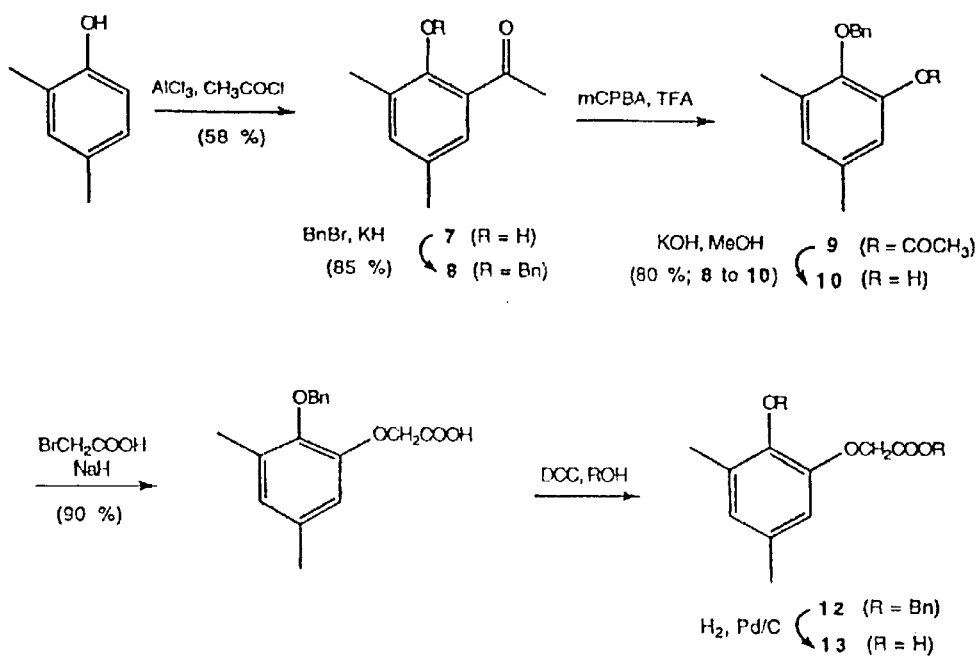
Fig. S4E

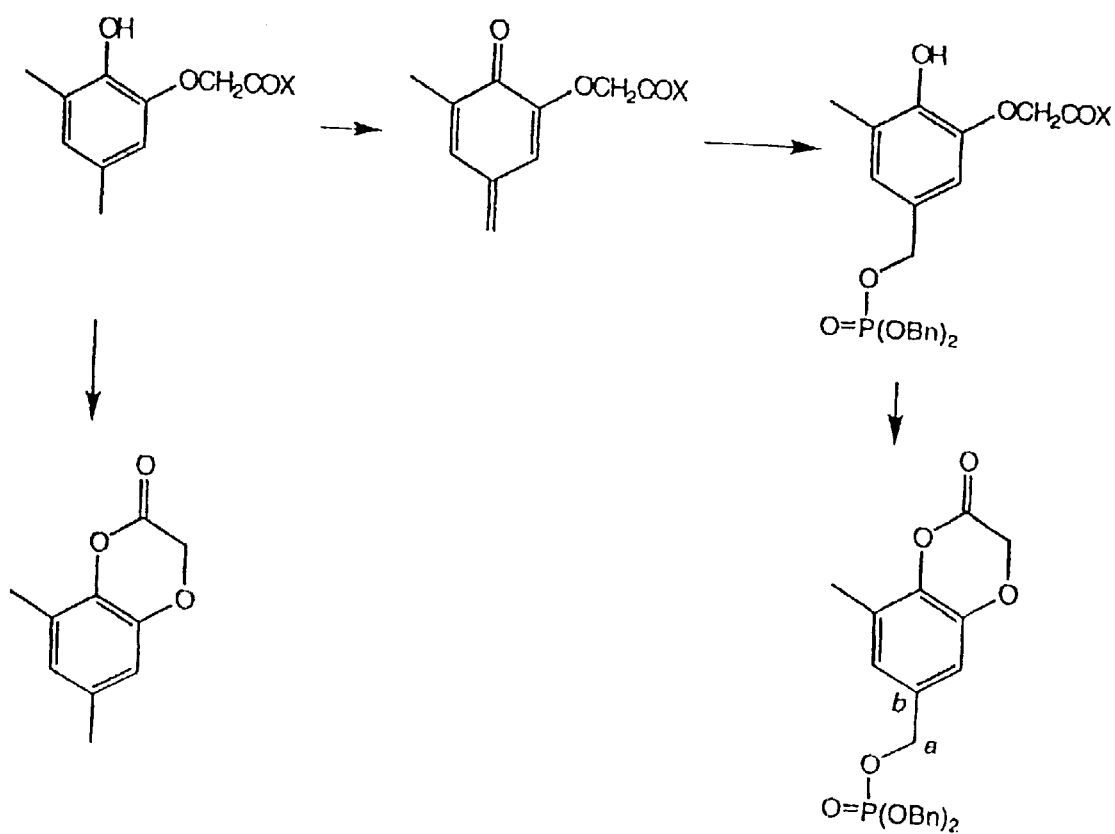
Fig. S5E

Control of Regioselectivity:

- Site-selectivity will be directed by hybridization of the complimentary delivering oligonucleotide.

Control of Chemoselectivity:

- Selectivity for the phosphodiester over minor or major groove reaction with bases will be directed by ammonium-phosphate ionic association.

- Tuning the ionic association directing force will be accomplished by altering the substituents on the ammonium group. It is expected that alkylation of minor groove nitrogens will increase with increased lipophilicity of the ammonium group.

- An alternate quinone methide-aziridinyl based reagent is also being developed which should allow more flexibility in tuning the lipophilic nature of the ammonium group.

Control of Stereoselectivity:

- Stereocontrol in the peralkylation reactions with the quinone methide reagent will take advantage of the natural asymmetry of the helical DNA structure. Asymmetric control will be examined with various heterogeneous complexes of the target oligonucleotide including:

a) Double-stranded complexes of DNA:backbone modified DNA (*e.g.*, DNA:PNA),
    b) Major groove bound complexes with DNA oligonucleotide (*e.g.*, triplex DNA),
    c) Minor groove bound complexes with DNA oligonucleotide (*e.g.*, distamycin).

Fig. 18E

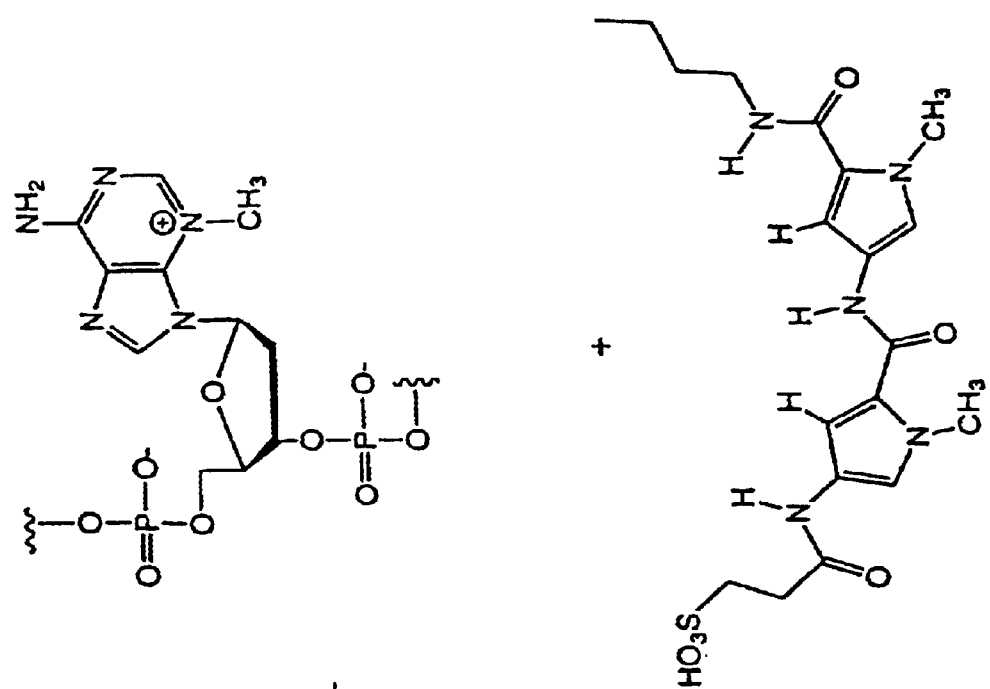
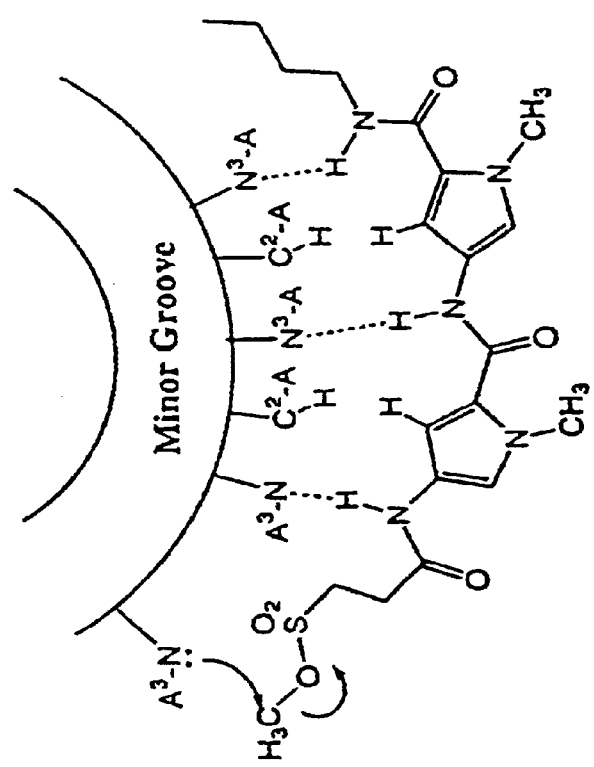
Fig. 20E

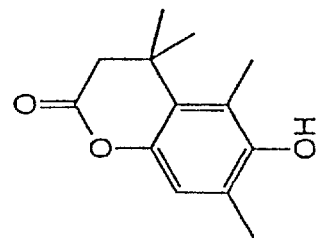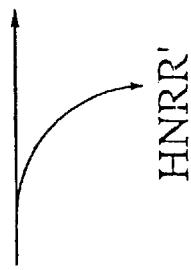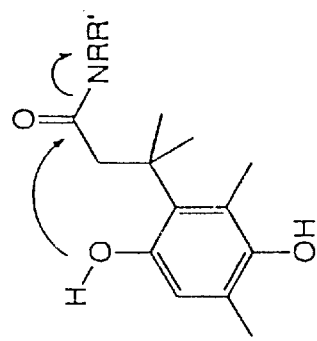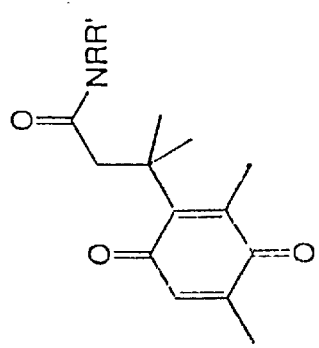
Fig. 21E

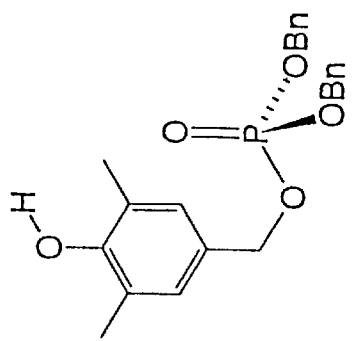
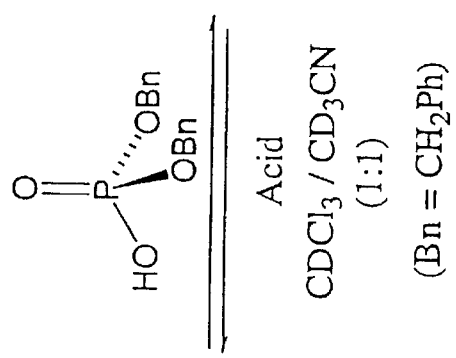
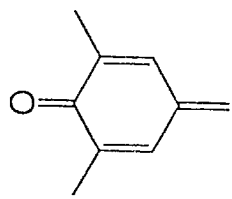
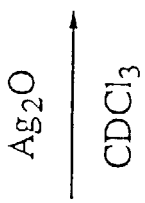
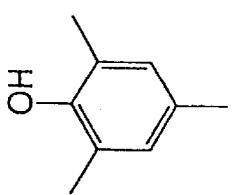
Fig. 32E

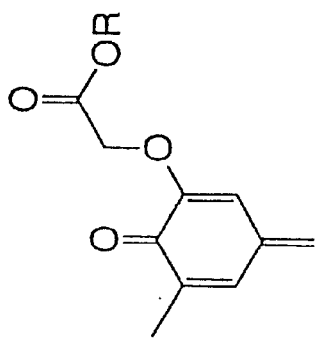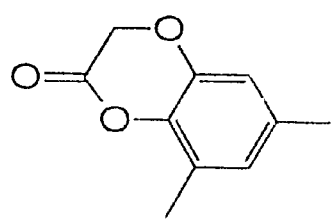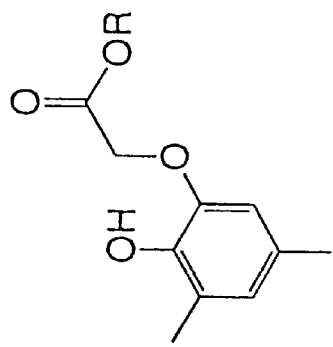
Fig. 42E

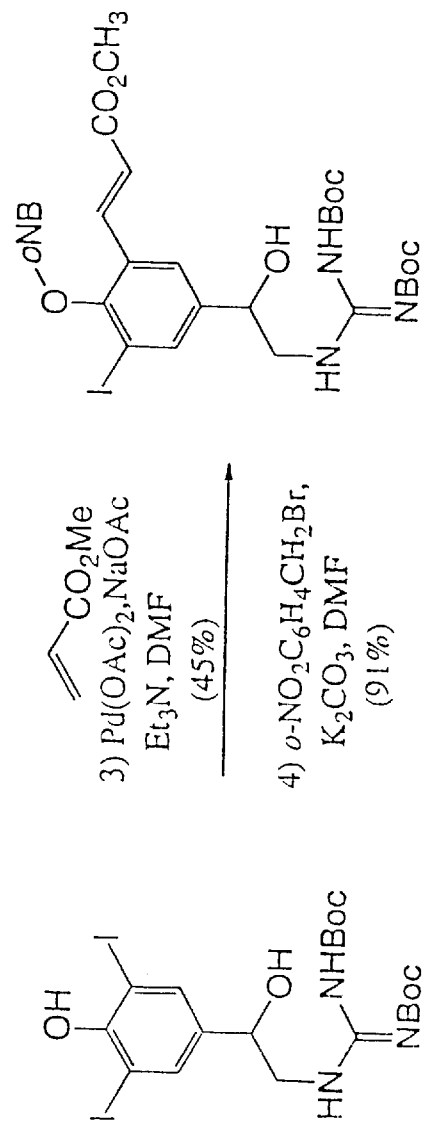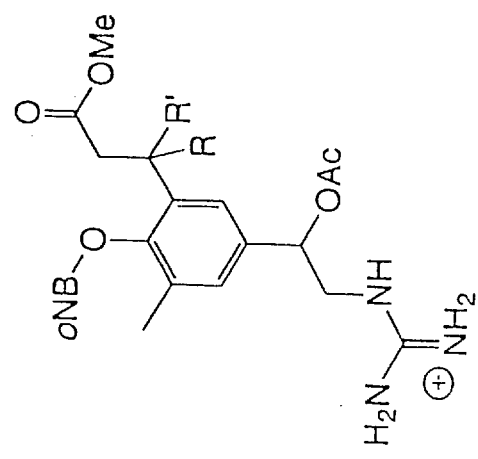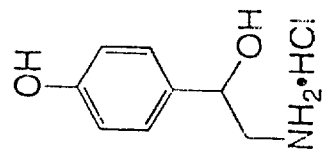
Fig. 48E

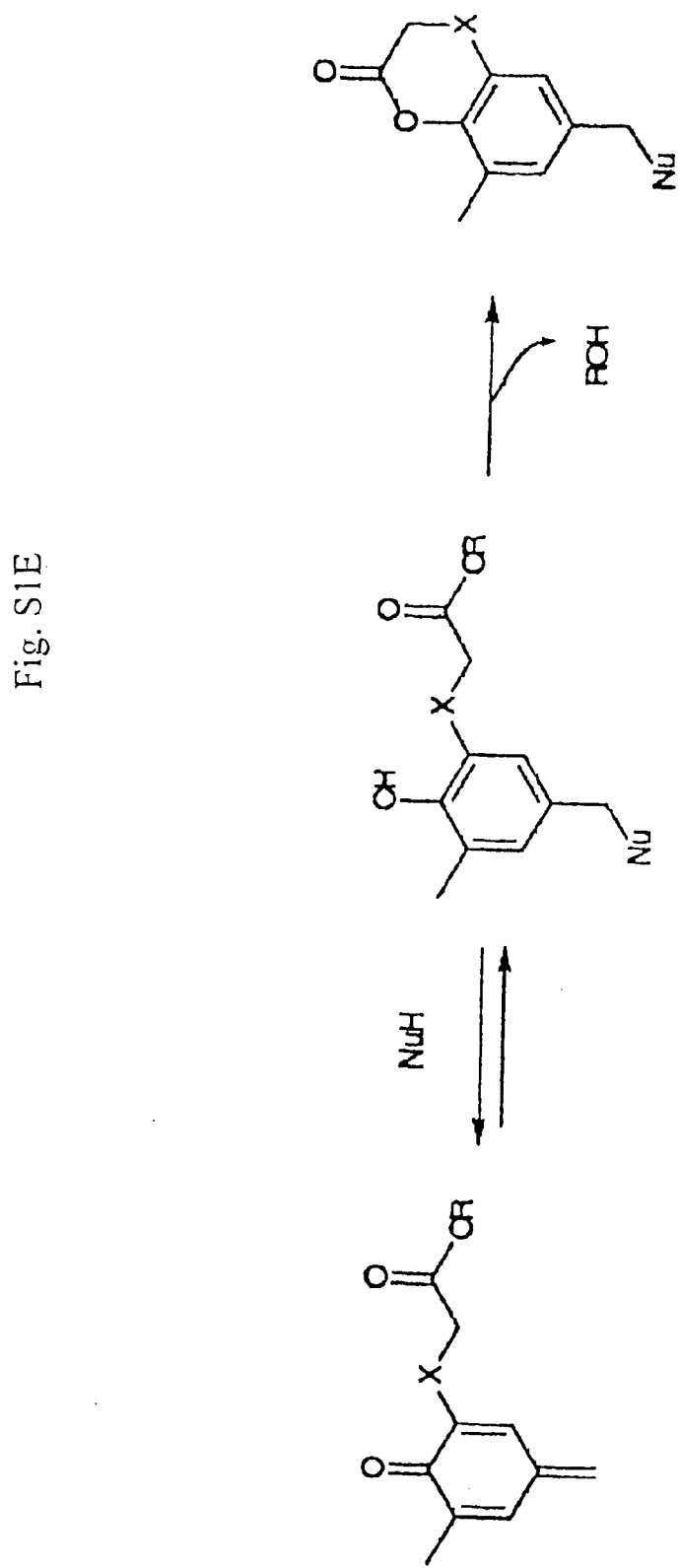
Fig. S1E

Fig. S2E
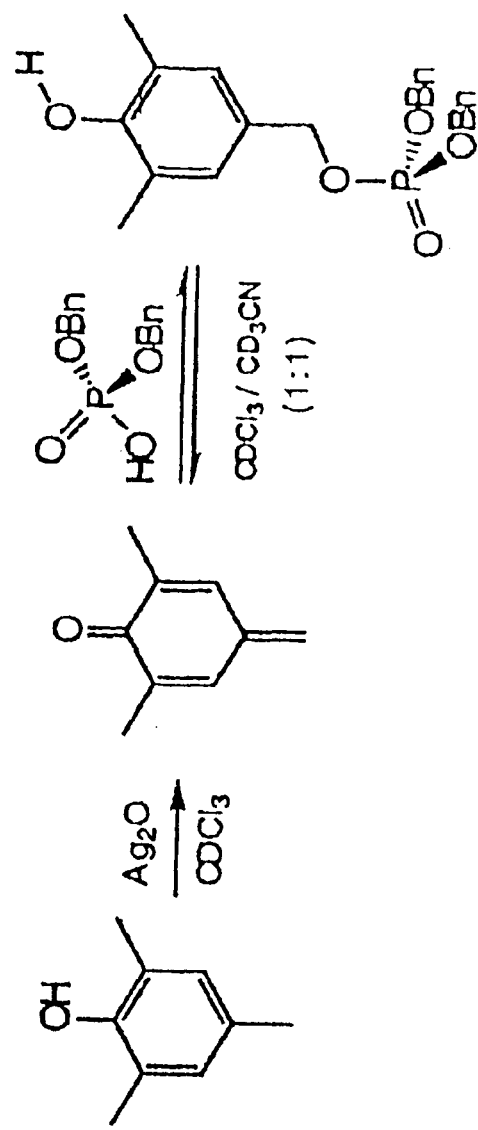

Fig. S3E
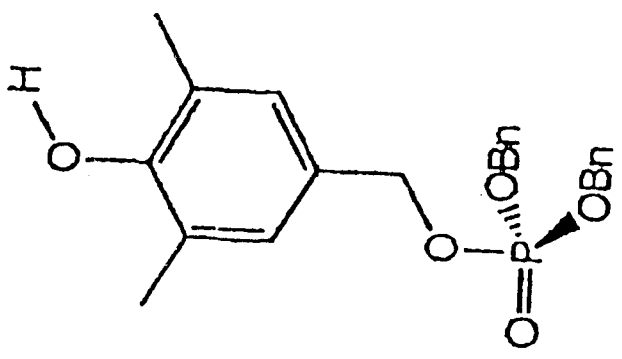
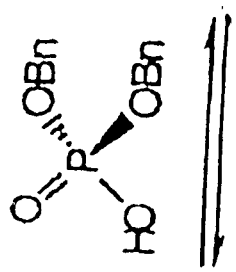
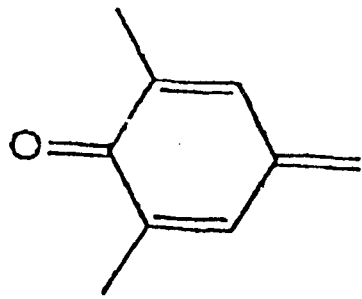
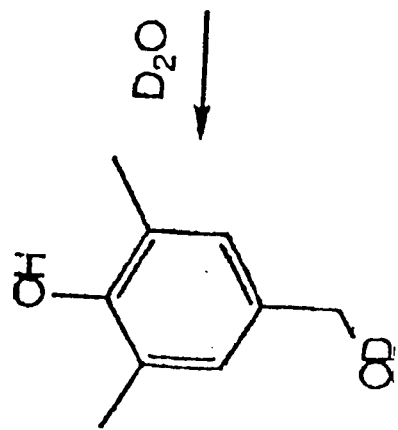

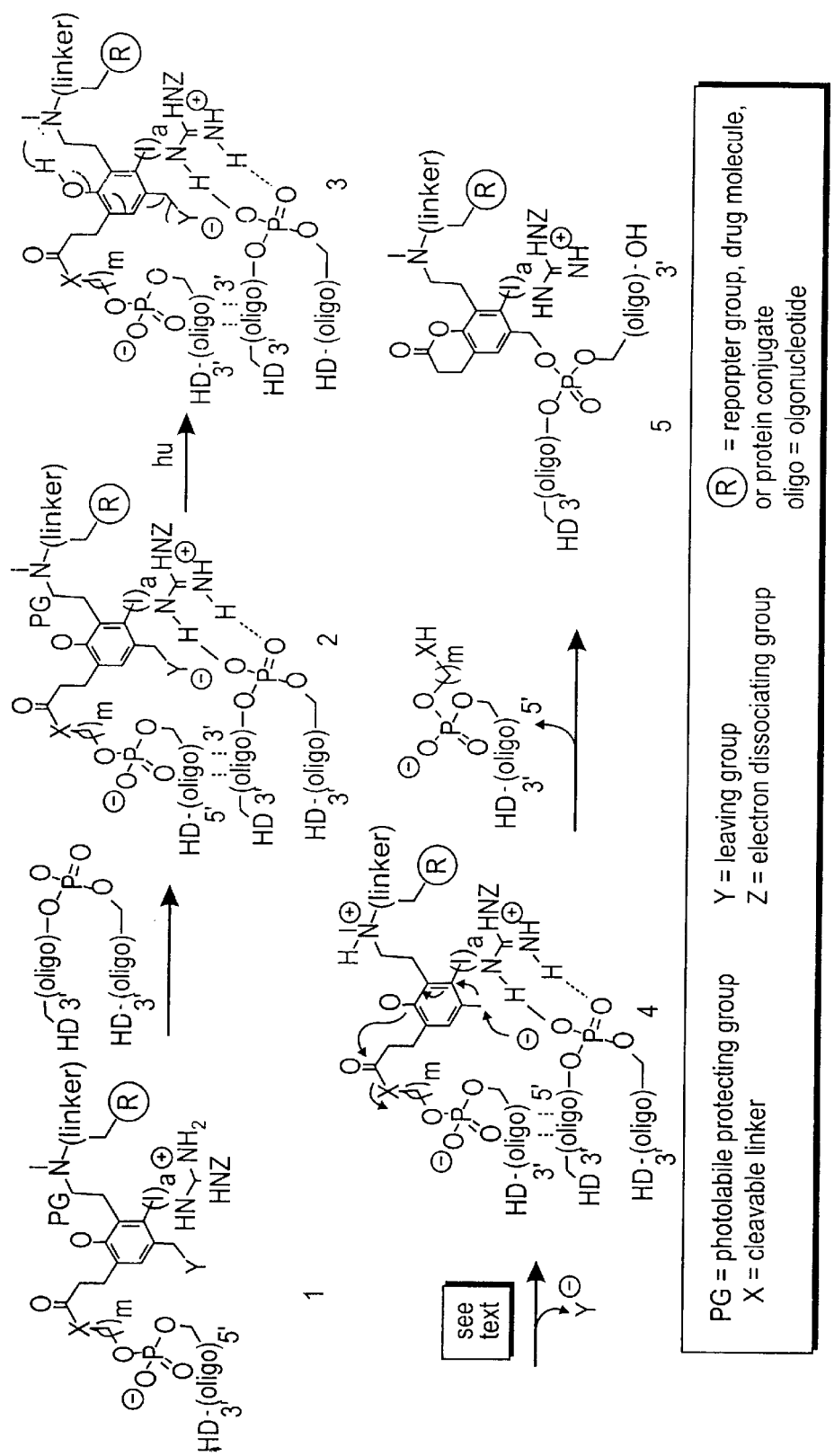
FIG. S1A

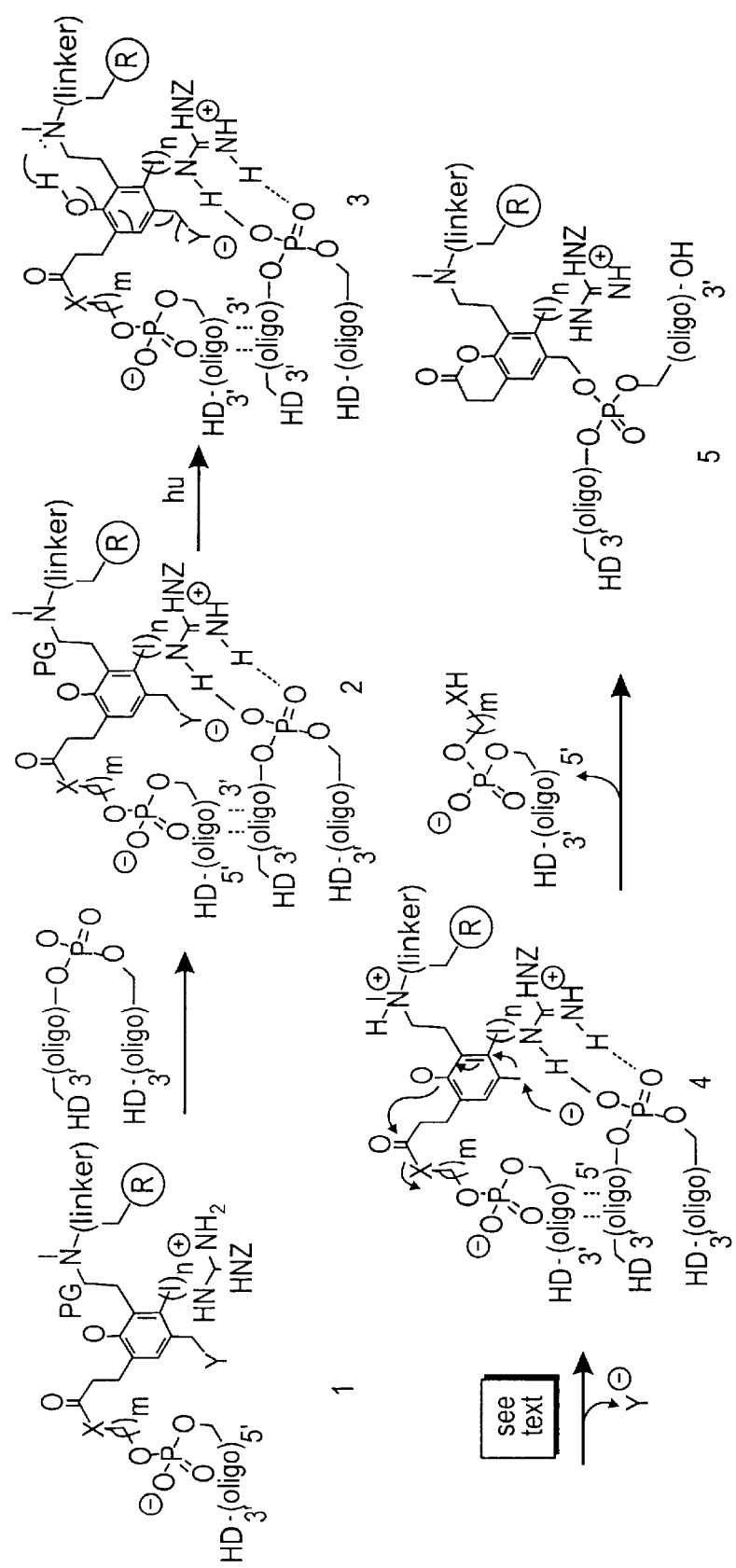
FIG. S1

Fig. S4
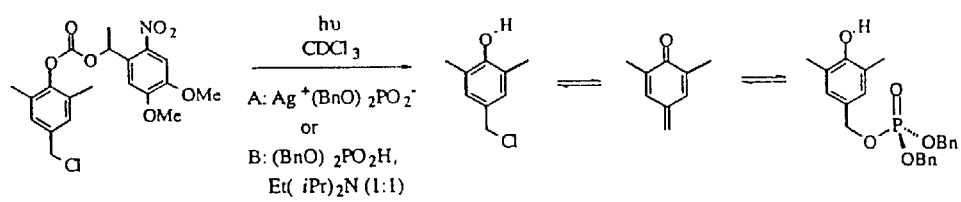

Fig. S7
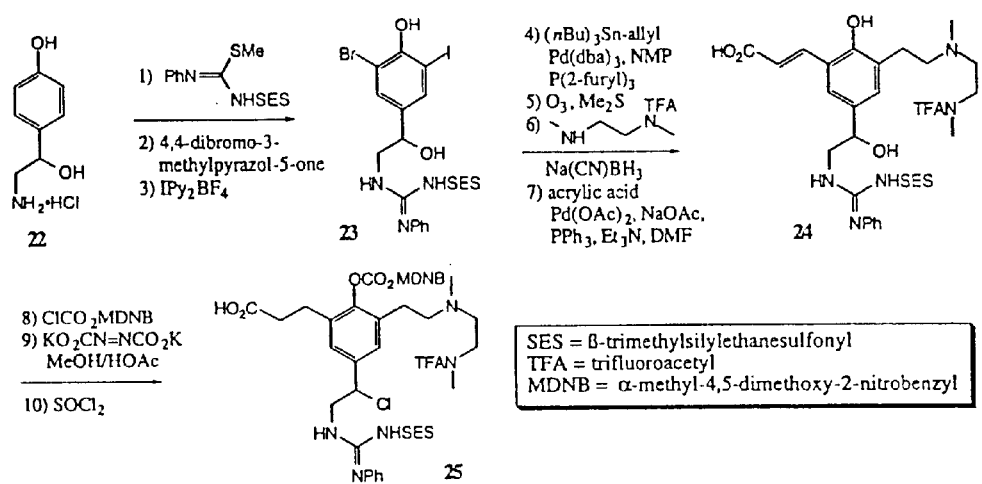
Fig. S8
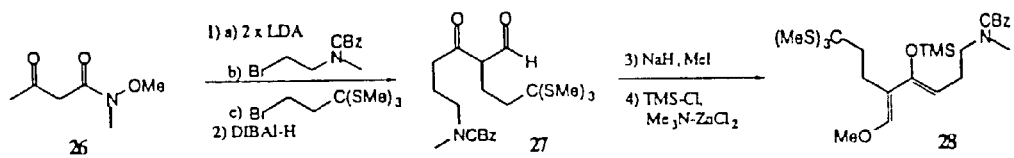

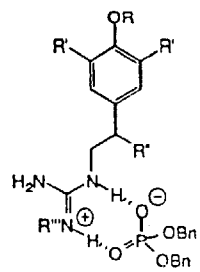
| Compound | R | R' | R" | R'" |
|---|---|---|---|---|
| 18 | H | H | H | H |
| 19 | H | H | OH | H |
| 20 | H | Me | H | H/Ph |
| 21 | MDNBC | Me | Cl | H/Ph |
Fig. 6
Fig. S6
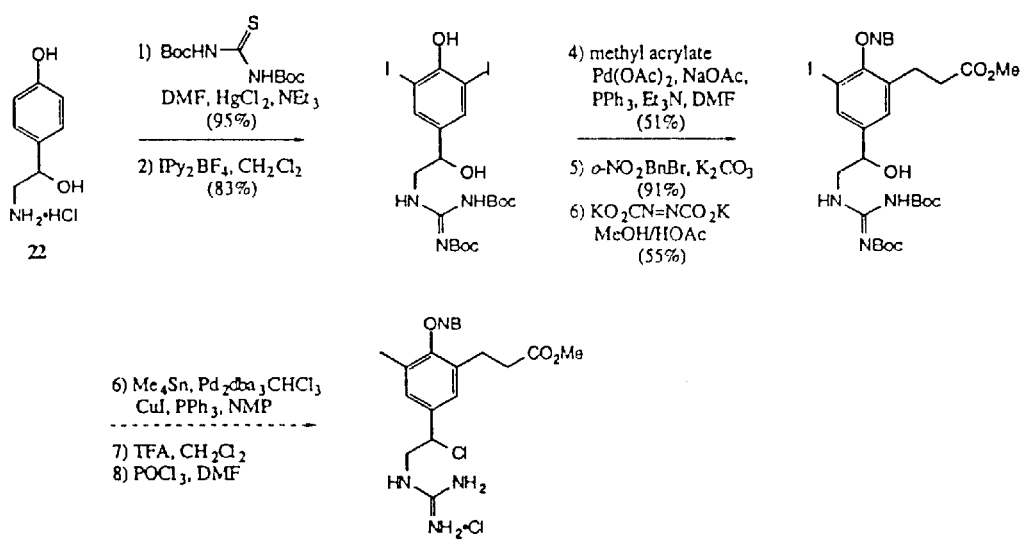

Fig. S9
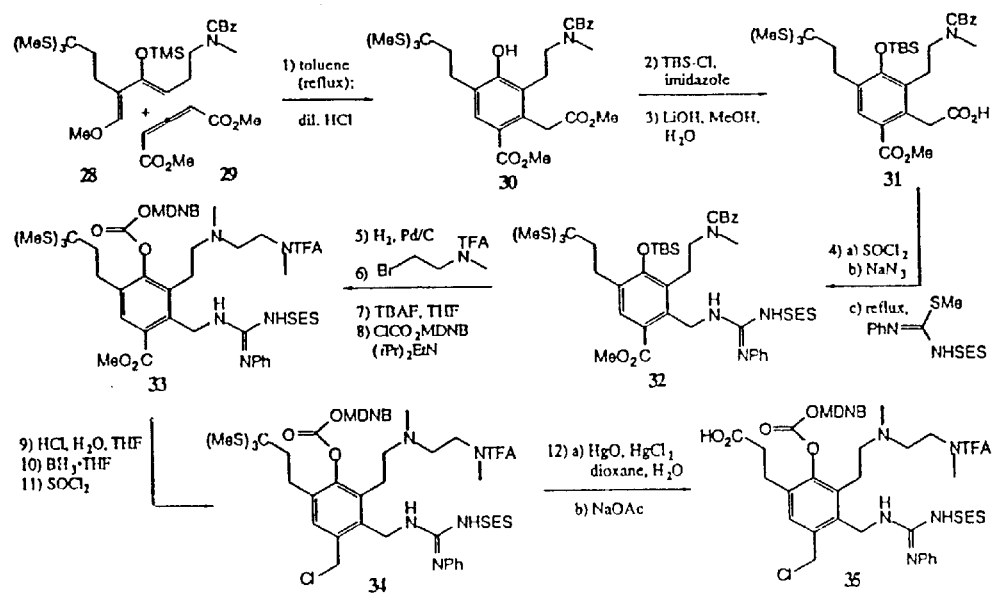
Fig. S10
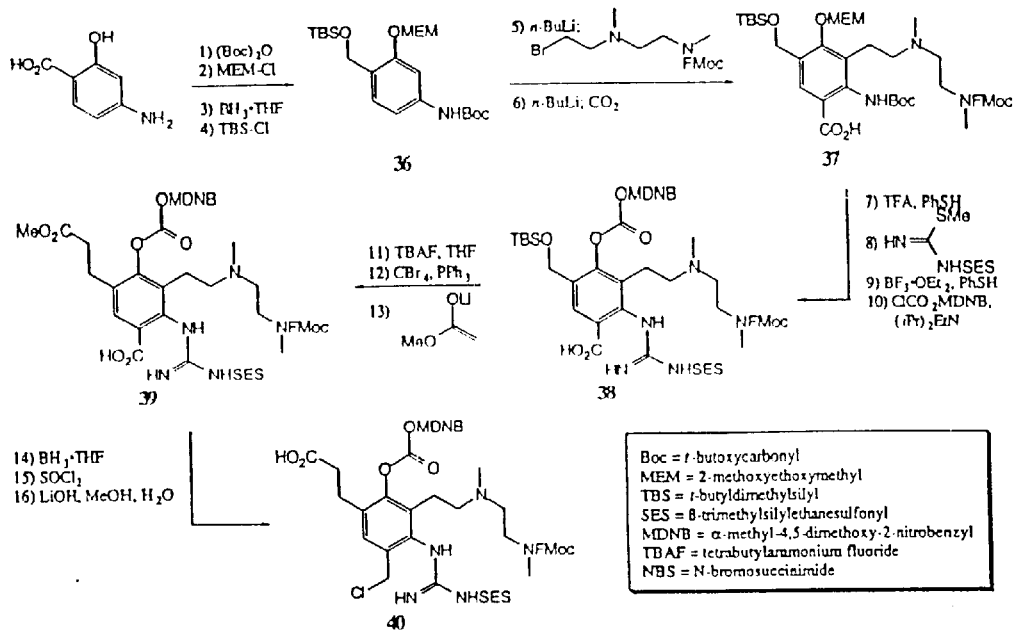

BIOMOLECULAR LABELING

CROSS-REFERENCE TO RELATED APPLICATIONS

This Application is a continuation-in-part of provisional application Ser. No. 60/041,883, filed Apr. 11, 1997, abandoned and Ser. No. 09/057,957, filed Apr. 9, 1998, abandoned which are hereby incorporated by reference.

STATEMENT REGARDING FEDERALLY SPONSORED RESEARCH OR DEVELOPMENT

REFERENCE TO A MICROFICHE APPENDIX

Not Applicable.

DESCRIPTION OF THE INVENTION

This research is developing a synthetic method and in vivo designed reagent for the chemoselective, covalent modification of the phosphodiester group in nucleic acid polymers. Successful alkylation of phosphodiesters to form stable phosphotriesters has been accomplished through the development of chemistry based on the reactive paraquinone methide. The systematic analysis of model compounds is being used to add increasingly higher levels of selectivity to the alkylating methodology. The design of these model compounds is evolving to incorporate the necessary functionality to achieve the development of a final reagent which will be used for selective in vitro modification of a single phosphodiester group within a DNA or RNA target. This final reagent is designed to allow the delivery of a variety of reporter groups, drug agents or protein conjugates to DNA or RNA targets. This methodology would allow for the molecular level study of protein-nucleic acid interactions in such complex systems as the chromatin, where molecular level understanding is still very limited due to the complex, multi-protein machinery which operates at this level. This would also lead to an innovative approach for site-selective drug delivery to nucleic acid targets. Lastly, this methodology has the potential for transcription control through the site-selective delivery of transcriptional activators to genetic targets.

This proposal focuses on the synthesis and analysis of the model compounds and reactions which are being developed in the process of optimizing the reagent design. This research is providing a detailed understanding of various chemical reactions and molecular interactions. The knowledge gained and compounds produced in the process of this research are providing new synthetic methodology for nucleic acid chemistry and compounds for nucleic acid modification. This proposal describes the research necessary up to the total synthesis of a fully functionalized labeling reagent and its characterization.

1. Specific Aims

Rapid progress in sequencing the human genome[1] opens new doors for potential technological developments for studying and treating disease at the foundational genetic level. One area of such potential development is the in vivo chemical modification of genomic DNA for diagnostics, therapeutics, and the study of biological processes. This requires progress in several areas of biomedical technology. Advances in oligonucleotide delivery to cells[2] and sequence-specific recognition of DNA[3] are two key areas. Our research program is targeting an unexplored area for the development of an innovative, chemical means to covalently deliver a variety of reporter groups, drug agents, or proteins to DNA. The ability to site-specifically attach such moieties to DNA would allow various genetic-based, biological studies to be conducted[4] and provide a new means for efficient diagnostics[5], therapeutics[6] and biological control at the genetic level[7].

Covalent modification of the phosphodiester group would be of most interest as it is the common, repeating, nucleophilic functional group throughout nucleic acid polymers. Whereas covalent modification of the nucleic acid bases generally leads to strand cleavage through depurination and will disrupt base pairing by interfering with hydrogen bonding, modification of the phosphate will likely have less effect on nucleic acid structure and function (FIG. 1).

This proposal will present the foundational research necessary for development of such a chemical reagent to accomplish this overall goal. This research is developing a variety of useful chemistry, synthetic methodology, and compounds in pursuit of the long-term goal.

The final in vivo designed reagent will covalently transfer attached molecules to a target phosphate group of a nucleic acid polymer (FIG. S1). The reagent is designed around a quinone methide with its bimodal electrophilic and a nucleophilic reactivity. The design features include:

An independently tethered delivering oligonucleotide and molecule to be transferred (1, loligo and R, respectively, FIG. S1). These are appended to a DNA synthesizer, machine-ready core reagent using standard automated, solid-phase, synthetic protocol for simplicity, efficiency and versatility.

Phosphate specificity through a guanidinium-phosphate complex (2). The guanidinium group will be substituted as needed to lower it nucleophilicity and prevent intramolecular reaction.

"Caged" reactivity initiated by proteolysis to afford the quinone methide precursor (3).

An intramolecular tertiary amine may be incorporated if it proves beneficial to assist 1,6-elimination[8] to afford the intermediate quinone methide (4).

Alkylation of the phosphodiester with the quinone methide resulting in the in vitro release of the delivering oligonucleotide through lactonization to accomplish the transfer step (4 to 5). The oligonucleotide tether is designed to be cleaved at a slower rate than 1,6-elimination occurs. The intramolecular conjugate acid will afford stability to the trialkylphosphate prior to lactonization.

Formation of a covalently stable trialkylphosphate upon lactone formation by trapping the ailcylated product (5) and preventing reaction reversibility.

The reagent is an affinity transfer alkylating reagent (ATAR) for labeling the phosphodiester of nucleic acids. The research program is designed to streamline development of the ATAR by optimizing the chemistry through independent model system studies. The final reagent will be suitable for general use by attaching any delivering oligonucleotide on an automated synthesizer followed by attachment of a desired reporter group[9], drug agent[10], or protein conjugate[11] on the solid support or post-synthetically. This provides a "user-friendly" reagent for use in modifying DNA, studying various nucleic acidprotein interactions, and for drug delivery applications.

The chemistry required for the ATAR is being developed through a variety of small molecule model studies. Each study requires minimal synthesis in order to independently investigate the various chemical aspects of the ATAR for optimization. The project has been designed so that the short-term model studies can be carried out by undergraduate research assistants. Progressively more complex studies are underway in order to coordinate the compatibility of the chemical reactions for optimal control of all aspects of the ATAR design. The chemistry necessary for the total syntheses of fully functionalized derivatives for incorporation into the ATAR on a DNA synthesizer is being developed in the course of these model studies. The multiple small component contributions required for this project make it an optimal training ground for short-term undergraduate research. This proposal maps out the investigations for development of the chemistry of the ATAR focusing on the model system syntheses and studies. Although the overall goal of this research is the envisioned applications of the ATAR mentioned above[4-7], this will be beyond the time frame for which present funding is sought.

Several significant subset developments result from the pursuit of the overall research goal. One will be a simplified synthetic method[12,13] for site selective alkylation and peralkylation of oligonucleotide phosphodiesters to produce trialkylphosphate modified oligonucleotides for various uses.[14,15,5] This backbone modification affords enhanced hybridization properties[16], antisense/antigene applications[17,18] and peralkylations of the phosphodiesters will alter an oligonucleotides solubility properties for use in large-scale solution phase oligonucleotide synthesis. This research has already afforded a useful synthetic method for modifying phosphodiesters with the formation, isolation and fall characterization of trialkylphosphates[19]. Some aspects of commercial potential for this methodology are being pursued with industrial support[20]. A non-specific chemical nuclease is being developed in conjunction with this research and a method for the site-selective hydrolytic cleavage of DNA[21,22].

2. Background and Significance

Heterobifunctional crosslinking reagents. containing a cleavable linker have been developed for studying protein-protein interactions[23]. These reagents require an invasive chemical step to transfer the probe molecule from the delivering species to the target protein. This limits their use to in vitro applications. The ATAR we are developing will involve an in vitro cleavage step of the initially formed crosslinked complex in order to release the delivering oligonucleotide. This forms a DNA target which has been covalently modified with a small molecule carrying the independently attached label. The independent synthetic attachment of both the delivering oligonucleotide and the desired reporter group, drug agent, or protein provides a versatile ATAR for various applications.

One example of a reagent which transfers a methyl group from a nucleic acid binding reagent to a nucleic acid base in vitro comes from the work of Gold and coworkers[24]. They produced a methylating reagent by tethering methyl sulfonates to a dipeptide lexitropsin, an A/T-rich minor groove binder. This reagent allowed methylation of the adenine-N3 selectively, resulting in the release of the lexitropsin sulfonic acid byproduct. The goal of this proposal is to define a method to extend this type of in vitro transfer chemistry beyond methylation to the transfer of a large variety of reporter groups or drug molecules. This will be accomplished by having them tethered to a reactive quinone methide[25,26] which will initiate nucleophilic attack followed by the in vitro release of the delivering molecule. Further, the ATAR being developed will be latently reactive upon photolysis after binding to the target site in order to minimize secondary alkylation reactions. It will also target the phosphate residue of nucleic acids in order to minimize perturbation of the bases, leaving the nucleic acid free for hybridization.

Although the phosphate residue of nucleic acids is not the chemoselective site for alkylation by many routinely used electrophilic reagents[27], in vitro ailcylation of the phosphodiester to afford phosphotriesters is observed. Ethylnitrosourea (GNU) shows the highest selectivity for phosphotriester formation relative to methylnitrosourea (MNU), dimethylsulfate (DMS) and ethylmethanesulfonate[28]. Expressed in terms of total DNA alkylation, the extent of phosphodiester alkylation by ENU has been estimated to be between $59\%^{28a}$ and $70\%^{28c}$.

A quinone methide is an effective ailcylating agent with a dialkylphosphate (see Preliminary Results). A quinone methide (FIG. 2) is a potent electrophile due to its highly polarized nature. Rearomatization of the quinone methide ring is a strong driving force for reaction[29]. This relatively hard electrophile is a good alkylating agent for the hard phosphate oxygen[30].

Skibo and coworkers have recently developed a molecule (5, FIG. 3) that alkylates the phosphate residue of nucleic acids[31]. This molecule contains a binding region which recognizes the adenine-thymine (A-T) base pair (and to a lesser extent the guanine-cytosine (G-C) base pair). The alkylating region is composed of an aziridium moiety for selective phosphate alkylation (6, FIG. 3) instead of normal alkylation of N-7[32].

Day and coworkers attempted to develop a reagent for alkylation of DNA phosphate groups using para-bromomethylbeazoyl choline iodide[33]. Unfortunately, it was later reported the reagent was polymerizing and phosphate alkylation was not occurring[34]. This work suggests the challenge in finding a strong enough electrophile to selectively react with a phosphate. As indicated, we have already shown that quinone methides alkylate dialkylphosphates in an aqueous environment.

The guanidinium functional group is extensively used in biological systems and various artificial receptors for phosphate recognition and binding[35]. This type of ionic association of cationic amine residues with DNA has been successfully used by other researchers in order to enhance binding to DNA[36]. As charge-charge attractions are the strongest noncovalent molecular interactions, salt bridges between nucleic acid phosphates and positively charged amino acid side chains are individually the highest strength interactions in protein-nucleic acid interactions[37].

The ATAR we are developing takes advantage of this type of guanidinium-phosphate ionic association to direct the alkylation process. The precursor to the quinone methide will incorporate a guanidinium residue to enhance the effective concentration of the phosphodiester. The guanidinium group may associate with other nucleic acid sites, such as the bases[38]; however, the thermodynamic preference for two point hydrogen bonding and charge pairing of a guanidinium-phosphate complex is well accepted[35,37].

3. Preliminary Results

Various model system studies are being conducted to develop the chemistry necessary for the ATAR. Below are nine key results which contribute to the ATAR development. In the area of in vivo design, the importance of a compound comes only with proven function. This of ten delays publication of foundational work until the significance of the chemistry is verified. The formation of isolated, fully characterized trialkylphosphates has been accomplished to provide a useful synthetic approach for modifying phosphodiesters. Due to this recent demonstration of function, publication of these results are in progress[19] and publication of the foundational work which supported it will follow[39]. There is presently a provisional patent covering many of these developments[40]. Some aspects of commercial potential of the phosphotriester forming reactions are being pursued with industrial support[20].

The small scale of these model studies as individual components of the projects overall goals make the research readily suited to undergraduate research. In less than two years of effort on this project, five different undergraduate and three graduate students have been involved at different times.

3.1. Quinone methide alkylation of a phosphodiester to form a phosphotriester. Studies of a quinone methide with a dialkylphosphate have been conducted[39a] 2,4,6-Trimethylphenol was quantitatively converted to quinone methide 7 with AgzO[41] and dibenzylphosphoric acid was added to produce phosphotriester 8 as the exclusive product (FIG. S2)[41].

3.2. Phosphotriester product is favored upon protonation. Formation of 8 is an equilibrium process. Trialkylphosphate 8 is favored under acidic conditions which protonate the quinone methide oxygen leading to the phenol. However, under basic conditions where the phenol is deprotonated or conditions acidic enough to protonate the phosphotriester oxygen, 7 is favored[39a]. As initially seen by the effect of various acids in the pKa range shown in FIG. S3, this should favor phosphotriester formation under biologically relevant conditions near pH 7.

3.3 Kinetic favorability of phosphotriester formation over hydrolysis in the presence of water. The reaction of quinone methide 7 and two equivalents of dibenzylphosphoric acid in the presence of excess water (~200 equivalents for a homogeneous solution) afforded only trialkylphosphate 8 as the product in the equilibrium by 1H NMR analysis. Minor amounts of the benzyl alcohol hydrolysis product was evident by 1H NMIR analysis after 18 hours at ambient temperature. Trialkylphosphate 8 is the kinetic product. A similar amount of 8 is produced in the presence of a much higher concentration of water (3,000 equivalents forming a bilayer) at ambient temperature after 30 minutes. However, the benzyl alcohol hydration product begins to drain off the kinetic ally formed 8 affording complete conversion to benzyl alcohol after 18 hours. Hydrolysis to benzyl alcohol appears to be the thermodynamic product[39]. Similar results of quinone methides reacting with amino acid derivatives under aqueous conditions have been reported by other researchers[43].

3.4. Hydrolytic stability of an acetylated trialkylphosphate derivative. The effect of protonation on the alkylation reaction above, and the trialkylphosphate being the kinetic product, suggested trapping of the phosphate alkylated DNA as lactone derivative 4 (FIG. S1) should be favored over hydrolysis (to afford a benzyl alcohol) under physiological oconditions. Investigation of the stability of lactone trapped trialkylphosphate product was the next step. The high stability of independently synthesized 9[44] (FIG. 4) in water (pH 6.5, 40° C., overnight) demonstrates the expected stability of the lactone product 4 (FIG. S1) which will result from the ATAR phosphate alkylation reaction[39b].

3.5. Trapping stable phosphotriesters through tandem lactonization after quinone methide alkylation of a phosphodiester. The isolation of stable, fully characterized products has been imperative to the development of useful synthetic methodology from this research. This has now been accomplished[19]. Variety of ester derivatives have been synthesized to study the requirements for trapping the trialkylphosphate through lactonization. Characterizable quinone methide intermediates are prepared via Ag2O or PbO2 oxidation. It proved necessary to synthesize derivatives with an oxygen at the ortho-position (catechol derivatives, 10a, FIG. 5) to exclude the formation of ortho-quinone methides upon oxidation if the esters were tethered through a methylene at the ortho-position (10b, R2=H, H, FIG. 5). Attempts at making secondary or tertiary substituted tethers at the ortho-position (10b, R2=H, CH3 or CH3, CH3, FIG. 5) resulted in facile lactonization (gem-dialkyl effect) circumventing oxidation to the quinone methide. These catechol derivatives may provide a beneficial modification to the ATAR design. An oxygen at the ortho-position of a para quinone methide appears to increase the reactivity of the quinone methide towards nucleophilic addition[45,46]. The ortho-oxygen is expected to affect the rate of the lactonization reaction and the stability of the lactone product towards hydrolysis. This catechol-type system (10a) will be compared to the corresponding phenol system with an ortho-alkyl tether (10b). The quinone methide from the latter systems will be formed by 1,6-elimination of a benzylic leaving group.

The ester derivatives were made in five steps from 2,4-dimethylphenol[47]. These esters include three classes: high, intermediate and low reactive derivatives (see FIG. S3). The high reactive esters lactonized to afford 12 under the mildly basic conditions of oxidation. The low reactive derivatives were oxidized to the corresponding quinone methide 13 and underwent dibenzylphosphate addition; however, were not able to lactonize under the alkylation conditions. The intermediate reactive derivatives were successfully oxidized to para-quinone methide intermediate 13, alkylated the dibenzylphosplate to 14, and lactonized to afford trapped trialkylphosphate product 15 (FIG. S3).

This now provides a useful synthetic approach towards the covalent functionalization of phosphodiesters. The key, fundamental reactions of the designed ATAR reagent have been successfully demonstrated. The details of these investigations are being submitted for publications[1] 9. The alkylation of nucleotide derivatives are presently being studied having obtained enough of various required dinucleotides for NMR analysis of the phosphodiester alkylation[48].
[1]9

3.6. Quinone methide formation through photolytic-initiated 1,6-elimination followed by phosphodiester alkylation. After significant effort, the conditions necessary for photolytic removal of a protecting group followed by 1,6-elimination to afford the para-quinone methide and reaction with dibenzylphosphate has been accomplished. Although there are numerous reports of reactions which occur through the presumed formation of quinone methide intermediates by 1,6-elimination processes[26,49,50] to our knowledge this is the first case of caged, photolytically-activated p-quinone methide formation via elimination with characterization[39c,51]. Multiple derivatives have been synthesized as discussed below (point 8, FIG. T2). The first successful reaction was accomplished using 16 (FIG. S4). Photolysis of 16 (150W xenon arc lamp, BiCI3/HCl filter, S2 ambient) was monitored by 1H NMR in CDCl3 with either: (A) one equivalent of Ag~(BnO)2PO~-salt, or (B) one equivalent of (i-Pr)2EtNH~(BnO)2PO2-salt. After photolysis for one hour, nearly all of 16 was deprotected to form a mixture of phenol 17, quinone methide 7 and trialkylphosphate 8 in approximately 2:1:1 ratio, respectively. This photolytic-initiated reaction did not go to completion, but appears to form an equilibrium mixture of 17:7:8 under these conditions. Note that under aqueous conditions for which the ATAR is being designed to operate, the chloride will not be a competitive nucleophile, and will rapidly diffuse away from the quinone methide. Preliminary experiments having water present show no sign of equilibrium back to 17. This experiment did not have the benefit of an intramolecular trap to drain off the kinetic preferred trialkylphosphate or the assistance of a phosphate-directing guanidinium group.

3.7. Hydrolytic stability of the quinone methide precursor and photolytic stability of the quinone methide intermediate and the trialkylphosphate product. Experiments have demonstrated the benefit of a carbonate protected phenol (e.g., 16, FIG. S4) for greatly increasing the stability of the benzylchloride. Hydrolysis of quinone methide precursors has been a problem with many quinone methide-based, biologically reactive molecules.[26,43,49] The carbonate protected 16 has shown no sign of hydrolysis at 250° C. in 33% D20/CD3CN for two days. Related benzyl protected derivatives hydrolyze relatively rapidly[39].

Due to the precedent for photolytic-induced homolytic reactions occurring with derivatives containing benzylic leaving groups, 53 and the appearance of various byproducts in earlier reactions attempted, an investigation of the photolytic stability of the intermediate quinone methide and the triallcylphosphate product was undertaken. Pre-formed quinone methide 7 was photolyzed under conditions used to afford 8 above (FIG. S4), and no reaction was evident by 1H NMR analysis after 3 hours. Similarly, trialkylphosphate 8 was photolyzed under the same conditions and showed no sign of reaction after 3 hours.

3.8. Studies of various combinations of photolabile protecting groups with different benzylic leaving groups for quinone methide formation. Successful conditions for producing identifiable quinone methide derivatives through photolytic-initiated 1,6-elimination reactions have now been realized[39C]. This led to the synthesis of derivatives containing either the o-nitrobeazyl (NB), the a-methyl-3,4-dimethoxy-2-nitrobenzylcarbonate (DMNBC) or the dimethoxybenzoin carbonate (DMBC) protecting group[54,55] with a variety of leaving groups at the benzylic position (FIG. T2)[56]. These derivatives are being examined to determine effects of the different substituents on their hydrolytic stability[39c,43], the rates of quinone methide formation and the alkylation reaction rates[45,49]. These particular derivatives allow correlation with other systems being used to study the quinone methide ailcylation reaction and the lactonization reaction.

3.9. Competitive guanidine cydlization: Phosphotriester formation with a quinone methide and a phosphodiester-ethylguanidinium salt. A possible guanidine 5-exo-trig cyclization on the quinone methide of the designed ATAR was realized. This potential competition is under examination and approaches to prevent it, if necessary, are being developed (see 4.1). Initial results[57] and a thorough literature search suggest this may be negligible[58,59]. The initial analysis looked at the effect of ethylguanidinium on the dibenzylphosphate alkylation reaction with quinone methide 7. As shown in FIG. S5, 0.5 equivalents of ethylguanidiniumdibenzylphosphate salt (18) in 8:1 DMSO-d6/D20 was added to a solution of quinone methide 7 in CDCl3. Due to solubility problems, NMR integration shows approximately 0.3 equivalents of 18 remained in solution. Within 30 minutes at ambient temperature, the same equilibrium of 7:8 was apparent which was formed without the ethylguanidinium present (i.e., 2:1 of 7:8, FIG. S2). Normalizing the reaction to the total amount of 18 present (0.3 equiv.), a 2:1 ratio of the equilibrium mixture of quinone methide 7 to trialkylphosphate 8 appears as an overall 10% formation of 8 by 1H NMR integration. Again, the presence of D20 had no effect on the kinetic formation of 8; however, with no intramolecular trap to drain off the kinetically formed 8, over the next several hours the presence of benzyl alcohol increased. At no point in the reaction was there any evidence of the ethyl guanidine adding to the quinone methide.[60,61]

Although this experiment examined an intermolecular reaction and the competitive cyclization reaction in the ATAR will be intramolecular, it should be realized that there was a 1:1 ratio of the phosphate and guanidine present for reaction with the quinone methide in this experiment. In the ATAR, the complexation of the guanidinium with the phosphodiester will similarly result in a 1:1 ratio of the two components in proximity of the quinone methide. Effects of hydrogen bonding lowering the nucleophihicity of the phosphate while increasing the nucleophilicity of the guanidine were present equally in the above experiment as they will be in the ATAR-DNA alkylation reaction so these effects would also still result in the expected preference for phosphodiester alkylation.

4. Research Design and Methods

Completion of the model studies described above and those following will accomplish the design optimization of the individual ATAR components. Studies with increasingly more complex systems are beginning to coordinate the reactions into a functional derivative.

4.1. Investigations of quinone methides with tethered guanidine functional groups. Model systems are being investigated to determine the effect of a tethered guanidinium in directing the phosphodiester alkylation reaction. Our initial efforts have focused on the use of two commercially available amines tyramine and octopamine, which were converted to their respective guanidinium-phosphate salt derivatives 18 and 19 (FIG. 6. Oxidation of 18 (and abis-Boc guanidine derivative) has not succeeded using Ag2O, PbO2, or DDQ. The inability to oxidize p-cresol suggests the 2,6-dimethyl derivative may be necessary. We recently accomplished a Stille coupling in a related 2,6-diiododerivative[63] and are preparing 20 for quinone methide formation through oxidation[64a]. A separate route to synthesize 20 has been developed by an undergraduate researcher and is in its final step for completion[64b]. The 1,6-elimination of unactivated benzyl alcohol 19 to afford quinone methide has yet to succeed using acidic thermolysis. Derivative 21 is being prepared for the more facile 1,6-elimination to form the quinone methide[64c].

The experiment reported above (FIG. S5) suggests that cyclization of guanidine on the quinone methide may not occur with the guanidiium-phosphate salt complex. Should this occur, adjusting the nucleophilicity of the guanidine should alleviate this possible competition. Based on reported pKa values for various substituted guanidines 8,[65] a phenyl guanidine (10.8) is sufficiently less basic than a methyl guanidine (14.1). The nucleophilicity should be similarly weakened while still favoring the guanidinium form. Phenyl-substituted guanidines 20 and 21 (R'''=Ph, FIG. 6) are being synthesized[5] to examine this effect.[67]

4.2. Incorporation of a guanidinium group and the ortho-tethered ester for lactonization. The synthesis of a derivative which will examine the effect of both the guanidinium group for phosphate specificity and the ortho-tethered ester for lactonization to trap the trialkylphosphate is being synthesized according to FIG. S6. Although results since the initiation of this synthesis may require changes in the protecting group strategy,[68] all of the reactions have already been worked out in other model systems so the completion of this derivative is expected without complications.

Examination of this model system in reactions with phosphodiesters will allow determination of the concerted efficiency of the guanidinium-phosphate complexation for alkylation specificity and trapping of the trialkylphosphate as the lactone for product stabilization. Note that the methyl ester will initially be attempted as the lactonization is expected to be more efficient with the all carbon tether as opposed to the catechol system which has already been optimized (see section 3.5)[19]. If necessary, the lactonization rate can be increased through Heck reaction with methylmethacrylate (FIG. S6, step four). This will place methyl groups on the ester tether and increase the rate of lactonization.[69]

4.3. Incorporating a proton shuttle into the ATAR. Some preliminary experiments suggest incorporating a tertiary methylamine into the tether ortho to the phenol may help facilitate the ATAR reactivity. Having an estimated pKa of 9.8,8 this will act as a proton shuttle to assist quinone methide formation through deprotonation for 1,6-elimination, the conjugate acid will help to activate the quinone methide through reprotonation, and it will assist in the lactonization reaction by deprotonation of the phenol. This will have little competition with guanidine protonation, so is expected to show no deleterious effects. Analysis of this design feature will be investigated in model systems incorporating this modification. These will be synthesized using methods shown in the total syntheses below. If this modification proves unnecessary, the total syntheses below will be simplified, but will be shown with the amine to exemplify the more challenging approach.

4.4. Positioning of the guanidine group for optimal phosphate recognition and quinone methide alkylation. An additional set of model studies will be carried out if proven necessary based on the initial system being investigated (system A, FIG. 7). The three systems are shown in FIG. 7 based on the position of the guanidiium group. Note that each system has at least one tautomer where phosphate addition will be more favored.[70] The flexible, non-static nature of these non-covalent interactions should be realized.

Model system A (FIG. 7) will be examined through the studies described above. Analysis of systems B and C (FIG. 7) will be carried out if there are deficiencies in system A. The synthesis of model systems B and C will be readily accomplished by modification of the synthetic approaches described below (sections 4.5, B and C). The synthesis of these model systems will therefore not be described separately, as the formation of simplified derivatives to examine the guanidine position effect can readily be seen from examination of the total syntheses which will be described below.

4.5. Syntheses of functionalized ATAR model systems. Much of the chemistry for synthesizing ATAR derivatives is being developed through the various model system studies. Three different fully functionalized DNA-synthesizer machine-ready ATAR derivatives may be synthesized. These are described below. Note that not all of these systems will be necessary. The model studies described above will define which system will be optimal and whether or not the tethered proton shuttle will be beneficial. The syntheses described below will produce the most difficult ATAR model systems. The system which may be most optimal based on model studies should therefore be no more difficult than any one of the syntheses described below. Should the incorporation of a proton shuttle prove to be of no benefit, then each of the syntheses below will be readily simplified.

(A) An ATAR derivative with the guanidine at the exocydic methylene of the quinone niethide. DNA synthesizer machine-ready derivative 25 will be prepared in ten steps from octopamine (22, FIG. S7). Most of the key steps have already proven effective in model studies. The synthesis involves a Rathke guanylation,[55] and ortho-bromination[71] followed by iodination[72] to make 23 for the Stile allylation selectively with the more reactive aryliodide.[73] This will be converted to the amine through ozonolysis[74] and reductive amination.[75] The Heck reaction with acrylic acid will afford 24.[76] The diimide reduction[77] for reducing the alkene has already been accomplished in a model study without affecting the nitrobenzyl group.

(B) An ATAR derivative with a meta-benzylic guanidine substituent. A machine-ready derivative having the guanidine at the meta-benzylic position will be synthesized using a more convergent approach with a Diels-Alder reaction as the key step. A highly functionalized Danishefskytype diene[78] will be synthesized in four steps from the dianion of acetoacetic amide 26 (FIG. S8)[79]. Dianion akylation[80] will afford 27 which will be reduced to the aldehyde[81] and converted to diene 28 by the standard approach.[82]

There is good precedent for the success of the cycloaddition of diene 28 with allene 29 to produce phenol 30 (FIG. S9).[83] Phenol 30 will be converted to machine-ready derivative 35 in 11 steps. Resonance effect allows for the selective hydrolysis of the benzylic methyl ester of 30.[84] A tandem Curtius rearrangement-Rathke reaction with in vitro trapping of the amine as the protected guanidine[66] will be examined.[85] The B-trimethylsilylethanesulfonyl (SES) protected guanidine[86] will be stable throughout the synthesis, but cleaved with fluoride ion after solid-phase synthesis without hydrolyzing the carbonate (MDNB) group on the phenol. The final conversion of the methyl-trimethylsulfide to the carboxylic acid will be accomplished as in Schreiber's total synthesis of cyclotheonamide B with related functionality in the molecule.[87]

(C) An ATAR derivative with a meta-guanidine substituent. If validated in model studies, a machine-ready derivative having the guanidine directly on the benzene ring will be prepared by one of two approaches. (1) A simple modification of the above approach using methyl acetylenedicarboxylate as the dienophile.[82] (2) A directed ortho-lithiation starting from 4-amino-salicylic acid taking advantage of a MEM[88] and Boc[89] protecting group to assure regioselectivity to 37 (FIG. S10).[90] Most of the other steps are repetitive of those in the above syntheses or readily carried out using standard chemistry.

4.6. Evaluation with nucleotide oligomers. The following studies will be incorporated as time permits during the requested finding period. These investigations will be discussed in chronological order, and will be accomplished to the extent allowable during this time frame.

4.6.1. Nucleotide alkylation studies. Prior to attaching the phosphodiester alkylating reagents to oligonucleotides for site-selective delivery, reactions will be run using the appropriate derivative synthesized above[91] with dinucleotides for complete product characterization and reaction optimization.[48,92] Dodecanucleotides will then be examined for peralkylation. The presence of the guanidinium groups in the alkylated polymer will maintain the water solubility of the trialkylphosphate product.[93] The reversal of charge will reverse the polarity necessary for PAGE analysis or slow the migration of partially alkylated oligonucleotides.[36] Assessing the degree of alkylation of the whole oligonucleotides can be determined qualitatively by gel migration analyses using PAGE on the 5'-32P labeled oligos.[94,95,96] Initial digestion of the oligonucleotides from the alkylation reaction with snake venom phosphodiesterase and/or calf intestine alkaline phosphatase will result in cleavage of the oligonucleotides only at unmodified phosphodiester linkages, as phosphotriester linkages are known to be stable to degradation.[16a] HPLC analysis of the resulting products for the degree of allcylation will assess if there was any regioselectivity.[97] The degree of alkylation will be further analyzed by high resolution mass spectrometry (MALDI-TOF). NMR analysis will be attempted to determine chemo- and possibly diastereo-selectivity's and for assessing the structural characteristics of the products.[98] Crystallization of the products for x-ray diffraction analysis may succeed with the guanidinium group incorporated.

4.6.2. Oligonucleotide attachment. The delivery oligonucleotide of desired sequence will be synthesized on an automated DNA synthesizer according to standard protocol.[99] Modifying oligonucleotides with any desired linker is common practice[17d,e,g,h,i]. A C12 chain length phosphoramidite will be synthesized[100] and attached to the oligonucleotide[99,101]. A standard esterification reaction will attach the ATAR derivative as synthesized above to the linker-OH on the solid support[102]. Mild alkaline hydrolysis of the TFA-protected amine[103] will allow the attachment of the desired reporter group, drug agent, or protein conjugate. Some examples of reporter groups for initial studies of oligonucleotide modification using this ATAR include: fluorescein-5-isothiocyanate,[104] the EDTA-Fe(TI) moiety[105], and tris(2,2'-bipyridine) ruthenium(II) (Ru(bpy)$32+$[106]. Complete protecting group removal and cleavage from the solid-support[107] will afford a functional ATAR[108]. Drugs[6,10] and derivatized proteins[7,11] will be attached similarly. The resulting ATAR derivatives will be purified by HPLC. The derivatized oligonucleotides will be characterized by enzymatic digestion and HPLC analysis against coinjections of standard solutions of the nucleoside components and a reagent standard with the attached linker. An exact mass will also be obtained. ATAR attachment will be confirmed by UV analysis.[109]

Affinity cleavage experiments can be conducted with the EDTA-e(II) group attached to the ATAR for analysis of labeling both single- and double-strand target DNA according to established methods[3,110]. Analysis of the diffusible cleavage pattern on the DNA to which the ATAR has been delivered will allow assessment of the structural characteristics of the ATAR-DNA interactions.

4.7. Future studies. The ability to modify nucleosomal DNA will allow various crosslinking and autocleavage investigations to be conducted for enhancing our understanding of DNA-protein interactions in the chromatin[4]. Transcriptional regulation will be studied by using the ATAR to attach transcriptional regulator GCN5p[7] and other transcriptional activators to selected sites on DNA[7b]. It will also be of interest to study how drugs known to bind to, and react with DNA will be affected by their covalent attachment through the ATAR.[111]

5. Human Subjects: None
6. Vertebrate Animals: None
7. Literature Cited (1) For a complete resource covering many aspects of the human genome see the Genome Database (GDB) hosted at Johns Hopkins University (http://gdbwww.gdb.orgl): Fasman, K. H.; Letovsky, S. I., Li, P.; Cottingham, R. W.; Kingsbury, D. T. "The GDB Human Genome Database Anno 1997," *Nucleic Acids Res.* 1997, 25, 72–80.

(2)
   (a) Leonetti, J. P.; Degols, G.; Clarenc, J. P.; Mechti, N.; Lebleu, B. "Cell Delivery and Mechanism of Action of Antisense Oligonucleotides," *Prog. Nucleic Acids Res. Mol. Bid.* 1993, 44, 143–66.
   (b) Zon, G. "Brief Overview of Control of Genetic Expression by Antisense Oligonucleotides and In Vivo Applications," *Molec. Neurobiol.* 1995, 10, 219–29.

(3)
   (a) Thuong, N. G.; Héléne, C. "Sequence-Specific Recognition and Modification of DoubleHelical DNA by Oligonucleotides," *Angew. Chem. Int. Ed. Engl.* 1993, 32, 666–90.
   (b) Dervan, P. B. "Reagents for the Site-Specific Cleavage of Megabase DNA," *Nature* 1992, 359, 87.
   (c) Dervan, P. B. "Design of Sequence Specific DNA Binding Molecules," *Science* 1986, 232, 464.

(4) A system such as being proposed will be particularly valuable for providing information at the molecular level in multi-protein complexes interacting with nucleic acids. These would include the complex protein-nucleic acid interactions of the chromatin involved in chromosome condensation-decondensation, DNA replication, transcription, transcription regulation and DNA repair. Molecular level details in such complex systems are difficult to achieve by existing biochemical techniques and advances in molecular biology require innovative approaches to begin to develop a more thorough molecular level understanding of the chromosomal protein machinery. For example, the presumed role of histone H 1 in transcriptional repression might be studied by site-specifically modifying a target DNA binding sequence with crosslinking and redox activated cleaving functionality for mapping DNA-histone H1 interactions:
   (a) Paranjape, S. M.; Kamakaka, R. T.; Kadonaga, J. T. "Role of Chromatin Structure in the Regulation of Transcription by RNA Polymerase II," *Annu. Rev. Biochem.* 1994, 63, 265–97.
   (b) Felsenfeld, G. "Chromatin as an Essential Part of the Transcriptional Mechanism," *Nature* 1992, 355, 219–24.
   (c) Halmer, L.; Gruss, C. "Influence of Histone H1 on the in vitro Replication of DNA and Chromatin," *Nucleic Acids Res.* 1995, 23, 773–78.

(5) The ability to label a hybridization-recognized sequence of DNA should afford an efficient approach to genetic diagnostics from blood samples. The chemistry being developed will allow the efficient synthesis of multiply-labeled oligonucleotides which can be used for genetic diagnostics by methods such as fluorescence in-situ hybridization (FISH).
   (a) Brenner, M.; Dunlay, T. "Fluorescence In vitro Hybridization. Hardware and Software Implications in the Research Laboratory," *Amer. Laboratory* 1995, 55–58.
   (b) For lanthanide-labeled DNA probes, see: Lövgren, T.; Hurskainen, P.; Dahlén, P. in *Nonisotopic DNA Probe Techniques*, Kricka, L. J., Ed.; Academic Press, Inc.: San Diego; 1992, pp. 227–274.

(6) A particularly appealing application would be in the area of site-specific drug delivery to genetic targets. The non-specific deliterious effects of chemotherapy on healthy cells could be alleviated using such a system to covalently deliver an antitumor antibiotic directly to a target DNA sequence.

(7) Innovative experiments which could be attempted with such a system include modifying nucleosomal DNA with transcriptional regulator GCN5p. This transcriptional regulator functions as a complex with two other proteins (ADA2p and,ADA3p). It has recently been found to be a histone acetyltransferase. Histone hyperacetylation is thought to facilitate transcription by chromatin disruption, but it is not clear whether the hi stone hyperacetylation is a result of chromatin disruption during the transcription process, or an initiator. This regulatory complex with GCN5p is recruited to a specific gene through interactions with other DNA binding transcription factors. A system such as being proposed would allow site-specific delivery of this regulatory protein to a particular chromatin site. This could then recruit the regulatory complex and other transcription factors and thereby initiate transcription of a selective gene. Obviously, such an approach could be used to regulate many cellular functions through selective control of genetic transcription. For leading references see:

(a) Wolffe, A. P.; Pruss, D. "Targeting Chromatin Disruption: Transcription Regulatorg that Acetylate Histones," *Cell* 1996, 84, 817–19.

(b) Ptashne, M.; Gann, A. "Transcriptional activation by recruitment," *Nature* 1997, 386, 569–77.

(8) Although only a very crude measure, estimated pKa values calculated from the effects of various related substituted derivatives suggest that the proton shuttle processes proposed should occur as drawn in scheme 1. The relevant pKa values (H2O, 25° C.) include: 2,4,6-trimethylphenol (10.88), 3-aminophenol (9.83), m-cresol (10.00), phenol (9.99), Et2MeN (10.4), phenethylamine (9.83), ethylamine (10.63), guanidine (14.38), methylguanidine (14.1), phenylguanidine (10.77). From these values, pKa estimates in the ATAR may be approximated assuming additivity of substituent effects. The approximated pKa would be: 10.7 for the phenoxide with a 3-amino group on the ring (the effect of a 3-amino on the pKa of phenol is ApKa=–0.16; thus approximating from the pKa of 2,4,6-trimethylphenol=10.88–0.16=10.7, other values are determined in a similar way), 10.9 for the phenoxide with the 3beazylic-amino group, 9.8 for the tertiary amine, 10.8 for the guanidine directly substituted on the arene ring, 10.5 for the benzylic guanidine with a phenyl substituent. The pKa values are from *Lange's Handbook of Chemistry*, Dean, J. A, Ed.; McGraw-Hill: N.Y. 1992, 14th edition.

(9) Reporter groups would include fluorescent probes (For example, see: Haugland, R. P. *Molecular Probes: Handbook of Fluorescent Probes and Research Chemicals*, Larison, K. D., Ed.; 1995–1997, 6th Edition, Molecular Probes, Inc., Eugene, Oreg.), probes used for recognition of a specific species such as biotin/avidin and antibodies, luminescent probes, probes which are chemically or redox reactive, radionuclear probes, and magnetic moieties.

(a) Wilbur, D. S. "Radiohalogenation of Proteins: An Overview of Radionuclides, Labeling Methods, and Reagents for Conjugate Labeling," *Bioconjugate Chem.* 1992, 3, 433–471.

(b) Peters, K.; Richards, F. M. "Chemical Cross-linking: Reagents and Problems in Studies of Membrane Structure," *Ann. Rev. Biochem.* 1977, 46, 523–51.

(c) Ji, T. H. "The Application of Chemical Cross linking for Studies on Cell Membranes and the Identification of Surface Reporterg," *Biochim. Biophys. Acta* 1979, 559, 39–69.).

(10) For examples of drugs which could be readily attached, see a listing of anticancer agents along with associated references in: Calbiochem Biochemical and Immunochemical 1996/97 Catalog, p. 539, San Diego, Calif.

(11) For an example of protein conjugation to an oligonucleotide for directing nuclease activity, see: Pei, D.; Corey, D. R.; Schultz, P. G. "Site-specific Cleavage of Duplex DNA by a Semi-synthetic Nuclease via Triple-helix Formation," *Proc. Nat. Acad. Sci. USA* 1990, 87, 9858.

(12) For conventional synthesis of phosphate modified oligonucleotides, see:

(a) Hayakawa, Y.; Hirose, M.; Hayakawa, M.; Noyori, R. "General Synthesis and Binding Affinity of Position-Selective Phosphonodiester- and Phosphotriester-Incorporated Oligodeoxyribonucleotides," *J. Org. Chem.* 1995, 60, 925–30.

(b) Hayakawa, Y.; Wakabayashi, S.; Kato, H.; Noyori, R. "The Allylic Protection Method in Solid-Phase Oligonucleotide Synthesis. An Efficient Preparation of Solid-Anchored DNA Oligomers," *J. Am. Chem. Soc.* 1990, 112, 1691–96.

(c) Kuijpers, W. H. A.; Huskens, J.; Koole, L. H.; Van Boeckel, C. A. A. "Synthesis of Well-Defined Phosphate-Methylated DNA Fragments: the Application of Potassium Carbonate in Methanol as Deprotecting Reagent," *Nucleic Acids Res.* 1990, 18, 5197–205.

(d) Alul, R. H.; Singman, C. N.; Zhang, G.; Letsinger, R. L. "Oxalyl-CPG: A Labile Support for the Synthesis of Sensitive Oligonucleotide Derivatives," *Nucleic Acids Res.* 1991, 19, 1527–32.

(e) Froehler, B. C. "Deoxynucleoside H-Phosphonate Diester Intermediates in the Synthesis of Internucleotide Phosphate Analogues," *Tetrahedron Let.* 1986, 27, 5575–78.

(13) For additional synthesis reviews see:

(a) Beaucage, S. L.; Iyer, R. P. "Advances in the Synthesis of Oligonucleotides by the Phosphoramidite Approach," *Tetrahedron* 1992, 48, 2223–2311.

(b) Hobbs, J. B. "Nucleotides and Nucleic Acids," *Organophosphorus Chemistry* 1990, 21, 201–321.

(c) Sonveaux, E. "The Organic Chemistry Underlying DNA Synthesis," *Bioorg. Chem.* 1986, 14, 274–325.

(14) Studies using phosphate triester modified oligos for duplex structure studies with RNA and DNA:

(a) Letsinger, R. L.; Bach, S. A.; Eadie, J. S. "Effects of Pendant Groups at Phosphorus on Binding Properties of d-ApA Analogues," *Nucleic Acids Res.* 1986, 14, 3487–99.

(b) Summers, M. F.; Powell, C.; Egan, W.; Byrd, R. A.; Wilson, W. D.; Zon, G. "Alkyl Phosphotriester Modified Oligodeoxyribonucleotides. VI. NMR and UV Spectroscopic Studies of Ethyl Phosphotriester (Et) Modified Rp-Rp and Sp-Sp Duplexes, {d[GGAA(Et)TTCC]}2," *Nucleic Acids Res.* 1986, 14, 7421–37.

(c) Pramanick, P.; Kan, L. "NMR Study of the Effect of Sugar-phosphate Backbone Ethylation on the Stability and Conformation of DNA Double Helix," *Biochemistry* 1987, 26, 3807–12.

(d) Koole, L. H.; van Genderen, M. H. P.; Buck, H. M. "A Parallel Right-Handed Duplex of the Hexamer d(TpTpTpTpTpT) with Phosphate Triester Linkages," *J. Am. Chem. Soc.* 1987, 109, 3916–21 *[The synthetic chemistry and hybridization data reported in this 1987 paper differed from that described later and subsequently retracted by Buck, H. M.; Moody, H. M.; Quaedflieg, P. J. L. M.; Koole, L. H.; van Genderen, M. H. P.; Smit, L.; Jurriaans, S.; Geelen, J. L. M. C.; Goudsmit, J. "Inhibition of HIV-1 Infectivity by Phosphate-Methylated DNA: Retraction," *Science* 1990, 250, 125–26 (also see: Maddox, J. "Dutch Cure for AIDS is Discredited," *Nature* 1990, 347, 411).].

(e) Quaedflieg, P. J. L. M.; Koole, L. H.; van Genderen, M. H. P.; Buck, H. M. "A structural Study of Phosphate-methylated d(CpG)n and d(GpC)n DNA oligomers. Implications of Phosphate Shielding for the Isomerization of B-DNA into Z-DNA," *Recl. Trav Chim Pay-Bas* 1989, 108, 421–23.

(f) Quaedflieg, P. J. L. M.; Broeders, N. L. H. L.; Koole, L. H.; van Genderen, M. H. P.; Buck, H. M. "Conformation of the Phosphate-methylated DNA Dinucleotides d(CpC) and d(TpC). Formation of a Parallel Miniduplex Exclusively for the S-Configuration at Phosphorus," *J. Org. Chem.* 1990, 55, 122–27.

(g) Quaedflieg, P. J. L. M.; van der Heiden, A. P.; Koole, L. H.; Coenen, A. J. J. M.; van der Wal, S.; Meijer, E. M. "Synthesis and Conformational Analysis of Phosphate-methylated RNA Dinucleotides,". *J. Org. Chem.* 1991, 56, 5846–59.

(15) Using modified triester phosphate oligos as probes for elucidating specific interactions with proteins:

(a) Weinfeld, M.; Drake, A. F.; Saunders, J. K.; Paterson, M. C. "Stereospecific Removal of Methyl Phosphotriesters from DNA by an *Escherichia coliada*+Extract," *Nucleic Acids Res.* 1985, 13, 7067–77.

(b) Gallo, K. A.; Shao, K; Phillips, L. R.; Regan, J. B.; Kozielkiewicz, M.; Uznanski, B.; Stec, W. J.; Zon, G. "Alkyl Phosphotriester Modified Oligodeoxyribonucleotides. V. Synthesis and Absolute Configuration of Rp and Sp Diastereomers of an Ethyl Phosphotriester (Et) Modified EcoRI Recognition Sequence, d[GGAA(Et)TTCC]. A Synthetic Approach to Regio- and Stereospecific Ethylationinterference Studies," *Nucleic Acids Res.* 1986, 14, 7405–20.

(c) Koziollciewicz, M.; Stec, W. J. "Application of Phosphate-backbone-modified Oligonucleotides in the Studies on EcoRI Endonuclease Mechanism of Action," *Biochemistry* 1992, 31, 9460–66.

(16)

(a) Miller, P. S.; Fang, K. N.; Kondo, N. S.; Ts'O, P.O.P. "Synthesis and Properties of Adenine and Thymidine Nucleoside Alkyl Phosphotriesters, the Neutral Analogs of Dinucleoside Monophosphates," *J. Am. Chem. Soc.* 1971, 93, 6657–65.

(b) Miller, P. S.; Barrett, J. C.; Ts'O, P.O.P. "Synthesis of Oligodeoxyribo-nucleotide Ethyl Phosphotriesters and Their Specific Complex Formation with Transfer Ribonucleic Acid," *Biochemistry* 1974, 13, 4887–96 (and the following paper in that journal as well).

(c) Pless, R. C.; Ts'O, P.O.P. "Duplex Formation of a Nonionic Oligo(deoxythymidylate) Analogue [Heptadeoxythymidylyl-(3'-5')-deoxythymidine Heptaethyl Ester (d-[Tp(Et)17T)] with Poly (deoxyadenylate). Evaluationof the Electrostatic Interaction," *Biochemistry* 1977, 16, 1239–50.

(d) Miller, P. S.; Braiterman, L. T.; Ts'O, P.O.P. "Effects of a Trinucleotide Ethyl Phosphotriester, G'''p(Et)G''' (Et)U, on Manmmalian Cells in Culture," *Biochemistry* 1977, 16, 1988–96.

(e) Petrenko, V. A.; Pozdnyakov, P. l.; Kipriyanov, S. M.; Boldyrev, A. N.; Semyonova, L. N.; Sivolobova, G. F. "Site-localized Mutagenesis Directed by Phosphotriester Analogs of Oligonucleotides," *Bioorg. Khim.* 1986, 12, 1088–1100.

(f) Asseline, U.; Barbier, C.; Thuong, N. T. "Oligothymidylates Comportant La Structure Alternee Alkylphosphotriester-phosphodiester et Lies de Facon Covalente a un Agent Intercalant," *Phosphorus Sulfur* 1986, 26, 63–73.

(g) Marcus-Sekura, C. J.; Woerner, A. M.; Shinozuka, K.; Zon, G.; Quinnan, Jr., G. V. "Comparative Inhibition of Cloramphenicol Acyltransferase Gene Expression by Antisense Oligonucleotide Analogs Having Alkyl Phosphotriester, Methylphosphonate and Phosphorothioate Linkages," *Nucleic Acids Res.* 1987, 15, 5749–63.

(h) see ref. 6a.

(i) Koole, L. H.; van Genderen, M. H. P.; Reiniers, R. G.; Buck, H. M. "Enhanced Stability of a Watson and Crick DNA Duplex Structure by Methylation of the Phosphate Groups in One Strand," *Proc. K Ned. Akad. Wet. B* 1987, 90, 41–6.*

(j) Petrenko, V. A.; Kipriyanov, S. M.; Boldyrev, A. N.; Pozdnyakov, P. I. "Mutagenesis Directed by Phosphotriester Analogues of Oligonucleotides: a Way to Site-specific Mutagenesis In Vivo," *FEBS Lett.* 1988, 238, 109–12.

(k) Durand, M. Maurizot, J. C.: Asseline, U.; Barbier, C.; Thuong, N. T.; Héléne, C. "Oligothymidylates Covalently Linked to an Acridine Derivative and with Modified Phosphodiester Backbone; Circular Dichroism Studies of Their Interactions with Complementary Sequences," *Nucleic Acids Res.* 1989, 17, 1823–36.

(17) For recent reviews see:

(a) Zon, G. "Brief Overview of Control of Genetic Expression by Antisense Oligonucleotides and In Vivo Applications," *Mol. Neurobiology* 1995, 10, 219–29.

(b) Kiely, J. S. "Recent Advances in Antisense Technology," *Ann. Rep. Med. Chem.* 1994, 29, 297–306.

(c) Stein, C. A.; Cheng, Y.-C. "Antisense Oligonucleotides as Therapeutic Agents-Is the Bullet Really Magic," *Science* 1993, 261, 1004–11.

(d) Varma, R. S. "Synthesis of Oligonucleotide Analogues with Modified Backbones," *SYNLETT* 1993, 621–37.

(e) Beaucage, S. L.; Iyer, R. P. "The Functionalization of Oligonucleotides Via Phosphoramidite Derivatives," *Tetrahedron* 1993, 49, 1925–63.

(f) Toulmé, J. J. in Antisense RNA and DNA; Murray, J. A. H., Ed.; Wiley, Inc.: New York, 1992, pp 175–94.

(g) IEnglisch, U.; Gauss, D. H. "Chemically Modified Oligonucleotides as Probes and Inhibitors," *Angew. Chem. Int. Ed. Engl.* 1991, 30, 613–722.

(h) Uhlmann, E.; Peyman, A. "Antisense Oligonucleotides: A New Therapeutic Principle," *Chem. Rev.* 1990, 90, 543–84.

(i) Goodchild, J. "Conjugates of Oligonucleotides and Modified Oligonucleotides: A Review of Their Synthesis and Properties," *Bioconjugate Chem.* 1990, 1, 165–87.

(j) Héléne, C.; Toulmé, J.-J. "Specific Regulation of Gene Expression by Antisense, Sense, and Antigene Nucleic Acids," *Biochim. Biophys. Acta* 1990, 1049, 99–125.

(k) Goodchild, J. "Inhibition of Gene Expression by Oligonucleotides," in Oligonucleotides: Antigenge Inhibitors of Gene Expression; Cohen, J. S., Ed.; MacMillan Press; London, 1989, pp. 53–77.

(l) Zon, G. "Oligonucleotide Analogues as Potential Chemotherapeutic Agents," *Pharm. Res.* 1988, 5, 539–49.

(m) Stein, C. A.; Cohen, J. S. "Oligonucleotides as Inhibitors of Gene Expression: a Review," *Cancer Res.* 1988, 48, 2659–68.

(n) Miller, P. S.; Ts'O, P.O.P. "Oligonucleotide Inhibitors of Gene Expression in Living Cells: New Opportunities in Drug Design," *Annu. Rep. Med. Chem.* 1988, 23, 295–304.

(o) Miller, P. S.; Agris, C. H.; Blake, K. R.; Murakami, A.; Spitz, S. A.; Reddy, M. P.; Ts'O, P.O.P. "Nonionic Oligonucleotide Analogs as New Tools for Studies on the Structure and Function of Nucleic Acids in Living Cells," in Nucleic Acids: The Vectors of Life; Pullman, B.; Jorter, J., Eds.; D. Reidel Publishing Co.: Dordrecht, Netherlands; 1983, pp. 521–35.

(18) A review bas proposed the use of the acronym SNAIGE (Synthetic or Small Nucleic Acid Interfering with Gene Expression) as a term for describing the various approaches to genetic regulation with oligonucleotides: Leonetti, J. P.; Degols, G.; Clarenc, J. P.; Mechti, N.; Lebleu, B. "Cell Delivery and Mechanism of Action of Antisense Oligonucleotides," *Prog. Nucl. Acid Res.* 1993, 44, 143–66.

(19) Zhou, Q.; Turnbull, K. D. "Phosphotriesters from Tandem Phosphodiester Alkylation with Quinone Methides Followed by Lactonization," manuscript near completion for submission to: *J. Am. Chem. Soc.* 1997, 119.

(20) Reliable Biopharmaceuticals (St. Louis, Mo.), a supplier of oligonucleotide derivatives for antisense and antigene applications, has expressed interest in this work. We are conducting preliminary experiments to determine the potential for collaborative development of synthetic methodology for oligonucleotide modification.

(21) Sigman, D. S.; Mazunider, A.; Perrin, D. M. "Chemical Nucleases," *Chem. Rev.* 1993, 93, 2295–316.

(22) More recent examples include:
(a) Jubian, V.; Dixon, R. P.; Hamilton, A. D. "Molecular Recognition and Catalysis. Acceleration of Phosphodiester Cleavage by a Simple Hydrogen-Bonding Receptor," *J. Am. Chem. Soc.* 1992, 114, 1120–21.
(b) Browne, K. A.; Bruice, T. C. "Chemistry of Phosphodiesters, DNA and Models. 2. The Hydrolysis of Bis(8-hydroxyquinoline) Phosphate in the Absence and Presence of Metal Ions," *J. Amer. Chem. Soc.* 1992, 114, 4951–58.
(c) Smith, J.; Ariga, K.; Anslyn, E. V. "Enhanced Ilmidazole-Catalyzed RNA Cleavage Induced by a Bis-Allcylguanidimum Receptor," *J. Am. Chem. Soc.* 1993, 115, 362–64.
(d) Takasaki, B. K.; Chin, J. "Synergistic Effect Between La(lfl) and Hydrogen Peroxide in Phosphate Diester Cleavage," *J. Am. Chem. Soc.* 1993, 115, 9337–38.
(e) Hall, J. Husken, D.; Pieles, U.; Moser, H. E.; Haner, R. *Chemistry & Biology* 1994, 1, 185–90.
(f) Bashkin, J. K.; Frolova, E. I.; Sampath, U. "Sequence-Specific Cleavage of HIV MRNA by a Ribozyme Mimic," *J. Am. Chem. Soc.* 1994, 116, 5981–82.
(g) Magda, D.; Miller, R. A.; Sessler, J. L.; Iverson, B. L. "Site-Specific Hydrolysis of RNA by Europium(m) Texaphyrin Conjugated to a Synthetic Oligodeoxyribonucleotide," *J. Am. Chem. Soc.* 1994, 116, 7439–40.
(h) Linkletter, B.; Chin, J. "Rapid Hydrolysis of RNA with a $Cu^{II}$ Complex," *Angew. Chem. Int. Ed. Engl.* 1995, 34, 472–74.

(23)
(a) Wilbur, D. S. "Radiohalogenation of Proteins: An Overview of Radionuclides, Labeling Methods, and Reagents for Conjugate Labelling," *Bioconjugate Chem.* 1992, 3, 433–471.
(b) Peters, K.; Richards, F. M. "Chemical Cross-linking: Reagents and Problems in Studies of Membrane Structure," *Ann. Rev. Biochem.* 1977, 46, 523–51.
(c) Ji, T. H. "The Application of Chemical Crosslinking for Studies on Cell Membranes and the Identification of Surface Reporters," *Biochim. Biophys. Acta* 1979, 559, 39–69.

(24) Zhang, Y.; Chen, F.-X.; Mehta, P.; Gold, B. "Groove- and Sequence-Selective Alkylation of DNA by Sulfonate Esters Tethered to Lexitropsins," *Biochemistry* 1993, 32, 7954–65.

(25) For reviews on quinone methides, see:
(a) Volod'kin, A. A.; Ershov, V. V. *Russian Chem. Rev.* 1988, 57, 336.
(b) Gruenanger, P. in *Houben-Weyl Methoden der Organischen Chemie* (Vol. VII/3b) Mueller, E.; Bayer, D., Eds.; G. Thieme Verlag: Stuttgart, 1979, pp. 395–521.
(c) Wagner, H.-U.; Gompper, R. in *The Chemistry of Quinonoid Compounds* (Vol. I) Patai, S., Ed.; John Wiley & Sons: New York, 1974, pp. 1145–1178.
(d) Turner, A. B. *Quart. Rev.* 1965, 18, 347.

(26) More recent, elegant examples for biomolecule alkylation include:
(a) Chatterjee, M.; Rokita, S. E. "The Role of a Quinone Methide in the Sequence Specific Alkylation of DNA," *J. Am. Chem. Soc.* 1994, 116, 1690–97.
(b) Li, T.; Zeng, Q.; Rokita, S. E. "Target-Promoted Alkylation of DNA," *Bioconjugate Chem.* 1994, 5, 497–500.
(c) Meyers, J. K.; Cohen, J. D.; Widlanski, T. S. "Substituent Effects on the Mechanism-Based Inactivation of Prostatic Acid Phosphatase," *J. Am. Chem. Soc.* 1995, 117, 11049–54.
(d) Myers, J. K.; Widlanski, T. S. "Mechanism-Based Inactivation of Prostatic Acid Phosphatase," *Science* 1993, 262, 1451–53.
(e) Wang, Q.; Dechert, U.; Jirik, F.; Withers, S. G. "suicide Inactivation of Human Prostatic Acid Phosphatase and a Phosphotyrosine Phosphatase," *Biochem. Biophys. Res. Commun.* 1994, 200, 577–83.

(27) For reviews see:
(a) Sega, G. A. "A Review of the Genetic Effects of Ethyl Methanesulfonate," *Mutation Res.* 1984, 134, 113–42.
(b) Hoffmann, G. R. "Genetic Effects of Dimethyl Sulfate, Diethyl Sulfate, and Related Compounds," *Mutation Res.* 1980, 75, 63–129.
(c) Digenis, G. A.; Issidorides, C. H. "Some Biochemical Aspects of N-Nitroso Compounds," *Bioorganic Chem.* 1979, 8, 97–137.

(28)
(a) Swenson, D. H.; Lawley, P. D. "Alkylation of Deoxyribonucleic Acid by Carcinogens Dimethylsulfate, Ethyl Methanesulfonate, N-Ethyl-N-nitrosourea and N-Methyl-N-nitrosourea," *Biochem. J.* 1978, 171, 575–87.
(b) Jensen, D. E.; Reed, D. J. "Reaction of DNA with Alkylating Agents. Quantitation of Alkylation by Ethylnitrosourea of Oxygen and Nitrogen Sites on Poly [dA-dT] Including Phosphotriester Formation," *Biochemistry* 1978, 17, 5098–107.
(c) Sun, L.; Singer, B. "The Specificity of Different Classes of Ethylating Agents Towards Various Sites of HeLa DNA in vitro and in vivo," *Biochemistry* 1975, 14, 1795–1802.

(29) Angle, S. R.; Arnaiz, D. O.; Boyce, J. P.; Frutos, R. P.; Louie, M. S.; Mattson-Arnaiz, H. L.; Rainier, J. D.; Turnbull, K. D.; Yang, W. "Formation of Carbon-Carbon Bonds via Quinone MethideInitiated Cycization Reactions," *J. Org. Chem.* 1994, 59, 6322–6337.
(30) *Organic Synthesis,* Smith, M. B.; McGraw-Hill, Inc.: New York; 1994, pp. 108–119.
(31) Schulz, W. G.; Nieman, R. A.; Skibo, E. B. "Evidence for DNA Phosphate Backbone Alkylation and Cleavage by Pyrrolo[1,2-a]benzimidazoles: Small Molecules Capable of Causing Base-Pair-Specific Phosphodiester Bond Hydrolysis," *Proc. Natl. Acad. Sci. USA* 1995, 92, 11854–58.
(32)
  (a) Tomasz, M.; Lipman, R. "Alkylation Reactions of Mitomycin C at Acid pH," *J. Am. Chem. Soc.* 1979, 101, 6063–67.
  (b) Iyengar, B. S.; Dorr, T. R.; Remers, W. A.; Kowal, C. D. "Nucleotide Derivatives of 2,7-Diaxninomitosene," *J. Med. Chem.* 1988, 31, 1579–85.
(33) Gohil, R. N.; Roth, A. C.; Day, R. A. "Reversible Covalent Modification of DNA," *Arch. Biochem. Biophys.* 1974, 165, 297–312.
(34) Bhat, G., Roth, A. C.; Day, R. A. "Extrinsic Cotton Effect and Helix-Coil Transition in a DNAPolycation Complex," *Biopolymers* 1977, 16, 1713–24.
(35) For a thorough review, see: Hannon, C. L.; Anslyn, E. V. "The Guanidinium Group: Its Biological Role and Synthetic Analogs," *Bioorg. Chem. Frontiers* 1993, 3, 193–255.
(36) For additional examples, see:
  (a) Blasko, A.; Dempcy, R. O.; Minyat, E. E.; Bruice, T. C. "Association of Short-Strand DNA Oligomers with Guanidiium-Linked Nucleosides. A Kinetic and Thermodynamic Study," *J. Am. Chem. Soc.* 1996, 118, 7892–99.
  (b) Dempcy, R. O.; Browne, K. A.; Bruice, T. C. "Synthesis of the Polycation Thymidyl DNG, Its Fidelity in Binding Polyanionic DNA/RNA, and the Stability and Nature of the Hybrid Complexes," *J. Am. Chem. Soc.* 1995, 117, 6140.
  (c) Hashimoto, H.; Nelson, M. G.; Switzer, C. "Formation of Chimeric Duplexes Between Zwitteriomc and Natural DNA," *J. Org. Chem.* 1993, 58, 4194–95.
  (d) Hashimoto, H.; Nelson, M. G.; Switzer, C. "Zwitterionic DNA," *J. Am. Chem. Soc.* 1993, LL5, 7128–34.
  (e) Letsinger, R. L.; Singman, C. N.; Histand, G.; Salunkhe, M. "Cationic Oligonucleotides," *J. Am. Chem. Soc.* 1988, 115, 7128.
    (1) Furberg, S.; Solbakk, J. "On the Stereochemistry of the Interaction Between Nucleic Acids and Basic Protein Side Chains," Acta Chem. Scand. B 1974, 28, 481–83.
(37) Saenger, W. *Principles of Nucleic Acid Structure,* Springer-Verlag: New York, 1984, pp. 385–431.
(38) Pullman, B. "Molecular Mechanisms of Specificity in DNA-Antitumor Drug Interactions," in *Advances in Drug Research,* Testa, B., Ed.; Academic Press; London; Vol. 18, 1989, pp. 1–113.
(39)
  (a) Zhou, Q.; Turnbull, K. D. "Equilibrium Control in Phosphodiester Alkylation with Quinone Methides," manuscript in preparation for submission to: *J. Org. Chem.* 1997, 62.
  (b) Zhou, Q.; Dyer, R. G.; Turnbull, K. D. "A Study of Triallcylphosphate Hydrolysis Rates Related to a DNA Modifying Reagent," manuscript in preparation for submission to: *J. Org. Chem.* 1997, 62.
  (c) Dyer, R. G.; Turnbull, K. D. "Photolytic-Initiated Formation of Quinone Methides for Phosphodiester Alkylation," manuscript in preparation.

(40) Patent Pending for "Biomolecular Labeling" (Apr. 4, 1997).
(41) Dyall, L. K.; Winstein, S. "Nuclear Magnetic Resonance Spectra and Characterization of Some Quinone Methides," *J. Am. Chem. Soc.* 1972, 94, 2196–99.
(42) Product identity was readily apparent from the distinct 3-bond phosphorus-hydrogen coupling constant of 8.2 Hz for the two different types of benzylic resonances in the 1H NMR spectra with an integrated ratio of 2:1. 1H NMR (CDCl3/CD3CN (1:1), 300 MHz) ~7.30 (in, 10H, 2(C6HS)), 6.87 (s, 2H, C6H2), 4.95 (d, J=8.2 Hz, 4H, 2(CII2Ph)), 4.84 (d, J=8.2 Hz, 2H, CLi2Ar), 2.13 (s, 6H, 2(CH3)).
(43) For leading references, see: McCracken, P. G.; Bolton, J. L.; Thatcher, G. R. J. "Covalent Modification of Proteins and Peptides by the Quinone Methide from 2-tert-Butyl-4,6-dimethylphenol: Selectivity and Reactivity with Respect to Competitive Hydration," *J. Org. Chem.* 1997, 62, 1820–25.
(44) Acylation of 3,5-dimethyl-4-hydroxybenzaldehyde followed by $NaBH_4$ reduction and phosphorylation of the benzyl alcohol afforded 9 (FIG. 4).
  (a) The phosphorylation reaction was a modification of: Silverberg, J. J.; Dillon, J. L.; Vemishetti, P. "A Simple, Rapid and Efficient Protocol for the Selective Phosphorylation of Phenols with Dibenzylphosphite," *Tetrahedron Lett.* 1996, 37, 771–74.
  (b) A recent paper reports on the hydrolytic stability of benzyltrialkylphosphates and the effects of various substituents on the phenyl ring: Meier, C.; Habel, L. W.; Baizarini, J.; De Clercq, E. "5',5'-Di-O-nucleosyl-O'-benzylphosphotriesters as Potential Prodrugs of 3'-Azido-2',3'-dideoxythymidine-5'-monophosphate," *Liebigs Ann* 1995, 2203–08.
(45) Studies of various electron-donating and electron-withdrawing substituents on the quinone methide ring and at the benzylic methylene have demonstrated their influence on quinone methide formation, reactivity and product stability:
  (a) Bolton, J. L.; Comeau, E.; Vukomanovic, V. "The Influence of 4-Alkyl Substituents on the Formation and Reactivity of 2-Methoxy-Quinone Methides: Evidence That Extended $\pi$-Conjugation Stabilizes the Quinone Methide Formed From Eugenol," *Chem-Biol. Interactions* 1995, 95, 279–90.
  (b) Thompson, D. C.; Perera, K. "Inhibition of Mitochondrial Respiration by a Para-Quinone Methide," *Biochem. Biophys. Res. Commun.* 1995, 209, 6–11.
  (c) Lycka, A.; Snobl, D.; Koutek, B.; Pavlickova, L.; Soucek, M. "13C NMR Study of Substituted Quinone Methides. 2- and 2,6-Substituted Fuchsones," *Coll. Czech. Chem. Commun.* 1981, 46, 1775–87.
  (d) Velek, J.; Koutek, B.; Musil, L.; Vasickova, S.; Soucek, M. "IR Spectra of Some Quinone Methides. A Study of the ortho-Effect," *Coll. Czech. Chem. Commun.* 1981, 46, 873–83.
(46)
  (a) Turnbull, K. D. "para-Quinone.Methides: Chemistry and Exploitation as Intermediates for the Intramolecular Formation of Carbon-Carbon Bonds and Investigations into the Chemistry and Synthesis of Neolignans Via a Proposed Intermediate in Their Biosynthesis," *Ph.D. Dissertation,* University of California, Riverside, 1991.
  (b) Angle, S. R.; Turnbull, K. D. "Para-Quinone Methide Initiated Cycization Reactions," *J. Am. Chem. Soc.,* 1989, 111, 1136.

(47) A Fries rearrangement on 2,4-dimethylphenol followed by benzylation of the phenol, a BaeyerVilliger oxidation, and saponification of the intermediate acetate on workup afforded the required monoprotected catechol. A substitution reaction with bromoacetic acid provided the intermediate carboxylic acid which was converted to the desired etser derivatives through carbodiimide activation in the presence of the required alcohol. The dimethylamide derivative was produced directly from addition of bromoacetamide followed by methylation. Hydrogenolysis provided the various derivatives of 11 shown in the table of scheme 3 for oxidation to the desired quinone methides.

(48) Reliable Biopharmaceuticals, St. Loius, Mo., has generously donated multi-milligram quantities of TpT (with and without protecting groups) and CpA (with and without protecting groups) for the purpose of these studies.

(49) Wakselman, M. "1,4- and 1,6-Eliminations from Hydroxy- and Amino-substituted Benzyl Systems: Chemical and Biochemical Applications," *Nouv. J. Chim.* 1983, 7, 439–47.

(50)
(a) Kanamathareddy, S.; Gutsche, C. D. "Calixarenes: Selective Functionalization and Bridge Building," *J. Org. Chem.* 1995, 60, 6070–75.
(b) Adam, I.; Sharma, S. K.; Gutsche, C. D. "The Quinonemethide Route to Mono- and Tetrasubstituted Calix [4]arenes," *J. Org. Chem.* 1994, 59, 3716–20.
(c) Note that even aniline has been eliminated to produce quinone methides: Angle, S. R.; Yang, W. "Synthesis and Chemistry of a Quinone Methide Model for Anthracycline Antitumor Antibiotics," *J. Am. Chem. Soc.* 1990, 112, 4524–28.

(51) Quinone methides have been generated by laser flash photolysis (266 nm) of phenolic benzyl alcohols and the UV of the transient intermediate was presumed to be the quinone methide. These are differentiated from caged quinone methide precursors which can be irradiated at wavelengths outside 350 nm in order to be useful in the presence of biological molecules: Diao, L.; Yang, C.; Wan, P. "Quinone Methide Intermediates from the Photolysis of Hydroxybenzyl Alcohols in Aqueous Solution," *J. Am. Chem. Soc.* 1995, 117, 5369–70.

(52) This allows transmission of >350 nm wavelength which will prevent absorbance of biological aromatics.

(53) Fleming, S. A.; Jensen, A. W. "Substituent Effects on the Photocleavage of Beazyl-Sulfur Bonds. Observation of the Meta-Effect" *J. Org. Chem.* 1996, 61, 7040–44, and references therein.

(54)
(a) Dimethoxybenzoin: Pirrung, M. C. Shuey, S. W. "Photoremovable Protecting Groups for Phosphorylation of Chiral Alcohols. Asymmetric Synthesis of Phosphotriesters of (−)-3',5'-Dimethoxybenzoin," *J. Org. Chem.* 1994, 59, 3890–97.
(b) Sheehan, J. C.; Wilson, R. M.; Oxford, A. W. "The Photolysis of Methoxy-Substituted Benzoin Esters. A Photosensitive Protecting Group for Carboxylic Acids," *J. Am. Chem. Soc.* 1971, 93, 7222–28.
(c) a-Methyl-4,5-dimethoxy-2-nitrobenzyl: Marriott, G. "Caged Protein Conjugates and Light-Directed Generation of Protein Activity: Preparation, Photoactivation, and Spectroscopic Characterization of Caged G-Actin Conjugates," *Biochemistry* 1994, 33, 9092–97.
(d) a-Carboxy-2-nitrobenzyl: Gee, K. R.; Wieboldt, R.; Hess, G. P. "Synthesis and Photochemistry of a New Photolabile Derivative of GABA. Neurotransmitter Release and Receptor Inactivation in the Microsecond Time Region," *J. Am. Chem. Soc.* 1994, 116, 8366–67.

(55) For reviews of photolabile protecting groups, see:
(a) Adams, S. R.; Tsien, R. Y. "Controlling Cell Chemistry with Caged Compounds," *Annu. Rev. Physiol.* 1993, 55, 755–84.
(b) Gurney, A. M.; Lester, H. A. "Light Flash Physiology with Synthetic Photosensitive Compounds," *Physiol. Rev.* 1987, 67, 583–615.
(c) Pillai, V. N. R. "Photoremovable Protecting Groups in Organic Synthesis," *Synthesis* 1980, 1–26.

(56)
(a) Derivatives with dimethyl substituents and a benzylic methyl (R, $R^1$, $R^{11}$=Me) were prepared by acylation of 2,6-dimethylphenol followed by a Fries rearrangement to the 4-methylketone derivative followed by protection with o-nitrobenzyl bromide and NaBH4 reduction to the benzyl alcohol derivative. The benzyl alcohol was converted to the acetate, trifluoromethyl acetate, bromide or chloride through literature methods.
(b) Derivatives with no substituents (R, $R^1$, $R^{11}$=H) were made by protection of 4-hydroxybenzaldehyde with o-nitrobenzyl bromide and reductive amination with the desired dialkylanuine.
(c) The methoxy substituted derivative (R, $R^{11}$=H, R=OMe) were made by protecting vanillin with o-nitrobenzyl bromide, NaBH4 reduction and conversion to the chloride with N-chlorosuccinimide.
(d) Dimethyl substituted derivatives with no benzylic alkyl group (R, $R^1$=Me, $R^{11}$=H) were prepared from protection of 3,5-dimethyl-4-hydroxybenzaldehyde with the alcohol of the desired photolabile protecting group in the presence of triphosgene to afford the carbonate protected benzaldehyde. NaBH4 reduction and conversion to the acetate or chloride afforded the desired products.

(57) Besides the experiment reported (FIG. S5), we have run several experiments with guanylated octopamine (structure at right) trying to induce quinone methide formation via dehydration. This has been attempted in refluxing TFA with no sign of any type of reaction. We have also obtained preliminary results on the benzylic chlorination of this compound in DMF with phosphoryl chloride. NMR evidence suggests quantitative conversion to the benzyl chloride with no cyclization of the guanidine. Treatment of this intermediate with NaOH resulted in apparent B-elimination to the styrene, but no sign of cyclization was evident by 1H NMR.

(58) Athough the possibility for this cyclization is readily apparent, a thorough examination of the natural product, synthetic, and medicinal literature has thus far failed to turn up an example of a cyclization such as could occur in any of our proposed ATAR systems (a 3 to 7-exo-tet or trig depending on which system and whether the quinone methide precursor or the quinone methide is cyclizing (see A, B, or C in section 4.3)). Although there are limited examples of guanidine SN2 or conjugate addition reactions, these require deprotonation under strong basic conditions or electrophilic activation under acidic conditions [For a recent example of an SN2 reaction see: Vaidyanathan, G.; Zalutsky, M. R. "A New Route to Guanidines from Bromoalkanes," *J. Org. Chem.* 1997, 62, 4867–69.]. Guanidine condensation reactions are well precedented and a useful means for making heterocyclic structures and in natural product synthesis and generally require acid or base catalysis to drive the reactions [For leading references, see:
(a) ref 35.
(b) Yamamoto, Y.; Kojima, S. "Synthesis and Chemistry of Guanidine Derivatives," in *The Chemistry of Amidines and Amidates,* Patai, S.; Rappoport, Z., Eds.; John Wiley & Sons: N.Y. 1991, 485–526.
(c) Berlinck, R. G. S. "Natural Guanidine Derivatives," *Nat. Prod. Rep.* 1996, 377–409.].

(59) One example of a natural product which has been isolated which has the potential to undergo a 5-exo-trig cyclization was found. This is martinelline: (Witherup, K. M.; Ransom, R. W.; Graham, A. C.; Bernard, A. M.; Salvatore, M. J.; Lumma, W. C.; Anderson, P. S.; Pitzenberger, S. M.; Varga, S. L. "Martinelline and Martinellic Acid, Novel G-Protein linked Receptor Antagonist from the Tropical Plant Martinella iquitosensis (Bignoniaceae)," *J. Am. Chem. Soc.* 1995, 117, 6682–85.). Although this was not specifically sought out, the natural product was isolated as the 3×TFA salt and stable to the extraction, characterization and assaying processes. A small amount of the correponding acid which would result from cleavage of the ester bond was also present; but the authors were uncertain if it was an artifact or natural. It was reported as a natural product.

(60) This is definitively stated as all the components produced in the reaction mixture have been independently characterized by 1H NMR, and there is no visible sign of any new benzylic resonances, or ethyl resonances which would identify the addition of the ethyl guanidine to the quinone methide.

(61) It is believed that cyclization will not be a concern in the ATAR as long as the guanidine is protonated. Guanidine deprotection will be the final step in our synthetic protocol and will result in the protonated guanidinium ATAR which will remain under aqueous conditions for all uses.

(62) Bernatowicz, M. S.; Wu, Y.; Matsueda, G. R. "1H-Pyrrazole-1-carboxamidine Hydrochloride: An Attractive Reagent for Guanylation of Arnines and Its Application to Peptide Synthesis," *J. Org. Chem.* 1992, 57, 2497–502.

(63) Iodination of phthalimide-protected octopamine followed by a Stille reaction with tetramethyltin has been accomplished in approx. 98% yield for the two steps.

(64) Three approaches are underway in order to establish different chemistry which will be utilized for more advanced derivatives:
(a) Graduate student Tony Hudgens has accomplished the diiodination of octopamine followed by Stille methylation, guanylation, and protection of the phenol as the silyl ether. He is presently optimizing a benzyl alcohol reduction and deprotection sequence to afford 20 (R'''=H). These steps have already been accomplished in related systems.
(b) Another approach, nearly complete, is being carried out by Mr. Damon Arinitage, a senior Honor's student in our laboratories. This has involved a condensation of nitromethane with benzyl-protected 3,5-dimethyl-4-hydroxy benzaldehyde followed by dehydration according to a literature procedure (Wollenberg, R. H.; Miller, S. J. "Nitroalkane Synthesis. A Convenient Method for Aldehyde Reductive Nitromethylation," *Tetehedron Lett.* 1978, 35, 3219–22.). Hydrogenation accomplishes the debenzylation, stryrene reduction, and reduction of the nitro to the amine. The amine is being guanylated using standard procedures to afford 20 (R'''=H).
(c) An approach to 21 being carried out by graduate student Tony Hudgens is nearly identical to the approach described above (64a to make 20), except the phenol is protected as the o-nitrobenzyl carbonate and the benzyl alcohol is converted to the benzyl chloride by procedures already established in the group.

(65) Yamamoto, Y.; Kojima, S "Synthesis and Chemistry of Guanidine Derivatives," in *The Chemistry of Amidines and Amidates,* Patai, S.; Rappoport, Z., Eds.; John Wiley & Sons: N.Y. 1991, 485–526.

(66) Cliffe, 1. A. "Functions Containing an Iminocarbonyl Group and any Element Other Than a Halogen or a Chalcogen," in *Comprehensive Organic Functional Group Transformations,* Gilchrist, T. L., Ed.; Pergamon: U.K. 1995, 639–75.

(67) The potential for a phenyl substituent to increase intercalation is realized. As the phenyl group itself is not very polar in nature, this should not be a favored interaction.

(68) The o-nitrobenzyl carbonate protection of the phenol has proven more effective at stablizing the benzyl chloride towards hydrolysis in the final product. The Boc protecting groups are difficult to remove in high yield, so bringing the amine through as the phthaloyl-protected derivative with deprotection after the Stilie methylation followed by guanylation and then chlorination as shown has proven the preferred route in other systems (see footnote 64c and 64a).

(69)
(a) Wang, B.; Liu, S.; Borchardt, R. T. "Development of a Novel Redox-Sensitive Protecting Group for Amines Which Utilizes a Facilitated Lactonization Reaction," *J. Org. Chem.* 1995, 60, 539–43.
(b) Cauwberghs, S.; De Clercq, P. J.; Tinant, B.; Declercq, J. P. "Factors Affecting Ease of Ring Formation. The Effect of Anchoring Substition on the Rate of an Intramolecular Diels-Alder Reaction with Furan-Diene," *Tetrahedron Lett.* 1988, 29, 2493–96.

(70) Molecular modeling (MM2) minimizations on these systems suggest there will be no steric or conformational constraints to addition of the phosphodiester to the quinone methide from the favored conformations. The highly flexible directionality and tautomerizing nature of hydrogen bonding make modeling of the transition state of little predictive value.

(71) Although we have been using more traditional brominations, we will try a new procedure which is reported to give 5% or less of the dibromo-product with phenols. Mashraqui, S. H.; Mudaliar, C. D.; Hariharasubrah-manian, H. "4,4-Dimethyl-3-methylpyrazol-5-one: New Applications for Selective Monobromination of Phenols and Oxidation of Sulfides to Sulfoxides," *Tettrahedron Lett.* 1997, 38, 4865–68.

(72) Barluenga, J.; Garcia-Martin, M. A.; Gonzalez, J. M.; Clapes, P.; Valencia, G. "Iodination of Aromatic Residues in Peptides by Reaction with JPy2BF4," *J. Chem. Soc. Chem. Commun.* 1996, 1505–06.

(73) Scott, W. J. "The Stille Reaction," *Org. React.* 1997, 50, 1–652.

(74) Pappas, J. J.; Keaveney, W. P.; Gancher, E.; Berger, M. "A New and Convenient Method for Converting Olefins to Aldehydes," *Tetrahedron Lett.* 1966, 4273–78.

(75) Borch, R. F.; Bernstein, M. D.; Durst, H. D. "The Cyanohydridoborate Anion as a Selective Reducing Agent," *J. Am. Chem. Soc.* 1971, 93, 2897–904.

(76) De Maijere, A.; Meyer, F. E. "Fine Feathers Make Fine Birds: The Heck Reaction In Modern Garb," *Angew. Chem. Int. Ed. Eng.* 1994, 33, 2379–411.

(77) Pasto, D. J.; Taylor, R. T. "Reduction with Diimide," *Org. React.* 1991, 40, 91–155.

(78) Danishefsky, S. "Siloxy Dienes in Total Synthesis," *Acc. Chem. Res.* 1981, 14, 400–406.

(79) Sibi, M. P.; Stessman, C. C.; Schultz, J. A.; Christensen, J. W.; Lu, J.; Marvin, M. "A Convenient Synthesis of N-Methoxy-N-methylamides From Carboxylic Acids," *Synth. Commun.* 1995, 25, 1255–64.

(80) Thompson, C. M.; Green, D. L. C. "Recent Advances in Dianion Chemistry," *Tetrahedron*, 1991, 47, 4223–85.

(81) Sibi, M. P. "Applications of N-Methoxy-N-methylamides in Synthesis," *Org. Prep. Proced. Int.* 1993, 23, 15.

(82) Danishefsky, S.; Yan, C.-F.; Singh, R. K.; Gammill, R. B.; McCurry, P. M.; Fritsch, N.; Clardy, J. "Derivatives of 1-Methoxy-3-trimethylsilyloxy-1,3-butadiene for Diels-Alder Reactions," *J. Am. Chem. Soc.* 1979, 101, 7001–008.

(83) Danishefsky has examined the cycloaddition reactions of sterically bulky dienes similar to 28 with methyl substituents at the 2- and 4-positions 82. Despite the increased sterics, reaction through the s-cis conformation is still a facile process. The same researchers demonstrated the use of dimethyl allene-1,3-dicarboxylate (29) as a dienophile in reactions with Danishefsky's diene to afford high regioselectivity and yield of a benzene derivative with a substitution pattern similar to our target 82.

(84) Euranto, E. K. in *The Chemistry of Carboxylic Acids and Esters,* Patal, S., Ed.; Interscience Publishers: N.Y. 1969, pp. 505–588.

(85) This will be similar to Overman's tandem Curtius-carbamylation reaction: Overman, L. E.; Taylor, G. F.; Petty, C. B.; Jessup, P. J. "trans-1-N~Acylamino-1,3-dienes: Preparation From Dienoic Acid," *J. Org. Chem.* 1978, 43, 2164–67.

(86)
 (a) Sulfonamides are the most stable amine protecting group; however, unlike most sulfonamides, this derivative is readily deprotected with fluoride ion. This will be particularly imperative as it will be the final protecting group removed in the synthesis of the fully functionalized ATAR. Weinreb, S. M.; Demko, D. M.; Lessen, T. A. "B-trimethylsilylethanesulfonyl Chloride (SES-Cl): A new Reagent for Protection of Amines," *Tetrahedron Lett* 1986, 27, 2099–2102.
 (b) Alternatively, a more acid labile sulfonamide protecting group (Pmc) will be used: Ramage, R., Green, J., Blake, A. J. "An Acid Labile Arginine Derivative for Peptide Synthesis: NG~2,2,5,7, 8~Pentamethylchroman-6-sulfonyl-L-arginine," *Tetrahedron* 1991, 47, 6353–70.

(87) Hagihara, M.; Schreiber, S. L. "Reassignment of Stereochemistry and Total Synthesis of Thrombin Inhibitor Cyclotheonamide B," *J. Am. Chem. Soc.* 1992, 114, 6570–71.

(88) *Chem. Pharm. Bull.* 1984, 33, 1016.

(89) Sharp, M. J.; Cheng, W.; Snieckus, V. "Synthetic Connections to the Aromatic Directed Metallation Reaction. Functionalized Aryl Boronic Acids by Ipso Borodesilylation. General Syntheses of Unsymmetrical Biphenyls and m-Terphenyls," *Tetrahedron Lett.* 1987, 28, 5093–96.

(90) A Heck approach as previously described will be used if the amine-containing functionality proves unnecessary.

(91) The guanidine will be deprotected on a derivative having an ester for lactonization.

(92) The products of these reactions will be useful in all future studies for correlation with ATAR alkylated products which can be digested down to the enzymatically protected trialkylphosphate dinucleotide components.

(93) If necessary, product analysis will take advantage of procedures used for purifying hydrophobic methylphosphonate modified oligonucleotides: Lin, S.-B.; Chang, G.-W.; Teh, G.-W. Lin, K.-I.; Au, L. C. "A Simple and Rapid Method for Purification of Oligodeoxyribonucleoside Methylphosphonates," *Biotechniques* 1993, 14, 795–98.

(94) Sambrook, J.; Fritsch, E. F.; Maniatis, T. *Molecular Cloning 2nd Ed.* (Cold Springs Harbor Laboratory, Cold Springs Harbor, N.Y., 1989).

(95) The higher the degree of alkylation, the slower the oligo should migrate; or if the polarity is reversed, the faster they will migrate. This will be quantified by densitometry of the autoradiography to allow determination of the degree of alkylation.

(96) Alternatively, HPLC will also allow resolution and quantification of the relative degree of alkylation.

(97) i.e., Is there a difference in degree of alkylation at the ends or the middle of the oligonucleotide?

(98) Diastereomers afford differing $^{31}P$ resonance signals. An NMR nano-probe would greatly facilitate these analyses, and funding for such an upgrade will be sought.
 (a) Löschner, T.; Engels, J, W. "Diastereomeric Dinucleoside-methylphosphonates: Determination of Configuration with the 2-D NMR ROESY Technique," *Nucleic Acids Res.* 1990, 18, 5083–88.
 (b) Summers, M. F.; Powell, C.; Egan, W.; Byrd, R. A.; Wilson, W. D.; Zon, G. "Alkyl Phosphotriester Modified Oligodeoxyribonucleotides. VI. NMR and UV Spectroscopic Studies of Ethyl Phosphotriester (Et) Modified Rp-Rp and Sp-Sp Duplexes, {d[GGAA(Et)TTCC]}2," *Nucleic Acids Res.* 1986, 14, 7421–37.
 (c) Pramanik, P.; Kan, L. "NMR Study of the Effect of Sugar-phosphate Backbone Ethylation on the Stability and Conformation of DNA Double Helix," *Biochemistry* 1987, 26, 3807–12.

(99) Oligonucleotides will be synthesized on an automated synthesizer and purified according to standard protocols:
 (a) Beaucage, S. L.; Caruthers, M. H. *Tetrahedron Lett.* 1981, 22, 1859.
 (b) Sinha, N. D.; Biernat, J.; McManus, J.; Koster, H. *Nucleic Acids Res.* 1984, 12, 4539–57.

(100) The commercially available 1,12-dodecanediol will be protected as the 4,4'-dimethoxytrityl ether (Khorana, H. G. *Pure Appl. Chem.* 1968, 17, 349.) and converted to the synthesizer-ready phosphoramidite according to standard protocol (Gait, M. J., Ed., *Oligonucleotide Synthesis, A Practical Approach,* IRL Press: New York; 1990, pp. 41–45.).

(101) Based on modeling estimates, an initial linker will have 16 atoms from the 5'-phosphate oxygen of the oligonucleotide to the benzyl ring of the reagent.

(102) Oakley, M. G.; Turnbull, K. D.; Dervan, P. B. "Synthesis of a Hybrid Protein Containing the Iron-Binding Ligand of Bleomycin and the DNA-Binding Domain of Hin," *Bioconjugate Chem.* 1994, 5, 242–47.

(103) Bergeron, R. J.; McManis, J. J. *J. Org. Chem.* 1988, 53, 3108. This can be accomplished without hydrolyzing a methyl ester, so the oligonucleQtide attachment will remain unharmed.

(104) Telser, J.; Cruickshank, K. A.; Morrison, L. E.; Netzel, T. L. "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements," *J. Am. Chem. Soc.* 1989, 111, 6966–76.

(105) Han, H.; Dervan, P. B. "Visualization of RNA Tertiary Structure by RNA-EDTA.Fe(II) Autocleavage: Analysis of tRNA$^{Phe}$ with Uridine-EDTA.Fe(II) at Position 47," *Proc. Natl. Acad. Sci. USA* 1994, 91, 4955–59

(106) Telser, J.; Cruickshank, K. A.; Schanze, K. S.; Netzel, T. L. "DNA Oligomers and Duplexes Containing a Covalently Attached Derivative of Tris(2,2'-bipyridine) ruthenium(II): Synthesis and Characterization by Thermodynamic and Optical Spectroscopic Measurements," *J. Am. Chem. Soc.* 1989, 111, 7221–26.

(107) The standard deprotection methods will be tested in model systems first (ammonium hydroxide), and if necessary, more mild deprotection methods have been developed for solid-support oligonucleotide deprotection and cleavage of alkali-labile oligonucleotides such as with 5% K2C03 in MeOH. 12c A more labile oxallyl-CPG solid-support linkage can be used with this deprotection methodology. 12d Alternatively, in conjunction with the oxallyl-CPG, an allyloxy protection scheme can be used throughout the oligonucleotide for mild catalytic palladium deprotection, 12b which the carbonate and ester will be stable towards.

(108) A post-synthetic methodology could also be used to functionalize the deprotected and cleaved, modified oligonucleotide in solution.

(109) The absorbance ratio at 260 nm (for DNA) versus 350 nm (for the reagent).

(110) The protocol for triple helix formation and analysis by affmity cleavage is very well developed, see:
   (a) Greenberg, W. A.; Dervan, P. B. "Energetics of Formation of Sixteen Triple Helical Complexes Which Vary at a Single Position Within a Purine Motif," *J. Am. Chem. Soc.* 1995, 117, 5016–22.

(111) Kennard, O.; Hunter, W. N. "Single-Crystal X-Ray Diffraction Studies of Oligonucleotides and Oligonucleotide-Drug Complexes," *Angew. Chem. Int. Ed. Engl.* 1991, 30, 1254–77.

A. Research Plan

1. Introduction

Rapid progress in sequencing the human genome[1A] opens new doors for potential technological developments for studying and treating disease at the foundational genetic level. One area of such potential development is the in vivo chemical modification of genomic DNA for diagnostics, therapeutics, and the study of biological processes. This requires progress in several areas of biomedical technology. Advances in oligonucleotide delivery to cells[2A] and sequence-specific recognition of DNA[3A] are two key areas. Our research program is targeting an unexplored area for the development of an innovative, chemical means to covalently deliver a variety of reporter groups, drug agents, or proteins to DNA. The ability to site-specifically attach such moieties to DNA would allow various genetic-based, biological studies to be conducted[4A] and provide a new means for efficient diagnostics,[5A] therapeutics[6A] and biological control at the genetic level.[7A]

Covalent modification of the phosphodiester group would be of most interest as it is the common, repeating, nucleophilic functional group throughout nucleic acid polymers. Whereas covalent modification of the nucleic acid bases generally leads to strand cleavage through depurination and will disrupt base pairing by interfering with hydrogen bonding, modification of the phosphate will have less effect on nucleic acid structure and function (FIG. 1A).

This proposal will present the foundational research necessary for development of such a chemical reagent to accomplish this overall goal. This research is developing a variety of useful chemistry, synthetic methodology, and technologically applicable compounds in pursuit of the long-termn goal.

This de vivo designed reagent will covalently transfer attached molecules to a target phosphate group of a nucleic acid polymer (FIG. 1A). The reagent is designed around a quinone methide with its bimodal electrophilic and a nucleophilic reactivity. The design features include:

An independently tethered delivering oligonucleotide and molecule to be transferred (1, oligo and R, respectively, FIG. 1A). These are appended to a DNA synthesizer, machine-ready core reagent using standard automated, solid-phase, synthetic protocol for efficiency and versatility.

Phosphate specificity through a guanidinium-phosphate complex (2). The guanidinium group will be substituted as needed to lower its nucleophilicity and prevent intramolecular reaction.

"Caged" reactivity initiated by photolysis to afford the quinone methide precursor (3).

An intramolecular tertiary amine may be incorporated if it proves beneficial to assist 1,6-elimination[8] to afford the intermediate quinone methide (4).

Alkylation of the phosphodiester with the quinone methide resulting in the in situ release of the delivering oligonucleotide through lactonization to accomplish the transfer step (4 to 5). The oligonucleotide tether is designed to be cleaved at a slower rate than 1,6-elimination occurs. The intramolecular conjugate acid will afford stability to the trialkylphosphate prior to lactonization.

Formation of a covalently stable trialkylphosphate upon lactone formation by trapping the alkylated product (5) and preventing reaction reversibility.

The reagent is an affinity transfer alkylating reagent (ATAR) for labeling the phosphodiester of nucleic acids. The research program is designed to streamline development of the ATAR by optimizing the chemistry through independent model system studies. The final reagent will be suitable for general use by attaching any delivering oligonucleotide on an automated synthesizer followed by attachment of a desired reporter group,[9A] drug agent,[10A] or protein conjugate[11A] on the solid support or post-synthetically. This provides a "user-friendly" reagent for use in modifying DNA, studying various nucleic acid-protein interactions, and for drug delivery applications.

The chemistry required for the ATAR is being developed through a variety of small molecule model studies. Each study requires minimal synthesis in order to independently investigate the various chemical aspects of the ATAR for optimization. Progressively more complex studies are underway in order to coordinate the compatibility of the chemical reactions for optimal control of all aspects of the ATAR design. The chemistry necessary for the total syntheses of fully functionalized derivatives for incorporation into the ATAR on a DNA synthesizer is being developed in the course of these model studies. This proposal maps out the investigations for development of the chemistry of the ATAR focusing on the model system syntheses and studies. Although the overall goal of this research is the envisioned applications of the ATAR mentioned above,[4A-7A] this will be beyond the time frame for which present funding is sought.

Several significant subset developments result from the pursuit of the overall research goal. One will be a simplified synthetic method[12A,13A] for site selective alkylation and peralkylation of oligonucleotide phosphodiesters to produce trialkylphosphate modified oligonucleotides for various uses.[14A,15A,5A] This backbone modification affords enhanced hybridization properties[16A] and antisense/antigene applications.[17A,18A] This research has already afforded a useful synthetic method for modifying phosphodiesters with the formation, isolation and fall characterization of trialkylphosphates.[19A] Some aspects of commercial potential for this methodology are being pursued with industrial support.[20A] A non-specific chemical nuclease is being developed in conjunction with this research and a method for the site-selective hydrolytic cleavage of DNA.[21A,22A]

2. Background and Significance

Heterobifunctional crosslinking reagents containing a cleavable linker have been developed for studying protein-protein interactions;[23A] These reagents require an invasive chemical step to transfer the probe molecule from the delivering species to the target protein. This limits their use to in vitro applications. The ATAR we are developing will involve an in vitro cleavage step of the initially formed crosslinked complex in order to release the delivering oligonucleotide. This forms a DNA target which has been covalently modified with a small molecule carrying the independently attached label. The independent synthetic attachment of both the delivering oligonucleotide and the desired reporter group, drug agent, or protein provides a versatile ATAR for various applications.

One example of a reagent which transfers a methyl group from a nucleic acid binding reagent to a nucleic acid base in vitro comes from the work of Gold and coworkers.[24A] They produced a methylating reagent by tethering methyl sulfonates to a dipeptide lexitropsin, an A/T-rich minor groove binder. This reagent allowed methylation ot the adenin-N3 selectively, resulting in the iclease ot the lexitropsin sulfonic acid byproduct. The goal of this proposal is to define a method to extend this type of in vitro transfer chemistry beyond methylation to the transfer of a large variety of reporter groups or drug molecules. This will be accomplished by having them tethered to a ieactive quinorie methide[25A,26A] which will initiate nucleophilic attack followed by the in situ release of the delivering molecule. Further, the ATAR being developed will be latently reactive upon photolysis after binding to the target site in order to minimize secondary alkylation reactions. It will also target the phosphate residue of nucleic acids in order to mimnnze perturbalion of the bases, leaving the nucleic acid free for hybridization.

Although the phosphate residue of nucleic acids is not the chemoselective site for alkylation by many routinely used electrophilic reagents,[27A] in situ alkylation of the phosphodiester to afford phosphotnesters is observed. Ethylnitrosourea (ENU) shows the highest selectivity for phosphotriester formation relative to methylnitrosourea (MNU), dimethylsulfate (DMS) and ethylmerhanesultonate[28A] Expressed in terms of total DNA alkylation, the extent of phosphodiester alkylation by ENU has been estimated to be between 59%[28A] and 7Q%.[28A]

A quinone methide is an effective alkylating agent with a dialkylphosphate (see Preliminary Results). A quinone methide (FIG. 2A) is a potent electrophile due to its highly polarized nature. Rearomatization of the quinone methide ring is a strong driving force for reaction.[29A] This relatively hard electrophile is a good alkylating agent for the hard phosphate oxygen.[30A]

Skibo and coworkers have recently developed a molecule (5, FIG. 3A) that alkylates the phosphate residue of nucleic acids.[31A] This molecule contains a binding region which recognizes the adenine.thymine (A.T) base pair (and to a lesser extent the guanine.cytosine (G.C) base pair). The alkylating region is composed of an aziridinium moiety for selective phosphate alkylation (6, FIG. 3A) instead of normal alkylation of N-7.[32A]

Day and coworkers attempted to develop a reagent for alkylation of DNA phosphate group using para-bromomethylbenzoyl choline iodide.[31A] Unfortunately, it was later reported the reagent was polyinerizing and phosphate alkylation was not occurring.[34A] This work suggests the challenge in finding a strong enough electrophile to selectively react with a phosphate. As indicated, we have already shown that quinone methides alkylate dialkylphosphates in an aqueous environment.

The guanidinium functional group is extensively used in biological systems and various artificial receptors for phosphate recognition and binding.[35A] This type of ionic association of cationic amine residues with DNA has been successfully used by other researchers in order to enhance binding to DNA.[36A] As charge-charge attractions are the strongest noncovalent molecular interactions, salt bridges between nucleic acid phosphates and positively charged amino acid side chains are individually the highest strength interactions in protein-nucleic acid interactions.[17A]

The ATAR we are developing takes advantage of this type of guanidinium-phosphate ionic association to direct the alkylation process. The precursor to the quinone methide will incorporate a guanidinium residue to enhance the effective concentration of the phosphodiester. The guanidinium group may associate with other nucleic acid sites, such as the bases;[35A] however, the thermodynamic preference for two point hydrogen bonding and charge pairing of a guanidinium-phosphate complex is well accepted.[35A,37A]

3. Preliminary Results

Various model system studies are being conducted to develop the chemistry necessary for the ATAR. Below are nine key results which contribute to the ATAR development. In the area of de novo design, the importance of a compound comes only with proven function. This often delays publication of foundational work until the significance of the chemistry is verified. The formation of isolated, fully characterized trialkylphosphates has been accomplished to provide a useful synthetic approach for modifying phosphodiesters. Due to this recent demonstration of function, publication of these results are in progress,[19A] and publication of the foundational work which supported it will follow.[39A] There is presently a provisional patent covering many of these developments.[40A] Some aspects of commercial potential of the phosphotriester forming reactions are being pursued with industrial support.[20A]

(1) Quinone methide alkylation of a phosphodiester to form a phosphotriester. Studies of a quinone methide with a dialkylphosphate have been conducted 2,4,6-Trimethylphenol was quantitatively converted to quinone methide 7 with $Ag_2O$[41A] and dibenzyl-phosphoric acid was added to produce phosphotriester 8 as the exclusive product (FIG. S2A).[42A]

(2) Phosphotriester product is favored upon protonation. Formation of 8 is an equilibrium process. Trialkylphosphate 8 is favored under acidic conditions which protonate the quinone methide oxygen leading to the phenol. However, under basic conditions where the phenol is deprotonated or conditions acidic enough to protonate the phosphotriester oxygen, 7 is favored. As initially seen by the effect of various acids in the $pK_a$ range shown in FIG. T1A, this should favor phosphotriester formation under biologically relevant conditions near pH 7.

(3) Kinetic favorability of phosphotriester formation over hydrolysis in the presence of water. The reaction of quinone methide 7 and two equivalents of dibenzylphosphoric acid in the presence of excess water (~200 equivalents for a homogeneous solution) afforded only trialkylphosphate 8 as the product in the equilibrium by $^1$H NMR analysis. Minor amounts of the benzyl alcohol hydrolysis product was evident by $^1$H NMR analysis after 18 hours ai ambient temperature. Trialkylphosphate 8 is the kinetic product. A similar amount of 8 is produced in the presence of a much higher concentration of water (3,000 equivalents forming a bilayer) at ambient temperature after 30 minutes. However, the benzyl alcohol hydration product begins to drain off the kinetically formed 8 affording complete conversion to benzyl alcohol after 18 hours. Hydrolysis to benzyl alcohol appears to be the thermodynamic product. Similar results of quinone methides reacting with amino acid derivatives under aqueous conditions have been reported by other researchers.[43A]

(4) Hydrolytic stability of an acetylated trialkylphosphate derivative. The effect of protonation on the alkylation reaction above and that the trialkylphosphate is the kinetic product suggested trapping of the phosphate alkylated DNA as lactone derivative 4 (FIG. S1A) should be favored over hydrolysis (to afford a benzyl alcohol) under physiological conditions. Investigation of the stability of lactone trapped trialkylphosphate product was the next step. The high stability of independently synthesized $9^{44}$ (FIG. 4A) in water (pH 6.5, 40° C., overnight) demonstrates the expected stability of the lactone product 4 (FIG. S1A) which will result from the ATAR phosphate alkylation reaction.

(5) Trapping stable phosphotriesters through tandem lactonization after quinone methide alkylation of a phosphodiester. The isolation of stable, fully characterized products has been imperative to the development of useful synthetic methodology from this research. This has now been accomplished.[19A] A variety of ester derivatives have been synthesized to study the requirements for trapping the trialkylphosphate through lactonization.

Characterizable quinone methide intermediates are prepared via $Ag_2O$ or $PbO_2$ oxidation. It proved necessary to synthesize derivatives with an oxygen at the ortho-position (catechol derivatives, 10a, FIG. 5A) to exclude the formation of ortho-quinone methides upon oxidation if the esters were tethered through a methylene at the ortho-position (10b, $R_2$=H, H, FIG. 5A). Attempts at making secondary or tertiary substituted tethers at the ortho-position (10b, $R_2$=H, $CH_3$ or $CH_3$, $CH_3$, FIG. 5A) resulted in facile lactonization (gem-dialkyl effect) circumventing oxidation to the quinone methide. These catechol derivatives may provide a beneficial modification to the ATAR design. An oxygen at the ortho-position of a para-quinone methide appears to increase the reactivity of the quinone methide towards nucleophilic addition.[45A,46A] The ortho-oxygen is expected to affect the rate of the lactonization reaction and the stability of the lactone product towards hydrolysis. This catechol-type system (10a) will be compared to the corresponding phenol system with an ortho-alkyl tether (10b). The quinone methide from the latter systems will be formed by 1,6-elimination of a benzylic leaving group.

The ester derivatives were made in five steps from 2,4-dimethylphenol.[47] These esters include three classes: high, intermediate and low reactive derivatives (see table insert of FIG. S3A). The high reactive esters lactonized to afford 12 under the mildly basic conditions of oxidation. The low reactive derivatives were oxidized to the corresponding quinone methide 13 and underwent dibenzylphosphate addition; however, were not able to lactonize under the alkylation conditions. The intermediate reactive derivatives were successfully oxidized to para-quinone methide intermediate 13, alkylated the dibenzylphosphate to 14, and lactonized to afford trapped trialkylphosphate product 15 (FIG. S3A).

This now provides a useful synthetic approach towards the covalent functionalization of phosphodiesters. The key, fundamental reactions of the designed ATAR reagent have been successfully demonstrated. The details of these investigations are being submitted for publication.[19A] The alkylation of nucleotide derivatives are presently being studied having obtained enough of various required dinucleotides for NMR analysis of the phosphodiester alkylation.[48A]

(6) Quinone methide formation through photolytic-initiated 1,6-elimination followed by phosphodiester alkylation. After significant effort, the conditions necessary for photolytic removal of a protecting group followed by 1,6-elimination to afford the para-quinone methide and reaction with dibenzylphosphate has been accomplished. Although there are numerous reports of reactions which occur through the presumed formation of quinone methide intermediates by 1,6-elimination processes,[26A,49A,50A] to our knowledge this is the first case of caged, photolytically-activated p-quinone methide formation via elimination with characterization.[39A,51A]

Multiple derivatives have been synthesized as discussed below (point 8, FIG. T2A). The first successful reaction was accomplished using 16 (FIG. S4A). Photolysis of 16 (150 W xenon arc lamp, $BiCl_3$/HCl filter,[52A] ambient) was monitored by $^1$H NMR in $CDCl_3$ with either: (A) one equivalent of $Ag^+(BnO)_2PO_2^-$ salt, or (B) one equivalent of $(i-Pr)_2EtNH^+(BnO)_2PO_2^-$ salt. After photolysis for one hour, nearly all of 16 was deprotected to form a mixture of phenol 17, quinone methide 7 and trialkylphosphate 8 in approximately 2:1:1 ratio, respectively. This photolytic-initiated reaction did not go to completion, but appears to form an equilibrium mixture of 17:7:8 under these conditions. Note that under aqueous conditions for which the ATAR is being designed to operate, the chloride will not be a competitive nucleophile, and will rapidly diffuse away from the quinone methide. Preliminary experiments having water present show no sign of equilibrium back to 17. This experiment did not have the benefit of an intramolecular trap to drain off the kinetic preferred trialkylphosphate or the assistance of a phosphate-directing guanidinium group.

(7) Hydrolytic stability of the quinone methide precursor and photolytic stability of the quinone methide intermediate and the trialkylphosphate product. Experiments have demonstrated the benefit of a carbonate protected phenol (e.g., 16, FIG. S4A) for greatly increasing the stability of the benzylchloride. Hydrolysis of quinone methide precursors has been a problem with many quinone methide-based, biologically reactive molecules.[26A,43A,49A] The carbonate protected 16 has shown no sign of hydrolysis at 25° C. in 33% $D_2O/CD_3CN$ for two days. Related benzyl protected derivatives hydrolyze relatively rapidly.

Due to the precedent for photolytic-induced homolytic reactions occurring with derivatives containing benzylic leaving groups,[53A] and the appearance of various byproducts in earlier reactions attempted, an investigation of the photolytic stability of the intermediate quinone methide and the trialkylphosphate product was undertaken. Pre-formed quinone methide 7 was photolyzed under conditions used to afford 8 above (FIG. S4A), and no reaction was evident by $^1$H NMR analysis after 3 hours. Similarly, trialkylphosphate 8 was photolyzed under the same conditions and showed no sign of reaction after 3 hours.

(8) Studies of various combinations of photolabile protecting groups with different benzylic leaving groups for quinone methide formation. Successful conditions for producing identifiable quinone methide derivatives through photolytic-initiated 1,6-elimination reactions have now been realized.[39A] This led to the synthesis of derivatives containing either the o-nitrobenzyl (NB), the a-methyl-3,4-dimethoxy-2-nitrobenzylcarbonate (DMNBC) or the dimethoxybenzoin carbonate (DMBC) protecting group[54A, 55A] with a variety of leaving groups at the benzylic position (FIG. T2A).[56A] These derivatives are being examined to determine effects of the different substituents on their hydrolytic stability,[39A,43A] the rates of quinone methide formation and the alkylation reaction rates.[45,49] These particular derivatives allow correlation with other systems being used to study the quinone methide alkylation reaction and the lactonization reaction.

(9) Competitive guanidine cyclization: Phosphotriester formation with a quinone methide and a phosphodiester-ethylguanidinium salt. Apossible guanidine 5-exo-trig cyclization on the quinone methide of the designed ATAR was realized. This potential competition is under examination and approaches to prevent it, if necessary, are being developed (see 4.1). Initial results[57A] and a thorough literature search suggest this may be negligible[58A,59A]

The initial analysis looked at the effect of ethylguanidinium on the dibenzylphosphate alkylation reaction with quinone methide 7. As shown in scheme 5, 0.5 equivalents of ethylguanidinium-dibenzylphosphate salt (18) in 8:1 DMSO-$d_6$D$_2$O was added to a solution of quinone methide 7 in CDCl$_3$. Due to solubility problems, NMR integration shows approximately 0.3 equivalents of 18 remained in solution. Within 30 minutes at ambient temperature, the same equilibrium of 7:8 was apparent which was formed without the ethylguanidinium present (i.e., 2:1 of 7:8, FIG. S2A). Normalizing the reaction to the total amount of 18 present (0.3 equiv.), a 2:1 ratio of the equilibrium mixture of quinone methide 7 to trialkylphosphate 8 appears as an overall 10% formation of 8 by $^1$H NMR integration. Again, the presence of D$_2$O had no effect on the kinetic formation of 8; however, with no intramolecular trap to drain off the kinetically formed 8, over the next several hours the presence of benzyl alcohol increased. At no point in the reaction was there any evidence of the ethyl guanidine adding to the quinone methide.[60A,61A]

Although this experiment examined an intermolecular reaction and the competitive cyclization reaction in the ATAR will be intramolecular, it should be realized that there was a 1:1 ratio of the phosphate and guanidine present for reaction with the quinone methide in this experiment. In the ATAR, the complexation of the guanidinium with the phosphodiester will similarly result in a 1:1 ratio of the two components in proximity of the quinone methide. Effects of hydrogen bonding lowering the nucleophilicity of the phosphate while increasing the nucleophilicity of the guanidine were present equally in the above experiment as they will be in the ATAR-DNA alkylation reaction so these effects would also still result in the expected preference for phosphodiester alkylation.

4. Methods and Procedures

Completion of the model studies described above and the following will accomplish the design optimization of the individual ATAR components. Studies with increasingly more complex systems are beginning to coordinate the reactions into a functional derivative. Although all the studies can not be delineated, the synthesis of more complex derivatives represents the approach to be used to prepare derivatives for optimization of each component incorporated into the ATAR.

4.1. Investigations of quinone methides with tethered guanidine functional groups. Model systems are being investigated to determine the effect of a tethered guanidinium in directing the phosphodiester alkylation reaction. Our initial efforts have focused on the use of two commercially available amines: tyramine and octopamine, which were converted to their respective guanidinium-phosphate salt derivatives 18 and 19 (FIG. 6A).[62A] Oxidation of 18 (and a bis-Boc guanidine derivative) has not succeeded using Ag$_2$O, PbO$_2$, or DDQ. The inability to oxidize p-cresol suggests the 2,6-dimethyl derivative may be necessary. We recently accomplished a Stille coupling in a related 2,6-diiododerivative[63A] and are preparing 20 for quinone methide formation through oxidation. The 1,6-elimination of 19 to afford quinone methide has yet to succeed using acidic thermolysis. Derivative 21 is being prepared for more facile 1,6-elimination.[64A]

The experiment reported above (FIG. S5A) suggests that cyclization of guanidine on the quinone methide may not occur with the guanidinium-phosphate salt complex. Should this occur, adjusting the nucleophilicity of the guanidine should alleviate this possible competition. Based on reported pK$_a$ values for various substituted guanidines,[8A,65A] a phenyl guanidine (10.8) is sufficiently less basic than a methyl guanidine (14.1). The nucleophilicity should be similarly weakened while still favoring the guanidinium form. Phenyl-substituted guanidines 20 and 21 (R'''=Ph, FIG. 6A) are being synthesized[66A] to examine this effect.[67A]

4.2. Incorporating a proton shuffle into the ATAR. Some preliminary experiments suggest incorporating a tertiary methylamine into the tether ortho to the phenol may help facilitate the ATAR reactivity. Having an estimated pKa of 9.8,[8A] this will act as a proton shuttle to assist quinone methide formation through deprotonation for 1,6-elimination, the conjugate acid will help to activate the quinone methide through reprotonation, and it will assist in the lactonization reaction by deprotonation of the phenol. This will have little competition with guanidine protonation, so is expected to show no deleterious effects. Analysis of this design feature will be investigated in model systems incorporating this modification. These will be synthesized using methods shown in the total syntheses below. If this modification proves unnecessary, the total syntheses below will be simplified, but will be shown with the amine to exemplify the more challenging approach.

4.3. Syntheses of functionalized ATAR model systems. Much of the chemistry for synthesizing ATAR derivatives is being developed through the various model system studies. Three different fully functionalized DNA-synthesizer machine-ready ATAR derivatives may be synthesized. The three systems are shown below based on the position of the guanidinium group. Note that each system has at least one tautomer where phosphate addition will be more favored. The flexible, non-static nature of these non-covalent interactions should be realized.[68A] (FIG. 7A)

(A) An ATAR derivative with the guanidine at the exocyclic methylene of the quinone methide. DNA synthesizer machine-ready derivative 25 will be prepared in ten steps from octopamine (22,FIG. S6A). Most of the key steps have already proven effective in model studies. The synthesis involves a Rathke guanylation,[66A] and ortho-bromination[69A] followed by iodination[70A] to make 23 for the Stille allylation selectively with the more reactive aryliodide.[71A] This will be converted to the amine through ozonolysis[72A] and reductive amination.[73A] The Heck reaction with acrylic acid will afford 24.[74A] The diimide reduction[75A] for reducing the alkene has already been accomplished in a model study without affecting the nitrobenzyl group.

(B) An ATAR derivative with a meta-benzylic guanidine substituent. A machineready derivative having the guanidine at the meta-benzylic position will be synthesized using a more convergent approach with a Diels-Alder reaction as the key step. A highly functionalized Danishefsky-type diene[76A] will be synthesized in four steps from the dianion of acetoacetic amide 26 (FIG. S7A)[77A] Dianion akylation[78A] will afford 27 which will be reduced to the aldehyde[79A] and converted to diene 28 by the standard approach.[80A]

There is good precedent for the success of the cycloaddition of diene 28 with allene 29 to produce phenol 30 (FIG. S8A).[81A] Phenol 30 will be converted to machine-ready derivative 35 in 11 steps. Resonance effect allows for the selective hydrolysis of the benzylic methyl ester of 30.[82A] A tandem Curtius rearrangement-Rathke reaction with in situ trapping of the amine as the protected guanidine[66] will be examined.[83A] The B-trimethylsilylethanesulfonyl (SES) protected guanidine[84A] will be stable throughout the synthesis, but cleaved with fluoride ion after solid-phase synthesis without hydrolyzing the carbonate (MDNB) group on the phenol. The final conversion of the methyltrimethylsulfide to the carboxylic acid will be accomplished as in Schreiber's total synthesis of cyclotheonamide B with related functionality in the molecule.[85A]

(C) An ATAR derivative with a meta-guanidine substituent. If validated in model studies, a machine-ready derivative having the guanidine directly on the benzene ring will be prepared by one of two approaches. (1) A simple modification of the above approach using methyl acetylenedicarboxylate as the dienophile.[80A] (2) A directed ortho-lithiation starting from 4-aminosalicylic acid taking advantage of a MEM[86A] and Boc[87A] protecting group to assure regioselectivity.[88A]

4.4. Nucleotide alkylation studies. Prior to attaching the phosphodiester alkylating reagents to oligonucleotides for site-selective delivery, reactions will be run using the appropriate derivative synthesized above[89A] with dinucleotides for complete product characterization and reaction optimization.[48A,90A] Dodecanucleotides will then be examined for peralkylation. The presence of the guanidinium groups in the alkylated polymer should maintain the water solubility of the trialkylphosphate product.[91A] The reversal of charge will reverse the polarity necessary for PAGE analysis or slow the migration of partially alkylated oligonucleotides.[36A] Assessing the degree of alkylation of the whole oligonucleotides can be determined qualitatively by gel migration analyses using PAGE on the 5'-$^{32}$p labeled oligos.[92A,93A,94A] Initial digestion of the oligonucleotides from the alkylation reaction with snake venom phosphodiesterase and/or calf intestine alkaline phosphatase will result in cleavage of the oligonucleotides only at unmodified phosphodiester linkages, as phosphotriester linkages are known to be stable to degradation.[16A] HPLC analysis of the resulting products for the degree of alkylation will assess if there was any regioselectivity.[95A] The degree of alkylation will be further analyzed by high resolution mass spectrometry (MALDITOF). NMR analysis will be attempted to determine chemo- and possibly diastereo-selectivity's and for assessing the structural characteristics of the products.[96A] Crystallization of the products for x-ray diffraction analysis may succeed with the guanidinium group incorporated.

4.5. Oligonucleotide attachment. The delivery oligonucleotide of desired sequence will be synthesized on an automated DNA synthesizer according to standard protocol.[97A] Modifying oligonucleotides with any desired linker is common practice.[17A] A $C_{12}$ chain length phosphoramidite will be synthesized[98A] and attached to the oligonucleotide.[96A,99A] A standard esterification reaction will attach the ATAR derivative as synthesized above to the linker-OH on the solid support.[100A] Mild alkaline hydrolysis of the TFA-protected amine[101A] will allow the attachment of the desired reporter group, drug agent, or protein conjugate. Some examples of reporter groups for initial studies of oligonucleotide modification using this ATAR include: fluorescein-5-isotholocyanate,[102A] the EDTA.Fe(II) moiety,[103A] and tris (2,2'-bipyridine)ruthenium (II) $(Ru(bpy)_{32}$.[104A] Complete protecting group removal and cleavage from the solid-support[105A] will afford a functional ATAR.[106A] Drugs[6A,10A] and derivatized proteins[7A,11A] will be attached similarly. The resulting ATAR derivatives will be purified by HPLC. The derivatized oligonucleotides will be characterized by enzymatic digestion and HJPLC analysis against coinjections of standard solutions of the nucleoside components and a reagent standard with the attached linker. An exact mass will also be obtained. ATAR attachment will be confirmed by UV analysis.[107A]

Affinity cleavage experiments canbe conducted with the EDTA.Fe(II) group attached to the ATAR for analysis of labeling both single- and double-strand target DNA according to established methods.[34,108A] Analysis of the diffusible cleavage pattern on the DNA to which the ATAR has been delivered will allow assessment of the structural characteristics of the ATAR-DNA interactions.

4.6. Future studies. The ability to modify nucleosomal DNA will allow various crosslinking and autocleavage investigations to be conducted for enhancing our understanding of DNA-protein interactions in the chromatin.[4A] Transcriptional regulation will be studied by using the ATAR to attach transcriptional regulator GCN5p[7A] and other transcriptional activators to selected sites on DNA.[7A] It will also be of interest to study how drugs known to bind to, and react with DNA will be affected by their covalent attachment through the ATAR.[109A]

(1A) For a complete resource covering many aspects of the human genome see the Genome Database (GDB) hosted at Johns Hopkins University (http://gdbwww.gdb.orgf): Fasman, K. H.; Letovsky, S. I.; Li, P.; Cottingham, R. W.; Kingsbury, D. T. "The GDB Human Genome Database Anno 1997," *Nucleic Acids Res.* 1997, 25, 72–80.

(2A) (a) Leonetti, J. P.; Degols, G.; Clarenc, J. P.; Mechti, N.; Lebleu, B. "Cell Delivery and Mechanism of Action of Antisense Oligonucleotides," *Prog. Nucleic Acids Res. McI. Biol.* 1993, 44, 143–66. (b) Zon, G. "Brief Overview of Control of Genetic Expression by Antisense Oligonucleotides and In Vivo Applications," *Molec. Neurobiol.* 1995, 10, 219–29.

(3A) (a) Thuong, N. G.; Héléne, C. "Sequence-Specific Recognition and Modification of Double-Helical DNA Oligonucleotides," *Angew. Chem. Int. Ed. Engl.* 1993, 32,666–90. (b) Dervan, P. R. "Reagents for the Site-Specific Cleavage of Megabase DNA," *Nature* 1992, 359, 87. (c) Dervan, P. R. "Design of Sequence Specific DNA Binding Molecules," *Science* 1986, 232, 464.

(4A) A system such as being proposed will be particularly valuable for providing information at the molecular level in multi-protein complexes interacting with nucleic acids. These would include the complex protein-nucleic acid interactions of the chromatin involved in chromosome condensation-decondensation, DNA replication, transcription, transcription regulation and DNA repair. Molecular level details in such complex systems are difficult to achieve by existing biochemical techniques and advances in molecular biology require innovative approaches to begin to develop a more thorough molecular level understanding of the chromosomal protein machinery. For example, the presumed role of histone H1 in transcriptional repression might be studied by site-specifically modifying a target DNA binding sequence with crosslinking and redox activated cleaving functionality for mapping DNA-histone H1 interactions: (a) Paranjape,S. M.; Kamakaka, R. T.; Kadonaga, J. T. "Role of Chromatin Structure in the Regulation of Transcription by RNA Polymerase II," *Annu. Rev. Biochem.* 1994, 63,265–97. (b) Felsenfeld, G. "Chromatinas an Essential Part of the Transcriptlonal Mechanism," *Nature* 1992, 355, 219–24. (c) Halmer, L.; Gruss, C. "Influence of Histone H1 on the in vitro Replication of DNA and Chromatin," *Nucleic Acids Res.* 1995, 23, 773–78.

(5A) The ability to label a hybridization-recognized sequence of DNA should afford an efficient approach to genetic diagnostics from blood samples. The chemistry being developed will allow the efficient synthesis of multiply-labeled oligonucleotides which can he used for genetic diagnostics by methods such as fluorescence in-situ hybridization (FISH). (a) Brenner, M.; Dunlay, T. "Fluorescence In vitro Hybridization. Hardware and Software Implications in the Research Laboratory," *Amer. Laboratory* 1995, 55–58. (b) For lanthanide-labeled DNA probes, see: Lövgren, T.; Hurskainen, P.; Dahlén, P. in *Nonisotopic DNA Probe Techniques,* Kricka, L. J., Ed.; Academic Press, Inc.: San Diego; 1992, pp. 227–274.

(6A) A particularly appealing application would be in the area of site-specific drug delivery to genetic targets. The non-specific deliterious effects of chemotherapy on healthy cells could be alleviated using such a system to covalently deliver an antitumor antibiotic directly to a target DNA sequence.

(7A) Innovative experiments which could be attempted with such a system include modifying nucleosomal DNA with transcriptional regulator GCN5p. This transcriptional regulator functions as a complex with two other proteins (ADA2p and ADA3p). It has recently been found to be a histone acetyltransferase. Histone hyperacetylation is thought to facilitate transcription by chromatin disruption, but it is not clear whether the histone hyperacetylation is a result of chromatin disruption during the transcription process, or an initiator. This regulatory complex with GCN5p is recruited to a specific gene through interactions with other DNA binding transcripttion factors. A system such as being proposed would allow site-specific delivery of this regulatory protein to a particular chromatin site. This could then recruit the regulatory complex and other transcription factors and thereby initiate transcription of a selective gene. Obviously, such an approach could be used to regulate many cellular functions through selective control of genetic transcription. For leading references see: (a) Wolfe, A. P.; Pruss, D. "Targeting Chromatin Disruption: Transcription Regulators that Acetylate Histones," *Cell* 1996, 84, 817–19. (b) Ptashne, M.; Gann, A. "Transcriptional activation by recruitment," *Nature* 1997, 386, 569–77.

(8A) Although only a very crude measure, estimated $pK_a$ values calculated from the effects of various related substituted derivatives suggest that the proton shuttle processes proposed should occur as drawn in scheme 1. The relevant $pK_a$ values ($H_2O$, 25° C.) include: 2,4,6-trimethylphenol (10.88), 3-aminophenol (9.83), m-cresol (10.00), phenol (9.99), $Et_2MeN$ (10.4), phenethylamine (9.83), ethylamine (10.63), guanidine (14.38), methylguanidine (14.1), phenylguanidine (10.77). From these values, $pK_a$ estimates in the ATAR may be approximated assuming additivity of substituent effects. The approximated $pK_a$ would be: 10.7 for the phenoxide with a 3-amino group on the ring (the effect of a 3-amino on the $pK_a$ of phenol is $\Delta pK_a=-0.16$; thus approximating from the $pK_a$ of 2,4,6-trimethylphenol=10.88–0.16=10.7, other values are determined in a similar way), 10.9 for the phenoxide with the 3-benzylic-amino group, 9.8 for the tertiary amine, 10.8 for the guanidine directly substituted on the arene ring, 10.5 for the benzylic guanidine with a phenyl substituent. The $pK_a$ values are from *Lange's Handbook of Chemistry,* Dean, J. A, Ed.; McGraw-Hill: N.Y. 1992, 14th edition.

(9A) Reporter groups would include fluorescent probes (For example, see: Haugland, R. P. Molecular Probes: *Handbook of Fluorescent Probes and Research Chemicals,* Larison, K. D., Ed.; 1995–1997, 6th Edition, Molecular Probes, Inc., Eugene, Oreg.), probes used for recognition of a specific species such as biotin/avidin and antibodies, luminescent probes, probes which are chemically or redox reactive, radionuclear probes, and magnetic moieties ((a) Wilbur, D. S. "Radiohalogenation of Proteins: An Overview of Radionuclides, Labeling Methods, and Reagents for Conjugate Labeling," *Bioconjugate Chem.* 1992, 3, 433–471. (b) Peters, K.; Richards, F. M. "Chemical Crosslinking: Reagents and Problems in Studies of Membrane Structure," *Ann. Rev. Biochem.* 1977, 46, 523–51. (c) Ji, T. H. "The Application of Chemical Crosslinking for Studies on Cell Membranes and the Identification of Surface Reporters," *Biochim. Biophys. Acta* 1979, 559, 39–69.).

(10A) For examples of drugs which could be readily attached, see a listing of anticancer agents along with associated references in: Calbiochem Biochemical and Immunochemical 1996/97 Catalog, p. 539, San Diego, Calif.

(11A) For an example of protein conjugation to an oligonucleotide for directing nuclease activity, see: Pei, D.; Corey, D. R.; Schultz, P. G. "Site-specific Cleavage of Duplex DNA by a Semi-synthetic Nuclease via Triple-helix Formation," *Proc. Nat. Acad. Sci. USA* 1990, 87, 9858.

(12A) For conventional synthesis of phosphate modified oligonucleotides, see: (a) Hayakawa, Y.; Hirose, M.; Hayakawa, M.; Noyori, R. "General Synthesis and Binding Affinity of Position-Selective Phosphonodiester- and Phosphotriester-Incorporated Oligodeoxyribonucleotides," *J. Org. Chem.* 1995, 69, 925–30. (b) Hayakawa, Y.; Wakabayashi, S.; Kato, H.; Noyori, R. "The Allylic Protection Method in Solid-Phase Oligonucleotide Synthesis. An Efficient Preparation of Solid-Anchored DNA Oligomers," *J. Am. Chem. Soc.* 1990, 112, 1691–96. (c) Kujipers, W. H. A.; Huskens, J.; Koole, L. H.; van Boeckel, C. A. A. "Synthesis of Well-Defined Phosphate-Methylated DNA Fragments: the Application of Potassium Carbonate in Methanol as Deprotecting Reagent," *Nucleic Acids Res.* 1990, 18, 5197–205. (d) Alul, R. H.; Singman, C. N.; Zhang, G.; Letsinger, R. L. "Oxalyl-CPG: A Labile Support for the Synthesis of Sensitive Oligonucleotide Derivatives," *Nucleic Acids Res.* 1991, 19, 1527–32. (e) Froehler, B. C. "Deoxynucleoside H-Phosphonate Diester Intermnediates in the Synthesis of Internucleotide Phosphate Analogues," *Tetrahedron Left.* 1986, 27, 557–78.

(13A) For additional synthesis reviews see: (a) Beaucage, S. L.; Iyer, R. P. "Advances in the Synthesis of Oligonucleotides by the Phosphoramidite Approach," *Tetrahedron* 1992, 48, 2223–2311. (1,) Hobbs, J. B. "Nucleotides and Nucleic Acids," *Organophosphorus Chemistry* 1990, 21, 201–321. (c) Sonveaux, E. "The Organic Chemistry Underlying DNA Synthesis," *Bioorg. Chem.* 1986, 14, 274–325.

(14A) Studies using phosphate triester modified oligos for duplex structure studies with RNA and DNA: (a) Letsinger, R. L.; Bach, S. A.; Eadie, J. S. "Effects of Pendant Groups at Phosphorus on Binding Properties of d-ApA Analogues," *Nucleic Acids Res.* 1986, 14,3487–99. (b) Summers, M. F.; Powell, C.; Egan, W.; Byrd, R. A.; Wilson, W. D.; Zon, G. "Alkyl Phosphotriester Modified Oligodeoxyribonucleotides. VI. NMR and UV Spectroscopic Studies of Ethyl Phosphotriester (Et) Modified Rp-Rp and Sp-Sp Duplexes, {d[GGAA(Et)TTCC]}$_2$," *Nucleic Acids Res.* 1986, 14, 7421–37. (c) Pramanik, P.; Kan, L. "NMR Study of the Effect of Sugar-phosphate Backbone Ethylation on the Stability and Conformation of DNA Double Helix," *Biochemistry* 1987, 26, 3807–12. (d) Koole, L. H.; van Genderen, M H Buck, H. M. "A Parallel Right-Handed Duplex of the Hexamer d(TpTpTpTpTpT) with Phosphate Triester Linkages," *J. Am. Chem. Soc.* 1987, 109, 3916–21 *[The synthetic chemistry and hybridization data reported in this 1987 paper differed from that described later and subsequently retracted by Buck, H. M.; Moody, H. M.; Quaedflieg, P. J. L. M.; Koole, L. H.; van Genderen, M. H. P.; Smit, L. Jurriaans, S. Geelen, J. L. M. C.; Goudsmit, J. "Inhibition of HIV-1 Infectivity by Phosphate-Methylated DNA: Retraction," *Science* 1990, 250, 125–26 (also see: Maddox, J. "Dutch Cure for AIDS is Discredited," *Nature* 1990, 347, 411).]. (e) Quaedflieg, P. J. L. M.; Koole, L. H.; van Genderen, M. H. P.; Buck, H. M. "A structural Study of Phosphate-methylated d(CpG)$_n$ and d(GpC)$_n$ DNA oligomers. Implications of Phosphate Shielding for the Isomerization of B-DNA into Z-DNA," *Recl. Trav. Chim. Pay-Bas* 1989, 108, 421–23. (f) Quaedflieg, P. J. L. M.; Broeders, N. L. H. L.; Koole, L. H.; van Genderen, M. H. P.; Buck, H. M. "Conformation of the Phosphate-methylated DNA Dinucleotides d(Cp,C) and d(TpC). Formation of a Parallel Miniduplex Exclusively for the S-Configuration at Phosphorus," *J. Org. Chem.* 1990, 55, 122–27. (g) Quaedflieg, P. J. L.; van der Heiden, A. P.; Koole, L. H.; Coenen, A. J. J. M.; van der Wal, S.; Meijer, E. M. "Synthesis and Conformational Analysis of Phosphate-methylated RNA Dinucleotides," *J. Org. Chem.* 1991, 56, 5846–59.

(15A) Using modified triester phosphate oligos as probes for elucidating specific interactions with proteins: (a) Weinfeld, M.; Drake, A. F.; Saunders, J. K.; Paterson, M. C. "Stereospecific Removal of Methyl Phosphotriesters from DNA by an *Escherichia coli* ada$^+$Extract," *Nucleic Acids Res.* 1985, 13, 7067–77. (b) Gallo, K. A.; Shao, K; Phillips, L. R.; Regan, J. B.; Kozielkiewicz, M.; Uznanski, B.; Stec, W. J.; Zon, G. "Alkyl Phosphotriester Modified Oligodeoxyribonucleotides. V. Synthesis and Absolute Configuration of Rp and Sp, Diastereomers of an Ethyl Phosphotriester (Et) Modified EcoRI Recognition Sequence, d[GGAA(Et)TTCC]. A Synthetic Approach to Regio and Stereospecific Ethylation-interference Studies," *Nucleic Acids Res.* 1986, 14, 7405–20. (c) Kbziolkiewicz, M.; Stec, W. J. "Application of Phosphate-backbone-modified Oligonucleotides in the Studies on EcoRI Endonuclease Mechanism of Action," *Biochemistry* 1992, 31, 9460–66.

(16A) (a) Miller, P. S.; Fang, K. N.; Kondo, N. S.; Ts'O, P.O P. "Synthesis and Properties of Adenine and Thymidine Nucleoside Alkyl Phosphotriesters, the Neutral Analogs of Dinucleoside Monophosphates," *J. Am. Chem. Soc.* 1971, 93, 6657–65. (b) Milrer, P. S.; Barrett, J. C.; Ts'O, P.O.P. "Synthesis of Oligodeoxyribo-nucleotide Ethyl Phosphotriesters and Their Specific Complex Formation with Transfer Ribonucleic Acid," *Biochemistry* 1974, 13, 4887–96 (and the following paper in that journal as well). (c) Pless, R. C.; Ts'O, P.O.P. "Duplex Formation of a Nonionic Oligo(deoxythymidylate) Analogue [Heptadeoxythymidylyl-(3'-5')-deoxythymidine Hepta-ethyl Ester (d-[Tp(Et)]$_7$T)] with Poly(deoxyadenylate. Evaluation of the Electrostatic Interaction," *Biochemistry* 1977, 16, 1239–50. (d) Miller, P. S.; Braiterman, L. T.; Ts'O, P.O.P. "Effects of a Trinucleotide Ethyl Phosphotriester, G'''p(Et)G'''(Et)U, on Mammalian Cells in Culture," *Biochemistty* 1977, 16, 1988–96. (e) Petrenko, V. A.; Pozdnyakov, P. I.; Kipriyanov,S. M.; Boldyrev, A. N.; Semyonova, L. N.; Sivolobova, G. F. "Site-localized Mutagenesis Directed by Phosphotriester Analogs of Oligonucleotides," *Bioorg. Khim.* 1986, 12, 1088–1100. (f) Asseline, U.; Barbier, C.; Thuong, N. T. "Oligothymidylates Comportant La Structure Alternee AIkylphosphotriester-phosphodiester et Lies de Facon Covalente a un Agent Intercalant," *Phosphorus Sulfur* 1986, 26, 63–73. (g) Marcus-Sekura, C. J.; Woerner, A. M.; Shinozuka, K.; Zon, G.; Quinnan, Jr., G. V. "Comparative Inhibition of Cloramphenicol Acyltransferase Gene Expression by Antisense Oligonucleotide Analogs Having Alkyl Phosphotriester, Methylphosphonate and Phosphorothioate Linkages," *Nucleic Acids Res.* 1987, 15, 5749–63. (h) see ref. 6a. (i) Koole, L. H.; van Genderen, MIH.P.; Reiniers, R. G.; Buck, H. M. "Enhanced Stability of a Watson and Crick DNA Duplex Structure by Methylation of the Phosphate Groups in One Strand," *Proc. K. Ned. Akad. Wet. B* 1987, 90, 41–6.* (j) Petrenko, V. A.; Kipriyanov, S. M.; Boldyrev, A. N.; Pozdnyakov, P. I. "Mutagenesis Directed by Phosphotriester Analogues of Oligonucleotides: a Way to Site-specific Mutagenesis In Vivo," *FEBS Lett.* 1988, 23,109–12. (k) Durand, Maunizot, J. C.; Asseline, U.; Barbier, C.; Thuong, N. T.; Héléne, C. "Oligothymidylates Covalently Linked to an Acridine Derivative and with Modified Phosphodiester Backbone: Circular Dichroism Studies of Their Interactions with Complementary Sequences," *Nucleic Acids Res.* 1989, 17, 1823–36.

(17A) For recent reviews see: (a) Zon, G. "Brief Overview of Control of Genetic Expression by Antisense Oligonucleotides and In Vivo Applications," *Mol. Neurobiology* 1995, 10, 219–29. (b) Kiely, T. S. "Recent Advances in Antisense Technology," *Ann. Rep. Med. Chem.* 1994, 29,297–306. (c) Stein, C. A.; Cheng, Y.-C. "Antisense Oligonucleotides as Therapeutic Agents-Is the Bullet Really Magic," *Science* 1993, 261, 1004–11. (d) Varma, R. S. "Synthesis of Oligonucleotide Analogues with Modified Backbones," *SYNLETT* 1993, 621–37. (e) Beaucage, S. L.; Iyer, R. P. "The Functionalization of Oligonucleotides Via Phosphoramidite Derivatives," *Tetrahedron* 1993, 49, 1925–63. (f) Toulmé, J. J. in *Antisense RNA and DNA;* Murray, J. A. H., Ed.; Wiley, Inc.: New York, 1992, pp 175–94. (g) Englisch, U.; Gauss, D. H. "Chemically Modified Oligonucleotides as Probes and Inhibitors," *Angew. Chem. Int. Ed. Engl.* 1991, 30, 613–722. (h) Uhlmann, E.; Peyman, A. "Antisense Oligonucleotides: A New Therapeutic Principle," *Chem. Rev.* 1990, 90, 543–84. (i) Goodchild, J. "Conjugates of Oligonucleotides and Modified Oligonucleotides: A Review of Their Synthesis and Properties," *Bioconjugate Chem.* 1990, 1, 165–87. (j) Héléne, C.; Toulmé, J.-J. "Specific Regulation of Gene Expression by Antisense, Sense, and Antigene Nucleic Acids," *Biochim. Biophys. Acta* 1990, 1049, 99–125. (k) Goodchild, J. "Inhibition of Gene Expression by Oligonucleotides," in *Oligonucleotides: Antisense Inhibitors of Gene Expression;* Cohen, 1.5., Ed.; McMillan Press: London, 1989, pp. 53–771 (l) Zon, G. "Oligonucleotide Analogues as Potential Chemotherapeutic Agents," *Pharm. Res.* 1988, 5, 539–49. (m) Stein, C. A.; Cohen, J. S. "Oligonucleotides as Inhibitors of Gene Expression: a Review," *Cancer Res.* 1988, 48, 2659–68. (n) Miller, P. S.; Ts'O, P.O.P. "Oligonucleotide Inhibitors of Gene Expression in Living Cells: New Opportunities in Drug Design," *Annu. Rep. Med. Chem.* 1988, 23, 295–304. (o) Miller, P. S.; Agris, C. H.; Blake, K. R.; Murakami, A.; Spitz, S. A.; Reddy, M. P.; Ts'O, P.O.P. "Nonionic Oligonucleotide Analogs as New Tools for Studies on the Structure and Function of Nucleic Acids in Living Cells," in *Nucleic Acids: The Vectors of Life;* Pullman, B.; Jortner, J., Eds.; D. Reidel Publishing Co.: Dordrecht, Netherlands; 1983, pp. 521–35.

(18A) A review has proposed the use of the acronym SNAIGE (Synthetic or Small Nucleic Acid Interfering with Gene Expression) as a term for describing the various approaches to genetic regulation with oligonucleotides; Leonetti, J. P.; Degols, G.; Clarenc, J. P.; Mechti, N.; Lebleu, B. "Cell Delivery and Mechanism of Action of Antisense Oligonucleotides," *Prog. Nucl. Acid Res.* 1993, 44, 143–66.

(19A) Zhou, Q.; Turnbull, K. D. "Phosphotriesters from Tandem Phosphodiester Alkylation with Quinone Methides Followed by Lactonization," manuscript near completion for submission to: *J. Am. Chem. Soc.* 1997, 119.

(20A) Reliable Biopharmaceuticals (St. Louis, Mo.), a supplier of oligonucleotide derivatives for antisense and antigene applications, has expressed interest in this work. We are conducting preliminary experiments to determine the potential for collaborative development of synthetic methodology for oligonucleotide modification.

21A) Sigman, D. S.; Mazumder, A.; Pemn, D. M. "Chemical Nucleases," *Chem. Rev.* 1993, 93, 2295–316.

(22A) More recent examples include: (a) Jubian, V.; Dixon, R. P.; Hamilton, A. D. "Molecular Recognition and Catalysis. Acceleration of Phosphodiester Cleavage by a Simple Hydrogen-Bonding Receptor," *J. Am. Chem. Soc.* 1992, 114, 1120–21. (b) Browne, K. A.; Bruice, T. C. "Chemistry of Phosphodiesters, DNA and Models. 2. The Hydrolysis of Bis(8-hydroxyquinoline) Phosphate in the Absence and Presence of Metal Ions," *J. Amer. Chem. Soc.* 1992, 114, 4951–58. (c) Smith, J.; Ariga, K.; Anslyn, E. V. "Enhanced Imidazole-Catalyzed RNA Cleavage Induced by aBis-Alkylguanidinium Receptor," *J. Am. Chem. Soc.* 1993, 115,362–64. (d) Takasaki, B. K.; Chin, J. "Synergistic Effect Between La(III) and Hydrogen Peroxide in Phosphate Diester Cleavage," *J. Am. Chem. Soc.* 1993, 115, 99337–38. (e) Hall, J. Husken, D.; Pieles, U.; Moser, H. E.; Haner, R. *Chemistry & Biology* 1994, 1, 185–90. (f) Bashkin, J. K.; Frolova, E. I.; Sampath, U. "Sequence-Specific Cleavage of HIV mRNA by a Ribozyme Mimic," *J. Am. Chem. Soc.* 1994, 116, 5981–82. (g)Magda, D.; Miller, R. A.; Sessler, J. L.; Iverson, B. L. "Site-Specific Hydrolysis of RNA by Europium(III) Texaphyrin Conjugated to a Synthetic Oligodeoxyribonucleotide," *J. Am. Chem. Soc.* 1994, 116, 7439–40. (h) Linkletter, B.; Chin, I. "Rapid Hydrolysis of RNA with a $Cu^{II}$ Complex," *Angew. Chem. Int. Ed. Engl.* 1995, 34, 472–74.

(23A) (a) Wilbur, D. S. "Radiohalogenation of Proteins: An Overview of Radionuclides, Labeling Methods, and Reagents for Conjugate Labeling," *Bioconjugate Chem.* 1992, 3, 433–471. (b) Peters, K., Richardg, F. M. "Chemical Crogg-linking: Reagents and Problems in Studies of Membrane Structure," *Ann. Rev. Biochem.* 1977, 46, 523–51. (c) Ji, T. H. "The Application of Chemical Crosslinking for Studies on Cell Membranes and the Identification of Surface Reporters," *Biochim. Biophys. Acta* 1979, 559, 39–69.

(24 A) Zhang, Y.; Chen, F.-X.; Mehta, P.; Gold, B. "Groove- and Sequence-Selective Alkylation of DNA by Sulfonate Esters Tethered to Lexitropsins," *Biochemistry* 1993, 32, 7954–65.

(25A) For reviews on quinone methides, see: (a) Volod'kin, A. A.; Ershov, V. V. *Russian Chem. Rev.* 1988, 57,336. (b) Gruenanger, P. in *Houben-Weyl Methoden der Organischen Chemie* (Vol. VII/3b) Mueller, E.; Bayer, O., Eds.; G. Thieme Verlag: Stuttgart, 1979, pp. 195–521. (c) Wagner, H.-U.; Gompper, R. in *The Chemistry of Quinonoid Compounds* (Vol. 1) Patai, S., Ed.; John Wiley & Sons: New York, 1974, pp. 1145–1178. (d) Turner, A. B. *Quart. Rev.* 1965, 18, 347.

(26A) More recent, elegant examples for biomolecule alkylation include: (a) Chatterjee, M.; Rokita, S. E. "The Role of a Quinone Methide in the Sequence Specific Alkylation of DNA," *J. Am. Chem. Soc.* 1994, 116, 1690–97. (b) Li, T.; Zeng, Q.; Rokita, S. E. "Target-Promoted Alkylation of DNA," *Bioconjugate Chem.* 1994, 5, 497–500. (c) Meyers, J. K.; Cohen, J. D.; Widlanski, T. S. "Substituent Effects on the Mechanism-Based Inactivation of Prostatic Acid Phosphatase," *J. Am. Chem. Soc.* 1995, 117, 11049–54. (d) Myers, J. K.; Widlanski, T. S. "Mechanism-Based Inactivation of Prostatic Acid Phosphatase," *Science* 1993, 262, 1451–53. (e) Wang, Q.; Dechert, U.; Jirik, F.; Withers, S. G. "Suicide Inactivation of Human Prostatic Acid Phosphatase and a Phosphotyrosine Phosphatase," *Biochem. Biophys. Res. Commun.* 1994, 200, 577–83.

(27A) For reviews see: (a) Sega, G. A. "A Review of the Genetic Effects of Ethyl Metianesulfonate," *Mutation Res.* 1984, 134, 113–42. (b) Hoffmann, G. R. "Genetic Effects of Dimethyl Sulfate, Diethyl Sulfate, and Related Compounds," *Mutation Res.* 1980, 75, 63–129. (c) Digenis, G. A.; Issidorides, C. H. "Some Biochemical Aspects of N-Nitroso Compounds," *Bioorganic Chem.* 1979, 8, 91–137.

(28A) (a) Swenson, D. H.; Lawley, P. D. "Alkylation of Deoxyribonucleic Acid by Carcinogens Dimethylsulfate, Ethyl Methanesulfonate, N-Ethyl-N-nirosourea and N-Methyl-N-nitrosourea," *Biochem. J.* 1978, 171, 575–87. (a) Jensen, D. E.; Reed, D. J. "Reaction of DNA with Alkylating Agents. Quantitation of Alkylation by Ethylnitrosourea of Oxygen and Nitrogen Sites on Poly [dA-dT] Including Phosphotriester Formation," *Biochemistry* 1978, 17, 5098–107. (c) Sun, L.; Singer, B. "The Specificity of Different Classes of Ethylating Agents Towards Various Sites of HeLa DNA in vitro and in vivo," *Biochemistry* 1975, 14, 1795–1802.

(29A) Angle, S. R.; Arnaiz, D. O.; Boyce, l. P.; Frutos, R. P.; Louie, M. S.; Mattson-Arnaiz, H. L.; Rainier, J. D.; Turnbull, K. D.; Yang, W. "Formation of Carbon-Carbon Bonds via Quinone Methide-Initiated Cyclization Reactions," *J. Org. Chem.* 1994, 59, 6322–6337.

(30A) *Organic Synthesis,* Smith, M. B.; McGraw-Hill, Inc.: New York; 1994, pp. 108–119.

(31A) Schulz, W. G.; Nieman, R. A.; Skibo, E. B. "Evidence for DNA Phosphate Backbone Alkylation and Cleavage by Pyrrolo[1,2-a]benzimidazoles: Small Molecules Capable of Causing Base-Pair-Specific Phosphodiester Bond Hydrolysis," *Proc. Natl. Acad. Sci. USA* 1995, 92, 11854–58.

(32A) (a) Tomasz, M.; Lipman, R. "Alkylation Reactions of Mitomycin C at Acid pH," *J. Am. Chem. Soc.* 1979, 101, 6063–67. (b) Iyengar, B. S.; Dorr, T. R.; Remers, W. A.; Kowal, C. D. "Nucleotide Derivatives of 2,7-Diaminomitosene," *J. Med. Chem.* 1986, 31, 1579–85.

(33A) Gohil, R. N.; Roth, A. C.; Day, R. A. "Reversible Covalent Modification of DNA," *Arch. Biochem. Biophys.* 1974, 165, 297–312.

(34A) Bhat, G.; Roth, A. C.; Day, R. A. "Extrinsic Cotton Effect and Helix-Coil Transition in a DNA-Polycation Complex," *Biopolymers* 1977, 16, 1713–24.

(35A) For a thorough review, see: Hannon, C. L.; Anslyn, E. V. "The Guanidinium Group: Its Biological Role and Synthetic Analogs," *Bioorg. Chem. Frontiers* 1993, 3, 193–255.

(36A) For additional examples, see: (a) Blaskó, A.; Dempcy, R. O.; Minyat, E. E.; Bruice, T. C. "Association of Short-Strand DNA Oligomers with Guanidinium-Linked Nucleosides. A Kinetic and Thermodynamic Study," *J. Am. Chem. Soc.* 1996, 118, 7892–99. (b) Dempcy, R. O.; Browne, K. A.; Bruice, T. C. "Synthesis of the Polycation Thymidyl DNG, Its Fidelity in Binding Polyanionic DNA/RNA, and the Stability and Nature of the Hybrid Complexes," *J. Am. Chem. Soc.* 1993, 117, 6140. (c) Hashimoto, H.; Nelson, M. G.; Switzer, C. "Formation of Chirneric Duplexes Between Zwitterionic and Natural DNA," *J. Org. Chem.* 1993, 58, 4194–95. (d) Hashimoto, H.; Nelson, M. G.; Switzer, C. "Zwitterionic DNA," *J. Am. Chem. Soc.* 1993, 115, 7128–34. (e) Letsinger, R. L.; Sinan, C. N.; Histand, G.; Salunkhe, M. "Cationic Oligonucleotides," *J. Am. Chem. Soc.* 1988, 155, 7128. (f) Furberg, S.; Solbakk, J. "On the Stereochemistry of the Interaction Between Nucleic Acids and Basic Protein Side Chains," *Acta Chem. Scand. B* 1974, 28,481–83.

(37A) Saenger, W. *Principles of Nucleic Acid Structure,* Springer-Verlag: New York, 1984, pp. 385–431.

(38A) Pullman, B. "Molecular Mechanisms of Specificity in DNA-Antitumor Drug Interactions," in *Advances in Drug Research,* Testa, B., Ed.; Academic Press: London; Vol. 18, 1989, pp. 1–113.

(39A) (a) Zhou, Q.; Turnbull, K. D. "Equilibrium Control in Phosphodiester Alkylation with Quinone Methides," manuscript in preparation for submission to: *J. Org. Chem.* 1997, 62. (b) Dyer, R. G.; Turnbull, K. D. "Photolytic-Initiated Formation of Quinone Methides for Phosphodiester Alkylation," manuscript in preparation.

(40A) Patent File number ARK0O7/97386 for "B iomolecular Labeling" (Apr. 11, 1997).

(41A) Dyall, L. K.; Winstein, S. "Nuclear Magnetic Resonance Spectra and Characterization of Some Quinone Methides," *J. Am. Chem. Soc.* 1972, 94, 2196–99.

(42A) Product identity was readily apparent from the distinct 3-bond phosphorus-hydrogen coupling constant of 8.2 Hz for the two different types of benzylic resonances in the $^1$H NMR spectra with an integrated ratio of 2:1. $^1$H NMR (CDCl$_3$/CD$_3$CN (1:1), 300 MHz) ∂7.30 (m, 10H, 2(C$_6$H$_5$)), 6.87 (s, 2H, C$_6$H$_2$), 4.95 (d, J=8.2 Hz, 4H, 2(CH$_2$Ph)), 4.84 (d, J=8.2 Hz, 2H, CH$_2$Ar), 2.13 (s, 6H, 2(CH$_3$).

(43A) For leading references, see: Mccracken; P. G.; Bolton, J. L.; Thatcher, G. R. J. "Covalent Modification of Proteins and Peptides by the Quinone Methide from 2-tert-Butyl-4,6-dimethylphenol: Selectivity and Reactivity with Respect to Competitive Hydration," *J. Org. Chem.* 1997, 62, 1820–25.

(44A) Acylation of 3,5-dimethyl-4-hydroxybenzaldehyde followed by NaBH$_4$ reduction and phosphorylation of the benzyl alcohol afforded 9 (FIG. 4). (a) The phosphorylation reaction was a modification of: Silverberg, J. J.; Dillon, J. L.; Vemishetti, P. "A Simple, Rapid and Efficient Protocol for the Selective Phosphorylation of Phenols with Dibenzylphosphite," *Tetrahedron Eett.* 1996, 37, 771–74. (b) A recent paper reports on the hydrolytic stability of benzyltrialkyphosphates and the effects of various substituents on the phenyl ring: Meier, C.; Habel, L. W.; Baizarim, J.; De Clercq, E. "5',5'-Di-O-nucleosyl-O'-benzylphosphotriesters as potential Prodrugs of 3'-Azido-2',3'-dideoxythymidine-5'-monophosphate," *Liebigs Ann* 1995, 2203–08

(45A) Studies of various electron-donating and electron-withdrawing substituents on the quinone methide ring and at the benzylic methylene have demonstrated their influence on quinone methide formation, reactivity and product stability: (a) Bolton, J. L.; Comeau, E.; Vukomanovic, V. "The Influence of 4-Alkyl Substituents on the Formation and Reactivity of 2-Methoxy-Quinone Methides: Evidence That Extended π-Conjugation Stabilizes the Quinone Methide Formed From Eugenol," *Chem-Biol. Interactions* 1995, 95, 279–90. (b) Thompson, D. C.; Perera, K. "Inhibition of Mitochondrial Respiration by a Para-Quinone Methide," *Biochem. Biophys. Res. Commun.* 1995, 209, 6–11. (c) Lycka, A.; Snobl, D.; Koutek, B.; Pavlickova, L.; Soucek, M. "13C NMR Study of Substituted Quinone Methides. 2- and 2,6-Substituted Fuchsones," *Coll. Czech. Chem. Commun.* 1981, 46, 1775–87. (d) Velek, J.; Koutek, B.; Musil, L.; Vasickova, S.; Soucek, M. "IR Spectra of Some Quinone Methides. A Study of the ortho-Effect," *Coll. Czech. Chem. Commun.* 1981, 46, 873–83.

(46A) (a) Turnbull, K. D. "para-Quinone Methides: Chemistry and Exploitation as Intermediates for the Intramolecular Formation of Carbon-Carbon Bonds ald Investigations into the Chemistry and Synthesis of Neolignans Via a Proposed Intermediate in Their Biosynthesis," *Ph.D. Dissertation,* University of California, Riverside, 1991. (b) Angle, S. R.; Turnbull, K. D. "Para-Quinone Methide Initiated Cyclization Reactions," *J. Am. Chem. Soc.* 1989, 111, 1136.

(47A) A Fries rearrangement on 2,4-dimethylphenol followed by benzylation of the phenol, a Baeyer-Villiger oxidation, and saponification of the intermediate acetate on workup afforded the required mono-protected catechol. A substitution reaction with bromoacetic acid provided the intermediate carboxylic acid which was converted to the desired etser derivatives through carbodiimide activation in the presence of the required alcohol. The dimethylamide derivative was produced directly from addition of bromoacetamide followed by methylation. Hydrogenolysis provided the various derivatives of 11 shown in the table of scheme 3 for oxidation to the desired quinone methides.

(48A) Reliable Biopharmaceuticals, St. Loius, Mo., has generously donated multi-milligram quantities of TpT (with and without protecting groups) and CpA (with and without protecting groups) for the purpose of these studies.

(49A) Wakselman, M. "1,4- and 1,6-Eliminations from Hydroy- and Amino substituted Benzyl Systems: Chemical and Biochemical Applications," *Nouv. J. Chim.* 1983, 7, 439–47.

(50A) (a) Kanamathareddy, S.; Gutsche, C. D. "Calixarenes: Selective Functionalization and Bridge Building," *J. Org. Chem.* 1995, 60, 6070–75. (b) Alam, I.; Sharma, S. K.; Gutsche, C. D. "The Quinonemethide Route to Mono and Tetrasubstituted Calix[4]arenes," *J. Org. Chem.* 1994, 59, 3716–20. (c) Note that even aniline has been eliminated to produce quinone methides: Angle, S. R.; Yang, W. "Synthesis and Chemistry of a Quinone Methide Model for Anthracycline Antitumor Antibiotics," *J. Am. Chem. Soc.* 1990, 112, 4524–28.

(51A) Quinone methides have been generated by laser flash photolysis (266 nm) of phenolic benzyl alcohols and the UV of the transient intermediate was presumed to be the quinone methide. These are differentiated from caged quinone methide precursors which can be irradiated at wavelengths outside 350 nm in order to be useful in the presence of biological molecules: Diao, L.; Yang, C.; Wan, P. "Quinone Methide Intermediates from the Photolysis of Hydroxybenzyl Alcohols in Aqueous Solution," *J. Am. Chem. Soc.* 1995, 117, 5369–70.

(52A) This allows transmission of >350 nm wavelength which will prevent absorbance of biological aromatics.

(53A) Fleming, S. A.; Jensen, A. W. "Substituent Effects on the Photocleavage of Benzyl-Sulfur Bonds. Observation of the 'Meta-Effect'" *J. Org. Chem.* 1996, 61, 7040–44, and references therein.

(54A) (a) Dimethoxybenzoin: Pirrung, M. C.; Shuey, S. W. "Photoremovable Protecting Groups for Phosphorylation of Chiral Alcohols. Asymmetric Synthesis of Phosphotriesters of (−)-3',5'-Dimethoxybenzoin," *J. Org. Chem.* 1994, 59, 3890–97. (b) Sheehan, J. C.; Wilson, R. M.; Oxford, A. W. "The Photolysis of MethoxySubstituted Benzoin Esters. A Photosensitive Protecting Group for Carboxylic Acids," *J. Am. Chem. Soc.* 1971, 93, 7222–28. (c) a-Methyl-4,5-dimethoxy-2-nitrobenzyl: Marriott, G. "Caged Protein Conjugates and Light-Directed Generation of Protein Activity: Preparation, Photoactivation, and Spectroscopic Characterization of Caged G-Actin Conjugates," *Biochemistry* 1994, 33, 9092–97. (d) a-Carboxy-2-nitrobenzyl: Gee, K. R.; Wieboldt, R.; Hess, G. P. "Synthesis and Photochemistry of a New Photolabile Derivative of GABA. Neurotransmitter Release and Receptor Inactivation in the Microsecond Time Region," *J. Am. Chem. Soc.* 1994, 116, 8366–67.

(55A) For reviews of photolabile protecting groups, see: (a) Adams, S. R.; Tsien, R. Y. "Controlling Cell Chemistry with Caged Compounds," *Annu. Rev. Physiol.* 1993, 55, 755.84. (b) Gurney, A. M.; Lester, H. A. "Light Flash Physiology with Synthetic Photosensitive Compounds," *Physiol. Rev.* 1987, 67, 583–617. (c) Pillai, V. N. R. "Photoremovable Protecting groups in Organic Synthesis," *Synthesis* 1980, 1–26.

(56A) (a) Derivatives with dimethyl substituents and a benzylic methyl (R, R', R"=Me) were prepared by acylation of 2,6-dimethylphenol followed by a Fries rearrangement to the 4-methylketone derivative followed by protection with o-nitrobenzyl bromide and $NaBH_4$ reduction to the benzyl alcohol derivative. The benzyl alcohol was converted to the acetate, trifluoromethyl acetate, bromide or chloride through literature methods. (b) Derivatives with no substituents (R, R', R"=H) were made by protection of 4-hydroxybenzaldehyde with o-nitrobenzyl bromide and reductive amination with the desired dialkylamine. (c) The methoxy substituted derivative (R, R"=H, R'=OMe) were made by protecting vanillin with o-nitrobenzyl bromide, $NaBH_4$ reduction and conversion to the chloride with N-chlorosuccinimide. (d) Dimethyl substituted derivatives with no benzylic alkyl group (R, R'=Me, R"=H) were prepared from protection of 3,5-dimethyl-4-hydroxybenzaldehyde with the alcohol of the desired photolabile protecting group in the presence of triphosgene to afford the carbonate protected benzaldehyde. $NaBH_4$ reduction and conversion to the acetate or chloride afforded the desired products.

(57A) Besides the experiment reported (scheme 5), we have run several experiments with guanylated octopamine (structure at right) trying to induce quinone methide formation via dehydration. This has been attempted in refluxing TFA with no sign of any type of reaction. We have also obtained preliminary results on the benzylic chlorination of this compound in DMF with phosphoryl chloride. NMR evidence suggests quantitative conversion to the benzyl chloride with no cyclization of the guanidine. Treatment of this intermediate with NaOH resulted in apparent β-elimination to the styrene, but no sign of cyclization was evident by $^1H$ NMR.

(58A) Athough the possibility for this cyclization is readily apparent, a thorough examination of the natural product, synthetic, and medicinal literature has thus far failed to turn up an example of a cyclization such as could occur in any of our proposed ATAR systems (a 3 to 7-exo-tet or trig depending on which system and whether the quinone methide precursor or the quinone methide is cyclizing (see A, B, or C in section 4.3)). Although there are limited examples of guanidine $S_N2$ or conjugate addition reactions, these require deprotonation under strong basic conditions or electrophilic activation under acidic conditions [For a recent example of an $S_N2$ reaction see: Vaidyanatban, C.; Zalutsky, M. R. "A New Route to Guanidines rom Bromoalkanes," *J. Org. Chem.* 1997, 62, 4867–69.]. Guanidine condensation reactions are well precedented and a useful means for making heterocyclic structures and in natural product synthesis and generally require acid or base catalysis to drive the reactions [For leading references, see: (a) ref 35. (b )Yamamoto, Y.; Kojima, S. "Synthesis and Chemistiy of Guanidine Derivatives," in *The Chemistry of Amidines and Amidates, Patai, S.; Rappoport, Z., Eds.; John Wiley & Sons: N.Y.* 1991, 485–526. (c) Berlinck, R. G. S. "Natural Guanidine Derivatives," *Nat. Prod. Rep.* 1996, 377–409.].

(59A) One example of a natural product which has been isolated which has the potential to undergo a 5-exo-trig cyclization was found. This is martinelline; (Witherup, K. M.; Ransom, R. W.; Graham, A. C.; Bernard, A. M.; Salvatore, M. J.; Lumma, W. C.; Anderson, P. S.; Pitzenberger, S. M.; Varga, S. L. "Martinelline and Martinellic Acid, Novel G-Protein linked Receptor Antagonist from the Tropical Plant *Martinella iquitosensis* (Bignoniaceae)," *J. Am. Chem. Soc.* 1995, 117, 6682–85.). Athough this was not specifically sought out, the natural product was isolated as the 3×TFA salt and stable to the extraction, characterization and assaying processes. A small amount of the correponding acid which would result from cleavage of the ester bond was also present; but the authors were uncertain if it was an artifact or natural. It was reported as a natural product.

(60A) This is definitively stated as all the components produced in the reaction mixture have been independently characterized by $^1H$ NMR, and there is no visible sign of any new benzylic resonances, or ethyl resonances which would identify the addition of the ethyl guanidine to the quinone methide.

(61A) It is believed that cyclization will not be a concern in the ATAR as long as the guanidine is protonated. Guanidine deprotection will be the final step in our synthetic protocol and will result in the protonated guanidinium ATAR which will remain under aqueous conditions for all uses.

(62A) Bernatowicz, M. S.; Wu, Y.; Matsueda, G. R. "1H-Pyrrazole-1-carboxamidine Hydrochloride: An Attractive Reagent for Guanylation of Amines and Its Application to Peptide Synthesis," *J. Org. Chem.* 1992, 57, 2497–502.

(63A) Iodination of phthalimide-protected octopamine followed by a Stille reaction with tetramethyltin has been accomplished in approx. 98% yield for the two steps.

(64A) Two approaches are underway: (1) Condensation of nitromethane with benzyl-protected 3,5-dimethyl-4-hydroxy benzaldehyde followed by in situ acylation of the resulting alcohol according to a literature preparation (Wollenberg, R. H.; Miller, S. J. "Nitroalkane Synthesis. A Convenient Method for Aldehyde Reductive Nitromethylation," *Tetehedron Lett.* 1978, 35, 3219–22.). Hydrogenation will debenzylate and reduce the nitro to the amine which will be guanylated using standard procedures and protected as the nitrobenzyl carbonate. (2) Diiodination of octopamine followed by Stile methylation, guanylation, protection of the phenol as the nitrobenzyl carbonate followed by chlorination of the benzylic alcohol. All of these steps have already been accomplished in related systems.

(65A) Yamamoto, Y.; Kojima, S "Synthesis and Chemistry of Guanidine Derivatives," in *The Chemistry of Amidines and Amidates*, Patai, S.; Rappoport, Z., Eds.; John Wiley & Sons: N.Y. 1991, 485–526.

(66A) Cliffe, I. A. "Functions Containing an Iminocarbonyl Group and any Element Other Than a Halogen or a Chalcogen," in *Comprehensive Organic Functional Group Transformations,* Gilchrist, T. L., Ed.; Pergamon: U.K. 1995, 639–75.

(67A) The potential for a phenyl substituent to increase intercalation is realized. As the phenyl group itself is not very polar in nature, this should not be a favored interaction.

(68A) Molecular modeling has not been carried out on these systems due to the highly flexible directionality and tautomerizing nature of hydrogen bonding.

(69A) Although we have been using more traditional brominations, we will try a new procedure which is reported to give 5% or less of the dibromo-product with phenols. Mashraqui, S. H.; Mudaliar, C. D.; Hariharasubrah-manian, H. "4,4-Dimethyl-3-methylpyrazol-5-one: New Applications for Selective Monobromination of Phenols and Oxidation of Sulfides to Sulfoxides," *Tetrahedron Lett.* 1997, 38, 4865–68.

(70A) Barluenga, J.; Garcia-Martin, M. A.; Gonzalez, J. M.; Clapes, P.; Valencia, G. "Iodination of Aromatic Residues in Peptides by Reaction with $IPy_2BF_4$," *J. Chem. Soc. Chem. Commun.* 1996, 1505–06.

(71A) Scott, W. J. "The Stille Reaction," *Org. React.* 1997 50, 1–652.

(72A) Pappas, J. J.; Keaveney, W. P.; Gancher, E.; Berger, M. "A New and Convenient Method for Converting Olefins to Aldehydes," *Tetrahedron Lett* 1966, 4273–78.

(73A) Borch, R. F.; Bernstein, M. D.; Durst, H. D. "The Cyanohydridoborate Anion as a Selective Reducing Agent," *J. Am. Chem. Soc.* 1971, 93, 2897–904.

(74A) De Maijere, A.; Meyer, F. E. "Fine Feathers Make Fine Birds: The Heck Reaction In Modern Garb," *Angew. Chem. Int. Ed. Engl.* 1994, 33, 2379–411.

(75A) Pasto, D. J.; Taylor, R. T. "Reduction with Diimide," *Org. React.* 1991, 40, 91–155.

(76A) Danishefsky, S. "Siloxy Dienes in Total. Synthesis," *Acc. Chem. Res.* 1981, 14, 400–406.

(77A) Sibi, M. P.; Stessman, C. C.; Schultz, J. A.; Christensen, J. W.; Lu, J.; Marvin, M. "A Convenient Synthesis of N-Methoxy-N-methylamides From Carboxylic Acids," *Synth. Commun.* 1995, 25, 1255–64.

(78A) Thompson, C. M.; Green, D. L. C. "Recent Advances in Dianion Chemistry," *Tetrahedron,* 1991, 47, 4223–85.

(79A) Sibi, M. P. "Applications of N-Methoxy-N-methylamides in Synthesis," *Org. Prep. Proced. Int.* 1993, 23, 15.

(80A) Danishefsky, S.; Yan, C.-F.; Singh, R. K.; Gammill, R. B.; McCurry, P. M.; Fritsch, N.; Clardy, J. "Derivatives of 1-Methoxy-3-trimethylsilyloxy-1,3-butadiene for Diels-Alder Reactions," *J. Am. Chem. Soc.* 1979, 101, 7001–008.

(81A) Danishefsky has examined the cycloaddition reactions of sterically bulky dienes similar to 28 with methyl substituents at the 2- and 4-positions.[80] Despite the increased sterics, reaction through the s-cis conformation is still a facile process. The same researchers demonstrated the use of dimethyl allene-1,3-dicarboxylate (29) as a dienophile in reactions with Danishefsky's diene to afford high regioselectivity and yield of a benzene derivative with a substitution pattern similar to our target.[80]

(82A) Euranto, E. K. in *The Chemistry of Carboxylic Acids and Esters,* Patai, S., Ed.; Interscience Publishers: N.Y. 1969, pp. 505–588.

(83A) This will be similar to Overman's tandem Curtius-carbamylation reaction: Overman, L. E.; Taylor, G. F.; Petty, C. B.; Jessup, P. J. "trans-1-N-Acylamino-1,3-dienes: Preparation From Dienoic Acid," *J. Org. Chem.* 1978, 43, 2164–67.

(84A) (a) Sulfonamides are the most stable amine protecting group; however, unlike most sulfonamides, this derivative is readily deprotected with fluoride ion. This will be particularly imperative as it will be the final protecting group removed in the synthesis of the fully functionalized ATAR. Weinreb, S. M.; Demko, D. M.; Lessen, T. A. "β-trimethylsilylethanesulfonyl Chloride (SES-Cl): A new Reagent for Protection of Amines," *Tetrahedron Lett* 1986, 27, 2099–2102. (b) Alternatively, a more acid labile sulfonamide protecting group (Pmc) will be used: Ramage, R.; Green, J.; Blake, A. J. "An Acid Labile Arginine Derivative for Peptide Synthesis: $N^G$-2,2,5,7,8-Pentamethylchroman-6-sulfonyl-L-argirine," *Tetrahedron* 1991,47, 6153–70.

(85A) Hagihara, M.; Schreiber, S. L. "Reassignment of Stereochemistry and Total Synthesis of Thrombin Inhibitor Cyclotheonamide B," *J. Am. Chem. Soc.* 1992, 114, 6570–71.

(86A) *Chem. Pharm. Bull.* 1984, 33, 1016.

(87A) Sharp, M. J.; Cheng, W.; Snieckus, V. "Synthetic Connections to the Aromatic Directed Metallation Reaction. Functionalized Aryl Boronic Acids by Ipso Borodesilylation. General Syntheses of Unsymmetrical Biphenyls and m-Terphenyls," *Tetrahedron Lett.* 1987, 28, 5093–96.

(88A) The synthesis would be accomplished as follows is shown in FIG. S9A.

(89A) The guanidine will be deprotected on a derivative having an ester for lactonization.

(90A) The products ofthese reactions will be useful in all future studies for correlation with ATAR alkylated products which can be digested down to the enzymatically protected trialkylphosphate dinucleotide components.

(91A) If necessary, product analysis will take advantage of procedures used for purifying hydrophobic methylphosphonate modified oligonucleotides: Lin, S.-B.; Chang, G.-W.; Teb, G.-W. Lin, K.-I.; Au, L.-C. "A Simple and Rapid Method for Purification of Oligodeoxyribonucleoside Methylphosphonates," *Biotechniques* 1993, 14, 795–98.

(92A) Sambrook, J.; Fritsch, E. F.; Maniatis, T. *Molecular Cloning 2nd Ed.* (Cold Springs Harbor Laboratory, Cold Springs Harbor, N.Y., 1989).

(93A) The higher the degree of alkylation, the slower the oligo should migrate; or if the polarity is reversed, the faster they will migrate. This will be quantified by densitometry of the autoradiography to allow determination of the degree of alkylation.

(94A) Alternatively, HPLC will also allow resolution and quantification of the relative degree of alkylation.

(95A) i.e., Is there a difference in degree of alkylation at the ends or the middle of the oligonucleotide?

(96A) Diastereomers afford differing $^{31}$P resonance signals. An NMR nano-probe would greatly facilitate these analyses, and finding for such an upgrade will be sought. (a) Löschner, T.; Engels, J, W. "Diastereomeric Dinucleoside-methylphosphonates: Determination of Configuration with the 2-D~NMR ROESY Technique," *Nuleic Acids Res.* 1990, 18,5083–88. (b) Summers, M. F.; Powell, C.; Egan, W.; Byrd, R. A.; Wilson, W. D.; Zon, G. "Alkyl Phosphotriester Modified Oligodeoxyribonucleotides. VI. NMR and UV Spectroscopic Studies of Ethyl Phosphotriester (Et) Modified Rp-Rp and Sp-Sp Duplexes, {d[GGAA(Et)TTCC]}$_2$" *Nucleic Acids Res.* 1986, 14, 7421–37. (c) Pramanik, P.; Kan, L. "NMR Study of the Effect of Sugar-phosphate Backbone Ethylation on the Stability and Conformation of DNA Double Helix," *Biochemistry* 1987, 26, 3807–12.

(97A) Oligonucleotides will be synthesized on an automated synthesizer and purified according to standard protocols: (a) Beaucage, S. L.; Caruthers, M. H. *Tetrahedron Lett.* 1981, 22, 1859. (b) Sinha, N. D.; Biemat, J.; McManus, J.; Koster, H. *Nucleic Acids Res.* 1984, 12, 4539–57.

(98A) The commercially available 1,12-dodecanediol will be protected as the 4,4'-dimethoxytrityl ether (Khorana, H. G. *Pure Appl. Chem.* 1968 17, 349.) and converted to the synthesizer-ready phosphoramidite according to standard protocol (Gait, M. J., Ed., *Oligonucleotide Synthesis, A Practical Approach,* IRL Press: New York; 1990, pp. 41–45.

(99A) Based on modeling estimates, an initial linker will have 16 atoms from the 5'-phosphate oxygen of the oligonucleotide to the benzyl ring of the reagent.

(100A) Oakley, M. G.; Turnbull, K. D.; Dervan, P. R. "Synthesis ofa Hybrid Protein Containing the Iron-Binding Ligand of Bleomycin and the DNA-Binding Domain of Hin," *Bioconjugate Chem.* 1994, 5, 242–47.

(101A) Bergeron, R. J.; McManis, J. J. *J. Org. Chem.* 1988, 53, 3108. This can be accomplished without hydrolyzing a methyl ester, so the oligonucleotide attachment will remain unharmed.

(102A) Telser, J.; Cruickshank, K. A.; Morrison, L. E.; Netzel, T. L. "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements," *J. Am. Chem. Soc.* 1989, 111, 6966–76.

(103A) Han, H.; Dervan, P. R. "Visualization of RNA Tertiary Structure by RNA-EDTA.Fe(II) Autocleavage: Analysis of tRNA$^{Phe}$ with Uridine-EDTA.Fe(II) at Position 47," *Proc. Natl. Acad. Sci. USA* 1994, 91, 4955–59

(104A) Telser, J.; Cruickshank, K. A.; Schanze, K. S.; Netzel, T. L. "DNA Oligomers and Duplexes Containing a Covalently Attached Derivative of Tris(2,2'-bipyridine) ruthenium(II): Synthesis and Characterization by Thermodynamic and Optical Spectroscopic Measurements," *J. Am. Chem. Soc.* 1989, 111, 7221–26.

(105A) The standard deprotection methods will be tested in model systems first (ammonium hydroxide), and if necessary, more mild deprotection methods have been developed for solid-support oligonucleotide deprotection and cleavage of alkali-labile oligonucleotides such as with 5% K$_2$CO$_3$ in MeOH.$^{12c}$ A more labile oxallyl-CPG solid-support linkage can be used with this deprotection methodology.$^{12d}$ Alternatively, in conjunction with the oxallyl-CPG, an allyloxy protection scheme can be used throughout the oligonucleotide for mild catalytic palladium deprotection,$^{12b}$ which the carbonate and ester will be stable towards.

(106A) A post-synthetic methodology could also be used to functionalize the deprotected and cleaved, modified oligonucleotide in solution.

(107A) The absorbance ratio at 260 nm (for DNA) versus 350 nm (for the reagent).

(108A) The protocol for triple helix formation and analysis by affinity cleavage is very well developed, see: (a) Greenberg, W. A.; Dervan, P. B. "Energetics of Formation of Sixteen Triple Helical Complexes Which Vary at a Single Position Within a Purine Motif," *J. Am. Chem. Soc.* 1995, 117,5016–22.

(109A) Kennard, O.; Hunter, W. N. "Single-Crystal X-Ray Diffraction Studies of Oligonucleotides and Oligonucleotide-Drug Complexes," *Angew. Chem. Int. Ed. Engl.* 1991, 30, 1254–77.

(110A) Professor Watkins, Chair of Journalism, has suggested the development of a workshop for professional journalists on "reporting science." She described such a workshop as a valuable service to the profession and that the Arkansas Press Association would likely endorse it.

(111A) Nadine Baum Teaching Grant

112A) Course and Curriculum Development

113A) I have received a great deal of help and advice in developing this course from Mrs. Ricki Lewis, a freelance science journalist who writes for a variety of professional scientific publications. She has expressed interest in being a part of such instruction.

114AA) Although there were only two of these presentations during the course, many written responses at the end of the course demonstrated the appeal of these presentations to the students.

Introduction

The prolific use of reactive quinone methide intermediates in organic and medicinal chemistry$^{1B,2B}$ warrants further optimization of their stability, reactivity, and chemoselectivity for expanding applications. In developing a research program around the application of quinone methides to drug delivery and biomolecular labeling,$^{2B,3B}$ we are studying various ways to control quinone methide formation for its use in biorelevant reactions.$^{4B}$ One goal of this research has been to develop a mild method for the latent formation of reactive quinone methide derivatives. Controlled formation of this alkylating intermediate would allow much higher target specificity. The most common method to form para-quinone methides for bio-alkylations is through 1,6-elimination of a benzylic leaving group from the corresponding phenol (2 to 3,FIG. S1B).$^3$ For latent formation of quinone methide 3, we considered the use of a protecting group which could be efficiently removed under biorelevant conditions. The reaction sequence would be initiated by removing the protecting group from the quinone methide precursor 1 to form the phenol 2 (FIG. S1B). Subsequent elimination of the leaving group produces quinone methide 3. The ability to initiate the latent formation of the quinone methide will improve selectivity in alkylation of the target bionucleophile to afford alkylated product 4.

The competitive pathway available to quinone methide precursor 1 in aqueous systems is hydrolysis to form benzyl alcohol 5. This has resulted in serious limitations to the use of quinone methides in biomolecular alkylation applications.[3] The rate of this competing hydrolysis pathway can be somewhat moderated by appropriate modification of the quinone methide precursor.

Meier and co-workers have conducted hydrolytic stability studies on the effect of ring substitution in benzylic trialkylphosphates and concluded that substitution by electron donating groups at the 4 position increases the potential for hydrolysis of a benzylic trialkylphosphate.[5] Most notable, in relation to our work, is that they were unable to isolate a benzylic trialkylphosphate having a 4-methoxy substituent. Widlanski and coworkers showed that the addition of a 2-nitro group to the ring (R=NO$_2$,FIG. S1B) improved the hydrolytic stability of a benzylic compound capable of forming a quinone methide through 1,6-elimination.[6] The stabilizing effect of a 2-nitro group allowed access to the quinone methide precursor having a bromide or chloride leaving group at the benzylic position (LG=Br or Cl,FIG. S1B).

Desiring a general, mild method for quinone methide formation under aqueous conditions, we investigated photolytic initiated 1,6-elimination reactions. Photolytic initiation at ≧350 nm wavelengths was considered ideal for a mild generation of a latent quinone methide for biomolecular labeling purposes. Photolabeling techniques have proven widely applicable in biochemistry.[7B] Our interest was in the use of 2-nitrobenzyl and α-methylnitroveratryl as photolabile protecting groups to be used for latent formation of quinone methides. The 2-nitrobenzyl protecting group has found widespread use in bioorganic and synthetic applications.[5B,8B,9B] The α-methylnitroveratryl protecting group is based on the 2-nitrobenzyl group but has more stable photolysis byproducts.[10A]

We wish to report the results of work in our laboratory on the hydrolytic stabilization of quinone methide precursors having benzylic leaving groups, and the latent generation of quinone methides via photolytic initiation. Based on previous investigations,[5A] an ether-linked protecting group on the quinone methide precursor (PG,FIG. S1B) was expected to be unstable towards hydrolysis. The use of an electron withdrawing group as a linker to the protecting group was expected to afford stability. Therefore, we desired to investigate the stabilizing effect of a carbonate linked photolabile protecting group versus an ether linkage in the quinone methide precursor. Our investigations required the synthesis of a series of quinone methide precursors with ether- and carbonate-linked photolabile protecting groups and bromide, chloride or fluoride leaving groups.

Results and Discussion

The synthesis of a series of related quinone methide precursors for our investigations was accomplished as outlined in FIG. T1B. Commercially available 4-hydroxy-3,5-dimethylbenzaldehyde (6) was protected as either the ether or the carbonate (7) by using the corresponding benzylbromide or chloroformate, respectively (FIG. T1B)." The bromide of the 2-nitrobenzyl group is commercially available while that of the α-methylnitroveratryl is available in one step from the alcohol.[12B] The necessary α-methylnitroveratryl alcohol was readily available upon nitration of the corresponding veratryl aldehyde[10B] followed by methyl acyl addition with trimethylaluminum.[13B] The cliloroformates required for carbonate formation are derived from the corresponding alcohols.[14B] After appropriate protection of 6, aldehyde 7 was then reduced to alcohol 8 with sodium borohydride.[15B] The resulting alcohol was transformed into the desired halide (9). The chloride is readily prepared using triphosgene.[16B]

$^a$i) 6, 2-nitrobenzylbromide, K$_2$CO$_3$, DMF, r.t., 2 h. ii) 6, a-methylnitroveratrylbromide, K$_2$CO$_3$, DMF, r.t., 44 h. iii) 6, 2nitrobenzylchloroformate, K$_2$CO$_3$, DMF, r.t., 1.5 h. iv) 6, a-methylnitroveratrylalcohol, triphosgene, py., CH$_2$Cl$_2$, −42 C-r.t., 16h.$^b$ NBE=2-Nitrobenzylether; MNVE=cc-Methylnitroveratrylether; NBC=2-Nitrobenzylcarbonate; MNVC=α-Methylnitroveratrylcarbonate.$^c$ NaBH$_4$, EtOH.$^d$ i) 8, triphosgene, py., CH$_2$Cl$_2$, r.t.

After forming each of the desired quinone methide precursors (9), they are being monitored for hydrolytic stability in various concentrations of water/acetonitrile at various temperatures (table 2). Solutions of the substrates (5 mM) in 5%, 10%, 33% and 50% water/acetonitrile at 25° C. are being monitored using capillary GC and 1H NMR analysis. Solutions of the substrates which are appropriately stable in 50% water/acetonitrile are then being monitored at temperatures of 25° C., 37° C. and 50° C. by capillary GC analysis. FIG. T2B shows the results of the hydrolysis half-lives for the various quinone methide precursors.

Preliminary results indicate that the ether-protected quinones methide precursors having a chloride leaving group at 22° C. in 33% D$_2$O/CD$_3$CN have a significantly shorter hydrolysis half-life compared to their carbonate-protected analogs. Additionally, a change in the protecting group from the 2-nitrobenzyl to the α-methylnitroveratryl resulted in an increase in the hydrolysis half-life of the quinone methide precursors having a chloride leaving group. The α-methylnitroveratryl carbonate protected substrate with a fluoride leaving group is expected to be the most stable to hydrolysis. The leaving groups within each class of protecting group (ether or carbonate) are anticipated to have hydrolysis half-lives in the order fluorine>chlorine>bromine. A change in the linking group from ether to carbonate is expected to result in a marked increase in the hydrolysis half-life regardless of the protecting group or leaving group used. This is believed to be the result of the electron withdrawing capacity of the carbonate group compared to the ether group.

EXPERIMENTAL 4-(2'-Nitrobenzyloxy)-3,5-dimethylbenzaldebyde (7b)

DMF (20 mL) at r.t. was added to a stirring mixture of 4-hydroxy-3,5-dimethylbenzaldehyde (0.500 g, 3.3 mmol), potassium carbonate (0.921 g, 6.6 mmol) and 2-nitrobenzylbromide (0.719 g, 3.3 mmol) and stirring was continued for 2 hours. The reaction was diluted with 5% NaHCO$_3$ (100 mL) and aqueous workup (Et$_2$O, MgSO$_4$) followed by concentration in vacuo yielded 7b (1.044 g, 88%) as a light yellow solid: $^1$H NMR (270 MHz, CDCl$_3$) d 2.29 (s, 6H), 5.24 (s, 2H), 7.49 (t, J=7.4 Hz, 1H), 7.55 (s, 2H), 7.74 (t, J=7.7 Hz, 1H), 8.11 (d, J=6.5 Hz, 1H), 8.14 (d, J=7.5 Hz, 1H), 9.85 (s, $^1$H); $^{13}$C NMR (68 MHz, CDCl$_3$) d 16.5, 70.2, 125.0, 128.3, 128.4, 130.9, 132.2, 132.8, 134.0, 134.3, 146.5, 160.7, 191.6.

4-(2'-Nitrobenzyloxy)-3,5-dimethylbenzyl alcohol (8b)

Sodium borohydride (15 mg, 0.39 mmol) followed by EtOH (0.4 mL) was added to a CDCl$_3$ (0.8 mL) solution of 7b (110 mg, 0.39 mmol) at r.t. After heating at 50 EC for 1 hour, the reaction mixture was quenched with 1 N HCl (2 mL) and aqueous workup (CH$_2$Cl$_2$, MgSO$_4$) followed by concentration in vacuo yielded 8b (112 mg, 99%) as a light yellow solid: $^1$H NMR (270 MHz, CDCl$_3$) d 2.26 (s, 6H), 4.57 (s, 2H), 5.21 (s, 2H), 7.04 (s, 2H), 7.49 (t, J=8 Hz, 1H), 7.75 (t, J=8 Hz, 1H), 8.15 (d, J=8 Hz, 1H), 8.18 (d, J=8 Hz, 1H); $^{13}$C NMR (68 MHz, CDCl$_3$) d 16.4, 64.9, 70.1, 124.9, 127.9, 128.2, 128.4, 131.1, 134.2, 134.8, 136.9, 146.6, 154.9.

4-(2'-Nitrobenzyloxy)-3,5-dimethylbenzylchloride (9b)

Pyridine (79 mL, 0.97 mmol) was added to a stirring mixture of 8b (112 mg, 0.39 mmol) and triphosgene (46 mg, 0.16 mmol) in CH$_2$Cl$_2$ (5 mL) at r.t. After 15 minutes, the reaction mixture was concentrated in vacuo. Flash chromatography (20 g, 5:1 hexanes/ethyl acetate) yielded 9b (81 mg, 68%) as a white solid: $^1$H NMR (270 MHz, CDCl$_3$) d 2.27 (s, 6H), 4.52 (s, 2H), 5.23(s, 2H), 7.09 (s, 2H), 7.51 (t, J=8.2 Hz, 1H), 7.76 (t, J=7.4 Hz, 1H), 8.17 (d, J=8.2 Hz, 1H), 8.18 (d, J=7.4 Hz, 1H); $^{13}$C NMR (68 MHz, CDCl$_3$) d 16.4, 46.2, 70.1, 124.9, 128.2, 128.4, 129.5, 131.5, 133.5, 134.2, 134.7, 146.6, 155.6.

4-(a'-Methyl-2'-nitro-4',5'-dimethoxybenzyloxy)-3,5-dimethylbenzaldehyde (7e)

DMF (5 mL) at r.t. was added to a stirring mixture of 4-hydroxy-3,5-dimethylbenzaldehyde (116 mg, 0.78 mmol), potassium carbonate (214 mg, 1.55 mmol) and a-methyl-2-nitro-4,5-dimethoxybenzyl bromide (169 mg, 0.58 mmol) and stirring was continued for 44 hours. The reaction was diluted with 5% NaHCO$_3$ (100 mL) and aqueous workup (Et$_2$O, MgSO$_4$) followed by concentration in vacuo yielded a yellow oil which was purified by flash chromatography (20 g, 5:1 hexanes/ethyl acetate) to yield 7e (125 mg, 60%) as a yellow oil: $^1$H NMR (270 MHz, CDCl$_3$) d 1.56 (d, J=6.2 Hz, 3H), 2.22 (s, 6H), 3.92 (s, 3H), 4.01 (s, 3H), 5.83 (q, J=6.2 Hz, 1H), 7.49 s, 3H), 7.57 (s, 1H), 9.81 (s, 1H); $^{13}$C NMR (68 MHz, CDCl$_3$) d 17.6, 23.5, 56.4, 56.5, 76.6, 107.5, 109.0, 131.1, 131.7, 132.1, 134.5, 139.0, 148.1, 153.8, 160.5, 191.5.

4-(a'-Methyl-2'-nitro-4',5'-dimethoxybenzyloxy)-3,5-dimethylbenzyl alcohol (8e)

Added EtOH (0.5 mL) at r.t. to a mixture of 7e (50 mg, 0.14 mmol) and sodium borohydride (5 mg, 0.14 mmol) and allowed to sit for 1 hour. The reaction was quenched with 1 m HCl (0.5 mL) and poured into 5% NaHCO$_3$ (15 mL). Aqueous workup (Et$_2$O, MgSO$_4$) followed by concentration in vacuo yielded 8e (27 mg, 54%) as a yellow oil: $^1$H NMR (270 MHz, CDCl$_3$) d 1.56 (d, J=6.2 Hz, 3H), 2.18 (s, 6H), 3.95 (s, 3H), 4.04 (s, 3H), 4.56 (s, 2H), 5.73 (q, J=6.2 Hz, lH), 7.00 (s, 2H), 7.55 (s, 1H), 7.59 (s, 1H); $^{13}$C NMR (68 MHz, CDCl$_3$) d 17.6, 23.4, 56.4, 56.5, 65.1, 76.2, 107.5, 109.2, 128.1, 131.0, 135.4, 136.1, 139.0, 147.9, 153.8, 154.6.

4-(a'-Methyl-2'-nitro-4',S'-dimethoxybenzyloxy)-3,5-dimethylbenzyl chloride (9e)

Pyridine (15 mL, 0.19 mmol) was added to a stirring mixture of 8e (27 mg, 0.07 mmol) and triphosgene (27 mg, 0.09 mmol) in a mixture of CDCl$_3$ (1 mL) and CH$_2$Cl$_2$ (2 mL) at r.t. After 1 hour, the reaction mixture was filtered through a pad of silica gel (5 g, 3 cm) washing with CH$_2$Cl$_2$ (25 mL) and concentrated in vacuo to yield pure 9e (24 mg, 86%) as a yellow oil: $^1$H NMR (270 MHz, CDCl$_3$) d 1.57 (d, J=6.2 Hz, 3H), 2.18 (s, 6H), 3.95 (s, 3H), 4.03 (s, 4.03 (s, 3H), 4.49 (s, 2H), 5.74 (q, J=6.2 Hz, 1H), 7.03 (s, 2H), 7.54 (s, 1H), 7.60 (s, 1H); $^{13}$C NMR (68 MHz, CDCl$_3$) d 17.6, 23.5, 46.2, 56.4, 56.5, 76.2, 107.5, 109.1, 129.6, 131.3, 132.7, 135.3, 139.0, 147.9, 153.8, 155.3.

4-(2'-nitrobenzyloxycarbonyloxy)-3,5-dimethylbenzaldehyde (7h)

A solution of 2-nitrobenzylchloroformate (215 mg, 1 mmol) in CH$_2$Cl$_2$ (1 mL) was added to a stirring mixture of 4-hydroxy-3,5-dimethylbenzaldehyde (150 mg, 1 mmol) and potassium carbonate (276 mg, 2 mmol) in DMF (4 mL) at r.t. After stirring for 1.5 hours, the reaction mixture was quenched by pouring into 5% NaHCO$_3$ (80 mL). Aqueous worktap (Et$_2$O, MgSO$_4$) and concentration in vacuo afforded a light yellow solid which was purified by flash chromatography (20 g, CH$_2$Cl$_2$) to yield 7h (247 mg, 75%) as a light yellow solid: $^1$H NMR (270 MHz, CDCl$_3$) d 2.22 (s, 6H), 5.66 (s, 2H), 7.45–7.50 (in, IH), 7.53 (s, 2H), 7.66 (d, J=3.9 Hz, 2H), 8.08 (d, J=7.9 Hz, 1H); $^{13B}$C NMR (68 MHz, CDCl$_3$) d 16.1, 67.3, 125.4, 129.0, 129.5, 130.4, 131.0, 131.6, 134.1, 134.4, 147.4, 151.9, 152.7, 191.4.

4-(2'-nitrobenzyloxycarbonyloxy)-3,5-dimethylbenzyl alcohol (8h)

Added EtOH (0.5 mL) at r.t. to a mixture of 7h (100 mg, 0.3 mmol) and sodium borohydride (12 mg, 0.3 mmol) and then refluxed for 5 minutes. Quenched reaction with 1 m HCl (0.5 mL) and poured into 5% NaHCO$_3$ (15 mL). Aqueous workup (Et$_2$O, MgSO$_4$) followed by concentration in vacuo afforded a yellow oil which was purified by flash chromatography (20 g. 1:1 hexanes/ethyl acetate) to yield 8h (56 mg, 56%) as a crystalline solid: $^1$H NMR (270 MHz, (CDCl$_3$) d 2.19 (s, 6H), 4.56 (s, 2H), 5.69 (s, 2H), 7.04 (s, 2H), 7.49–7.55 (m, 1H), 7.69–7.72 (m, 2H), 8.15 (d, J=7.9 Hz, 1H); $^{13}$C NMR (68 MHz, CDCl$_3$) d 16.1, 64.7, 66.9, 125.4, 127.5, 128.8, 129.3, 130.3, 131.6, 134.1, 138.9, 147.3, 147.69, 152.7.

4-(2'-nitrobenzyloxycarbonyloxy)-3,5-dimethylbenzyl chloride (9h):

Pyridine (34 mL, 0.42 mmol) was added to a stirring mixture of 8h (56 mg, 0.17 mmol) and triphosgene (60 mg, 0.20 mmol) in a mixture of CDCl$_3$ (1 mL) and CH$_2$Cl$_2$ (2.5 mL) at r.t. After 45 minutes, the reaction mixture was filtered through a pad of silica gel (5 g, 3 cm) washing with CH$_2$Cl$_2$ (20 mL) and concentrated in vacuo to yield pure 9h (53 mg, 90%) as a clear oil which became an off-white solid on addition of hexane: $^1$H NMR (270 MHz, CDCl$_3$) d 2.20 (s, 6H), 4.50 (s, 2H), 5.70 (s, 2H), 7.09 (s, 2H), 7.50–7.56 (m, 1H), 7.69–7.72 (m, 2H), 8.16 (d, J=7.9 Hz, LH); $^{13}$C NMR (68 MHz, CDCl$_3$) d 16.1, 64.7, 66.9, 125.4, 127.5, 128.8, 129.3, 130.3, 131.6, 134.1, 138.9, 147.3, 147.69, 152.7.

4-(a'-Methyl-2'-nitro-4',5'-dimethoxybenzyloxycarbonyloxy)-3,5-dimethylbenzaldehyde (7k)

Triphosgene (0.224 g, 0.7 mmol) in CH$_2$Cl$_2$ (10 inL) at r.t. was added to a-methyl-2-nitro-4,5-dimethoxybenzyl alcohol (0.500 g, 2.2 mmol) and pyridine (0.534 inL, 6.6 mmol) in $CH_2Cl_2$ (20 mL) at −42 EC ($CH_3CN/CO_2$). After 2 hours, 4-hydroxy-3,5-diinethylbenzaldehyde (0.330 g, 2.2 mmol) and pyridine (0.534 mL, 6.6 inmol) in $CH_2Cl_2$ (10 mL) at r.t. was added and the mixture was allowed to slowly warm to r.t. overnight. The reaction mixture was quenched with saturated ammoniuin chloride (80 mL) and aqueous workup ($CH_2Cl_2$, $MgSO_4$) followed by concentration in vacuo afforded a brown solid which was recrystallized (EtOH) to yield 7k (431.9 mg, 49%) as a cream colored solid: $^1$H NMR (270 MHz, $CDCl_3$) d 1.76 (d, J=6.4 Hz, 3H), 2.18 (s, 6H), 3.93 (s, 3H), 3.98 (s, 3H), 6.47 (q, J=6.4 Hz, 1H), 7.11 (s, 1H), 7.55 (s, 2H), 7.59 (s, 1H), 9.88 (s, 1H); $^{13}$C NMR (68 MHz, CDCl3) d 16.2, 22.0, 56.5, 56.6, 73.6, 107.5, 107.8, 130.4, 131.5, 132.0, 134.3, 140.1, 148.4, 151.2, 152.7, 153.8, 191.4.

4-(a'-Methyl-2'-nitro-4',5'-dimethoxybenzyloxycarbonyloxy)-3,5-dimethylbenzyl alcohol (8k)

Sodium borohydride (9 ing, 0.25 inmol) followed by EtOH (0.5 mL) was added to 7k (100 mg, 0.25 mmol) in $CH_2Cl_2$ (2 mL) at r.t. and then refluxed for 30 minutes. Aqueous workup ($CH_2Cl_2$, $MgSO_4$) followed by concentration in vacuo yielded 8k (75 mg, 75%) as a light yellow solid: $^1$H NMR (270 MHz, CDCl3) d 1.68 (d, J=6.4 Hz, 3H), 2.03 (s, 6H), 3.86 (s, 3H), 3.91 (s, 3H), 4.45 (s, 2H), 6.39 (q, J=6.4 Hz, 1H), 6.92 (s, 2H), 7.06 (s, 1H), 7.52 (s, 1H); $^{13}$C NMR (68 MHz, $CDCl_3$) d 16.0, 21.9, 56.3, 56.4, 64.4, 73.0, 107.4, 107.6, 127.2, 129.9, 132.3, 138.7, 139.8, 147.4, 148.1, 151.7, 153.7.

4-(a'-Methyl-2'-nitro-4'-5'-dimethoxybenzyloxycarbonyloxy)-3,5-dimethylbenzyl chloride (9k)

Pyridine (30 inL, 0.37 mmol) was added to a stirring mixture of 8k (60 mg, 0.15 mmol) and triphosgene (18 mg, 0.06 mmol) in $CH_2Cl_2$ (5 mL) at r.t. After 15 minutes, the reaction mixture was concentrated in vacuo. Flash chromatography (8 g, 5:1 hexanes/ethyl acetate) yielded 9k (48 mg, 76%) as an off-white solid: $^1$H NMR (270 MHz, $CDCl_3$) d 1.75 (d, J=6.4 Hz, 3H), 2.11 (s, 6H), 3.94 (s, 3H), 3.97 (s, 3H), 4.47 (s, 2H), 6.46 (q, J=6.4 Hz, 1H), 7.05 (s, 2H), 7.11 (s, 1H), 7.59 (s, IH).

References

1B Reviews on Quinone Methides: (a) Grauenanger, P. *Methoden der Organisch Chemie*, Houben-Weyl, 4th edition, 1979, 395–52 1. (b) Peter, M. G. *Angew. Chem. Int. Ed. Engl.* 1989, 28, 5550.1.

2B For more recent, elegant examples of quinone methides in biomolecular alkylation, see: (a) Chatterjee, M.; Rokita, S. E. *J. Am. Chem. Soc.* 1994, 116, 1690. (b) Li, T.; Zeng, Q.; Rokita, S. E. *Bioconjugate Chem.* 1994, 5, 497. (c) Meyers, I. K.; Cohen, J. D.; Widlanski, T. S. *J. Am. Chem. Soc.* 1995, 117, 11049. (d) Myers, J. K.; Widlanski, T. S. *Science* 1993, 262, 1451. (e) Wang, Q.; Dechert, U.; Jirik, F.; Withers, S. G. *Biochem. Biophys. Res. Commun.* 1994, 200, 577. (f) Rokita, S. E.; Yang, J; Pande, P.; Greenberg, W. A. *J. Org. Chem.* 1997, 62, 3010. (g) Angle, S. T.; Ralnier, J. D.; Woytowicz, C. *J. Org. Chem.* 1997, 62, 5884. (h) Skibo, E. B.; Gordon, S.; Bess, L.; Boruah, R.; Heileman, M. *J. Med. Chem.* 1997, 40, 1327–1339.

3B Wakselman, M. *Nouv. J. Chim.*, 1983, 7, 439–447.

4B McCracken, P. G.; Bolton, J. L.; Thatcher, G. R. J. *J. Org. Chem.* 1997, 62, 1820–25.

5B Meier, C.; Habel, L. W.; Balzarmni, J.; De Clercq, E. *Liebigs Ann.*, 1995, 2203–2208.

6B Meyers, J. K.; Cohen, J. D.; Widlanski, T. S. *J. Am. Chem. Soc.*, 1995, 117, 11049–11054.

7B. Brunner, J. *Annu. Rev. Biochem.* 1993, 62, 483–514.

8B Amit, B.; Hazum, E.; Fridkin, M.; Patchornik, A. *Int. J. Peptide Protein Res.*, 1977, 9, 91–96.

9B Pillai, V. N. R. *Synthesis*, 1980, 1–26.

10B Holmes, C. *J. Org. Chem.*, 1997, 62, 2370–2380.

11B Venuti, M. C.; Loe, B. E.; Jones, G. H.; Young, J. M. *J. Med. Chem.*, 1988, 31, 2132–2136.

12B Lan, A. J. Y.; Heuckeroth, R. O.; Mariano, P. S. *J. Am. Chem. Soc.*, 1987, 109, 2738–2745.

13B Teague, S. J. *Tetrahedron Letters*, 1996, 37, 5751–5754.

14B McGall, G. H.; Barone, A. D.; Diggelmann, M.; Fodor, S. P. A.; Gentalen E.; Ngo, N. *J. Am. Chem. Soc.*, 1997, 119, 5081–5090.

15B Dai-Ho, G.; Moriano, P. S. *J. Org. Chem.*, 1988, 53, 5113–5127.

16B Goren, Z.; Heeg, M. J.; Mobashery, S. *J. Org. Chem.*, 1991, 56, 7196–7199.

Introduction

As genomic sequence data continues to proliferate, [1C] there is increased significance placed on technology which allows selective modification of nucleic acids[2C] for studying and manipulating genetic structure and function. We are developing a general reagent designed to functionalize nucleic acid polymers selectively at the phosphodiester group through alkylation to afford the phosphotriester (FIG. 1C)[3C] The generality of the reagent will be based on the ability to independently attach the desired functionalizing moieties to the alkylating reagent. The designed reagent can then be used as a probe for nucleic acid structure, nucleic acid-protein interactions, drug delivery, or as a means to modify the nucleic acid target for controlled function. The development of this general nucleotide modifying reagent required investigation into alkylating chemistry which would be selective for the relatively weak nucleophilic phosphodiester in the presence of the nucleic acid bases. We chose to develop this alkylating reagent around the well precedented alkylating ability of quinone methides.[4C,5C]

The versatile para-quinone methide, represented by para-benzoquinone methide (1,FIG. 2C), shows increased electrophilic reactivity as a conjugate addition vinologue due to the driving force towards rearomatization.[6C] In developing a research program around the application of quinone methides to drug delivery and biomolecular labeling, we are studying various ways to control product formation in quinone methide reactions.

Directing selectivity towards the phosphodiester was envisioned to be most readily accomplished by incorporation of a phosphate binding moiety in close proximity to the alkylating site on the quinone methide. For this purpose we chose a guanidinium group for well precedented phosphate binding.[7C] This lead to the design of 2 and 3 as precursors for our alkylating studies (FIG. S1C). These molecules were designed to associate with phosphodiesters through guanidinium-phosphate salts 4 and 5. The desired quinone methide 6 will be oxidatively produced[8C] from 5 to study the alkylation reaction leading to phophotriester 7. The alkylation reaction will also be studied by deprotection of 4 followed by in situ 1,6-elimination to afford quinone methide 6[5C,9C,10C]. These two approaches will allow mechanistic confirmation of the alkylation reactions by preformation and characterization of the quinone methide through oxidation of 5 and provide a mild method for biorelevant quinone methide formation by use of a photolabile protecting group in 4 for quinone methide formation via elimination.

Results and Discussion

The initial model compounds for investigation were synthesized by a procedure that will allow flexibility for future modifications. Commercially available octopamine hydrochloride 8 was used as the starting material, providing the basic framework of our reagent (FIG. S2C). Phthalimide protection of the primary amine followed by bis, ortho iodination with Barluenga's reagent[11C] ($LPy_2BF_4$) 10 in very good yield. A catalytic palladium/copper Stille reaction[12C] led to dimethyl analog 11. Protection of phenol 11 with the photolabile ortho-nitrobenzyl protecting group was accomplished under standard conditions. Phthalimide deprotection with hydrazine yielded the primary amine 13 which was converted directly into the guanidinium hydrochloride 14 after reacting with 1H-pyrazole-1-carboxaniidine hydrochloride.[13C] The final step was the conversion of the benzylic alcohol into the desired leaving group. Phosphorous oxychloride provided an easy and convenient means to convert the alcohol into the corresponding benzyl chloride 15.

The synthesis of our model systems has been accomplished. We are currently evaluating these model systems for phosphate alkylation by photolysis reactions on system 2 in the presence of dibenzyl phosphate salts. We are also conducting test reactions on 3 by direct oxidation with DDQ. Once optimal reaction conditions have been found, test reactions using more complex nucleotide dimers will be conducted.

Conclusion

From the results of the experiments above, the directing effect of the guanidinium group on phosphodiesters will be compared to corresponding alkylation reactions using quinone methide derivatives without a guanidinium group.

Materials and Methods 4-(2-N-Phthaloyl-1-hydroxyethyl)phenol (9)

N-(ethoxycarbonyl)phthalimide (1.092 g. 4.98 mmol) was added to a vigorously stirring solution of octopamine hydrochloride 8 (0.727 g, 3.83 mmol) and sodium carbonate (0.811 g, 7.65 mmol) in water (20 ml). The resulting solution was vigorously stirred overnight, during this time the crude white product precipitated. After filtration, the product was washed with water (3×3 ml) giving analytically pure 9 (0.879 g, 81%) as a white solid: mp ° C.; $^1$H NMR (270 MHz, $DMSOd_6$) δ9.33 (s, 1H, ArO$\underline{H}$), 7.84(m, 4H, Pth), 7.14(d, J=8.4 Hz, 2H Ar—$\underline{H}$), 6.69(d, J=8.4 Hz, 2H, Ar—$\underline{H}$), 5.47(d, I=4.1 Hz, 1H, RO$\underline{H}$), 4.79 (1H, m, ArCH(O$\underline{H}$)), 3.65 (2H, m, C$\underline{H}_2$NPth); $^{13}$C NMR (67.5 MHz, DMSO-$d_6$) δ168.6, 157.4, 134.9, 133.3, 132.2, 127.7. 123.4, 115.4, 69.4, 45.8;

4-(2-N-Phthaloyl-1-hydroxyethyl)-2,6-diiodophenol (10)

Bis(pyridine)iodonium(I)tetrafluoroborate (1.828 g. 4.92 mmol) was added to a stirring solution of 9 (0.633 g, 2.23 mmol) in $CH_2Cl_2$ (15 ml) and DMSO (5 ml). The resulting homogenous solution quickly changed to a light yellow color. After stirring under a nitrogen atmosphere for 1 h, an aqueous workup was preformed. The yellowish organic extract was washed with 5% aqueous sodium thiosulfate resulting in a clear solution, which was then dried over $MgSO_4$. Evaporation under reduced pressure yielded pure 10 (1.137 g. 95%) as an off-white solid: mp ° C.; $^1$H NMR (270 MHz, DMSO-$d_6$) δ7.86(m, 4H, Pth), 7.66(s, 2H, Ar—$\underline{H}$), 5.72(d, 1=4.4 Hz, 1H, O—$\underline{H}$), 4.75 (m, 1H, ArC$\underline{H}$(OH)), 3.62 (m, 2H, C$\underline{H}_2$—NPth); $^{13}$C NMR (67.5 MHz, DMSO-$d_6$) δ168.4, 155.2, 138.9, 137.2, 134.9, 132.0, 123.5, 87.2, 67.9, 40.1;

4-(2-N-Phthaloyl-1-hydroxyethyl)-2,6-dimethylphenol (11)

$Pd_2dba_3CHCl_3$ (27 mg, 0.026 mmol), CuI (17.3 mg, 0.091 mmol), and $PPh_3$ (50 mg, 0.191 mmol), were added to solution of 10 (0.500 g, 0.934 mmol) in 1-methyl-2-pyrrolidinone (1.5 ml). The mixture was annealed by heating to 80° C. for 10 min. under a nitrogen atmosphere. Tetramethyltin (400 mL, 2.9 mmol) was added to the stirring solution in the high pressure reaction tube. The reaction was heated to 80° C. for 3 h, followed by an aqueous workup. The crude product was purified by flash chromatography using a gradient from 10:1 to 1:1 hexane/EtOAc for elution, giving analytically pure 11 (302 mg, 92%) as a white solid: mp ° C.; $^1$H NMR (270 MHz, $CDCl_3$) δ7.76(m, 4H, Pth), 7.10(s, 2H, Ar—$\underline{H}$), 4.95 (m, 1H, ArC$\underline{H}$(OH)), 3.96 (m, 2H, C$\underline{H}_2$NPth), 2.28(s, 6H ArC$\underline{H}$s); $^{13}$C NMR (67.5 MHz, $CDCl_3$Acetone-$d_6$) δ169.0, 153.5, 134.9, 133.8, 133.0, 127.0, 124.6, 123.7, 71.2, 46.5, 16.7;

2-N-Phthaloyl-1-{3,5-dimethyl-4-[(2-nitrobenzyl)oxyjphenyl}-1-ethanol (12)

ortho-Nitrobenzylbromide (0.580 g 2.68 mmol), and $K_2CO_3$ (1.10 g, 7.96 mmol) were added to a stirring solution of phenol 11 (0.800 g, 2.57 mmol) in 15 ml DMF. The mixture was stirred for 4 hrs, followed by a standard aqueous work up giving pure 12 (1.079 g. 94%) as a offwhite solid: mp ° C.; $^1$H NMR (270 MHz, $CDCl_3$) δ7.86(m, 4H, Pth), 7.74(t, J=8.2 Hz, 1H, $\underline{Ar}NO_2$), 7.51(t, J=8.2 Hz, 1H, $\underline{Ar}NO_2$), 7.14(s, 2H, Ar—$\underline{H}$), 4.97 (m, 1H, ArC$\underline{H}$(OH)), 3.94 (m, 2H, C$\underline{H}_2$—NPth), 2.26(s, 6H, ArC$\underline{H}_3$); $^{13}$C NMR;

2-Amino-1-{3,5-dimethyl-4-[(2-nitrobenzyl)oxy]phenyl}-1-ethanol HCl (13)

2 mL of hydrazine hydrate was added to a stirring solution of compound 12 (0.519 g, 1.16 mmol) in 7 ml of methanol. The reaction was stirred for 5 hrs, after which the solvents were removed by roto-evaporated. An alkaline workup gave the crude amine which was converted to the hydrochloride salt and recrystalized from methanol/$CH_2Cl_2$ giving analytically pure 13 (0.410 g, 90%) as a white solid: mp, C; $^1$H NMR (270 MHz, MeOH-$d_4$) δ8.13 (dd, J=8.2 Hz, 2H, $\underline{Ar}NO_2$), 7.81 (t, J=8.2 Hz 1H $\underline{Ar}NO_2$), 7.59(t, J=8.2 Hz, 1H, $\underline{Ar}NO_2$), 7.13(s, 2H, Ar—$\underline{H}$), 5.17(s, 2H, ArOC$\underline{H}$Ar($NO_2$)), 4.83 (m, 1H, ArC$\underline{H}$(OH)), 3.03 (m, 2H, $CH_2$—$NH_3$), 2.26(s, 6H, ArC$\underline{H}_3$) $^3$C NMR (67.5 MHz, MeOH-$d_4$) δ, 155.4, 147.1, 136.9, 133.7, 133.6, 131.1, 128.8, 126.3, 124.4, 70.0, 69.2, 46.0, 15.2;

N-(2-{3,5-dimethyl-4-[(2-nitrobenzyl)oxy]phenyl-2-hydroxyethyl)guanidinium HCl (14)

1H-1-Carboxamidine hydrochloride (271 mg,1.85 mmol), and DIPEA (0.5 mL, 3.87 mmol) were added to a vigorously stirring solution of amine 13 (450 mg, 1.42 mmol) in DMF (1.5 ml). The reaction was stirred for 14 hrs then worked up by diluting with Et2O. The viscous oil was repeatedly washed with $Et_2O$, then recrystillized from $CH_2Cl$/MeOH$^2$ giving pure 14 (382 mg, 68%) as a off-white solid: $^1$H NMR (270 MHz, DMSO-d$_6$) δ8.16(d, J=8.2 Hz, 1H, ArNO$_2$) 8.03(d, J=8.2 Hz ArNO$_2$), 1H, 7.87(t, J=8.2 Hz, 1H ArNO$_2$), 7.66(t, J=8.2 Hz, 1H, ArNO$_2$), 7.45(t, J=5.2 Hz, 1H, RCH$_2$NH), 7.11(s, 2H, Ar—H), 5.80(d, J=4.1 Hz, LH RO—H), 5.14(s, 2H, ArOCH$_2$Ar(NO$_2$)), 4.60 (m, 1H, ArCH(OH)), 3.31 (m, 2H, CH2NH), 2.21(s, 6H, ArCH$_3$) $^{13}$C NMR (67.5 MHz, MeOH-d$_4$)δ159.3, 156.3, 148.2, 138.7, 135.1, 135.1, 132.1, 129.9, 129.6, 127.7, 125.8, 73.0, 71.3, 50.0, 16.8;

N-(2-Chloro-{3,5-dimethyl-4-[(2-nitrobenzyl)oxy] phenyl}ethyl)guanidinium HCl (15)

Phosphoryl Chloride (3.3 mL,3.54 mmol) was added to a solution of 14 (40.2 mg, 0.10 mmol) in DMF (1 ml). Following stirring under N$_2$ for 24 hrs, the cmde product was isolated by diluting with Et$_2$O. The product was then purified by recrystillization from CHCl$_3$Et$_2$O/EtOH. Giving pure compound 15 (31.2 mg, 74%) as an off-white solid: $^1$H NMR (270 MHz, MeCN d$_3$) δ8.14(d, 1H, I=8.2 Hz, ArNO$_2$), 8.07(d, J=8.2 Hz, 1H, ArNO$_2$), 7.81 (t, J=8.2 Hz, 1H, ArNO$_2$), 7.59(t, J=8.2 Hz, 1H, ArNO$_2$), 7.49(t, J=5.2 Hz, 1H, RCH$_2$NH), 7.19(s, 2H, Ar-H), 5.20.(s, 2H, ArOCH$_2$Ar(NO$_2$)), 5.04(m, 1H, ArCH(OH)), 3.71(m, 2H, CH$_2$—NH), 2.24(s, 6H, ArCH) $^{13}$C NMR (67.5 MHz, MeOHd$_4$) δ157.4, 156.1, 147.4, 134.1, 133.7, 133.4, 131.5, 128.8, 128.5, 127.9, 124.5, 70.1, 60.3, 48.3, 15.2;

References

1C For a complete resource covering many aspects of the human genome see the Genome Database (GDB) hosted at Johns Hopkins University (http://gdbwww.gdb.org/): Fasman, K. H.; Letovsky, S. I.; Li, P.; Cottingham, R. W.; Kingsbury, D. T. "The GDB Human Genome Database Anno 1997," Nucleic Acids Res. 1997, 25, 72–80

2C Coleman, R. S.; and Kesicki, E. A. "Template-Directed Cross-Linking of Oligonucleotides: Site-Specific Covalent Modification of dG-N7 within Duplex DNA," J. Org. Chem. 1995, 60, 6252–53.

3C For the only example of a reagent for selective phosphate alkylation, see: Schulz, W. G.; Nieman, R. A.; Skibo, E. B. "Evidence for DNA Phosphate Backbone Alkylation and Cleavage by Pyrrolo[1,2-a]benzimidazoles: Small Molecules Capable of Causing Base-Pair-Specific Phosphodiester Bond Hydrolysis," Proc. Natl. Acad. Sci. USA 1995, 92, 11854–58. For a previously attempted phosphate alkylation in DNA, see: Gohil, R. N.; Roth, A. C.; Day, R. A. "Reversible Covalent Modification of DNA," Arch. Biochem. Biophys. 1974, 165,297–312.; and the following retraction: Bhat, G.; Roth, A. C.; Day, R. A. "Extrinsic Cotton Effect and Helix-Coil Transition in a DNA-Polycation Complex," Biopolymers 1977, 16, 1713–24.

4C For reviews on quinone methides, see: (a) Volod'kin, A. A.; Ershov, V. V. Russian Chem. Rev. 1988, 57,336. (b) Gmenanger, P. in Houben-Weyl Methoden der Organischen Chemie (Vol. VII/3b) Mueller, E.; Bayer, O., Eds.; G. Thieme Verlag: Stuttgart, 1979, pp. 395–521. (c) Wagner, H.-U.; Gompper, R. in The Chemistry of Quinonoid Compounds (Vol. 1) Patai, S., Ed.; John Wiley & Sons: New York, 1974, pp. 1145–1178. (d) Turner, A. B. Quart. Rev. 1965, 18, 347.

5C More recent, elegant examples for biomolecule alkylation include: (a) Chatteree, M.; Rokita, S. E. "The Role of a Quinone Methide inthe Sequence Specific Alkylation of DNA," J. Am. Chem. Soc. 1994, 116, 1690–97. (b) Li, T.; Zeng, Q.; Rokita, S. E. "Target-Promoted Alkylation of DNA," Bioconjugate Chem. 1994, 5, 497–500. (c) Meyers, J. K.; Cohen, J. D.; Widlanski, T. S. "Substituent Effects on the Mechanism-Based Inactivation of Prostatic Acid Phosphatase," J. Am. Chem. Soc. 1995, 117, 11049–54. (d) Myers, J. K.; Widlanski, T. S. "Mechanism-Based Inactivation of Prostatic Acid Phosphatase," Science 1993, 262, 1451–53. (e) Wang, Q.; Dechert, U.; Jink, F.; Withers, S. G. "Suicide Inactivation of Human Prostatic Acid Phosphatase and a Phosphotyrosine Phosphatase," Biochem. Biophys. Res. Commun. 1994, 200, 577–83. (f) McCracken, P. G.; Bolton, J. L.; Thatcher, G. R. J. "Covalent modification of Proteins and Peptides by the Quinone Methide from 2-tert-Butyl-4,6-dimethylphenol: Selectivity and Reactivity with Respect to Competitive Hydration,"J. Org. Chem. 1997, 62, 1820–25. (g) Rokita, S. E.; Yang, J.; Pande, P.; Greenberg, W A. "Quinone Methide Alkylation of Deoxycytidine," J. Org. Chem. 1997, 62, 3010–12.

6C Angle, S. R.; Arnalz, D. O.; Boyce, J. P.; Frutos, R. P.; Louie, M. S.; Mattson-Arnaiz, H. L.; Rainier, J. D.; Tumbull, K. D.; Yang, W. "Formation of Carbon-Carbon Bonds via Quinone Methide-Initiated Cyclization Reactions," J. Org. Chem. 1994, 59, 6322–6337.

7C For a thorough review, see: Hannon, C. L.; Anslyn, E. V. "The Guanidinium Group: Its Biological Role and Synthetic Analogs," Bioorg. Chem. Frontiers 1993, 3, 193–255.

8C Dyall, L. K.; Winstein, S. "Nuclear Magnetic Resonance Spectra and Characterization of Some Quinone Methides," J. Am. Chem. Soc. 1972, 94, 2 196–99.

9C Wakselman, M. "1,4- and 1,6-Eliminations from Hydroxy- and Amino-substituted Benzyl Systems: Chemical and Biochemical Applications," Nouv. J. Chim. 1983, 7, 439–47.

10C (a) Kanamathareddy, S.; Gutsche, C. D. "Calixarenes: Selective Functionalization and Bridge Building," J. Org. Chem. 1995, 60, 6070–75. (b) Alam, I.; Sharma, S. K.; Gutsche, C. D. "The Quinonemethide Route to Mono- and Tetrasubstituted Calix[4]arenes," J. Org. Chem. 1994, 59,37 16–20. (c) Note that even aniline has been eliminated to produce quinone methides: Angle, S. R.; Yang, W. "Synthesis and Chemistry of a Quinone Methide Model for Anthracycline Antitumor Antibiotics," J. Am. Chem. Soc. 1990, 112, 4524–28.

11C Barluenga, J.; Garcia-Martin, M. A.; Gonzdlez, J. M.; Clapes, P.; Valencia, G. "Iodination of aromatic residues in peptides by reaction with IPy$_2$BF$_4$," J. Chem. Soc. Chem Commun., 1996, 1505–6.

12C Farina, V.; Kapadia, S.; Krishnan, B.; Wang, C.; Liebeskind, L. S. "On the nature of the "Copper Effect" in Stille Cross-Coupling," J. Org. Chem. 1994, 59, 5905–11.

13C Bernatowicz, M. S.; Wu, Y.; Matsueda, G. R. "1 H-Pyrazole-1-carboxamidine Hydrochloride: An Attractive Reagent for Guanylation of Anilnes and its Application to Peptide Synthesis," J. Org. Chem. 1992, 57,2497–2502.

1. Specific Aims

The overall goal of this research is to design and develop a chemical reagent for ultimate use under physiological conditions which will selectively alkylate a nucleophilic functional group of a biomolecule[1D] with a molecular label, reporter group or drug followed by the in situ release of the delivery molecule which acts as a taxi to deliver the label to the targeted biomolecular site of interest. The design is to transfer a functionalized label in vitro or in vivo specifically to one biomolecule by some affinity interaction and then release the delivering molecule so as to minimize perturbation of the molecular system under study. This will allow native processes such as intramolecular folding or interactions of the labeled biomolecule with a secondary biomolecule to be probed. This should provide a valuable tool for defining cellular processes as well as have potential therapeutic and drug delivery applications. The name given to to this reagent for reference purpose is an affinity transfer alkylating reagent.

The specific objective of this part of the research project is to target a phosphodiester functional group of nucleic acids for labeling or drug delivery. The goal is to develop an affinity transfer alkylating reagent for the in situ labeling of nucleic acid phosphodiesters to generate phosphotriesters carrying a reporter group or drug molecule under physiologically relevant conditions. Tfhe plan is to fully define the chemistry required for accomplishing this goal in small molecule model systems designed to investigate each aspect of the methodology. These model studies will progressively advance to more complex molecules so that the mechanistic details can be fully understood, the scope and limitations can be realized, and the reagent design can be optimized at each stage. Within the time frame of these investigations it is hoped to progress to the point of having an affinity transfer labeling reagent ready for future studies with DNA and to probe the structure of a complex biomolecular target such as a tRNA in vitro.

2. Background and Significance 2.1. Biomolecular Labeling

The understanding of cellular processes on a molecular level has increased dramatically in recent years. A variety of methodologies have evolved allowing the labeling of proteins and nucleic acids (FIG. 1D) with reporter groups (i. e., radiolabels, fluorescent or luminescent groups, antibody or binding substrates) and reactive functionality (i.e., oxidants, alkylators, carbene or nitrene precursors) (FIG. 2D) for the molecular probing of biological processes.[2D] There is now a variety of commercially available molecular probes which can readily be attached to biomolecules through thiol and amino groups.[3D] The initial goal of this research is to expand labeling techniques to include targeting dialkylphosphates and to introduce a non-invasive in vivo or in vitro methodology for accomplishing this. This same methodology could also be used as a reagent for drug delivery to specific nucleic acid targets.

2.2. Labeling a Phosphodiester Residue in Nucleic Acids: Phosphate Triesters

Modification ofthe phosphate residue of oligonucleotides has been an appealing target in the design of antisense/antigene/sense agents for potential therapeutic/diagnostic applications and as tools for molecular biological studies.[4D-7D] The neutralized alkylphosphate oligonucleotides have proven resistant to nucleases (therefore stable against cellular degradation), able to penetrate the cellular and nuclear membranes, and demonstrate increased stability in formation of Watson-Crick double helices with DNA and RNA.[8D]

Oligodeoxynucleotide phosphate triesters are routinely synthesized through several different routes.[4D,9D-12D] However, a particular concern with the synthesis of triester alkylphosphate oligonucleotides is stereocontrol at the chiral phosphate center.[13D-16D] In situ phosphate alkylation within the asymmetric environment of double or triple helical nucleic acids might afford a means for stereoselectivity. This issue will be addressed in the course of this proposed research.

Phosphate alkylation of DNA with a variety of alkylating reagents (carcinogenic compounds) is one of the mechanisms by which mutagenesis occurs.[17D,18D] One compound of particular interest to our proposed research was prepared by Day and coworkers for the selective alkylation of the DNA phosphate residue.[19D] Despite negative results with a later retraction of their interpretation of some results,[20D] their use of an ionic association of ammonium residues with DNA phosphodiesters attracted our attention and has been successfully used by other researchers in order to enhance binding to DNA.[21D]

Alkylation of a phosphodiester to form the triester is routinely accomplished under controlled organic reaction conditions.[22D] Trialkylphosphates are routinely used for drug delivery, reporter group release and suicide inhibition substrates.[22A-D]

To date, there have been no reports involving the in situ alkylation of the phosphate residue of nucleic acids for labeling or drug delivery. It is in this area the following research is aimed.

3. Statement of Cancer Relevance

This project is expected to impact cancer research in multiple areas. The successful development of the proposed chemical reagent for affinity transfer alkylation of the phosphate residue of nucleic acids and future developments towards the selective alkylation of other biomolecular residues should provide a chemical tool that will find uses in four primary areas of cancer research.

Firstly, the use of this reagent in vitro and potentially in vivo for the delivery and transfer of reporter groups to targeted nucleic acid sequences will aid molecular biologists in identifying and tracking molecular constituents involved in cancerous cell growth. This could be valuable in further understanding the genetic and developmental causes of cancer. Secondly, with increased understanding of mutant genetic sequences which identify potential cancer development, the ability to use this reagent to probe for and label these genetic sequences with a reporter group could aid in cancer diagnostics. Thirdly, this reagent could similarly be used to deliver antitumor drugs directly to a targeted genetic sequence of relevance to the molecular genetics of cancer and thereby induce its destructive effects at specific target sites. This could obviously have a significant impact on chemotherapy by lowering the nonspecific genetic damage induced by antitumor compounds. Lastly, as our understanding of the biological genetics of cancer is developed, a reagent such as that being proposed here might find uses in preventitive measures against cancer. In a manner similar to that described for delivery of antitumor compounds, this reagent might be used for delivering compounds which will disrupt genetic sequences related to cancer through alkylation, cleavage, or modification which will induce some enzymatic response resulting in excission of a faulty genetic code.

4. Research Design

FIG. S1D graphically represents the key aspects in the design of this affinity transfer alkylating reagent as follows:

Step 1: Site-specific delivery of the probe (R) to the carrier biomolecule (C) through a designed hybridization complex with delivery molecule (D). Step 2: Alkylation of the carrier biomolecule with a latent electrophile activated via photolysis. Step 3: In situ release of the delivery molecule upon alkylation through a cleavage reaction with a labile linker attaching the reagent to the delivery molecule. Step 4: Probing a structural or biomolecular interaction through the signalling or reactivity of the incorporated reporter group (R) (FIG. S1D). Step 4 might also involve a reaction with the target biomolecule when R is a reactive group such as an antitumor compound.

A reagent for phosphate alkylation in nucleic acids will employ an oligonucleotide complimentary to the target nucleic acid as the delivery molecule (D). The reagent development will focus on the chemical requirements for alkylation (step 2) and in situ release of the delivery molecule (step 3). The methodology will make use of the bifunctional electrophilicity and nucleophilicity of quinone methides.

Quinone methides are highly reactive electrophiles at the exocyclic methylene.[23,24] para-Quinone methides can be readily formed from phenols by elimination of a para-benzylic leaving group.[25D] As illustrated in FIG. S2D, phenol protection with a photo-labile protecting group (1) would allow the generation of phenoxide or phenol 2 under mild photolysis conditions followed by quinone methide formation (3) upon elimination of the benzylic leaving group. Alkylation of quinone methide 3 with the nucleophilic residue of the target biomolecule results in the generation of phenoxide 4. This can intramolecularly cleave an ortholinkage to afford 5, the covalently modified carrier biomolecule, and release the delivering molecule.

Examining a series of protected phenols (photolabile protecting groups) substituted with a variety of para-benzylic leaving groups (initially ainmonium groups) in conjunction with one of several types of cleavable linkers (i.e., ester, thioester, amide, carboxylate, carbamate) would allow optimization of the compatability of these functional groups. Specifically, model studies will focus on the rate of quinone methide formation and its reversibility versus the rate of linker cleavage, both requiring the phenolic/phenoxide precursor (2 and 4,FIG. S2D). Functionalizing this substrate such as to render it water soluble will allow its evaluation under physiologically relevant conditions. Preliminary limitations of this methodology can be examined by testing its reactivity with relevant biological nucleophiles (i.e., thiols, amines, alcohols, imidazoles, carboxylates, phosphodiesters) under various conditions.

5. Preliminary Results

Time Commitment to Present: Approximately 6 months

Preliminary results have been obtained on model systems which address a few key aspects of the proposed reagent for affinity transfer alkylation. These initial results include:

(1) Alkylation of a dialkylphosphate with quinone methide 6 to form trialkylphosphate 7 has been accomplished according to FIG. S3D.[26D]

(2) The hydrolytic stability of a trapped trialkylphosphate (acylated phenol 8,FIG. S4D) related to that which will be trapped out intramolecularly in the affinity transfer labeling reagent (5, FIG. S2D) is being investigated. This was prepared by an independent approach according to FIG. S4D.[27D,28D]

(3) The formation of a quinone methide via photolytic initiated deprotection of dibenzylphosphate ammonium salt 9 is presently under investigation (presumed mechanism is shown in FIG. S5D).[29D] Preliminary evidence suggests transient formation of quinone methide 6, however further studies are still necessary.[30D]

Precursor 9 was prepared as the dibenzylphosphate salt[29D] from the corresponding benzylamine 13 which was synthesized according to FIG. S6D.[31D]

6. Research Plan and Procedures 6.1. Continuation of Model Studies on Small Molecule Systems Initial Time Commitment: 6 months (prior to progressing to next stage). This research should be essentially completed by the grant start date.

Long-term Commitment: 1–2 years (for full study beyond the necessary groundwork)

We are presently continuing our studies with small molecule model systems in order to assess and optimize the development of the affinity transfer alkylating reagent at each stage. These studies are planned to progress as follows.

The role of the benzylic tertiary or quaternary ammonium leaving group is to increase the effective concentration of the quinone methide alkylating reagent in direct proximity of the targeted phosphodiester residue (FIG. 3D).[35D]

FIG. 3D. The ionic association of the tertiary or quaternary ammonium quinone methide precursor with dibenzylphosphate in order to accentuate phosphodiester alkylation.

Quinone methide formation by elimination of a para-benzylic quaternary ammonium leaving group has been accomplished by other researchers.[36D] We are presently examining alkylation of dibenzylphosphate with quinone methides produced from quaternary ammonium precursors in place of the tertiary ammonium precursors (FIG. 3D). We are also exploring methods for trapping the alkylated product phenoxide (11, FIG. S5D) as an acetate in order to afford a stable phosphotriester[38D] and more closely replicate the designed target reagent with a model system.

Additional studies with related model systems will assess changes such as the particular photolabile protecting group employed[37D-39D] and the substituents on the quaternary ammonium. The latter studies will allow optimization of its solubility properties, its ability to ionically associate with the phosphate, its capacity as a leaving group, and its nucleophilic reactivity upon elimination (reversibility). We are examining a tunable ammonium leaving group through the use of a para-substituted aniline derivative (FIG. 4D, presently a phenetidine derivative (X=OEt) has been prepared).[34D,40D]

Control reactions for assessing the benefit of ionic association on the phosphate alkylation reaction will include alternative, non-ionic leaving groups such as a bromide and ester derivatives (i.e., methanesulfonate and acetate).[41D] Other derivatives having benzylic substituents which will not eliminate to form a quinone methide will be used to assess competitive inhibition of the reaction and the effects of the decomposition products of photodeprotection.

FIG. 4D. A tunable quaternary ammonium leaving group where X can be an electron withdrawing or an eleoctron donating group. This can also be a tertiary axnmonium leaving group with a tunable pKa.

The effect of pH on the rate of the reaction will also need to be established. A variety of investigations into the effects of pH on nucleophilic addition reactions with quinone methides have been conducted.[42D] We will focus our studies on the pH range 6.7–8.1 using phosphate buffers. A water soluble quinone methide derivative will be synthesized as described below (18,FIG. S7D), except the ester will be hydrolyzed to afford the carboxylic acid. Kinetic runs can be monitored by UY-vis spectroscopy at 25° C. after photo-deprotection to form the transient quinone methide species in the presence of the desired nucleophile at constant temperature (±0.25° C.)[43D] We can also examine the effects of varying the ionic strengths on the rates of these reactions.[21D]

The delivering molecule cleavage in the affinity transfer reagent will also be assessed with model studies. The model system is designed to test the lactonization of the phenoxide with the delivering molecule linker to afford the phenolic lactone (4 to 5, FIG. S2D). These studies will require the synthesis of 19 which will be accomplished according to FIG. S7D.[44D]

A fully functionalized model system will be examined for functional group compatibility, product stabilitiy, and competitive reactions for reagent design optimization. The synthesis of 22 (FIG. S8D) can be accomplished by extending the chemistry described above to incorporate a phosphodiester by standard methods[50D] affording intermediate 21 followed by phosphate deprotection.

The initial goal will be to determine the efficacy of an ester (ethyl ester) as the cleavable linker. Subsequent studies will also assess the efficiency of an amide as the cleavable linker. Precedent for the displacement of an amide linker with a phenoxide-type species includes a recent report of a redox-sensitive protecting group which operated by the spontaneous release of an amine from an amide by lactonization of hydroquinone 24 reductively formed from corresponding quinone 23 (FIG. S9D).[51D]

Should a more labile linkage prove necessary, a carbonate or carbamate can be examined. This will require a modification to the approach shown above (FIG. S7D) or could be obtained using the approach shown in FIG. S10D.

6.2. Second Generation Development: Dinucleotide Phosphate Alkylation

Initial Time Commitment: 6 months (prior to progressing to next stage). This should be approximately where project will stand at grant start date.

Long-term Commitment: 1 year (for full study beyond the necessary groundwork)

Attention will next be given to alkylation of the phosphate residue of DNA and RNA. Initial investigations of these reactions will focus on protected nucleotides in order to determine chemoselectivity of the alkylation. Most of the required derivatives for these studies are either commercially available or can be readily obtained according to established procedures.[9-11D,50D,52D] With the base protected, examination of competitive alkylation with the 5'-hydroxyl can be assessed with a 3'-phosphate deoxyribonucleotide derivative. Competitive alkylation with the bases can similarly be assessed by examining 5'-dimethoxytrityl protected, 3'-phosphate deoxyribonucleotides of all four natural bases. Similarly, chemoselectivity with a 2'-hydroxyl of the ribonucleotide series can be examined by using a 5'-dimethoxytrityl, base protected, 3'-phosphate ribonucleotide. The characterization of the various products from these studies will rely predominantly on established NMR analysis techniques.[53D] These studies will not only help in determining chemoselectivity, which again is expected to be accentuated via the ammoniunm-phosphate ionic association, but will also afford valuable control derivatives for analysis of byproducts in further studies. Examination of the stability of the various phosphate triester nucleotides will also be assessed.[28D]

The alkylation and stability of the phosphate of dinucleotides will also be studied in order to allow a detailed analysis of reaction conditions and product characterization. The products of these reactions will be useful for standards in the investigations of reactions with larger oligonucleotides.

A series of 3',5'-unprotected dinucleotides will be analyzed incorporating all four nucleic acid bases [guanosine (G), cytosine (C), adenosine (A), and thymidine (T)] used in combinations which could potentially hybridize under the reaction conditions. These reactions will allow investigation of the effects of buffers, salts (nature and concentration of each), pH, and temperature on the rates and efficiency of the alkylation reaction. Investigations described previously for preliminary model studies can also be repeated in this system to assess the benefits of ionic association on the reaction, determination of the optimal photolabile protecting group and leaving group, and optimization of the phenoxide trap or cleavable linker for the reaction. These reactions will also allow the further assessment of chemoselectivity under in vitro conditions, where product analysis will be assisted by the characterization of the various possible alkylation products obtained from the previous model studies described above.

Particular concerns which will be addressed in these investigations include analysis of the effect of various buffers on the ability of the affinity transfer labeling reagent to ionically associate with the phosphate residue. Consideration of competitive buffer association with the phosphate residue relative to the ionic association of the affinity transfer labeling reagent with the phosphate residue will be addressed. Literature precedent fully supports the ionic association of ammonium and phosphate residues in a variety of common buffers.[5D] Also potential reaction of the buffer with the electrophilic quinone methide intermediate must be addressed. Again, there are many examples of nucleophilic additions to reactive quinone methide intermediates in a variety of buffers with no evidence for competition with buffers.[42D,55D] Effects of pH on the reaction will be particularly relevant in the case where a protonated amine is the leaving group. Changes in pH will also effect the rate of photolysis (including optimal wavelength for absorption) and the fate of the photodegradation byproducts, the stability of the phenoxide, the reactivity of the quinone methide, the nucleophilicity of the phosphate (the last three factors all having an impact on the rate of quinone methide formation), and the rate of phenoxide trapping/linker cleavage. Inclusion of various salts at differing concentrations may also effect the reaction in ways similar to those already mentioned. There is also precedent for ammonium/phosphate ionic association in the presence of other salts.[2D] All of these reactions, being conducted on relatively small molecules, should still be readily analyzed using NMR analysis ($^1$H and $^{31}$P).[53D] They can also be monitored and characterized by UV-vis and HPLC analysis to determine rates and identify products and potentially intermediates as well (low temperature NMR). A series of pertinent control reactions can also be examined in order to help define various mechanistic and reactivity aspects of the reaction. These control reactions will be described in the following section.

Investigations regarding stereoselectivity in the reaction at the dinucleotide stage can also be pursued. It has been demonstrated by Quaedflieg and coworkers that hybridization of a combination of methylphosphate triester dinucleotides occurs in water to afford the base paired duplexes.[56D] In this work, the diastereomers of the methylphosphate triester dinucleotides were separated[57D] to afford the Rp-Rp duplex and the Sp-Sp duplex. We could investigate the effect of hybridization of a series of methylphosphate triester dinucleotides on our photoinitiated alkylation reaction. By running the alkylation reaction in water on a hybridized duplex between the methylphosphate dinucleotide d(Ap$_{Me}$C)[58D] with the complementary dinucleotide d(GpT) at the appropriate temperature to maintain antiparallel duplex formation (31, FIG. 6D), we can assess the stereoselectivities in alkylation of the d(GpT) when hybridized to a complementary sequence which will not undergo reaction. These studies would require the analysis with both diastereomers of the methylphosphate dinucleotide.[6D] The product stability and conformational changes which occur upon alkylation of the dinucleotide in these hybridized duplexes will also be of interest (32, FIG. 6D). These studies will be more pertinent with longer oligonucleotides, but these dinucleotide systems will allow better product characterization. NMR analysis will allow the determination of diastereoselectivities (diastereomers afford differing $^{31D}$P resonance signals).$^{57D}$ 2D-NOE data will be helpful in assessing the structural characteristics of the products.$^{6D,59D}$ FIG. 6D. A methylphosphate d(Ap$_{Me}$C) hybridized with complementary d(GpT) [duplex 31] for the analysis of the photoinitiated alkylation reaction to afford the alkylated duplex 32.

Although these studies on dinucleotides are useful for a detailed mechanistic and product analysis, they still may not represent reactions of larger oligonucleotides. The ability of larger oligonucleotides to form characterizable helical structures and complementary oligonucleotides to hybridize into double (and even triple) helical structures will likely have significant impact on the course of the affinity transfer labeling reaction. The effects may be realized in chemo-, regio-, and stereoselectivity of the reaction.

6.3. Third Generation Development: Multiple Phosphate Alkylation of Oligonucleotides Initial Time Commitment: 1 year (prior to moving on to next stage)

Long-term Commitment: 2 years (for fall study beyond the necessary groundwork)

Our studies will next progress into examining reactions of the affinity transfer alkylating reagent with longer oligonucleotides. These will first focus on alkylation of multiple phosphate residues in single stranded DNA (ssDNA). All oligonucleotides can be designed and synthesized$^{60D}$ so as to control complementary hybridization. A special design feature will be incorporated into the oligonucleotides in order to facilitate product purification and will be described below. Initial studies will involve short oligonucleotides (4- to 8-mers) in order to facilitate product analysis. At this point in our studies, optimal conditions for the reaction should be realized. The reactions will be monitored by UV-vis analysis for hyperchromic effects with the nucleic acid bases and for observing changes in absorption of the photolabile protecting group and the quinone methide precursor and products which will be well characterized by this point in our studies. UV Hyperchromicity will allow assessment of the effects of alkylation on base-pair stacking interactions as the reduction in UV absorption is a well established sign of increased helical stacking.$^{61D}$ The latter results can be further compared with CD spectra which are especially sensitive to changes in the asymmetric surroundings of a chromophore.$^{62D}$ Progressing into studies involving oligonucleotides of complimentary design for forming double stranded DNA (dsDNA) will allow assessment of the effects of helicity on the alkylation reaction. It is known that dsDNA induces helical stacking with aromatic moieties which interact with it.$^{62D}$ This effect alone might help to promote the desired alkylation reaction with DNA, and should be evident by the UV hyperchromicity of the association complexes formed between the cationic alkylating reagent and DNA prior to reaction. This hyperchromic effect should also be evident in the alkylated product formed after the reaction in the UV spectra of the aromatic alkylating reagent which should align in a helical stack on the outer surface of the dsDNA. Comparison of data obtained from the alkylation on ssDNA with that from dsDNA should afford information regarding the effects of a more ordered helix on the reaction. This helical stacking of the aromatic groups of the triester on the outer surface of the dsDNA helix might also be evident by CD analysis in conjunction with the hyperchromic UV shifts. It will be of interest to determine what effect the alkylation will have in distorting the dsDNA as evidenced by changes in the 220–300 nm region of the CD spectrum.$^{63D}$ A series of accompanying control reactions will be delineated below.

Product purification will be conducted taking advantage of procedures used for purifying methylphosphonate modified oligonucleotides.$^{64D}$ In order to facilitate purification of the hydrophobic alkylated phosphate oligonucleotides produced in these reactions, the 5' phosphodiester linkage of each oligonucleotide will be protected as the allylphosphate triester during their synthesis. $^{10D}$ This protection methodology will allow for a completely deprotected oligonucleotide (except for the last 5' allylphosphotriester linkage) to be synthesized and used in the reactions. After the alkylation reactions, this 5' allylphosphate linkage can be selectively deprotected under mild palladium catalyzed conditions.$^{10D}$ The resulting oligonucleotide, having a single (assuming complete alkylation) 5' phosphodiester linkage, will be more readily solublized, purified by cation exchange resins (e.g., NH$_4$HCO$_3$ elution from a DEAE-cellulose column),$^{65D}$ and available for 5'-labeling with $^{32}$P using T4 polynucleotide kinase for polyacrylamide gel electrophoresis (PAGE).$^{60D}$ Product analysis will be carried out at multiple levels. Assessing the degree of alkylation of the oligonucleotides can be determined qualitatively by gel migration analyses using PAGE on 5'-$^{32}$P labeled oligos. The higher the degree of alkylation, the slower the oligo should migrate. For short oligonucleotides, partially alkylated products should resolve out and be quantified by densitometry or autoradiography to allow determination of the degree of alkylation. Alternatively, HPLC might also allow resolution and quantification of the relative degree of alkylation. Initial digestion of the oligonucleotides obtained from the alkylation reaction with snake venom phosphodiesterase AND/OR calf intestine alkaline phosphatase should result in cleavage of the oligonucleotides only at unmodified phosphodiester linkages, as phosphotriester linkages are known to be stable to degradation.$^{8D}$ HPLC analysis of the resulting products should allow determination of the degree of alkylation and if there was any regioselectivity (i.e., Is there a difference in degree of alkylation at the ends or the middle of the oligonucleotide?). The degree of alkylation could be further confirmed chemically by mass balance. This approach is dependent on the lower hydrolytic stability of the benzylic residue on the phosphate triester. Although there is precedent for the hydrolytic instability of benzylphosphates as opposed to other alkyl groups,$^{66D}$ the effect of the para-alkoxy substituent on the phenyl ring might slow the rate of hydrolysis$^{67D}$ and this question must first be resolved. However, assuming the benzylic alkyl substituent can be hydrolyzed (or hydrogenolyzed) selectively, then the difference in the hydrolyzed mass from the alkylated precursor mass should allow determination of the extent of alkylation.

Assessing stereoselectivity of the alkylation reaction on oligonucleotides might be accomplished by 2D-NMR$^{53D-59D}$ and possibly by an experimental enzymatic method as well. The resulting fractions from enzymatic digestion could be analyzed by 2D-NOE experiments in order to determine if any stereoselectivity occured in the reaction.$^{68D}$ Based on the extensive amount of NMR work in the literature related to diastereopure methylphosphate and methylphosphonate containing oliaonucleotides, it is hoped that analysis will be greatly facilitated by comparison to known examples.$^{6D,7D,13D,53D,59D}$ We will also attempt crystalization of alkylated products for characterization. A more experimental approach for analysis of stereoselectivity in the reactions involves the use of a methyltransferase enzyme, an E.coli Ada regulatory protein, which has demonstrated the ability to repair methylphosphotriester mutations in DNA.$^{7D,14D,69D}$ This repair enzyme has been shown to selectively repair the Sp-configuration of the methylphosphate DNA, presumably due to its presence in the major groove where the enzyme can also repair the thymidine 0–4 methylated mutation.[14D] This selectivity might allow determination of reaction stereoselectivity by treating the products with the enzyme and determining if dealkylation occurs. This approach is rather speculative and likely impractical as it is not known if the enzyme would accept a benzylic-type substituent in place of a methyl group. Further, this enzyme operates in a stoichiometric manner by alkylation of a cysteine residue in order to demethylate the phosphate, and it is not known how much of this enzyme would be available.

A variety of control reactions will be completed in order to help define the mechanism and determine the products of the reaction. These controls will include the use of an affinity transfer labeling reagent derivative without a photolabile protecting group (i.e., methyl phenol ether derivative 33, FIG. 7D) in order to examine the effects of this functionality and its photodegradation byproducts, and also to examine the possibility of an alkylation reaction through a direct displacement reaction at the benzylic position. This control will also assess the effect of ionic association with the oligonucleotide phosphate residues without consequent alkylation. A control reaction using a nonionic leaving group (i.e., benzylbromide derivative 34, FIG. 7D) will also be run in order to determine nonspecific reactions which cannot ionically associate with the phosphate residue. It may also be possible to determine the effective concentration of the quinone methide derived from the ammonium/phosphate salt complex by determining the concentration of 34 required to achieve equivalent rates of reaction with the phosphate upon photolytic activation. A prerequisite to this analysis would be determining the difference in rate of quinone methide formation between the ammonium derivatized quinone methide precursor and 34. The equilibrium constant for ionic association of the phosphate/ammonium complex would also be required (both of these values could be determined spectroscopically). The phosphate concentration could also be varied in the photoinitiated reaction with 34 in order to determine the effective concentration resulting from ionic association. An additional control reaction with a derivative that has no benzylic leaving group (i.e., p-methyl derivative 35, FIG. 7D) and thereby cannot form the quinone methide nor can it ionically associate with the phosphate residue will allow assessment of phenol and photodeprotection byproducts. Addition of an ammonium ion to the reaction mixture at varying concentrations will allow assessment of the effects of inhibition of ionic association on the reaction and possibly aid in determining the effective concentration of the quinone methide resulting from ionic association. A final control to be included will be an affinity transfer alkylating reagent derivative having no intramolecular phenoxide trap/delivering molecule linker. This will allow assessment of the effect of the phenoxide on the reaction.

FIG. 7D. Control reagents to be used for defining various aspects of the phosphate alkylation reaction.

The application benefits which can be derived from this first phase of investigations will involve the in situ, post-synthetic modification of DNA. These applications will be most relevant to antisense technology and should afford a new and efficient approach for the formation of phosphate triester modified oligonucleotides and a new approach for the multiple-labeling of oligonucleotides for hybridization studies.[70D] Potential future work might involve extension of this labeling methodology to other phosphate containing biomolecules.

6.4. Fourth Generation Development: Site-Specific Affinity Transfer Alkylating of Single Stranded DNA Initial Time Commitment: 6 months (prior to moving on to next stage)

Long-term Commitment: 2 years (for full study beyond the necessary groundwork)

The next phase of investigations will involve site-specific delivery of the reagent through an attached oligonucleotide in order to examine the transfer step in the development of this affinity transfer alkylating reagent. The reagent could be attached to a delivery oligonucleotide through several possible linkers.

The first linker attachment to be discussed will be a simple linker from a 5'-phosphate of the delivering oligonucleotide. There are a tremendous variety of linkers which have been reported,[4D] of which one will be proposed for use in these studies. However, it should be noted that many alternatives are available for oligonucleotide derivatization with a linker to the transfer affinity labeling reagent being developed. Based on modeling estimates, an initial linker will have 16 atoms from the 5'-phosphate oxygen of the oligonucleotide to the benzyl ring of the reagent. Commercially available 5'-modifiers can be purchased as the phosphoramidite for direct incorporation onto an oligonucleotide during automated synthesis. One readily available linker derivative is the 5'-amino modifier 36 with either a $C_6$ or a $C_{12}$ chain length (FIG. 8D).[71D] Although there are thiol and hydroxyl 5'-modifier phosphoramidites commercially available, the appropriate $C_{12}$ chain length phosphoramidites 37 and 38 will need to be synthesized.

FIG. 8D. 5'-Modifier phosphoramidites for linker attachment of oligonucleotides to the transfer affinity reagent.

These will be synthesized in a standard manner according to FIG. S11D. The commercially available diol or bromoalcohol 39[72D] will be protected as the benzoate ester 40 and the bromide converted to thiol 41 with sodium sulfhydride in DMSO in order to minimize thioether formation.[73D] The alcohol 40 and thiol 41 will then be protected as the 4,4'-dimethoxytrityl ethers,[74D] debenzoylated under mildly alkaline conditions[75D] and converted to the automated synthesizer-ready phosphoramidites 37 and 38 according to standard protocol (FIG. S11D).[76D] Following attachment of these phosphoramidite modifiers to the 5'-end of the desired oligonucleotides on the automated synthesizer, the trityl protecting groups will be removed according to standard protocol,[60D] and the oligo will be ready for attachment of the affinity transfer labeling reagent.

One potential drawback with this 5'-linker will be noted. The lack of control due to the high degree of flexibility of the linker affords little control over positioning of the alkylating species. This will be addressed by an alternative linker in a later section of this proposal (see 6.7). For our initial investigations into site-specific delivery of the transfer alkylating reagent the 5'-linker will nicely meet our objjectives based on the synthetic flexibility and ease of access with commercially available (or easily produced) derivatives, and their ready applicability to automated synthesis routines.

The transfer affinity reagent will be prepared initially with no reporter group incorporated. In subsequent investigations an Fe-EDTA complex will be incorporated as the reporter group on the affinity transfer alkylating reagent in order to effect DNA cleavage. Carboxylic acid 42 (FIG. S12D), obtained from the hydrolysis of 23 (FIG. S8D) will be activated for ester, amide, or thioester bond formation with 1-(3dimethylaxninopropyl)-3-ethylcarbodiimide hydrochloride (EDCD and 1-hydroxybenzotriazole (HOBt) in a manner similar to a procedure used by the PI to attach the iron-binding domain of bleomycin to the DNA-binding domain of HIN recombinase.[77D] This will require the fully protected, support-bound oligonucleotides having the free amine, alcohol or thiol (43, FIG. S12D) to be stirred at ambient temperature in DMF with the carboxylate activating reaction mixture until analysis of aliquots with indicator dyes reveals the consumption of the carboxylic acid or by ninhydrin analysis for the reaction with the amine. The derivatized oligonucleotide (44) will then be deprotected, cleaved from the solid support, and purified by RP-HPLC affording the ammonium acetate derivatized oligonucleotide 45 (FIG. S12D).[60D] For some experiments it may be desirable to $^{32}$P-label the 3' end of these derivatized oligonucleotides in order to allow analysis after the label transfer reactions. The derivatized oligonucleotides will be characterized by enzymatic digestion and HPLC analysis against coinjections of standard solutions of the nucleoside components and a reagent standard with the attached linker. An exact mass might also be possible by a technique such as laser desorption time-of-flight mass spectrometry. Confirmation of the successful attachment of the reagent should also be evident by the absorbance ratio at 260 nm (for DNA) versus that at 350 nm (for the reagent).

It is realized that the affinity transfer labeling reagent may readily self associate, and the impact of this potential complication will need to be determined, but some of the subsequent attachment methods to be discussed below may adequately circumvent this potential problem. The photolytically activated affinity transfer alkylating reaction will be accomplished by allowing prehybridization of the oligo-bound reagent with a synthesized complimentary target oligonucleotide labeled at the 5' end with $^{32}$P.[60D] The reagent bound delivering oligo's for these studies will be 8-nucleotides in length and the target sequence will be a 28-mer with the hybridization sequence 8-nucleotides in from the 5' end and 12-nucleotides in from the 3' end for reasons discussed below. The only sequence preference for the hybridization site will be to have C-G base pairs at the ends to prevent fraying of the duplex and to contain all four bases so as to test the generality of the labeling methodology. The reaction will be run under standard conditions in 20–50 mM potassium phosphate (pH 7.0), 100–500 mM NaCl, 25–37° C. Upon reaching hybridization equilibrium (30 min), the reaction will be initiated by photolysis of the reaction mixture in Pyrex glassware with a 150 W Xenon arc lamp using a 345 nm long filter. Analysis of both the delivering oligonucleotide ($^{32}$P-labeled at the 3' end) and the modified target strand ($^{32}$P-labeled at the 5' end) can be accomplished by denaturing polyacrylamide gel electrophoresis (PAGE) and densitometry or autoradiography. This should allow quantification of the products formed in the reactions. By running these gels with standards of the delivering oligonucleotide modified with the linker that would result after successful transfer of the labeling reagent (derived from 43, FIG. S10D), as well as both the starting oligonucleotides and their accompanying Maxam-Gilbert sequencing lanes, the reaction products should be identifiable by their gel shifts. The released delivery oligonucleotide should co-spot with the authentic material, and the phosphate alkylated product oligo should migrate slightly slower than the unmodified target strand due to the loss of one charged phosphate. As this may prove difficult to unambiguously identify, it may prove beneficial to append a reporter group to the labeling reagent which would allow its unique identification, such as a fluorescence tag, which will be discussed below.

Identifying the site of alkylation of the target strand will be accomplished by enzymatic digestion of the product strand and HPLC analysis. As previously mentioned, snake venom phosphodiesterase and alkaline phosphatase will not cleave a phosphotriester linkage; therefore, at the site of alkylation a dinucleotide sequence will result from the digestion. HPLC analysis of the digestion with coinjections of the various dinucleotide phosphotriesters produced in the earlier experiments on dinucleotides, will allow identification of the site(s) of alkylation. Isolation of a sufficient amount of the digested dinucleotide phosphotriesters might also allow 2D-NMR analysis in hopes of determining stereoselectivity of the alkylation reaction.

One analysis which will also be attempted is hydrolytic cleavage of the alkylated DNA target at the site of phosphotriester fomation. This will not only be a useful method for analyzing the amount and site of phosphate alkylation, but may have significant implications toward the potential for site-specific hydrolytic cleavage of DNA. The target site of the labeled DNA will be positioned so that if the site of alkylation is near the 5' end of the delivering strand, and cleavage at that site of alkylation on the labeled target strand can be hydrolytically induced, the resulting fragments will be of sufficiently differing lengths relative to themselves and the delivering oligo to allow identification based on PAGE mobility. This means that with an 8-mer delivering oligo the site of target alkylation should be 12-nucleotides from the 3' end and 16-nucleotides from the 5' end of the target strand. It has been shown that the rate of hydrolysis is increased at sites of phosphotriester modified DNA.[78] However, as previously mentioned, it has also been demonstrated that benzylphosphate esters hydrolyze more rapidly than other alkylphosphates,[66D] although the effect of the para-alkoxy substituent in the alkylation product with the labeling reagent may alter the hydrolysis rate.[67D] The hydrolytic stability of the alkylated DNA will therefore need to be determined. Should induceable cleavage occur at the site of phosphate alkylatlon, then autoraaiograph analysis of PAGE runs will allow determination and quantification of the site of alkylation.

Many of the same control reactions which were discussed in the preceeding section would also be applicable in these studies. Accompanying control reactions run with the target strand (all oligos $^{32}$P-labeled) should include; (1) a reaction without the attached reagent, but with the linker arm, (2) a reaction with an unmodified delivering oligonucleotide, (3) a reaction with free labeling reagent not attached to an oligonucleotide, (4) a fully functionalized delivery oligo with the attached reagent, but not photolyzed to initiate the reaction, (5) a reaction with the fullly functionalized delivery oligo and attached reagent and some other $^{32}$P-labeled random sequence to examine nonspecific reaction. Included with these control reactions should be a reaction with no target strand in order to probe self-reaction of the reagent derivatized delivering oligo (3'-$^{32}$P-labeled).

A series of experiments will need to be conducted in order to determine the effects of various parameters on the reaction. One series of experiments will vaiy the type and concentration of buffer used, one series will vary the salt concentration and introduce additional salts such as $MgCl_2$, one series will vary the pH of the reaction system, one series will vary the equilibration time prior to initiating reaction, and a final series will vary the temperature of the reaction (0 to 37° C.).

It may prove beneficial to include a flourescent tag attached to the labeling reagent as a handle for identification. Fluorescien is representative of a nonassociating organic fluorophore and has been used as the 5-isothiocyanate derivative to post-synthetically modify a primary amine linker attached to a fully deprotected oligonucleotide in 70% yield.[79D] A three step procedure from 18 should readily afford the necessary labeling precursor (FIG. S13D). Ozonolysis of 18 followed by a reductive workup[80D] will produce the aldehyde for a Wittig reaction under conditions which favor the (E)-olefin[81D] to give 47 after hydrolysis of the ethyl ester.

Coupling of the labeling reagent 47 to the oligonucleotide will then be accomplished as previously discussed (FIG. S12D) to afford amine derivative 48 (FIG. S14D). At this point the fluorescein-5-isothiocyanate could be added to the protected, support-bound modified oligonucleotide, or it could be added post-synthetically to the cleaved, deprotected oligo to afford 49 (FIG. S14D).[79D] A variety of other reporter groups could be attached at this stage as well. For example, the EDTA.Fe(II) moiety could be attached for cleavage analysis at the labeling site. This would be accomplished according to known chemistry also in a post-synthetic manner providing 50 (FIG. S14D).[82D] Another example of a reporter group which could be attached through amine 48 is a derivative of tris(2,2'-bipyridine) ruthenium (II) (Ru(bpy)$3^{2+}$).[83D] This would be accomplished using the activated bipyridine derivative succinimidyl-4-carboxy-4'-methyl-2,2'-bipyridine followed by reaction with Ru(bpy)2(H2O)$2^{2+}$ according to the established protocol[83D] to give the covalently attached derivative of Ru(bpy)$3^{2+51}$ (FIG. S14D). It should again be emphasized that the focus of the present research will be in developing the chemistry required to effect the affinity transfer alkylating methodology, and that the specific type of reporter molecules which might be used will be dependent on the investigations being pursued and the chemical compatibility of the reporter group with the chemistry necessary to attach it to the labeling reagent. As these examples would demonstrate, the standard mild protocols for labeling are easily compatible with the reagent being proposed. The limitations in reporter groups might be more associated with the specific types of molecular interactions they undergo at the target site. If there is potential to interfere with the delivering reagent or the target site through ionic association, then their use might be limited.

6.5. Fifth Generation Development: Site-Specific Affinity Transfer Alkylation of Double Stranded DNA Initial Time Commitment: 6 months (prior to moving on to next stage)

Long-term Commitment: 1–2 years (for full study beyond the necessary groundwork)

Site-specific affinity transfer alkylation will also be investigated with dsDNA through hybridization of the delivering oligonucleotide in a triple helix motif.[84D] For these investigations, all the previously detailed analyses and control reactions would be used with limitations in the base composition used for the delivering oligonucleotides as all pyrimidine (pyr) containing oligonucleotides would be used for targeting a purine (pur) tract of the dsDNA to form a pyripuripyr triple helix complex. One particular focus of these investigations will be in determining if either or both strands of the target DNA can be individually labeled. This will involve modification of the size of the linker which can be readily accomplished with slight modifications of the chemistry described previously (FIG. S13D). For these studies, an EDTA.Fe(II) reporter group would be attached to the labeling reagent (FIG. S14D). Attachment of EDTA.Fe (II) to small molecules has proven useful for structural studies of nucleic acids.[85D] The iron complexed carboxylates will not interfere in the ionic association of the reagent ammonium with DNA phosphate and should therefore pose no problems for these investigations.[86D] The reductively induced cleavage of DNA with the EDTA.Fe(II) reporter group upon addition of such reducing agents as dithiothreitol or sodium ascorbate will produce a distinguishable cleavage pattern due to the generation of a nonspecific diffusible oxidant (presumably hydroxyl radical). The characteristics of the cleavacre pattern will allow the determination of the sequence location of binding and which strand it is bound to.[87] This will be based on the size and amount of the resulting cleavage fragments affording asymmetric cleavage bands which will be visualized by high resolution PAGE on the cleavage reaction products when both strands of the dsDNA target are $^{32}$P end labeled.

6.6. Application of the Affinity Transfer Alkylating Reagent: Structural Mapping of a tRNA Through Autocleavage Initial Time Commitment: 6 months (prior to moving on to next stage)

Long-term Commitment: 1 year (for fall study beyond the necessary groundwork)

Although the primary focus at this stage in the development of this affinity transfer alkylating reagent is in determining the mechanism and selectivity of the alkylation chemistry and optimizing the design aspects of the reagent for eventual in vitro and in vivo performance, it will be helpful to field test the reagent in some application oriented investigations. For these initial studies it is of interest to apply the reagent towards a molecular structure analysis in a system which has been investigated by other methods to allow correlation with our methodology. An attractive candidate for this research would be a structural study of yeast phenylalanine tRNA. The three-dimensional structure of yeast tRNA$^{Phe}$ has been well characterized by X-ray crystallography and solution studies.[88D] Importantly, these structural studies have been reasonably well correlated to tRNA-EDTA.Fe(II) autocleavage investigations where EDTA derivatized uridine nucleogides have been incorporated into the tRNA structure.[82D] This combined foundation should afford us the opportunity to use the affinity transfer labeling reagent to introduce an EDTA.Fe(II) reporter group into the tRNA at selected sites and induce autocleavage by addition of dithiothreitol (DTT) to determine how well the resulting high resolution PAGE cleavage data correlates with the known structural studies. It should be noted again that the nonspecific diffusible oxidant produced by this autocleavage methodology allows the spatial position of the EDTA.Fe(II) species to be determined based on the cleavage at several nucleotide positions proximal in three-dimensional space. Analysis of the cleavage products by gel electrophoresis will then allow determination of the resulting fragments and their relative amounts which correlates to the vicinity of the cleavage site to the location of the EDTA.Fe moiety. Because autocleavage analysis has already been conducted on this tRNA, analysis with the affinity transfer labeling reagent should be greatly simplified.

The tRNA for these studies can be synthesized and $^{32}$P labeled according to published procedures.[82D] Labeling the tRNA will be accomplished by preparing a reagent derivatized oligonucleotide having the EDTA ligand attached as described previously. Targeting the phosphate residue of U47 (this base was derivatized for autocleavage by Han and Dervan) will allow a near correlation with published results.[82D] This requires the delivering oligonucleotide to have the sequence 5'-CCTCCAGATC-3' for 5' linker attachment of the labeling reagent. The tRNA will be denatured by heating at 70° C. followed by mixing the reagent derivatized delivering oligo and slow cooling to generate the hybridized complex 53 (scheme 15). The reaction will be initiated by photolysis as already described which should induce alkylation to afford complex 54 followed by lactonization of the resulting phenol via release of the delivering oligo to give labeled RNA 55 (FIG. S15D). The delivering oligo will be separated and the labeled RNA analyzed by PAGE, noting any decrease in gel mobility relative to unmodified tRNA which would suggest the alkylation of a phosphate residue. The labeled tRNA would then be allowed to renature by again heating to 70° C. and slowly cooling to room temperature prior to analysis which would presumably afford the EDTA labeled tRNA 56 (FIG. S15D).

The lead cleavage assay used by Han and Dervan will allow determination of any deleterious effects of the label on the folding of the tRNA to its native structure.[82] The autocleavage will then be induced by the addition of Fe(II) and DTT and the cleavage products analyzed by autoradiography of the high resolution denaturing polyacrylamide gels. The results will be correlated with Han and Dervan's results as well as other structural characterizations of the tRNA$^{Phe}$. These investigations should allow assessment of the accuracy and the efficiency of the label transfer process.

6.7. Future Development: Alternative Delivery Linker

A future goal likely not to be addressed in the time frame of these investigations.

The high degree of flexibility in using these oligonucleotide 5'-linkers for delivery of the transfer labeling reagent renders precise control over the possible positions for alkylation very difficult. As an alternative to this linker methodology, a linker from the 2'-oxygen of a guanosine ribose derivative will be developed which will offer much tighter restraints on where the alkylating reagent will be positioned. The fully functionalized nucleotide 52, which will be incorporated into a delivering oligonucleotide, is pictured in FIG. 9D. Reports of phosphoramidites of 2'-O-alkylamine derivatives of purines have been published and could therefore be readily accessed (five steps from the ribonucleoside to the phosphoramidite).[89D] This would result in an amine derivatized oligo which could be attached to the labeling reagent as already described. The 2'-O-linker is designed specifically for a guanosine nucleotide so that an amide functional group in the linker can hydrogen bond with the minor groove face of this purine base. Although this hydrogen bonding interaction is based on a cis-amide conformation, it is felt that this might be energetically favored as the presence of the alkyl linker at the 2'-oxygen will be displacing water molecules from the minor groove (an energetically costly process), which might be offset by the hydrogen bonding with the amide. These two hydrogen bonds will act to direct the linker across the minor groove and position the alkylating reagent in direct proximity to the complementary strand phosphate residue three base pairs to the 5'-side as illustrated in FIG. S16D. Also, due to the steric restraints in the minor groove of B-form DNA, all the bulky substituents of the labeling reagent will be forced out of the groove resulting in the favorable positioning of the ammonium ion towards the helix, which should help promote salt formation with the target phosphate residue and alkylation upon formation of the quinone methide. This positioning is based on modeling linker designs using space-filling models. Prior to actually embarking on a synthesis of such a linker, a more thorough modeling analysis will be carried out using Macromodel 4.5$^{90D}$ employing an MM$^2$ forcefield for the small molecule minimizations followed by the use of an AMBER forcefield for the minimizations within a DNA helix.

The effect of positioning the transfer labeling reagent across the minor groove should enforce a highly regioselective reaction with the phosphate residue. As shown below, upon photolysis the alkylating reagent should be transferred from the delivering oligonucleotide to the target strand at a single phosphate residue (FIG. S16D).

An additional unique feature of this approach through the minor groove might be realized in the alkylation stereoselectivity. As the approach with a 5'-linker will likely come from the least sterically hindered major groove side of the phosphate residue (confirmed with space-filling models), this approach may afford selectivity from the opposite side, and therefore may allow selective access for either diastereomer, depending on the linker used. Again, determination of stereoselectivity will be challenging. Two approaches are planned. We will isolate the products of alkylation by enzymatic digestion and HPLC isolation as described. We will attempt to varify the stereochemistry at the phosphorus center by 2D-NMR analysis on these isolated dinucleosides as described previously. An additional approach may be to attempt to crystallize the alkylated products using shorter oligonucleotides (6 to 8-mers). This will be possible with the 2'-O-linker derivatives because the alkylation reaction will occur at an internal site where the asymmetric helical environment can be maintained. Advantage can also be taken of the label in order to derivatize the site with a heavy atom to aid in crystallization.

6.8. Additional Future Developments

Additional future studies will explore alkylation of other nucleophilic residues common to biomolecules. Such targets will include amino residues of nucleic acid bases and various nucleophilic residues of amino acids. Investigations will initially target residues which are difficult to alkylate using other reagents in hopes of expanding the sites which might be sought for labeling or drug delivery targets. These investigations will progress from simple model systems to more complex targets in order to fully develop the chemistry in a manner similar to that described for this project.

7. Facilities

The University of Arkansas Fullbright College recently completed (June 1995) a 42,000 square foot, $9.2 million research facility for the Department of Chemistry and Biochemistry. Within this new research facility, the PI has one four-man lab (four 6 foot exhaust hoods with approximately 12 foot of bench space per man) for synthetic work with additional instrument and storage space in adjacent laboratories. An additional fourman lab is allocated for biorganic aspects of this work.

As part of the PI's start-up, we are nearly fully equipped (four-man lab) for the synthetic aspects of the project. For the bioorganic aspects of the project, we recently purchased two DNA synthesizers (an ABI 392 and a Milligen Biosearch 8600) and are beginning to purchase the associated purification equipment. We also have two Shimadzu HPLC's (single and double pump, one with an auto-injector, auto collector, variable wavelength detector and integrator), two Hitachi S-2000 UV-vis spectrophotometers (one with a thermostatted 6-cell changer for kinetics), and a scintillation counter (Pharmacia Wallac 1410).

The department has recently acquired a multinuclear, variable temperature 300 MHz Balker NMR, a formerly GE QE-300 MHz system, and a JEOL 270 MHz NMR system, all in newly renovated departmental space. In addition, a Varian 500 MHz multinuclear NMR, two Jeol 90 MHz multinuclear NMR's, an X-ray diffraction facility, a Hewlett-Packard 5982 EI/CI GC-MS, a Perkin-Elmer 287 JR and two Mattson RS 1 IR's, a Cary 218 UV-Vis spectrophotometer, and a Perkin-Elmer 440 fluorometer are provided by the department. All instrumentation use within the department is free of charge.

For molecular modeling studies, the department has a recently acquired CaChe 3.5 Worksystem. There is also a departmental Silicon Graphics W-4D25G-538 workstation with BioSym Insight, Discover, and Delphi software. In addition, Professor Julianto Pranata in the Chemistry department is equipped with workstations and software for running MacroModel 4.5, BOSS 3.1, AMBER 4.0 and MOPAC 6.00. The University computing center has an IBM mainframe with MIDNET link to Cray XMJP.

Secretarial and bookkeeping support are provided by the Department of Chemistry and Biochemistry. The department and university have high quality, professionally staffed glass, machine, and electronics shops for research support. We are presently searching for a replacement for our NMR technician who will be leaving in February, 1995. Within the department is also a fully stocked library of chemical and biochemical literature with well over 300 journal subscriptions.

8. References (1D) The term biomolecule is used throughout this proposal in a general sense to refer to proteins, nucleic acids, oligosaccharides, lipids, hormones and any such biologically relevant molecule which might be targeted for labeling.

(2D) (a) Kessler, C., Ed. *Nonradioactive Labeling and Detection of Biomolecules,* Springer-Verlag: Berlin, 1992. (b)Likhtenshtein, G. I. *Biophysical Labeling Methods in Molecular Biology,* Cambridge University Press. New York, 1993. (c) Brunner, J. "New Photolabeling and Crosslinking Methods," *Annu. Biochem. Rev.* 1993, 62, 483–514.

(3D) For example, see: Haugland, R. P. *Molecular Probes: Handbook of Fluorescent Probes and Research Chemicals,* Larison, K. D., Ed.; 1992–1994, 5th Edition, Molecular Probes, Inc., Eugene, Oreg.

(4D) For recent reviews see: (a) Zon, G. "Brief Overview of Control of Genetic Expression by Antisense Oligonucleotides and In Vivo Applications," *Mol. Neurobiology* 1995, 10, 219–29. (b) Kiely, J. S. "Recent Advances in Antisense Technology," *Ann. Rep. Med Chem.* 1994, 29,297–306. (c) Stein, C. A.; Cheng, Y.-C. "Antisense Oligonucleotides as Therapeutic Agents-Is the Bullet Really Magic," *Science* 1993, 261, 1004–11. (d) Varma, R. S. "Synthesis of Oligonucleotide Analogues with Modified Backbones," *SYNLETT* 1993, 621–37. (e) Beaucage, S. L.; Iyer, R. P. "The Functionalization of Oligonucleotides Via Phosphorarnidite Derivatives," *Tetrahedron* 1993, 49, 1925–63. (f) Toulmé, J. J. in Antisense RNA and DNA; Murray, J. A. H., Ed.; Wiley, Inc.: New York, 1992, pp 175–94. (g) Englisch, U.; Gauss, D. H. "Chemically Modified Oligonucleotides as Probes and Inhibitors," *Angew. Chem. Int. Ed. Engl.* 1991, 30, 613–722. (h) Uhlmann, E.; Peyman, A. "Antisense Oligonucleotides: A New Therapeutic Principle," *Chem. Rev.* 1990, 90, 543–84. (i) Goodchild, J. "Conjugates of Oligonucleotides and Modified Oligonucleotides: A Review of Their Synthesis and Properties," *Bioconjugate Chem.* 1990, 1, 1155–87. (j) Héléne, C.; Toulmé, J.-J. "Specific Regulation of Gene Expression by Antisense, Sense, and Antigene Nucleic Acids," *Biochim. Biophys. Acta* 1990, 1049, 99–125. (k) Goodchild, J. "Inhibition of Gene Expression by Oligonucleotides," in *Oligonucleotides: Antisense Inhibitors of Gene Expression;* Cohen, J. S., Ed:; MacMillan Press: London, 1989, pp. 53–77. (l) Zon, G. "Oligonucleotide Analogues as Potential Chemotherapeutic Agents," *Pharm. Res.* 1988, 5, 539–49. (m) Stein, C. A.; Cohen, J. S. "Oligonucleotides as Inhibitors of Gene Expression: a Review," *Cancer Res.* 1988, 48, 2659–68. (n) Miller, P. S.; Ts'O, P.O.P. "Oligonucleotide Inhibitors of Gene Expression in Living Cells: New Opportunities in Drug Design," *Annu. Rep. Med. Chem.* 1988, 23, 295–304. (o) Miller, P. S.; Agris, C. H.; Blake, K. R.; Murakami, A.; Spitz, S. A.; Reddy, M. P.; Ts'O, P.O.P. "Nonionic Oligonucleotide Analogs as New Tools for Studies on the Structure and Function of Nucleic Acids in Living Cells," in *Nucleic Acids: The Vectors of Life;* Pullman, B.; Jortner, J., Eds.; D. Reidel Publishing Co.: Dordrecht, Netherlands; 1983, pp. 521–35.

(5D) A recent review has proposed the use of the acronym SNAIGE (Synthetic or Small Nucleic Acid Interfering with Gene Expression) as a term for describing the various approaches to genetic regulation with oligonucleotides: Leonetti, J. P.; Degols, G.; Clarenc, J. P.; Mechti, N.; Lebleu, B. "Cell Delivery and Mechanism of Action of Antisense Oligonucleotides," *Prog. Nucl. Acid Res.* 1993, 44, 143–66.

(6D) Using phosphate triester modified oligos for duplex structure studies with RNA and DNA: (a) Letsinger, R. L.; Bach, S. A.; Eadie, J. S. "Effects of Pendant Groups at Phosphorus on Binding Properties of d-ApA Analogues," *Nucleic Acids Res.* 1986, 14, 3487–99. (b) Summers, M. F.; Powell, C.; Egan, W.; Byrd, R. A.; Wilson, W. D.; Zon, G. "Alkyl Phosphotriester Modified Oligodeoxyribonucleotides. VI. NMR and UV Spectroscopic Studies of Ethyl Phosphotriester (Et) Modified Rp-Rp and Sp-Sp Duplexes, $\{d[GGAA(Et)TTCC]\}_2$," *Nucleic Acids Res.* 1986, 14, 742 1–37.(c) Pramanik, P.; Kan, L. "NMR Study of the Effect of Sugar-phosphate Backbone Ethylation on the Stability and Conformation of DNA Double Helix" *Biochemistry* 1987 26, 1807–12. (d) Koole, L. H.; van Genderen, M. H. P.; Buck, H. M. "A Parallel Right-Handed Duplex of the Hexamer d(TpTpTpTpTpT) with Phosphate Triester Linkages," *J. Am. Chem. Soc.* 1987, 109, 3916–21 *[The synthetic chemistry and hybridization data reported in this 1987 paper differed from that described later and subsequently retracted by Buck, H. M.; Moody, H. M.; Quaedflieg, P. J. L. M.; Koole, L. H.; van Genderen, M. H. P.; Smit, L.; Jurriaans, S.; Geelen, J. L. M. C.; Goudsmit, J. "Inhibition of HIV-1 Infectivity by Phosphate-.Methylated DNA: Retraction," *Science* 1990, 250, 125–26 (also see: Maddox, J. "Dutch Cure for AIDS is Discredited," *Nature* 1990, 347, 411).]. (e) Quaedflieg, P. J. L. M.; Koole, L. H.; van Genderen, M. H. P.; Buck, H. M. "A structural Study of Phosphate-methylated d(CpG)n and d(GpC)nDNA oligomers. Implications of Phosphate Shielding for the Isomerization of B-DNA into Z-DNA," *Recl. Trav. Chim. Pay-Bas* 1989, 108, 421–23. (f) Quaedflieg, P. J. L. M.; Broeders, N. L. H. L.; Koole, L. H.; van Genderen, M. H. P.; Buck, H. M. "Conformation of the Phosphate-methylated DNA Dinucleotides d(CpC) and d(TpC). Formation of a Parallel Miniduplex Exclusively for the S-Configuration at Phosphorus," *J. Org. Chem.* 1990, 55, 122–27. (g) Quaedflieg, P. J. L. M.; van der Heiden, A. P.; Koole, L. H.; Coenen, A. J. J. M.; van der Wal, S.; Meijer, E. M. "Synthesis and Conformational Analysis of Phosphate-methylated RNA Dinucleotides," *J. Org. Chem.* 1991, 56, 5846–59.

(7D) Using modified triester phosphate oligos as probes for elucidating specific interactions with proteins: (a) Weinfeld, M.; Drake, A. F.; Saunders, J. K.; Paterson, M. C. "Stereospecific Removal of Methyl Phosphotriesters from DNA by an *Escherichia coli* ada$^+$ Extract," *Nucletc Acids Res.* 1985 13, 7067–77. b) Gallo, K. A.; Shao, K; Phillips, L. R.; Regan, J. B.; Kozielkiewicz, M.;

Uznanski, B.; Stec, W. J.; Zon, G. "Alkyl Phosphotriester Modified Oligodeoxyribonucleotides. V. Synthesis and Absolute Configuration of and Diastereomers of an Ethyl Phosphotriester (Et) Modified EcoRI Recognition Sequence, d[GGAA(Et)TTCC]. A Synthetic Approach to Regio- and Stereospecific Ethylation-interference Studies," *Nucleic Acids Res.* 1986, 14, 7405–20. (c) Koziolkiewicz, M.; Stec, W. J. "Application of Phosphate-backbone-modified Oligonucleotides in the Studies on EcoRI Endonuclease Mechanism of Action," *Biochemistry* 1992, 31, 9460–66.

(8D) (a) Miller, P. S.; Fang, K. N.; Kondo, N. S.; Ts'O, P.O.P. "Synthesis and Properties of Adenine and Thymidine Nucleoside Alkyl Phosphotriesters, the Neutral Analogs of Dinucleoside Monophosphates," *J. Am. Chem. Soc.* 1971, 93, 6657–65. (b) Miller, P. S.; Barrett, J. C.; Ts'O, P.O.P. "Synthesis of Oligodeoxyribonucleotide Ethyl Phosphotriesters and Their Specific Complex Formation with Transfer Ribonucleic Acid," *Biochemistry* 1974, 13, 4887–96 (and the following paper in that journal as well). (c) Pless, R. C.; Ts'O, P.O.P. "Duplex Formation of a Nonionic Oligo(deoxythymidylate) Analogue [Heptadeoxythymidylyl-(3'-5')-deoxythymidine Heptaethyl Ester (d-[Tp(Et)]$_7$T)] with Poly(deoxyadenylate). Evaluation of the Electrostatic Interaction," *Biochemistry* 1977, 16, 1239–50. (d) Miller, P. S.; Braiterman, L. T.; Ts'O, P.O.P. "Effects of a Trinucleotide Ethyl Phosphotriester, G$^m$p(Et)G$^m$(Et)U, on Mammalian Cells in Culture," *Biochemistry* 1977, 16, 1988–96. (e) Petrenko, V. A.; Pozdnyakov, P. I.; Kipriyanov, S. M.; Boldyrev, A. N.; Semyonova, L. N.; Sivolobova, G. F. "Site-localized Mutagenesis Directed by Phosphotriester Analogs of Oligonucleotides," *Bioorg. Khim.* 1986, 12, 1088–1100. (f) Asseline, U.; Barbier, C.; Thuong, N. T. "Oligothymidylates Comportant La Structure Alternee Alkylphosphotriester-phosphodiester et Lies de Facon Covalente a un Agent Intercalant," *Phosphorus Sulfur* 1986, 26, 63–73. (g) Marcus-Sekura, C. J.; Woerner, A. M.; Shinozuka, K.; Zon, G.; Quinnan, Jr., G. V. "Comparative Inhibition of Cloramphenicol Acyltransferase Gene Expression by Antisense Oligonucleotide Analogs Having Alkyl Phosphotriester, Methylphosphonate and Phosphorothioate Linkages," *Nucleic Acids Res.* 1987, 15, 5749–63. (h) see ref. 6a. (i) Koole, L. H.; van Genderen, M. H. P. Reinierg, R. G., Buck, H. M. "Enhanced Stability of a Watson and Crick DNA Duplex Structure by Methylation of the Phosphate Groups in One Strand," *Proc. K. Ned. Akad. Wet. B* 1987, 90, 41–6.* (j) Petrenko, V. A.; Kipriyanov, S. M.; Boldyrev, A. N.; Pozdnyakov, P.1. "Mutagenesis Directed by Phosphotriester Analogues of Oligonucleotides: a Way to Site-specific Mutagenesis In Vivo," *FEBS Lett.* 1988, 238, 109–12. (k) Durand, M. Maurizot, J. C.; Asseline, U.; Barbier, C.; Thuong, N. T.; Héléne, C. "Oligothymidylates Covalently Linked to an Acridine Derivative and with Modified Phosphodiester Backbone: Circular Dichroism Studies of Their Interactions with Complementary Sequences," *Nucleic Acids Res.* 1989, 17, 1823–36.

(9D) For additional synthesis reviews see: (a) Beaucage, S. L.; Iyer, R. P. "Advances in the Synthesis of Oligonucleotides by the Phosphoramidite Approach," *Tetrahedron* 1992, 48, 2221–2311. (b) Hobbs, J. B. "Nucleotides and Nucleic Acids," *Organophosphorus Chemistry* 1990, 21, 201–321. (c) Sonveaux, E. "The Organic Chemistry Underlying DNA Synthesis," *Bioorg. Chem.* 1986, 14, 274–325.

(10D) (a) Hayakawa, Y.; Hirose, M.; Hayakawa, M.; Noyori, R. "General Synthesis and Binding Affinity of Position-Selective Phosphonodiester- and Phosphotriester-Incorporated Oligodeoxynucleotides," *J. Org. Chem.* 1995, 60, 925–30. (b) Hayakawa, Y.; Wakabayashi, S.; Kato, H.; Noyori, R. "The Allylic Protection Method in Solid-Phase Oligonucleotide Synthesis. An Efficient Preparation of Solid-Anchored DNA Oligomers," *J. Am. Chem. Soc.* 1990, 112, 169 1–96. (c) Kuijpers, W. H. A.; Huskens, J.; Koole, L. H.; van Boeckel, C. A. A. "Synthesis of Well-Defined Phosphate-Methylated DNA Fragments: the Application of Potassium Carbonate in Methanol as Deprotecting Reagent," *Nucleic Acids Res.* 1990, 18, 5197–205.

(11D) Alul, R. H.; gingman, C. N.; Zhang, G.; Letsinger, R. L. "Oxalyl-CPG: A Labile Support for the Synthesis of Sensitive Oligonucleotide Derivatives," *Nucleic Acids Res.* 1991, 19, 1527–32.

(12D) Froehler, B. C. "Deoxynucleoside H-Phosphonate Diester Intermediates in the Synthesis of Internucleotide Phosphate Analogues," *Tetrahedron Lett.* 1986, 27, 5575–78.

(13D) For a recent review see: Lesnikowski, Z. J. "Stereocontrolled Synthesis of P-Chiral Analogues of Oligonucleotides," *Bioorganic Chem.* 1993, 21, 127–55.

(14D) It should be noted that diastereoresolution of the Rp-diastereomer of the methylphosphotriester thymidyl (3',5')thymidyl dinucleoside was accomplished with the use of a methyltransferase enzyme shown to possess diastereospecificity in demethylation of the $S_p$-configuration: (a) Hamblin, M. R.; Potter, B. V. L. "*E. coli* Ada Regulatory Protein Repairs the 5p Diastereomer of Alkylated DNA," *FEBS Lett.* 1985, 189, 315–17. (b) Also see ref. 7a.

(15D) Koziolkiewicz, M.; Wilk, A. in *Oligonucleotide Synthesis Protocols*; Agrawal, S., Ed.; Humana Press: 1993, pp.

(16D) One particular exception is the limited work of Ikehara and coworkers: Ohtsuka, E.; Shiraishi, M.; Ikehara, M. "Stereoselective Synthesis of Dinucleoside Phosphate Aryl Esters by Using New Condensing Reagents, Arenesulfonyl-5-(Pyridin-2-yl)-Tetrazole," *Tetrahedron* 1985, 41, 5271–77, and references cited therein.

(17D) For reviews see: (a) Sega, G. A. "A Review of the Genetic Effects of Ethyl Methanesulfonate," *Mutation Res.* 1984, 134, 113–42. (b)Hoffmann, G. R. "Genetic Effects of Dimethyl Sulfate, Diethyl Sulfate, and Related Compounds," *Mutation Res.* 1980, 75, 63–129. (c) Digenis, G. A.; Issidorides, C. H. "Some Biochemical Aspects of N-Nitroso Compounds," *Bioorganic Chem.* 1979, 8, 97–137.

(18D) (a) Swenson, D. H.; Lawley, P. D. "Alkylation of Deoxyribonucleic Acid by Carcinogens Dimethylsulfate, Ethyl Methanesulfonate, N-Ethyl-N-nitrosourea and N-Methyl-N-nitrosourea," *Biochem. J.* 1978, 171, 575–87. (b) Jensen, D. E.; Reed, D. J. "Reaction of DNA with Alkylating Agents. Quantitation of Alkylation by Ethylnitrosourea of Oxygen and Nitrogen Sites on Poly [dA-dT] Including Phosphotriester Formation," *Biochemistry* 1978, 17, 5098–107.

(19D) Gohil, R. N.; Roth, A. C.; Day, R. A. "Reversible Covalent Modification of DNA," *Arch. Biochem. Biophys.* 1974, 165, 297–312.

(20D) Bhat, G.; Roth, A. C.; Day, R. A. "Extrinsic Cotton Effect and Helix-Coil Transition in a DNAPolycation Complex," *Biopolymers* 1977, 16, 1713–24.

(21D) For recent examples, see: (a) Dempcy, R. O.; Browne, K. A.; Bruice, T. C. "Synthesis of the Polycation Thymidyl DNG, Its Fidelity in Binding Polyanionic DNA/RNA, and the Stability and Nature of the Hybrid Complexes," *J. Am. Chem. Soc.* 1995, 117, 6140. (b) Liang, G.; Encell, L.; Nelgon, M. G., Switzer, C.: Shuker, D. E. G.; Gold, B. "Role of Electrostatics in the Sequence-Selective Reaction of Charged Alkylating Agents with DNA," *J. Am. Chem. Soc.* 1995, 117, 10135–36. (c) Hashimoto, H.; Nelson, M. G.; Switzer, C. "Formation of Chimeric Duplexes Between Zwitterionic and Natural DNA," *J. Org. Chem.* 1993, 58, 4194–95. (d) Hashimoto, H.; Nelson, M. G.; Switzer, C. "Zwitterionic DNA," *J. Am. Chem. Soc.* 1993, 115, 7128–34. (e) Letsinger, R. L.; Singman, C. N.; Histand, G.; Salurikhe, M. "Cationic Oligonucleotides," *J. Am. Chem. Soc.* 1988, 115, 7128.

(22D) (a) Lefebvre, I.; Perigaud, C.; Pompon, A.; Aubertin, A.-M.; Girardet, J.-L.; Kim, A.; Gosselin, G.; Imbach, J. L. "Mononucleoside Phosphotriester Derivatives with S-Acyl-2-thioethyl Bioreversible Phosphate-Protecting Groups: Intracellular Delivery of 3'-Azido-2',3'-dideoxythyrnidine 5'-Monophosphate," *J. Med. Chem.* 1995, 38, 3941–50. (b) Meier, C.; Habel, L. W.; Balzarmni, J.; De Clercq, E. "5',5'-Di-O-nucleosyl-O'-benzylphosphotriesters as Potential Prodrugs of 3'-Azido-2',3'-dideoxythymidine-5'-monophosphate," *Liebigs Ann* 1995, 2203–08. (c) McGuigan, C.; Wang, Y.; Riley, P. A. "Synthesis and Biological Evaluation of Substituted Phosphate Triester Alkyl Lyso Phospholipids (ALP's) as Novel Potential Antineoplastic Agents," *FEBS Lett.* 1995, 372, 259–63. (d) Hong, S.-b.; Raushel, F. M. "Synthesis and Enzymatic Hydrolysis of a Light-Emitting Substrate for Phosphotriesterase," *Bioorg. Med. Chem Lett.* 1994, 4, 2705–08. (e) Ichikawa, Y.; Wong, C.-H. "Efficient Chemical Synthesis of GDP-fucose," *J. Org. Chem.* 1992, 57, 2943–46. (f) Meier, C.; Huynh-Dinh, T. "O-Alkyl-5',5'-Dinucleoside-Phosphate as Combined Prodrugs of Antiviral and Antibiotic Compounds," *Bioorg. Med. Chem. Lett.* 1991, 1, 527–30. (g) Neumann, J.-M.; Herv~, M.; Debouzy, J.-C.; Guerra, F. I.; Gouyette, C.; Dupraz, B.; Huynh-Dinh, T. "Synthesis and Transmembrane Transport Studies by NMR of a Glucosyl Phospholipid of Thyrnidine," *J. Am. Chem. Soc.* 1989, 111, 4270–77. (h) Ogilvie, K. K.; Beaucage, S. L., Gillen, M. F., Entwigtle, D. W. "Fluoride Ion Catalyzed Alkylation of Nucleic Acid Derivatives Using Trialkyl Phosphates, Dialkyl Sulfates and Akyl Methanesulfonates," *Nucleic Acids Res.* 1979, 6, 2261–73. (i) Griffin, B. E.; Haines, J. A.; Reese, C. B. "The Methylation of Adenylyl-(3'-5')-uridine and Uridylyl(3'-5')-adenosine with Diazomethane," *Biochim. Biophys. Acta* 1967, 142, 536–38.

(23D) For reviews on quinone methides, see: (a) Thompson, D. C.; Thompson, J. A.; Sugumaran, M.; Moldeus, P. "Biological and Toxicological Consequences of Quinone Methide Formation," *Chem.-Biol. Interactions* 1992, 86, 129–62. (b) Peter, M. G. "Chemical Modifications of Biopolymers by Quinones and Quinone Methides," *Angew. Chem. Int. Ed. Engl.* 1989, 28, 555–70. (c) Volod'kin, A. A.; Ershov, V. V. *Russian Chem. Rev.* 1988, 57, 336. (d) Gruenanger, P. in *Houben-Weyl Methoden der Organischen Chemie* (Vol. VII/3b) Mueller, E., Bayer, O., Eds.; G. Thieme Verlag: Stuttgart, 1979, pp. 395–521. (e) Wagner, H.-U.; Gompper, R. in *The Chemistry of Quinonoid Compounds* (Vol. 1) Patai, S., Ed.; John Wiley & Sons: New York, 1974, pp. 1145–1178. (f) Turner, A. B. *Quart. Rev.* 1965, 18, 347.

(24D) For leading references of a quinone methide designed to alkylate DNA, presumably at the bases, see: (a) Chatterjee, M.; Rokita, S. E. "The Role of a Quinone Methide in the Sequence Specific Alkylation of DNA," *J. Am. Chem. Soc.* 1994, 116, 1690–97. (b) Li, T.; Zeng, Q.; Rokita, S. E. "Target-Promoted Alkylation of DNA," *Bioconjugate Chem.* 1994, 5, 497–500.

(25D) Wakselman, M. "1,4- and 1,6-Elimination from Hydroxy- and Amino-Substituted Benzyi Systems: Chemical and Biochemical Applications," *NOUV. I. Chim.* 1983, 7, 439.

(26D) The quinone methide was formed using a slight modification of an established procedure (Dyall, L. K.; Winstein, S. "Nuclear Magnetic Resonance Spectra and Characterization of Some Quinone Methides," *J. Am. Chem. Soc.* 1972, 94, 2196–99.). [6: $^1$H NMR (CDCl$_3$, 300 MHz) $\partial$7.00 (s, 2H, 2(=CH)), 5.75 (s, 2H, =CH2), 2.03 (s, 6H, 2(CH3))]. Reaction of quinone methide 6 with 1 equivalent of dibenzylphosphate in CD$_3$CN/CDCl$_3$ afforded an equilibrium composed of ~50:50 ratio of 7:6+ dialkylphosphate. Under the reaction conditions this proved to be stable to hydrolysis for several hours upon addition of excess D$_{20}$. We are presently attempting to trap out the product as the acetylated phenol to model lactonization in the affinity labeling reagent. This will allow the equilibrium to be drained to product formation. Temperature and concentration dependence varified the equilibrium and confirmed the reaction was second order. [7: $^1$H NMR (CDCl$_3$/CD$_3$CN (1:1), 300 MHz) $\partial$7.22 (in, 10H, 2(C$_6$H$_5$)), 6.77 (s, 2H, C$_6$H$_2$), 5.87 (d, J=8.5 Hz, 4H, 2(C$\underline{H}_2$Ph)), 5.75 (d ,J=8.5 Hz, 2H, C$\underline{H}_2$Ar), 3.7 (br s, 1H, HOAr), 2.10 (s, 6H, 2(CH$_3$))].

(27D) The starting 4-acyloxybenzyl chloride was prepared according to established procedures in one step (Taylor, L. D.; Grasshoff, J. M.; Pluhar, M. "Use of o- and p-Hydroxybenzyl Functions as gBlocking Groups.

(38D) Alternative photolabile protecting groups include: (a) Dimethoxybenzoinyl: Pirrung, M. C.; Shuey, S. W. "Photoremovable Protecting Groups for Phosphorylation of Chiral Alcohols. Asymmetric Synthesis of Phosphotriesters of (–)-3',5'-Dimethoxybenzoin," *J. Org. Chem.* 1994, 59, 3890–97. (b) a-Carboxy-2nitrobenzyl; Gee, K. R.; Wieboldt, R.; Hess, G. P. "Synthesis and Photochemistry of a New Photolabile Derivative of GAB A. Neurotransmitter Release and Receptor Inactivation in the Microsecond Time Region," *J. Am. Chem. Soc.* 1994, 116, 8366–67. (c) a-Methyl-4,5-dimethoxy-2-nitrobenzyl: Marriott, G. "Caged Protein Conjugates and Light-Directed Generation of Protein Activity: Preparation, Photoactivation, and Spectroscopic Characterization of Caged G-Actin Conjugates," *Biochemistry* 1994, 33, 9092–97.

(39D) For reviews of photolabile protecting groups, see: (a) Adams, S. R.; Tsien, R. Y. "Controlling Cell Chemistry with Caged Compounds," *Annu. Rev. Physiol.* 1993, 55, 755–84. (b) Gurney, A. M.; Lester, H. A. "Light Flash Physiology with Synthetic Photosensitive Compounds," *Physiol. Rev.* 1987, 67, 583617. (c) Pillai., V. N. R. "Photoremovable Protecting Groups in Organic Synthesis," *Synthesis* 1980, 1–26.

(40D) Hall, N. F.; Sprinkle, M. R. "Relations Between the Structures and Strengths of Certain Organic Bases in Aqueous Solution," *J. Chem Soc.* 1932, 54, 19 16–32.

(41D) The benzylic bromide will be synthesized by reduction of the benzaldehyde precursor (NaBH4) and bromination of the resulting benzyl alcohol with trimethylsilyl-bromide (TMSBr). Ester derivatives can readily be produced from the benzyl alcohol.

(42D) (a) Hemmingson, J. A.; Leary, G. "The Chemistry of Reactive Lignin Intermediates. Part II. Addition Reactions of Vinyl-substituted Quinone Methides in Aqueous Solution," *J. Chem. Soc. Perkin II* 1975, 1584–87. (b) Leary, G.; Miller, I. J.; Thomas, W.; Woolhouse, A. D. "The Chemistry of Reactive Lignin Intermediates. Part 5. Rates of Reactions of Quinone Methides with Water, Alcohols, Phenols, and Carboxylic Acids," *J. Chem. Soc. Perkin II* 1977, 1737–39. (c) O'Shea, K. E.; Fox, M. A. "Pulse Radiolytic Kinetic Study of a-Methyl-Substituted Benzoquinone Radical Anions: A Possible Mechanistic Model for Bioreductive Alkylation," *J. Am. Chem. Soc.* 1991, 113, 611–15. (d) Skibo, E. B. "Formation and Fate of Benzimidazole-Based Quinone Methides. Influence of pH on Quinone Methide Fate," *J. Org. Chem.* 1992, 57, 5874–78. (e) Richard, J. P. "The Mechanism for the Uncatalyzed and Specific-Acid Catalyzed Reactions of a Simple Quinone Methide with Solvent and Halide Ions," *J. Am. Chem. Soc.* 1990, 112.

(43D) Monitoring for loss of the quinone methide (or its precursor) at constant temperature will allow the determination of rate constants for the reactions. From the equation, $$kt = 2.303 \log (A_0 A\infty)/(A_t - A\infty)$$

where A is the absorbance of the solution, kinetic plots will afford rate constants. We can also utilize $^1H$ and $^{31}P$ NMR for kinetic analysis.

(44D) Allylation of 4-hydroxybenzaldehyde followed by a Claisen rearrangement will afford 15.$^{45}$ Allylation of 15 followed by a second Claisen rearrangement will provide the symmetric bisallyl phenol which will be protected as the o-nitrobenzyl alcohol to give 16.$^{32}$ Hydroboration followed by protection of the benzylic alcohol as the t-butyldimethylsilylether$^{47}$ will provide 17. Reductive amination$^{33,48}$ with a dialkylamine followed by desilylation of the primary silylether, Jones oxidation49 and esterificatlon of the resulting carboxylic acid will afford amine.hydrochloride 18. Quaternization of the amine with iodoethane (or iodomethane)$^{34}$ will provide the desired quinone methide precursor 19.

(45D) (a) Waespe, H.-R.; Heimgartner, H.; Schmid, H.; Hansen, H.-J.; Paul, H.; Fischer, H. "Zur Photochemie von Allylarylathem," *Helv. Chim. Acta* 1978, 61, 401–29. (b) Tarbell, D. S.; Kincaid, J. F. "The Claisen Rearrangement. II. A Kinetic Study of the Rearrangement of Allyl 2,6-Dimethylphenyl Ether in Diphenyl Ether Solution," *J. Am. Chem. Soc.* 1940, 62, 728–31.

(46D) Brown, H. C. *Hydroboration,* Benjamin, W. A., New York, 1962.

(47D) Corey, E. J.; Venkateswarlu, A. J. "Protection of Hydroxyl Groups as tert-Butyldimethylsilyl Derivatives," *J. Am. Chem. Soc.* 1972, 94, 6190.

(48D) Lane, C. F. "Sodium Cyanoborohydride—A Highly Selective Reducing Agent for Organic Functional Groups," *Synthesis* 1975, 135–46.

(49D) Wiberg, K. B. "Oxidation in Organic Chemistry," *Academic Press,* 1965, Ch. 2.

(50D) (a) For examples of phosphorylation inthe presence of amines, see: Sinha, N. D.; Striepeke, S. "Oliaonucleotideg with Reporter Groups Attached to the 5"-Terminus," in *Oligonucleotides and Analogues: A Practical Approach,* Eckstein, F., Ed.; IRL Press: New York; 1991, pp. 185–210. (b) Alul, R. H.; Singman, C. N.; Zhang, O.; Letsinger, R. L. "Oxalyl-CPG: A Labile Support for the Synthesis of Sensitive Oligonucleotide Derivatives," *Nucleic Acids Res.* 1991, 19, 1527–32.

(51D) Wang, B.; Liu, S.; Borchardt, R. T. "Development of a Novel Redox-Sensitive Protecting Group for Ainines Which Utilizes a Facilitated Lactonization Reaction," *J. Org. Chem.* 1995, 60, 539–43.

(52D) *Oligonucleotide Synthesis. A Practical Approach* Gait, M. J., Ed.; IRL Press: Oxford; 1984.

(53D) (a) Wiimenga, S. S.; Mooren, M. M. W.; Hilbers, C. W. "NMR of Nuclelc Acids; From Spectrum to Structure," in *NMR of Macromolecules. A Practical Approach* Roberts, G. C. K., Ed.; IRL Press: Oxford, 1993, pp. 217–288. (b) Wtithrich, K. *NMR of Proteins and Nucleic Acids* John Wiley & Sons: New York, N.Y., 1986. (c) Srivastava, P. C.; Robin, R. K.; Meyer, P. B., Jr. in *Chemistry of Nucleosides and Nucleotides;* Townsend, L. B., Ed.; Plenum Press: New York, N.Y., 1988, vol. 1, pp. 113–282.

(54D) There is overwhelming precedent for the ainmoniumphosphate salt forming in various buffers. For some examples see references 19, 20, and 21 and references therein.

(55D) For leading references, see: (a) Chatteijee, M.; Rokita, S. E. "The Role of a Quinone Methide in the Sequence Specific Alkylation of DNA," *J. Am. Chem. Soc.* 1994, 116, 1690–97. (b) Li, T.; Zeng, Q.; Rokita, S. E. "Target-Promoted Alkylation of DNA," Bioconjugate Chem. 1994, 5, 497–500.

(56D) See ref 6f and references cited therein for an overview of these studies.

(57D) The separation and absolute configurational assignment of dinucleotide phosphate triesters is now well established. For a review see ref 13.

(58D) (a) Koole, L. H.; Moody, H. M.; Broeders, N. L. H. L.; Quaedflieg, P. J. L. M.; Kuijpers, W. H. A.; van Genderen, M. H. P.; Coenen, A. J. J. M.; van der Wal, S.; Buck, H. M. "Synthesis of Phosphate-Methylated DNA Fragments Using 9-Fluorenylmethoxycarbonyl as Transient Base Protecting Group," *J. Org. Chem.* 1989, 54, 1657–64. (b) For optional synthetic approaches to the methylphosphate dinucleotides see references 4–9.

(59D) Uischner, T.; Engels, J. W. "Diastereomeric Dinucleoside-methylphosphonates: Determination of Configuration with the 2-D NMR ROESY Technique," Nucleic Acids Res. 1990, 18, 5083–88.

(60D) Oligonucleotides will be synthesized on an automated synthesizer and purified according to standard protocols: (a) Beaucage, S. L.; Caruthers, M .H. *Tetrahedron Lett.* 1981, 22, 1859. (b) Sinha, N. D.; Biernat, J.; McManus, J.; Koster, H. *Nucleic Acids Res.* 1984, 12, 4539–57. (c) Sambrook, J.; Fritsch, E. F.; Maniatis, T. Molecular Cloning 2nd Ed. (Cold Springs Harbor Laboratory, Cold Springs Harbor, N.Y., 1989).

(61D) Saenger, W. *Principles of Nucleic Acid Structure,* Springer-Verlag: New York, 1984.

(62D) For a recent example see: Iverson, B. L.; Shreder, K.; Kr~Jl, V.; Sessler, J. L. "Phosphate Recognition by Sapphyrin. A New Approach to DNA Binding," J. Am. Chem. Soc. 1993, 115, 11022–23, and references cited therein. Based on personal conmunication with Professor Iverson, they now interpret their results as arising from helical stacking of the sapphyrin induced through its interaction with DNA.

(63D) Gray, D. M.; Ratliff, R. L.; Vaughan, M. R. Methods in Enzymology, Academic Press: San Diego, 1992; Vol. 211, pp 389–406.

(64D) Lin, S,-B.; Chang, G.-W.; Teh, G.-W. Lin, K.-I.; Au, L.-C. "A Simple and Rapid Method for Purification of Oligodeoxyribonucleoside Methylphosphonates," Biotechniques 1993, 14, 795–98.

(65D) Miller, P. S.; Reddy, M. P.; Murakami, A.; Blake, K. R.; Lin, S.-B.; Agris, C. H. Biochemistry 1986, 25, 5092–97.

(66D) (a) Brown, D. M.; Higson, H. M. "Phospholipids. Part I. The Hydrolysis of Some Esters of Cyclohexanediol Phosphates," *J. Chem. Soc.* 1957, 2034–41. (b) Cramer, F.; Kenner, G. W.; Hughes, N. A.; Todd, Sir A. "Nucleotides. Part XLII. The Preparation of the 2',5'- and 3',5'-Diphosphates of Adenosine," *J. Chem. Soc.* 1957, 3297–98. (c) Zervas, L.; Dilaris, I. "Dealkylation and Debenzylation of Triesters of Phosphoric Acid. Phosphorylation of Hydroxy and Amino Compounds," *J. Am. Chem. Soc.* 1955, 77, 5354–57. (d) Cox., J. R.; Ramsay, O. B. "Mechanisms of Nucleophilic Substitution in Phosphate Esters," *Chem. Rev.* 1964, 64, 317.

(67D) Gobel, M. W.; Bats, J. W.; Durner, G. "En Route to Synthetic Phosphodiesterases: Supramolecular Phosphoryl-Transfer Mediated by Amidinium Phosphate Contact Ion-Pairs," *Angew. Chem. Int. Ed. Engl.* 1992, 31, 207–09.

(68D) This complex NMR work can be done in collaboration with Professor Jim Hinton of this department whose expertise is in structural determination of proteins by NMP analysis.

(69D) (a) McCarthy, J. G.; Edington, B. V.; Schendel, P. F. "Inducible Repair of Phosphotriesters in *Escherichia coli*," *Proc. Natl. Acad. Sci. USA* 1983, 80, 7380–84. (b) McCarthy, T. V.; Lindahi, T. "Methyl Phosphotriesters in Alkylated DNA are Repaired by the Ada Regulatory Protein of *E. coli*," *Nucleic Acids Res.* 1985, 13, 2683–98. (c) Demple, B.; Sedgwick, B.; Robins, P.; Totty, N.; Waterfield, M. D.; Lindahi, T. "Active Site and Complete Sequence of the Suicidal Methyltransferase That Counters Alkylation Mutagenesis," *Proc. Natl. Acad. Sci. USA* 1985, 82, 2688–92. (d) Carter, C. A.; Kirk, M. C.; Ludlum, D. B. "Phosphotriester Formation by the Haloethylnitrosoureas and Repair of the Lesions by *E.coli* B521 Extracts," *Nucleic Acids Res.* 1988, 16, 5661–72.

(70D) (a) For example, in applications such as fluorescence in situ hybridization (FISH), see; Brenner, M.; Dunlay, T. "Fluorescence In situ Hybridization. Hardware and Software Implications in the Research Laboratory," *Am. Laboratory* 1995, 55–58. (b) For lanthanide-labeled DNA probes, see: Lovgren, T.; Hurskainen, P.; Dahlen P. in *Nonisotopic DNA Probe Techniques*, Kricka, L. J., Ed.; Academic Press, Inc.: San Diego; 1992, pp. 227–274.

(71D) Glen Research, 44901 Falcon Place, Sterling, Va. 22170.

(72D) Aldrich Chemical Co., 1001 West Saint Paul Avenue, Milwaukee, Wis. 53233.

(73D) Vasil'tsov, A. M.; Trofimov, B. A.; Amasova, S. V. "Synthesis of Thiols from Alkyl Halides and Sodium Hydrosulfide in Dimethyl Sulfoxide," *J. Org. Chem. USSR* 1983, 19, 1197.

(74D) Khorana, H. G. *Pure Appl. Chem.* 1968, 17, 349.

(75D) Mashimo, K.; Sato, Y. "Synthesis of Isoajmaline," Tetrahedron 1970, 26, 803.

(76D) Gait, M. J., Ed., *Oligonucleotide Synthesis, A Practical Approach*, IRL Press: New York; 1990, pp. 41–45.

(77D) Oakley, M. G.; Turnbull, K. D.; Dervan, P. B. "Synthesis of a Hybrid Protein Containing the Iron-Binding Ligand of Bleomycin and the DNA-Binding Domain of Hin," *Bioconjugate Chem.* 1994, 5, 242–47.

(78D) Shooter, K. V. "The Kinetics of the Alkaline Hydrolysis of Phosphotriesters in DNA," *Chem.-Biol. Interactions* 1976, 13, 151–63.

(79D) Telser, J.; Cruickshank, K. A.; Morrison, L. E.; Netzel, T. L. "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements," *J. Am. Chem. Soc.* 1989, 111, 6966–76.

(80D) Pappas, J. J.; Keaveney, W. P.; Gancher; E.; Berger, M. "A New and Convenient Method for Converting Olefins to Aldehydes," *Tetrahedron Lett.* 1966, 4273–78.

(81D) Bigot, Y. L.; Delmas, M.; Gaset, A. "A Simplified Wittig Synthesis Using Solid/Liquid Transfer Processes," *Synth. Coomun.* 1982, 12, 1115–20.

(82D) Han, H.; Dervan, P. B. "Visualization of RNA Tertiary Structure by RNA-EDTAoFe(II) Autocleavage: Analysis of tRNA$^{Phe}$ with Uridine-EDTA.Fe(II) at Position 47," *Proc. Natl. Acad. Sci. USA* 1994, 91, 4955–59.

(83D) Telser, J.; Cruickshank, K. A.; Schanze, K. S.; Netzel, T. L. "DNA Oligomers and Duplexes Containing a Covalently Attached Derivative of Tris(2,2'-bipyridine) ruthenium(II): Synthesis and Characterization by Thermodynamic and Optical Spectroscopic Measurements," *J. Am. Chem. Soc.* 1989, 111, 722 1–26.

(84D) For a recent review, see: Thuong, N. T.; Helene, C. "Sequence-Specific Recognition and Modification of Double-Helical DNA by Oligonucleotides," *Angew. Chem. Int. Ed. Engl.* 1993, 32, 666–690.

(85D) For a recent example and references to many prior examples see ref 84.

(86D) The protocol for triple helix formation and analysis by affinity cleavage is very well developed, see: Greenberg, W. A.; Dervan, P. B. "Energetics of Formation of Sixteen Triple Helical Complexes Which Vary at a Single Position Within a Purine Motif," *J. Am. Chem. Soc.* 1995, 117, 5016–22.

(87D) Dervan, P. B. "Design of Sequence-Specific DNA-Binding Molecules," *Science* 1986, 232, 464–71.

(88D) (a) Kim, S. H.; Quigley, G. J.; Suddath, F. L.; McPherson, A.; Sneden, D.; Kim, J. J.; Weinzierl, J.; Rich, A. *Science* 1973, 179, 285–88. (b) Hall, K. B.; Sampson, J. R.; Uhlenbeck, O. C.; Redfield, A. G. *Biochemistry* 1989, 28, 5794–801. (c) Latham, J. A.; Cech, T. R. *Science* 1989, 245, 276–82. (d) Huttenhofer, A.; Noller, H. F. *Proc. Natl. Acad. Sci. USA* 1992, 89, 7851–55.

(89D) Manoharan, M.; Guinosso, C. J.; Cook, P. D. "Novel Functionalization of the Sugar Moiety of Nucleic Acids for Multiple Labeling in the Minor Groove," *Tetrahedron Lett.* 1991, 32, 7171–74.

(90D) Clark Still, Columbia University, Department of Chemistry, New York, N.Y., 10027.

Progress in the development of a reagent to be used for site-specific phosphodiester labeling of DNA will be discussed. We are systematically optimizing the various components of 3 reagent designed to: (1) site-specifically recognize DNA with a linked, complimentary oligonucleotide, (2) crosslink to the target DNA through photo-initiated quinone methide formation and phosphate alkylation, (3) release the delivery oligonucleotide in situ, and (4) produce a covalently stable phosphotriester modified DNA canying an independently tethered reporter group.

The prolific use of reactive quinone methide intermediates in organic and medicinal chemistry warrants further optimization of their stability, reactivity, and chemoselectivity for expanding applications. The versatile para-quinone methide, represented by parabenzoquinone methide, shows increased electrophilic reactivity as a conjugate addition vinologue due to the driving force towards rearomatization. This molecule also shows bimodal reactivity having both an electrophilic exocyclic methylene and a nucleophilic phenoxide. In developing a research program around the application of quinone methides to drug delivery and biomolecular labeling, we are studying various ways to control product formation in quinonie methide reactions.

The addition of many nucleophiles to para-quinone methides is a reversible reaction. Quinone methide alkylation of weaker nucleophiles requires trapping of the kinetically favored addition product. We have examined intramolecular trapping of the quinone methide addition products (molecule 2) as a lactone (molecule 3) in order to provide product stability by withdrawing electron density form the phenolic oxygen to lower the propensity for reversibility.

Results and Discussion

Initial studies focused on quinone methide alkylation reactions relevant to nucleic acid polymers. Alkylation of a weakly nucleophilic phosphodiester derivative was modeled by using a dibenzylphosphodiester. Reaction of dibenzylphosphoric acid with para-quinone methide molecule 4, oxidatively formed from 2,4,6-trimethylphenol, 3 revealed that formation of phosphotriester molecule 5 is an equilibrium process. The use of the phosphoric acid was required in order to protonate phenol molecule 4 to afford a stable product, emphasizing the need to trap the addition product. Trialkylphosphate molecule 5 is favored under acidic conditions (pH2 to pH7) which protonate the quinone methide oxygen leading to the phenol. However, under basic conditions where the phenol is deprotonated or conditions acidic enough (pH,2) to protonate the phosphotriester oxygen, molecule 4 is favored.

The reaction of quinone methide molecule 4 and two equivalents of dibenzylphosphoric acid in the presence of excess water (~200 equivalents for a homogeneous solution) afforded only trialkylphosphate molecule 3 as the product in the equilibrium by 1H NMR analysis. Minor amounts of the benzyl alcohol hydrolysis product molecule 6 was evident by $^1$H NMR analysis after 18 hours at ambient temperature. Trialkylphosphate molecule 5 is the kinetic product. A similar amount of molecule 5 produced in the presence of a much higher concentration of water (3,000 equivalents forming a bilayer) at ambient temperature after 30 minutes. However, the benzyl alcohol hydration product molecule 6 begins to drain off the kinetically formed molecule 5 affording complete conversion to benzyl alcohol after 18 hours. Hydrolysis to benzyl alcohol appears to be the thermodynamic product. Similar results of quinone methides reacting with amino acid derivatives under aqueous conditions have been reported by other researchers. Again, this emphasized the need to trap the kinetic addition product to afford the desired phosphotriester.

Initial attempts at trapping the phosphotriester included a variety of intermolecular reactions with active acylating, silylating, and alkylating reagents. The highly reactive reagents generally reacted directly with the dibenzylphosphoric acid, or the less reactive reagents required basic conditions and the corresponding dibenzylphosphate salt which generally resulted in other quinone methide reaction pathways being preferred presumably due to the equilibrium strongly favoring the quinone methide under basic conditions.

Developing an intramolecular trap was restricted by limiting the studies to quinone methide intermediates which could be characterized to reduce the number of variables under study and minimize mechanistic speculation. This limited us to derivatives which could be chemo- and regio-specifically oxidized to the para-quinone methide. In order to avoid oxidative formation of orthoquinone methides, catechol precursors were used to make the desired quinone methide derivatives with a lactone forming trap appended.

A variety of esters were prepared. Benzyl ether molecule 10 was synthesized from 2,4-dimethylphenol by a Friedel-Craft acylation, followed by benzylation, a Baeyer-Villiger oxidation, and saponification of the intermediate acetate. A substitution reaction with bromoacetic acid provided carboxylic acid molecule 11 which was converted to the desired ester derivatives through carbodiimide activation in the presence of the required alcohol. Hydrogenolysis provided molecules 13a–13g for oxidation to the desired quinone methides. This approach was used to synthesize a series of quinone methide precursors with appended esters for lactone formation ranging from highly reactive to relatively nonreactive derivatives.

The more reactive arylester derivatives (molecule 13a) were found to lactonize directly upon treatment with either silver (I) oxide or lead (IV) oxide under the relatively mild basic conditions. The more stable alkyl ester (molecules 13e–13f) and amide (molecule 13g) precursors readily formed stable intermediate quinone methides (molecules 14e–14g) upon oxidation. Dibenzylphosphoric acid addition afforded molecules 15c–15g in equilibrium as evident by $^1$H NMR. However, cyclization to the trapped product molecule 16 did not occur under the reaction conditons.

Lactonization to the trapped phosphotriester molecule 16 was accomplished with derivatives of intermediate reactivity (molecules 13b–13d). The trapping process of the trialkylphosphate (molecules 15b–15d) was readily observed by $^1$H NMR analysis over a period of 48 h. The yield of molecule 16 by $^1$H NMR analysis was approximately 90%. The trapped product molecule 16 was isolated in 66% yield after purification on a DEAD cellulose column. The product molecule 16 was confirmed by $^1$H NMR through hydrogen-phosphorous coupling (benzylic protons: J=8 hz), 31P NMR (8.75 ppm versus dibenzylphosphoric acid 10.60 ppm) and 13C NMR through carbon-phosphorous coupling (carbon a and b of molecule 16 in FIG. 5: 2JC-P=5 Hz and 3JC-P=6 Hz). These couplings clearly identified the successful formation of molecule 16.

Materials and methods

General, Organic. All reactions were run under a nitrogen or an argon atmosphere in oven dried glassware, unless noted otherwise. All commercially available compounds were purchased from Aidrich Chemical Company, Milwaukee, Wis. or Lancaster Synthesis Inc., Windham, N.H. and used without purification, unless noted otherwise. All solvents were freshly distilled prior to use unless employed under aqueous conditions. Tetrahydrofuran (THF) and ether (Et$_2$O) were distilled from sodium/benzophenone. Dichloromethane (CH$_2$Cl$_2$), chloroform (CHCL$_3$), pyridine and triethylamine (ET$_3$N) were distilled from CaH$_2$. Methanol was distilled from magnesium. N,N-Dimethylformamide (DMF) was distilled from CaSO$_4$. Acetic anhydride was distilled under nitrogen. Molarities for alkyllithiums were established by titration with 2,5-dimethoxy benzyl alcohol. "Aqueous workup (solvent, drying agent)" in the experimental procedures refers to dilution of the reaction mixture with water, extraction of the aqueous layer multiple times with the designated organic solvent, washing the combined organic layers with brine, and drying over the indicated drying agent. "Concentration in vacuo" in the experimental procedures refers to isolation of product(s) from a solvent/product mixture by removal of the solvent under reduced pressure (water aspirator) with a Bychi Rotavapor. Flash chromatography was done on E. Merck Silica Gel #60, 230–400 mesh and analytical thin-layer chromatography (TLC) was performed on E. merck glass backed silica gel 60 plates, 0.25 mm thickness, with a 254 mm fluorescent indicator. NMR spectra were recorded on a BrYker AMX-300 NMR, a General Electric QE-300, or a JEOL 270 NMR; shifts reported are relative to internal tetramethylsilane; coupling constants (J) are reported in Hz and refer to apparent peak multiplicities and not true coupling constants; abbreviations used are as follows: s=singlet, d=doublet, t=triplet, m=multiplet.

Equilibrium Study

To a solution of 2,4,6-trimethyl phenol (2.1 mg, 15 mmol) in $CDCl_3$ (3.0 mL) was added silver(I)oxide (125 mg). The suspension was stirred at room temperature for 8 min, then was filtered through a glass-wool. The resulting green quinone methide solution (500 mL) was added to the dibenzylphosphoric acid solutions (0.5 equiv, 1.0 equiv, 2.0 equiv, or 3 equiv in 500 mL $CD_3CN$ respectively). The equilibrium constant was calculated by $H^1$ NMR intergration analysis at 25° C. constant temperature.

Ana. Data:

Quinone methide (2): $^1H$ NMR ($CDCl_3$) ¶ 6.98 (s, 2H, $C_6H2$), 5.74 (s, 2H, CH2), 2.00 (s, hH, 2CH3).

Trialkylphosphate (3) 1H NMR (1:1 CDCl3 and CD3CN) ¶7.31 (m, 10H, 2C6H5), 6.88 (s 2H, C6H2), 4.97 (d, J=7.67 Hz, 4H, 2CH2C6H5), 4.84 (d, J=8.41 Hz, 2H, CH2C6H2), 2.14 (s, hH, 2CH3).

3,5-Dimethyl-2-hydroxyacetophenone (7). To a solution of aluminium chloride (8.54 g, 64 mmol) in nitrobenzene (30 mL) was slowly added 2,4-dimehtylphenol (4.0 mL, 33 mmol) and acetyl chloride (2.4 mL, 33.7 mmol) in ice bath. The resulting solution was stirred at 48° C. under N2. After 24 h, the reaction solution was added into HCl solution (5N, 200 mL). The mixture was extracted with ethyl ether (3×200 mL). The organic layer was collected and then washed with NaOH solution (0.5 N, 200 mL), dried over MgSO4 and concentrated. Nitrobenzene was distilled off under reduced vacuum to afford 7 (3.125 g, 57.5% yield) as an off color solid.

1H NMR (CDCl3) ¶12.39 (s, 1H, OH), 7.35 (s, 1H, C6H2), 7.16 (s, 1H, C6H2), 2.60 (s, 3H, COCH3), 2.26 (s, 3H, CH3C6H2), 2.12 (s, 3H, CH3C6H2); 13C NMR d 205.2, 159.2, 138.7, 128.1, 127.4, 127.3, 118.4, 26.5, 20.2, 15.0.

2-Benzyloxy-3,5-dimethylacetophenone (8). To a solution of 3,5-dimethyl-2-hydroxyacetophenone (2.1574 g, 13.2 mmol) and benzylbromide (2.0 mL, 16.8 mmol) in DMF (15.0 mL) was slowly added potassium hydride solid (710 mg, 17.7 mmol) in ice-salt bath. After 12 h, the suspension was worked up with $NAHCO_3$ (100 mL) and ether (3×100 mL). The organic layer was dried over $MgSO_4$ and concentrated. Flash column (EtOAc in hexanes 2.5% to 4.5%) afforded 8 (2.845 g) in 85.1% yield as an oil.

$^1H$ NMR ($CDCl_3$) ¶7.40 (m, 5H, $C_6H_5$), 7.21 (s, 1H, $C_6H_2$), 7.13 (s, 1H, $C_6H_2$), 4.79 (s, 2H, $CH_2C_6H_5$), 2.56 (s, 3H, $COCH_3$), 2.30 (s, 3H, $CH_3C_6H_2$),2.28 (s, 3H, $CH_3C_6H_2$); 13C NMR d 205.2, 154.1, 137.1, 135.8, 134.1, 133.9, 132.3, 128.8, 128.5, 128.3, 127.8, 76.7, 30.4, 20.3, 15.8.

2-Benzyloxy-3,5-dimethylphenol (10). To a solution of 2-benzyloxy-3,5-dimethylacetophenone (2.8445 g, 11.2 mmol) in $CH_2Cl_2$ (25.0 mL) was added M-CPBA (65%, 6.10 g, 23.0 mmol). The resulting solution was cooled in ice bath and trifluoroacetice acid (0.86 mL, 11.2 mmol) was slowly added. The reguling suspension was stirred in dark. for 5 hs. The reaction solution was worked up with 10% $NaSO_3$ (100 ML) and $CH_2Cl_2$ (3×100 ml). The organic layer was washed with $NaHCO_3$, $H_2O$, brine, dried over $MgSO_4$ and concentrated. The residue was desolved in methanol (20 mL) and KOH solution (5 N, 20 mL) was added. The mixture was stirred for 12 h, then neutralized with 2 N Hcl and extracted with $CH_2Cl_2$ (3×100 mL). The organic layer was dried over $MgSO_4$ and concentrated. Flash column (EtOAc inhexanes 3% to 5%) afforded 10 (2.066 g) in 80.9% yield as an oil.

$^1H$ NMR ($CDCl_3$) ¶7.41 (m, 5H, C6H5), 6.59 (s, 1H, $C_6H_2$), 6.53 (s, 1H, $C_6H_2$), 4.85 (s, 2H, $CH_2C6H5$), 229 (s, 3H, $CH_3C6H_2$), 2.23 (s, 3H, $CH_3$, $C6H_2$); 13C NMR d 148.9, 142.2, 137.4, 134.8, 130.9, 129.1, 128.8, 128.4, 123.3, 113.9, 75.4, 20.7, 15.8.

(2-Benzyloxy-3,5-dimethyl) phenoxyacetic acid (11). To a suspension of 2-benzyloxy-3,5-dimethylphenol (1.500 g, 6.6 mmol) and sodium hydride (200 mg, 9.3 mmol) in DMF (10.0 mL) was cannulated a suspension of bromoacetic acid (1.097 g, 7.89 mmol) and sodium hydride (316 mg, 13.2 mmol) in DMF (10.0 mL). The resulting suspension was stirred for 12 h. The reaction solution was worked up with 2% acetic acid (100 mL) and ether (3×100 mL). The organic layer was washed with $H_2O$ (2×200 mL), brine, dried over MgSO4 and concentrated. Flash column (MeOH in $CH_2Cl_2$ 1% to 7%) afforded 11 (1.693 g) in 90.0% yield as a white solid.

$^1H$ NMR($CDCl_3$) ¶17.36 (m, 5H, C6H5), 6.68 (s, 1H, $C6H_2$), 6.59 (s, 1H, $C6H_2$), 4.97 (s, 2H, $CH_2C6H5$), 4.68 (s, 2H, $OCH_2COOH$), 2.26 (s, 3H, $CH_3C6H_2$) 2.19 (s 3H, $CH_3C6H_2$); 13C NMR d 173.2, 150.9, 144.9, 137.5, 134.4, 132.9, 128.7, 128.6, 128.4, 126.0, 114.3, 75.2, 67.0, 20.8, 15.7.

Methyl (2-benzyloxy-3,5-dimethyl) phenoxyacetate (12e). To a solution of methyl bromoacetate (54.5 mL, 0.58 mmol) in DMF (5.0 mL) was cannulated a suspension of 2-benzyloxy-3,5-dimethylphenol (110 mg, 0.48 mmol) and sodium hydride (40.0 mg) in DMF (10.0 mL). The resulting suspension was stirred for 12 H. The reaction solution was worked up with ether (3×100 mL). The organic layer was dried over MgSO4 and concentrated. Flash column (EtOAc in hexanes 7% to 10%) afforded 12e (118.2 mg) in 81.5% yield as an oil.

1H NMR ($CDCl_3$) ¶7.47–7.27 (m, 5H, C6H5), 6.62 (s 1H, C6H2), 6.52 (s, 1H, C6H2), 499 (s, 2H, $CH_2C6H5$), 4.66 (s, 2H, $OCH_2CO$), 3.78 (s, 3H, $CH_3OCO$), 2.24 (s, 3H, $CH_3C6H_2$); 13C NMR d 169.9, 150.7, 144.5, 138.0, 133.4, 132.4, 128.4, 128.3, 127.8, 124.9, 113.0, 74.5, 66.3, 52.1, 21.1, 16.1.

Methyl (2-hydroxy-3,5-dimethyl) phenoxyacetate (13e): To a solution of methyl (2-benzyloxy-3,5-dimethyl) phenoxyacetate (98.0 mg) in EtOAc (10.0 mL) was added palladium on activated caubon (10% 100 mg). The resulting suspension was hydrogenated under $H_2$ (55 psi) for 3 h. Palladium was removed through celite and the filtrate was concentrated to afford 13e (62.5 mg) in 91.2% yield as an oil.

1H NMR (CDCl3) ¶6.65 (s, 1H, $C6H_2$), 6.53 (s, 1H, $C6H_2$), 4.63 (s, 2H, $OCH_2CO$), 3.79 (s, 3H, $CH_3OCO$), 2.22 (s, 3H, $CH_3C6H_2$), 2.21 (s, 3H, $CH_3C6H_2$); 13C NMR d 171.0, 145.4, 143.2, 128.6, 126.0, 125.2, 114.2, 68.6, 52.5, 20.7, 15.6.

N,N-Dimethyl (2-benzyloxy-3,5-dimethyl) phenoxyacetamide (12 g): To a solution of methyl bromoacetamide (190.6 mg, 1.39 mmol) and of 2-benzyloxy-3,5-dimethylphenol (300.0 mg, 1.32 mmol) in DMF (5.0 mL) was potassium hydride (79.0 mg) in ice bath. The resulting suspension was stirred for 3 h. Then potassium hydride (270 mg, 5.2 equiv) and methyl idiode (1.0 mL, 12 equiv) was slowly added in ice bath. The suspension was stirred for 5 hs. The reaction solution was worked up with $NaHCO_3$ and $CH_2Cl_2$ (3×100 mL). The organic layer was dried over MgSO4 and concentrated. Flash column (MeOH in $CH_2Cl_2$ 4%) afforded 12G (333.7 mg) in 80.0% yield as an oil.

1H NMR (CDCl$_3$) ¶7.45–7.32 (m, 5H, C6H5), 6.62 (s, 2h, C6H$_2$), 4.96 (s, 2H, CH$_2$C6H5), 4.70 (s, 2H, OCH$_2$CO), 3.03 (s, 3H, CH$_3$N), 2.97 (s, 3H, CH$_3$N), 2.25 (s, 3H,CH$_3$C6H$_2$), 2.16 (s, 3H, CH$_3$C6H$_2$); 13C NMR d 167.9, 150.9, 144.3, 138.0, 133.6, 132.2, 128.3, 128.2, 127.8, 112.9, 74.6, 68.3, 36.6, 35.6, 21.2, 16.1.

N,N-Dimethyl (2-hydroxy-3,5-dimethyl) phenoxyacetamide (13 g): To a solution of N,N-dimethyl (2-benzyloxy-3,5-dimethyl) phenoxyacetamide (100 mg) in EtOAc (10.0 mL) was added palladium on activated carbon (10%, 100 mg). The resulting suspension was hydrogenated under H$_2$ (55 psi) for 3 h. Palladium was removed through celite and the filtrate was concentrasted to afford 13 g (74.0 mg) in 94.9% yield as an oil.

1H NMR (CDCl$_3$) ¶6.66 (s, 1H, C6H$_2$), 6.62 (s, 1H, C6H$_2$), 4.66 (s, 2H, OCH$_2$CO), 2.94 (s, 3H, CH3 N), 2.86 (s, 3H, CH$_3$N), 2.20 (s, 3H, CH$_3$C6H$_2$), 2.19 (s, 3H, CH$_3$C6H$_2$); 13C NMR d 170.2, 146.9, 145.3, 128.1, 126.8, 126.0, 117.7, 71.5, 35.7, 35.3, 20.5, 15.8.

1-Propyl (2-benzyloxy-3,5-dimethyl) phenoxyacetate (12f). To a suspension of (2-benzyloxy-3,5-dimethyl) phenoxyacetic acid (200 mg, 0.70 mmol) and 1,3-dicyclohexylcarbodimide (151.5 mg, 0.73 mmol) in CH$_2$Cl$_2$ (10.0 mL) was added pyridine (43.0 mL) and 1-propanol (57 mL). The suspension was stirred at room temperature for 12 h. The precipitation was filtered through filter paper and the filtrate was concentrated. Flash column (EtOAc in hexanes 3% to 5%) afforded 12f (111.5 mg) in 48.6% yield as an oil.

1H NMR (CDCl$_3$) ¶7.52–7.25 (m, 5H, C6H5), 6.62 (s, 1H, C6H$_2$), 6.53 (s, 1H, C6H$_2$), 5.01 (s, 2H, CH$_2$C6H5), 4.66 (s, 2H, OCH$_2$CO), 4.16 (t,J=6.68 Hz, 2H, OCH$_2$CH$_2$), 2.24 (s, 3H, CH$_3$C6H$_2$), 2.16 (s, 3H, CH$_3$C6H$_2$), 1.67 (h, J=7.42 Hz, 2H, OCH$_2$CH$_2$), 0.91 (t, J=7.67 Hz, 3H, OCH$_2$CH$_2$CH$_3$); 13C NMR d 169.2, 150.6, 144.4, 133.3, 132.3, 128.4, 128.3, 128.3, 127.8, 124.7, 112.9, 74.5, 66.7, 66.2, 21.9, 21.1, 16.1, 10.3.

1-Propyl (2-hydroxy-3,5-dimethyl) phenoxyacetate (13f). To a solution of 1-propyl (2-benzyloxy-3,5-dimethyl) phenoxyacetate (108.6 mg) in EtOAc (10.0 mL) was added palladium on activated carbon (10%, 50 mg). The resulting suspension was hydrogenated under H$_2$ (55 psi) for 3 h. Palladium was removed through celite and the filtrate was concentrated to afford 13f (78.0 mg) in 99.0% yield as an oil.

1H NMR (CDCl$_3$) ¶6.64 (s, 1H, C6H$_2$), 6.55 (s, 1H, C6H$_2$), 4.62 (s, 2H, OCH$_2$CO), 4.15 (t, J=6.70 Hz, 2H, OCH$_2$CH$_2$), 2.21 (s, 3H, CH$_3$C6H$_2$), 2.20 (s, 3H, CH$_3$C6H$_2$), 1.66 (h, J=7.18 Hz, 2H, OCH$_2$CH$_2$), 0.92 (t, J=7.42 Hz, 3H, OCH$_2$CH$_2$CH$_3$); 13C NMR d 171.1, 145.7, 143.4, 128.7, 126.1, 125.2, 114.5, 68.9, 67.3, 22.0, 20.7, 15.6, 10.2.

2-Chloroethyl (2'-benzyloxy-3',5'-dimethyl) phenoxyacetate (12d): To a suspension of (2-benzyloxy-3,5-dimethyl) phenoxyacetic acid (150 mg, 0.52 mmol) and 1,3-dicyclohexylcarbodimide (151.3 mg, 0.73 mmol) in CH$_2$Cl$_2$ (10.0 mL) was added pyridine (42.4 mL) and 2-chloroethanol (45.0 mL). The suspension was stirred at room temperature for 12 h. The precipitation was filtered through filter paper and the filtrate was concentrated. Flash column (EtOAc in hexanes 10%) afforded 12d (89.2 mg) in 47.5% yield as an oil.

1H NMR (CDCl$_3$) ¶7.51–7.27 (m, 5H, C6H5), 6.64 (s, 1H, C6H$_2$), 6.55 (s, 1H, C6H$_2$), 5.01 (s, 2H, CH$_2$C6H5), 4.72 (s, 2H, OCH$_2$CO), 4.44 (t, J=5.69 Hz, 2H, OCH$_2$CH$_2$Cl), 3.67 (t, J=5.44 Hz, 2H, OCH$_2$CH$_2$Cl), 2.25 (s, 3H, CH$_3$C6H$_2$), 2.17 (s, 3H, CH$_3$C6H$_2$); 13C NMR d 168.7, 150.5, 144.4, 137.9, 133.4, 132.4, 128.3, 128.3, 127.8, 125.0, 113.0, 74.5, 66.0, 64.5, 41.3, 21.1, 16.1.

2-chloroethyl (2'-hydroxy-3',5'-dimethyl) phenoxyacetate (13d): To a solution of 2-chloroethyl (2'-benzyloxy-3',5'-dimethyl) phenoxyacetate (74.0 mg) in EtOAc (10.0 mL) was added palladium on activated carbon (10%, 72 mg). The resulting suspension was hydrogenated under H$_2$ (55 psi) for 3 h. Palladium was removed through celite and the filtrate was concentrated to afford 13d (53.0 mg) in 96.6% yield as a off color solid.

1H NMR (CDCl$_3$) ¶6.65 (s, 1H, C6H$_2$), 6.55 (s, 1H, C6H$_2$), 4.86 (s, 2H, OCH$_2$CO), 4.44 (t, J=5.44 Hz, 2H, OCH$_2$CH$_2$CL), 3.69 (t, J=5.44 Hz, 2H, OCH$_2$CH$_2$Cl), 2.22 (s, 3H, CH$_3$C6H$_2$), 2.21 (s, 3H, CH$_3$C6H$_2$); 13C NMR d 170.2, 145.2, 143.1, 128.7, 126.0, 125.1, 113.9, 68.3, 64.9, 41.2, 20.7, 15.6.

2,2,2-Trichloroethyl (2'-benzyloxy-3',5'-dimethyl) phenoxyacetate (12c). To a suspension of (2-benzyloxy-3,5-dimethyl) phenoxyacetic acid (270 mg, 0.94 mmol) and 1,3-dicyclohexylcarbodimide (292.0 mg, 1.41 mmol) in CH$_2$Cl$_2$ (10.0 mL) was added pyridine (76.0 mL) and 2,2,2-trichloroethanol (117.0 mL). The suspension was stirred at room temperature for 12 h. The precipitation was filtered through filter paper and the filtrate was concentrated. Flash column (EtOAc in hexanes 5% to 10%) afforded 12c (311.1 mg) in 78.9% yield as an oil.

1H NMR (CDCl$_3$) ¶7.52–7.28 (m, 5H, C6H5), 6.67 (s, 1H, C6H$_2$), 6.60 (s, 1H, C6H$_2$), 5.04 (s, 2H, CH$_2$C6H5), 4.85 (s, 2H, OCH$_2$CO), 4.84 (s, 2H, OCH$_2$CCl$_3$), 2.26 (s, 3H, CH$_3$C6H$_2$), 2.19 (s, 3H, CH$_3$C6H$_2$); 13C NMR d 167.6, 150.3, 144.4, 137.8, 133.4, 132.5, 128.3, 128.3, 127.8, 125.1, 125.1, 113.1, 94.4. 74.6, 74.0, 65.8, 21.1, 16.1.

2,2,2-Trichloroethyl (2'-hydroxy-3'5'-dimethyl) phenoxyacetate (13c). To a solution 2,2,2-trichloroethyl (2'-benzyloxy-3',5'-dimethyl) phenoxyacetate (151.0 mg) in EtOAc (10.0 mL) was added palladium on activated carbon (10%, 72 mg). The resulting suspension was hydrogenated under H$_2$ (55 psi) for 3 h. Palladium was removed through celite and the filtrate was concentrated to afford 13c (97.8 mg) in 82.9% yield as a white solid.

1H NMR (CDCl$_3$) ¶6.65 (s, 1H, C6H$_2$), 6.54 (s, 1H, C6H$_2$), 4.83 (s, 2H, OCH$_2$CO), 4.80 (s, 2H,OCH$_2$CCl$_3$), 2.24 (s, 3H, CH$_3$C6H$_2$), 2.21 (s, 3H, CH$_3$, C6H$_2$).

2,2,2-Trifluoroethyl (2'-benzyloxy-3',5'-dimethyl) phenoxyacetate (12b). To a suspension of (2-benzyloxy-3,5-dimethyl) phenoxyacetic acid (150 mg, 0.52 mmol) and 1,3-dicyclohexylcarbodimide (151.3 mg, 0.73 mmol) in CH$_2$Cl$_2$ (10.0 mL) was added pyridine (43.0 mL) and 2,2,2-trifluoroethanol (46.0 mL). The suspension was stirred at room temperature for 12 h. The precipitation was filtered through filter paper and the filtrate was concentrated. Flash column (EtOAc in hexanes 10% to 15%) afforded 12b (138.0 mg) in 70.8% yield as an oil).

1H NMR (CDCl$_3$) ¶7.52–7.25 (m, 5H, C6H5), 6.66 (s, 1H, C6H$_2$), 6.54 (s, 1H, C6H$_2$), 4.99 (s, 2H, CH$_2$C6H5), 4.60 (s, 2H, OCH$_2$CO), 4.56 (q, J=8.41 Hz, 2H, OCH$_2$CF$_3$), 2.25 (s, 3H, CH$_3$C6H$_2$), 2.17 (s, 3H, CH$_3$C6H$_2$); 13C NMR d 167.7, 150.4, 144.6, 137.9, 133.5, 132.6, 128.3, 128.3, 127.9, 125.4, 122.7 (q, 1JC-F=277.3 Hz), 113.5, 74.7, 66.0, 60.6 (q, 2JC-F=36.7 Hz), 21.0, 16.1.

2,2,2-Trifluoroethyl (2'-hydroxy-3',5'-dimethyl) phenoxyacetate (13b). To a solution 2,2,2-trifluoroethyl (2'-benzyloxy-3',5'-dimethyl) phenoxyacetate (138.0 mg) in EtOAc (10 mL) was added palladium on activated carbon (10%, 92 mg). The resulting suspension was hydrogenated under H$_2$ (55 psi) for 3 h. Palladium was removed through celite and the filtrate was concentrated to afford 13b (93.5 mg) in 96.0% yield as a white solid.

1H NMR (CDCl$_3$) ¶6.65 (s, 1H, C6H$_2$), 6.52 (s, 1H, C6H$_2$), 4.74 (s, 2H, OCH$_2$CO), 4.55 (q, J=8.41 Hz, 2H,

OCH$_2$CF$_3$), 2.23 (s, 3H, CH$_3$C6H$_2$), 2.20 (s, 3H, CH$_3$C6H$_2$); 13C NMR d 68.9, 144.9, 142.9, 128.9, 126.1, 125.3, 122.6, (q, 1JC-F=277.2 Hz), 113.3, 67.7, 60.7 (q, 2JC-F=37.2 Hz), 20.8, 15.6.

Phenyl (2-benzyloxy-3,5-dimethyl) phenoxyacetate (12a): To a suspension of (2-benzyloxy-3,5-dimethyl) phenoxyacetic acid (100 mg, 0.35 mmol) and 1,3-dicyclohexyl-carbodimide (75.8 mg, 0.36 mmol) in CH$_2$Cl$_2$ (10 mL) was added pyridine (30.0 mL) and phenol (33.3 mg, 0.35 mmol). The suspension was stirred at room temperature for 12 h. The precipitation was filtered through filter paper and the filtrate was concentrated. Flash column (EtOAc in hexanex 5%) afforded 12a (102.3 mg) in 80.8% yield as an oil.

1 H NMR (CDCl$_3$) ¶7.52–7.11 (m, 10H, 2C6H5), 6.67 (s, 1H,C6H$_2$), 6.65 (s, 1H, C6H$_2$), 5.03 (s, 2H, CH$_2$C6H5), 4.91 (s, 2H, OCH$_2$CO), 2.28 (s, 3H, CH$_3$C6H$_2$), 2.19 (s, 3H, CH$_3$C6H$_2$); 13C NMR d 167.7, 150.7, 150.2, 144.6, 138.0, 133.6, 132.6, 129.6, 128.5, 128.4, 128.0, 126.3, 125.2, 121.4, 113.4, 74.7, 66.5, 21.2, 16.2.

Lactone (17): A suspension of phenyl (2-benzyloxy-3,5-dimethyl) phenoxyacetate (52.0 mg) and potassium carbonate (425 mg) in CH$_2$Cl$_2$ (10 mL) was stirred for 3 h. The reaction solution was diluted in CH$_2$Cl$_2$ (50 mL) and washed with water (60 mL). The organic layer was dried over MgSO4 and concentrated. Flash column (EtOAc inhexanes 2%) afforded 17 (25.5 mg) in 75.4% yield as a white solid.

1H NMR (CDCl$_3$) ¶668 (s, 1H, C6H$_2$), 6.67 (s, 1H, C6H$_2$), 4.60 (s, 2H, OCH$_2$CO), 2.25 (s, 6H, 2CH$_3$C6H$_2$); 13C NMR d 163.6, 142.0, 137.4, 134.6, 126.7, 125.5, 115.0, 64.7, 20.8, 15.0.

Trapped trialkylphosphate (16): To a solution of 2,2,2-trifluoroethyl (2'-hydroxy-3',5'-dimethyl) phenoxyacetate (21.2 mg, 0.076 mmol) in chloroform (25.0 mL) was added lead (IV) oxide (2.5 g) and acetic acid (3.3 mL). The suspension was stirred for 10 min and the solid was filtered. The resulting yellow solution was added to dibenzylphosphoric acid (42.4 mg, 2 equiv). The reaction solution was stirred at 25° C. for 20 h and then at 40° C. for 24 h. The reaction solution was passed through a DEAE-cellulose resin (dry, pretreated with chloroform) to afford the crude trapped trialkylphosphate 16 (23.0 mg) in 66% yield as an off-color solid.

1 H NMR (CD$_3$CN) ¶7.36–7.33 (m, 10H, 2C6H5), 6.86 (s, 2H, C6H$_2$), 5.01 (d, J=8.16 Hz, 4H, 2CH$_2$C6H5), 4.90 (d, J=8.66 Hz, 2H, CH$_2$C6H$_2$), 4.66 (s, 2H, OCH$_2$CO), 2.23 (s, 3H, CH$_3$); 31P NMR d 8.75.

References

Reviews on Qjuinone Methide: (a) Grauenanger, P. Methoden der Organisch Chemie, Houben-Weyl, 4th edition, 1979, 395–(b) Peter, M. G. Angew. Chem. Int. Ed. Engl. 1989, 28, 5550.1.

For more recent, elegant examples of quinone methide, see: (a) Chatterjee, M.; Rokita, S. E. J. Am. Chem. Soc. 1994, 116, 1690. (b) Li, T.; Zeng, Q.; Rokita, S. E. Bioconjugate Chem. 1994, 5, 497. (c) Meyers, J. K.; Cohen, J. D.; Widlanski, T. S. J. Am. Chem. Soc. 1995, 117, 11049. (d) Myers, J. K.; Widlanski, T. S. Science 1993, 262, 1451. (e) Wang, Q.; Dechert, U.; Jirik, F.; Withers, S. G. Biochem. Biophys. Res. Commun. 1994, 200, 577. (f) Rokita, S. E.; Yang, J; Pande, P.; Greenberg, W. A. J. Org. Chem. 1997, 62, 3010. (g) Angle, S. T.; Rainier, J. D.; Woytowicz, C. J. Org. Chem. 1997, 62, 5884.

Dyall, L. K.; Weistein, S. J. Am. Chem. Soc. 1972, 94, 2196.

For leading references, see: McCracken, P. G.; Bolton, J. L.; Thatcher, G. R. J. J. Org. Chem. 1997, 62, 1820.

Cullinane, J.; Edward, E. J. Appl. Chem. 1959, 134.

Venuti, M. C.; Loe, B. E.; Jones, G. H.; Young, J. M. J. Med. Chem. 1988, 31, 2132.

Koch, S.; Chamberlin, R. Syn. Comm. 1989, 19, 829.

Hassner, A.; Alexanian, V. Tetrahedron Lett. 1978 (46), 4475.

Rao, R.; Sucheta, K.; Reddy, G.; Rovi, D. Tetrahedron Lett. 1994, 35, 4415.

Winkle, M. R.; Lansinger, J. M.; Ronald, R. C. J. Chem. Soc., Chem. Commun. 1980.

FIG. S1 is a schematic representation of a reaction process.

Figure 2C:
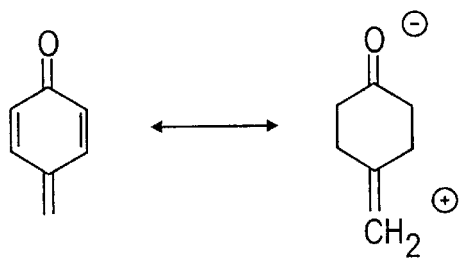
Figure 2:

FIG. 2 is a schematic representation of the resonance structure of para-benzoquinone methide reflects its dualistic reactivity characteristics.

Figure 3:
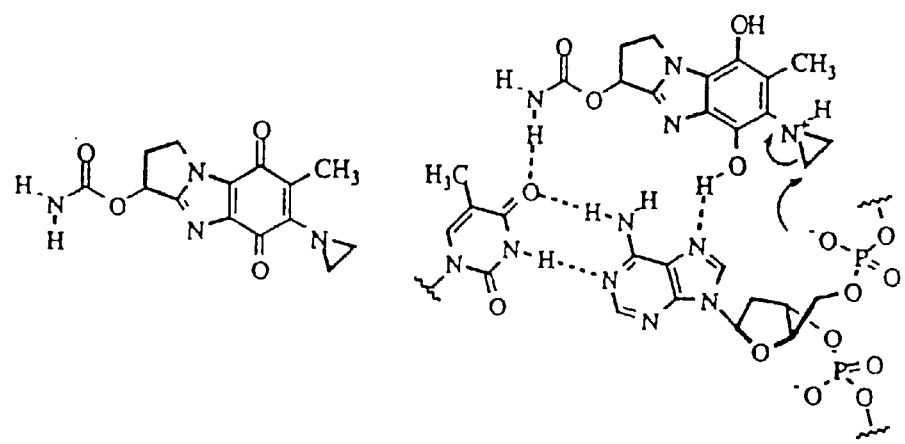

FIG. 3 is a schematic representation of Skibo's Pyrollo [1,2-a]benzimidazole 5 for selective alkylation at the 5'-phosphate group via the presumed complex 6.

FIG. T1 is a tabular representation of the effect of acid/base on equilibrium of 7:8.

FIG. S2 is a schematic representation of a reaction process.

Figure 4:
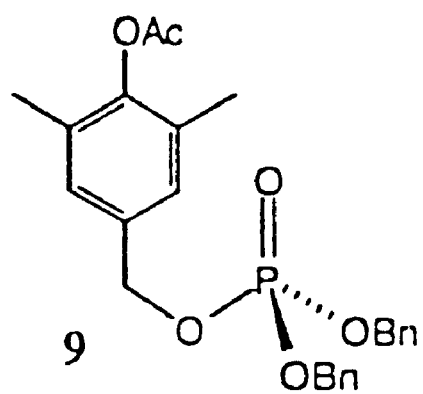

FIG. 4 is a schematic representation of a compound.

Figure 5:
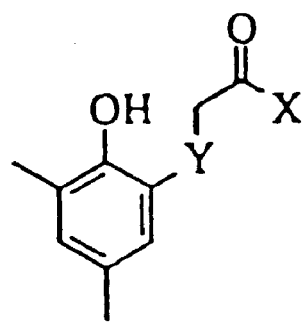

FIG. 5 is a schematic representation of a compound.

FIG. S3 is a schematic representation of a reaction process.

FIG. S4 is a schematic representation of a reaction process.

FIG. T2 is a tablular representation of a reaction process.

FIG. S5 is a schematic representation of a reaction process.

FIG. 6 is a schematic representation of a reaction process.

FIG. S6 is a schematic representation of a reaction process.

FIG. S7 is a schematic representation of a reaction process.

FIG. S8 is a schematic representation of a reaction process.

FIG. S9 is a schematic representation of a reaction process.

FIG. S10 is a schematic representation of a reaction process.

Figures 8, 9:
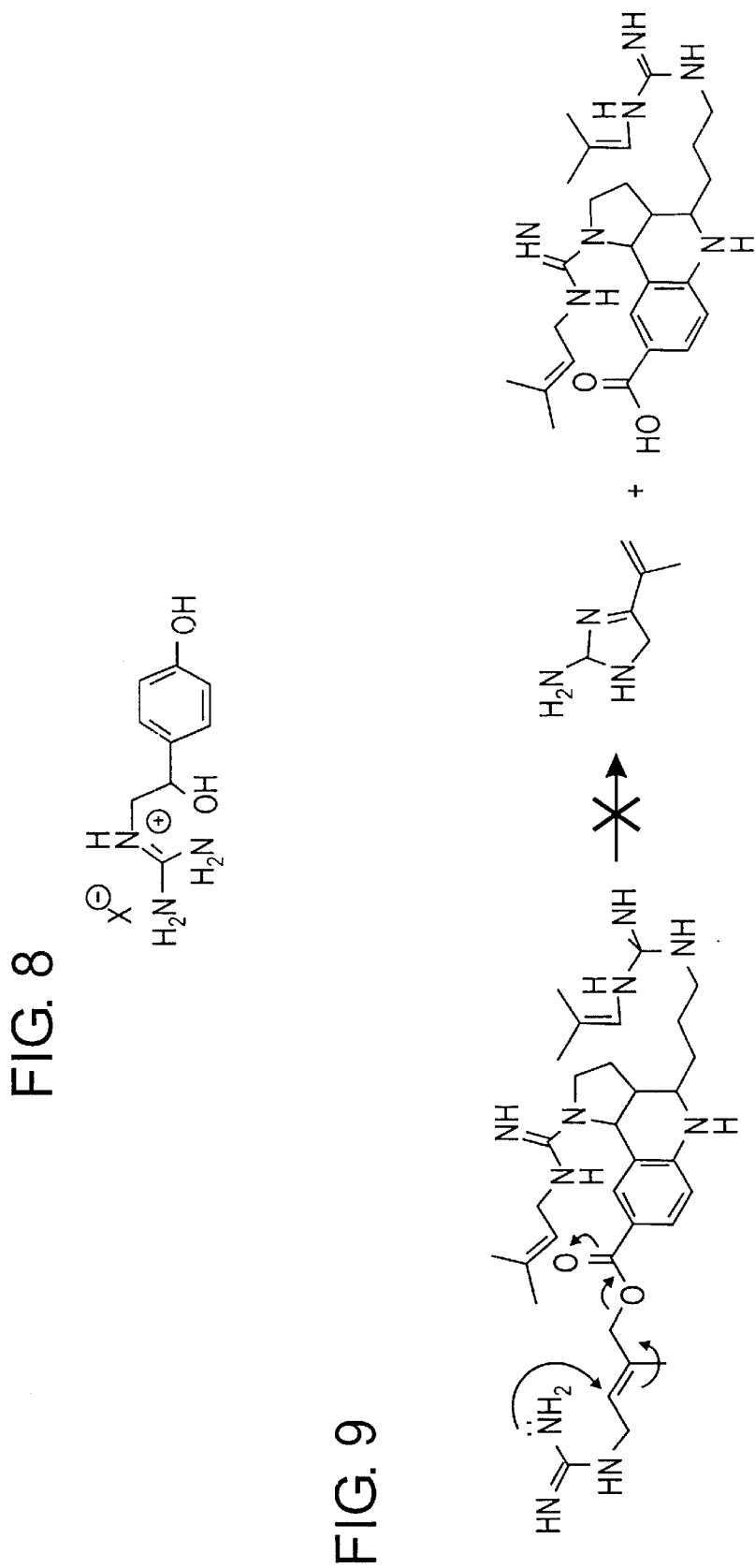

FIG. 8 is a schematic representation of a reaction process.

FIG. 9 is a schematic representation of a reaction process.

Figure 1:
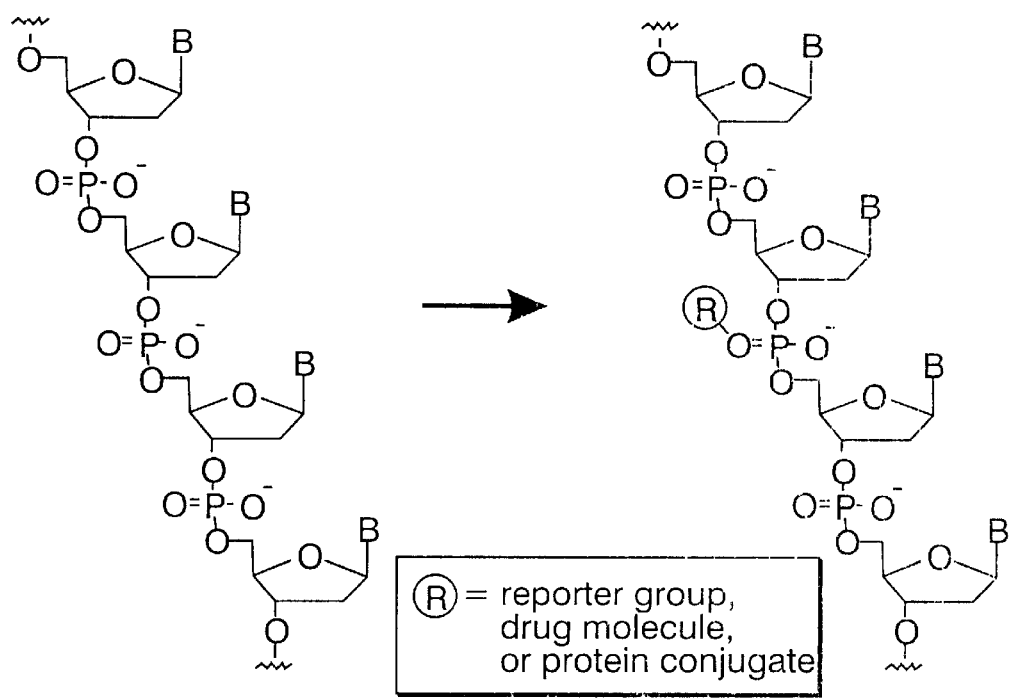
FIG. 1—Is a schematic representation of the Chemospecific and regiospecific labelinc of DNA through phosphodiester alkylation (B=base).
Figure 1A:
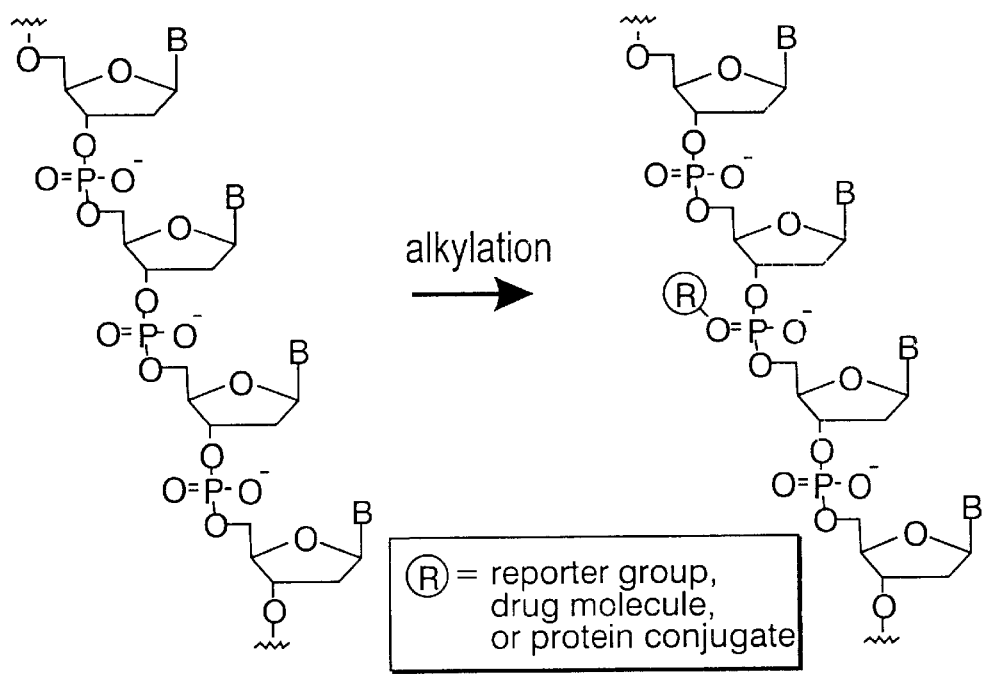

FIG. 1A. Chemospecific and regiospecific labeling of DNA through phosphodiester alkylation (B=base).

FIG. S1A is a schematic representation of a reaction process.

FIG. 2A. Is a schematic representation of a resonance structure of para-benzoquinone methide reflects its dualistic reactivity characteristics.

FIG. 3A is a schematic representation of Skibo's Pyrollo [1,2-a] benzimidazole 1 for selective alkylation at the 5'-phosphate group via the presumed complex 2.

FIG. S2A is a schematic representation of a reaction process.

FIG. T1 is a tablular representation of a reaction process.

FIG. 4A is a schematic representation of a reaction process.

FIG. 5A is a schematic representation of a reaction process.

FIG. S3A is a schematic representation of a reaction process.

FIG. S4A is a schematic representation of a reaction process.

FIG. T2A is a tablular representation of a reaction process.

FIG. S5A is a schematic representation of a reaction process.

Figure 6A:
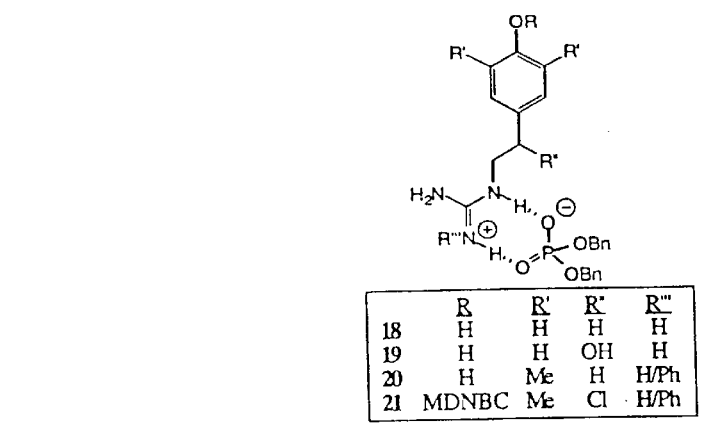

FIG. 6A is a schematic representation of a reaction process.

Figure 7A:
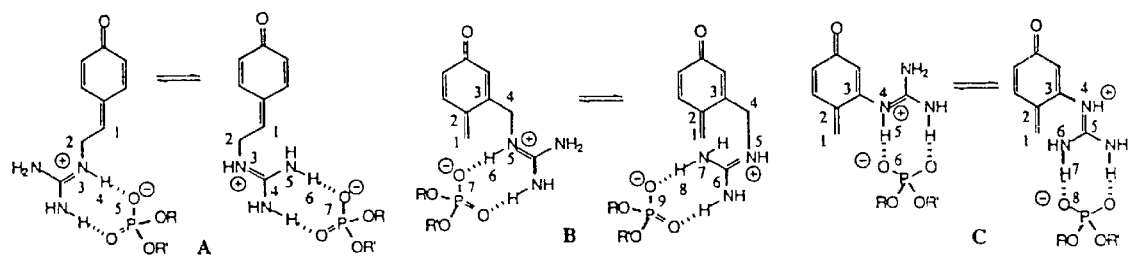

FIG. 7A is a schematic representation of a reaction process.

FIG. S6A is a schematic representation of Danishefky-type diene[76] will be synthesized in four steps from the dianion of acetoacetic amide 26 ( FIG. 34).[77] Dianion akylation[78] will afford 27 which will be reduced to the aldehyde[79] and converted to diene 28 by the standard approach.[80]

FIG. S7A. Is a schematic representation of there is good precedent for the success of the cycloaddition of diene 28 with allene 29 to produce phenol 30 (FIG. 35).[81]. Phenol 30 will be converted to machine-ready derivative 35.

FIG. S8A is a schematic representation of a reaction process.

FIG. T3A is a tablular representation of a reaction process.

FIG. S9A is a schematic representation of a reaction process.

FIG. S1B is a schematic representation of a reaction process.

FIG. T1B is a tablular representation of a reaction process.

FIG. T2B is a tablular representation of a reaction process.

Figure 1C:
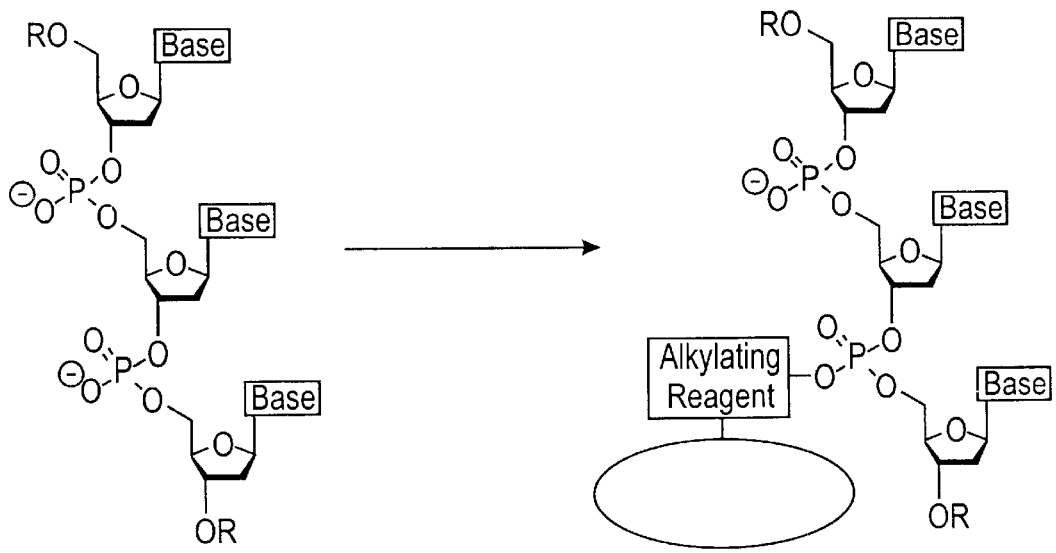

FIG. 1C is a schematic representation of the Functionalization of DNA through a general DNA phosphodiester alkylating reagent.

FIG. 2C is a schematic representation of resonance forms of para-benzoquinone methide.

FIG. S1C is a schematic representation of a reaction process.

FIG. S2C is a schematic representation of a reaction process.

FIG. 1D is a schematic representation of three catagories of standard methods for attaching chemical probes to biomolecules.[2a]

FIG. 2D is a schematic representation of general types of labeling reporter groups typically used in biomolecular investigations. The fluorescent probes table was duplicated from reference 3.

FIG. S1D is a schematic representation of a reaction process.

FIG. S2D is a schematic representation of a reaction process.

FIG. S4D is a schematic representation of the (1) Alkylation of a dialkylphosphate with quinone methide 6 to form trialkylphosphate 7 has been accomplished.

FIG. S4D is a schematic representation of the hydrolytic stability of a trapped trialkylphosphate related to that which will be trapped out intramolecularly in the affinity transfer labeling reagent.

FIG. S5D is a schematic representation of the formation of a quinone methide via photolytic initiated deprotection of dibenzylphosphate ammonium salt 9.

FIG. S6D is a schematic representation of a reaction process.

FIG. 3D is a schematic representation of a compound.

FIG. 4D is a schematic representation of a compound.

FIG. S7D is a schematic representation of a reaction process.

FIG. S8D is a schematic representation of a reaction process.

FIG. S9D is a schematic representation of a reaction process.

FIG. S10D is a schematic representation of a reaction process.

Figure 6D:
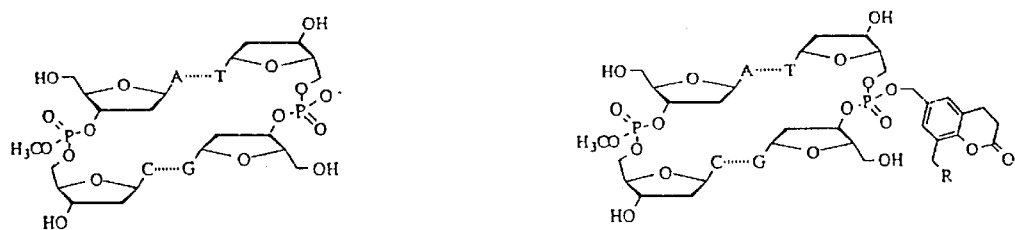

FIG. 6D is a schematic representation of a methylphosphate d(ApMeC) hybridized with complementary d(GpT) [duplex 31] for the analysis of the photoinitiated alkylation reaction to afford the alkylated duplex 32.

Figure 7D:
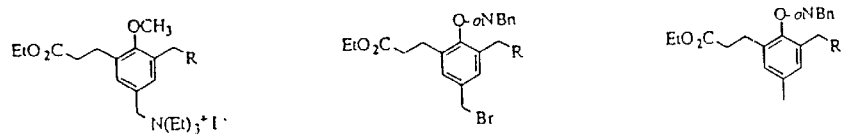

FIG. 7D is a schematic representation of control reagents to be used for defining various aspects of the phosphate alkylation reaction.

Figure 8E:
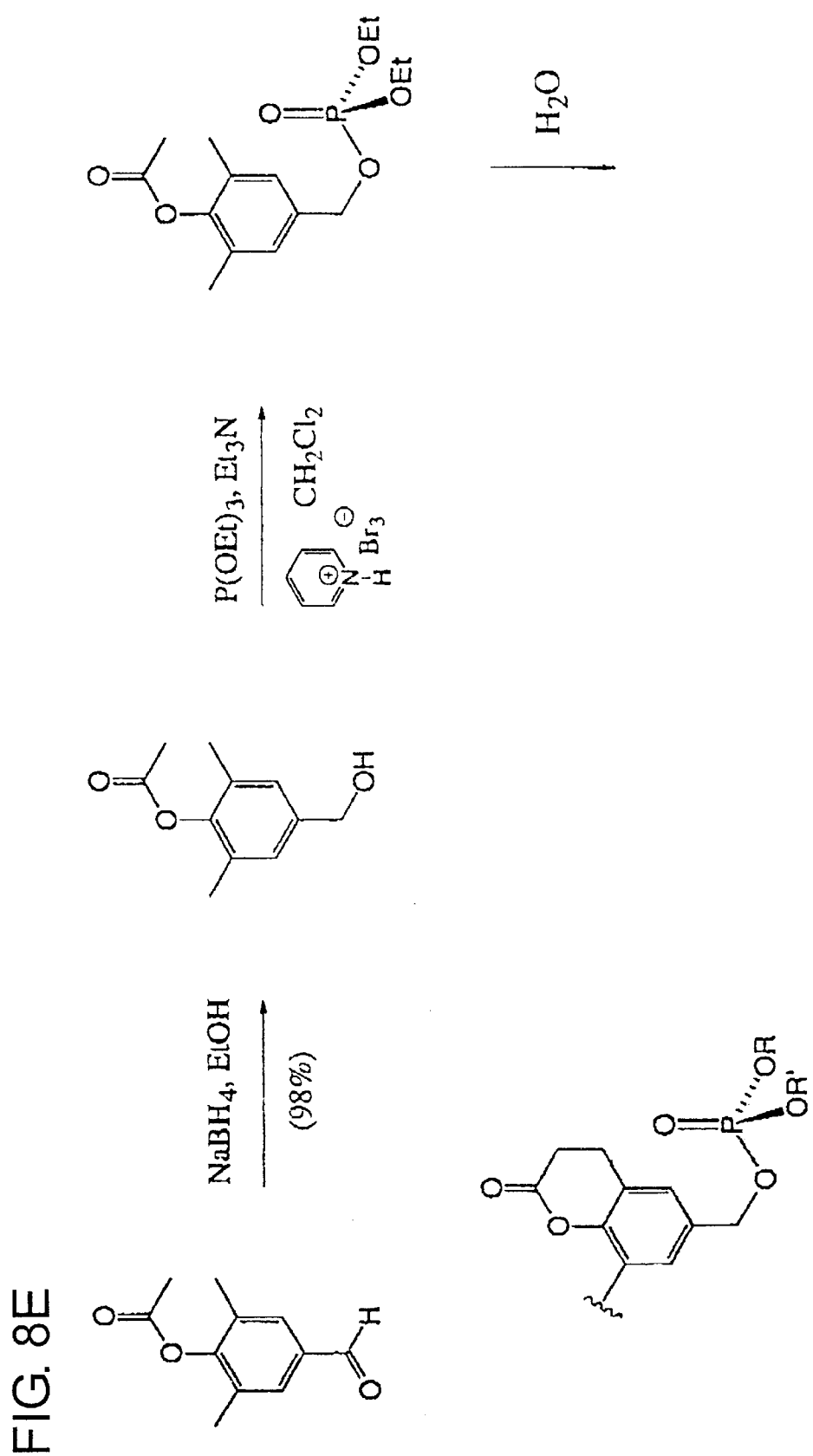
Figure 8D:
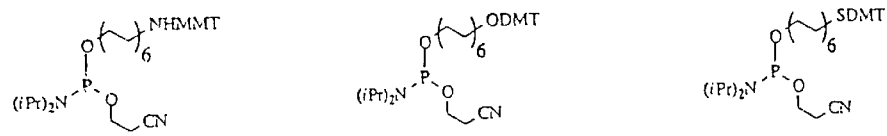

FIG. 8D is a schematic representation of 5'-Modifier phosphoramidites for linker attachmnent of oligonucleotides to the transfer affinity reagent.

FIG. S11D is a schematic representation of a reaction process.

FIG. S12D is a schematic representation of a reaction process.

FIG. S13D is a schematic representation of a reaction process.

FIG. S14D is a schematic representation of a reaction process.

FIG. S15D is a schematic representation of a reaction process.

FIG. 9D is a schematic representation of a 2'-O-linked transfer labeling reagent designed to be constrained across the minor groove for more controlled regioselectivity in labeling.

FIG. S16D is a schematic representation of a reaction process.

FIG. 1E is a schematic representation of a reaction process.

Figure 2E:
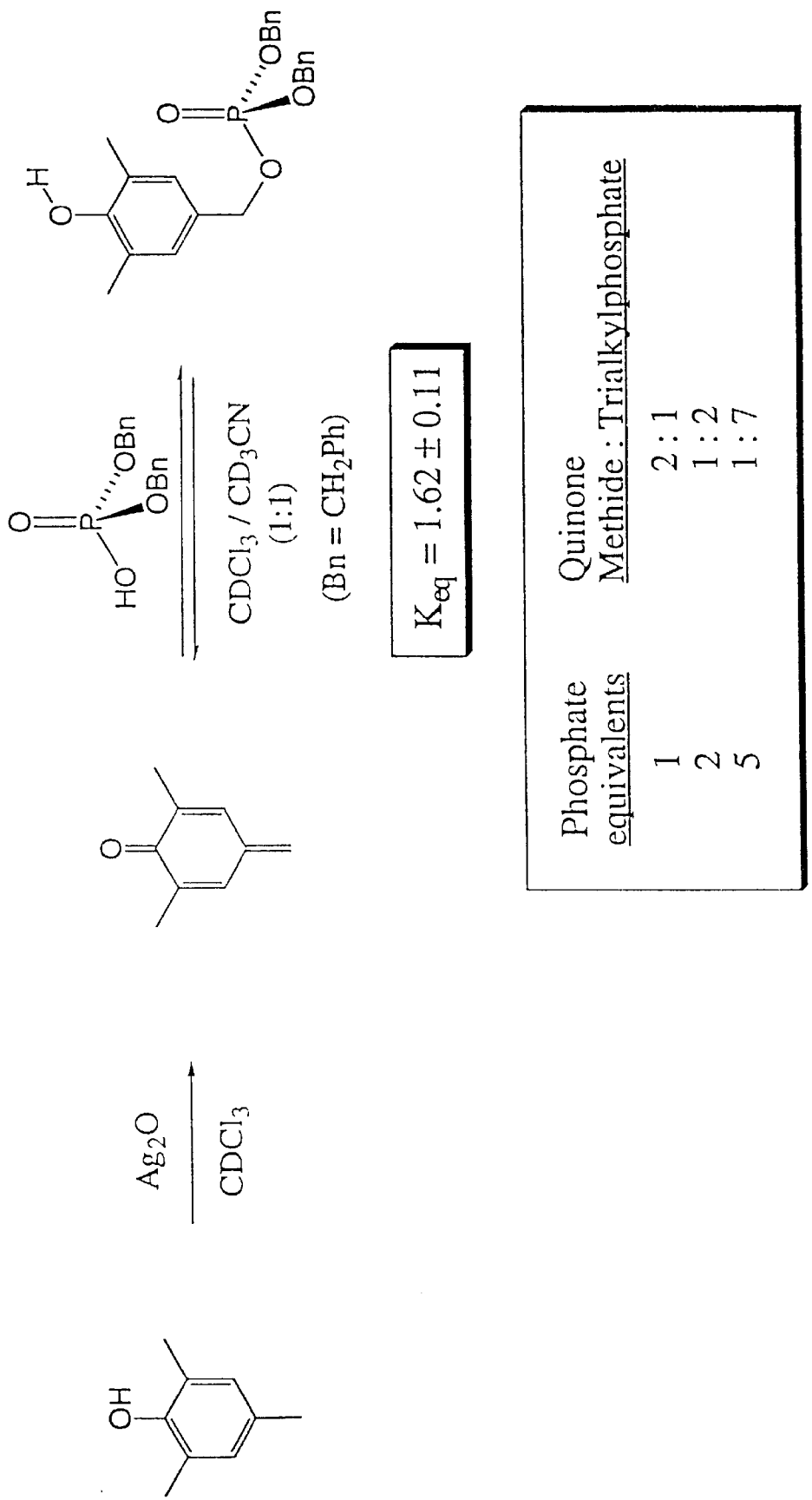

FIG. 2E is a schematic representation of a reaction process.

FIG. 3E is a schematic representation of a reaction process.

Figure 4E:
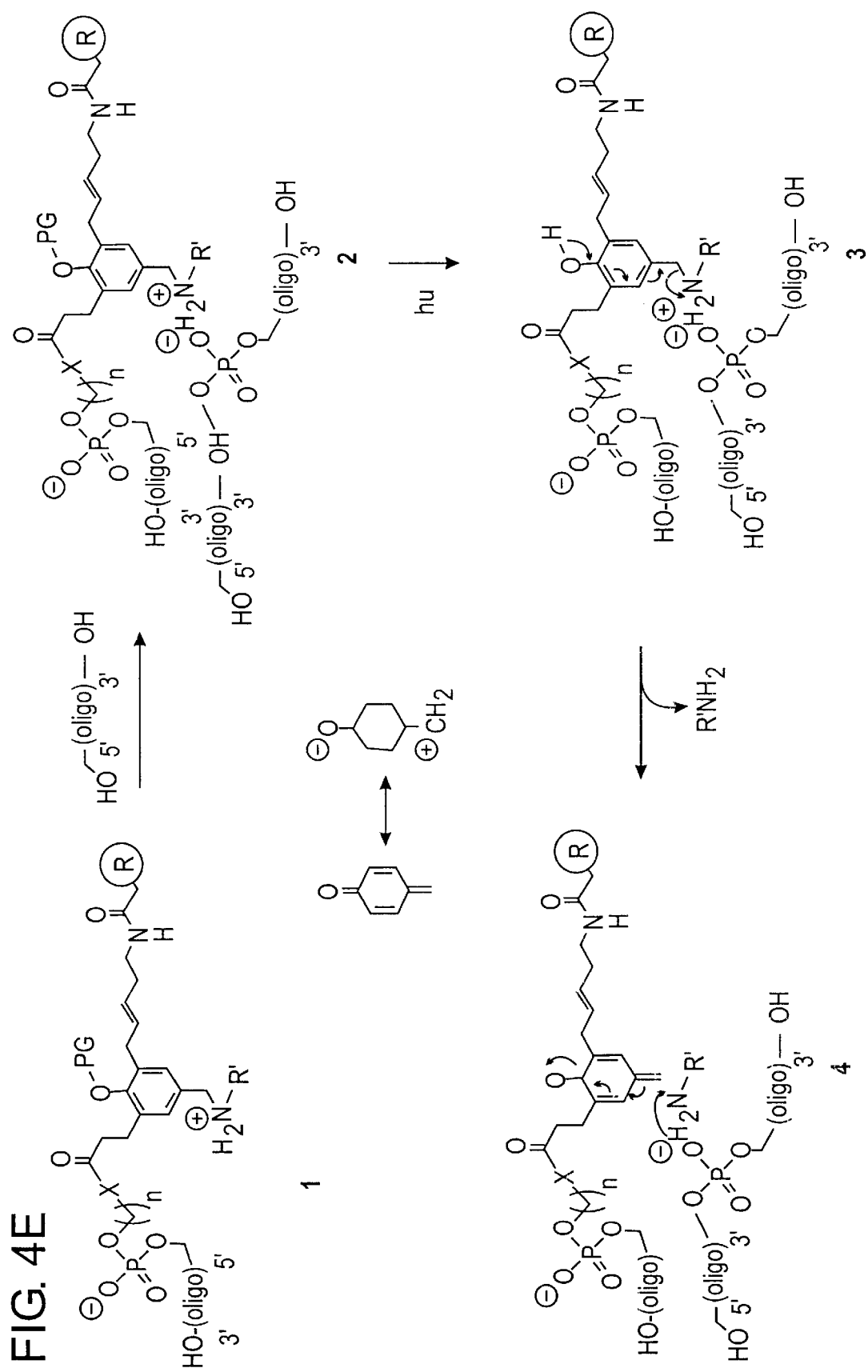

FIG. 4E is a schematic representation of a reaction process.

FIG. 4E is a schematic representation of a reaction process.

Figure 5E:
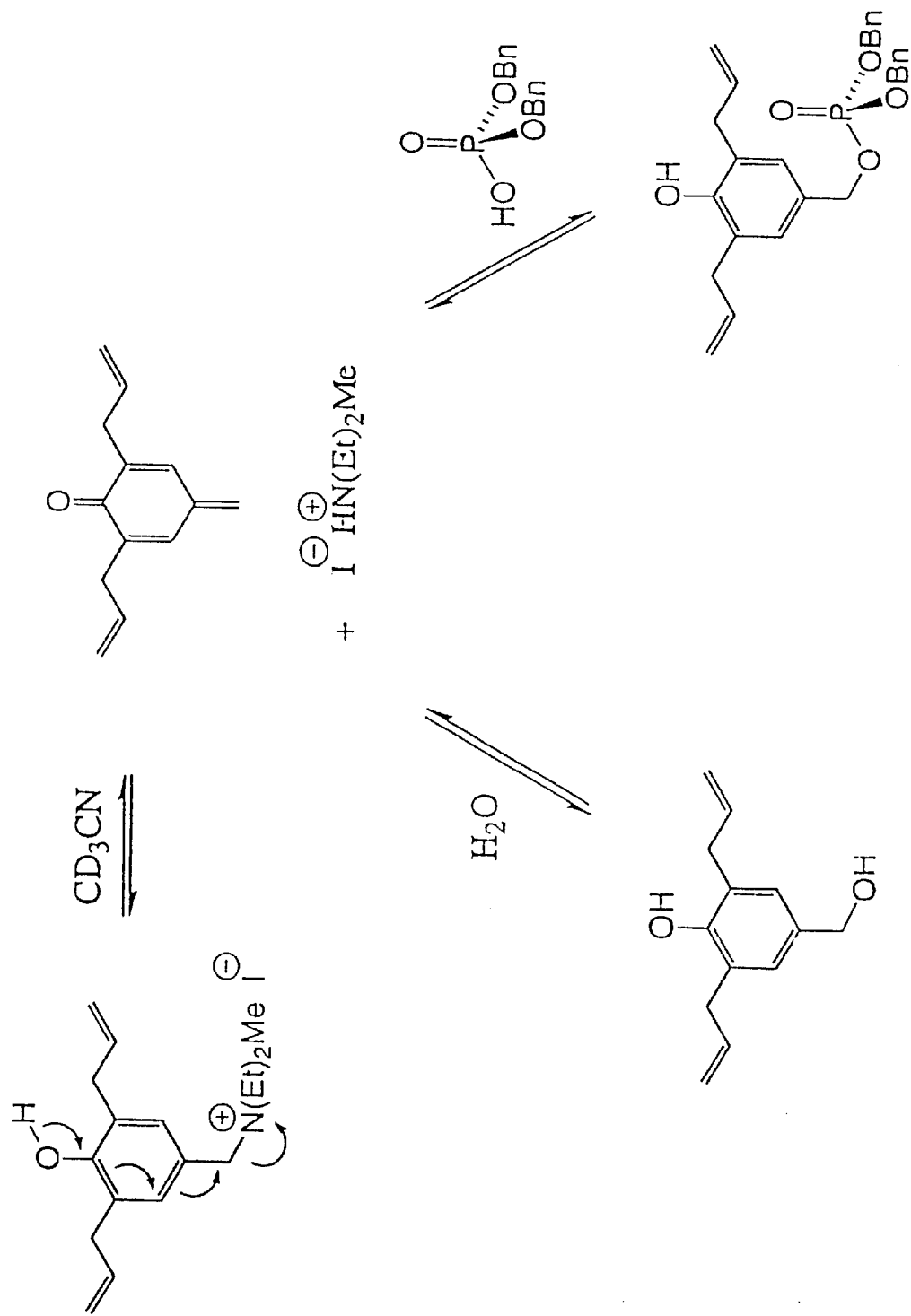

FIG. 5E is a schematic representation of a reaction process.

Figure 6E:
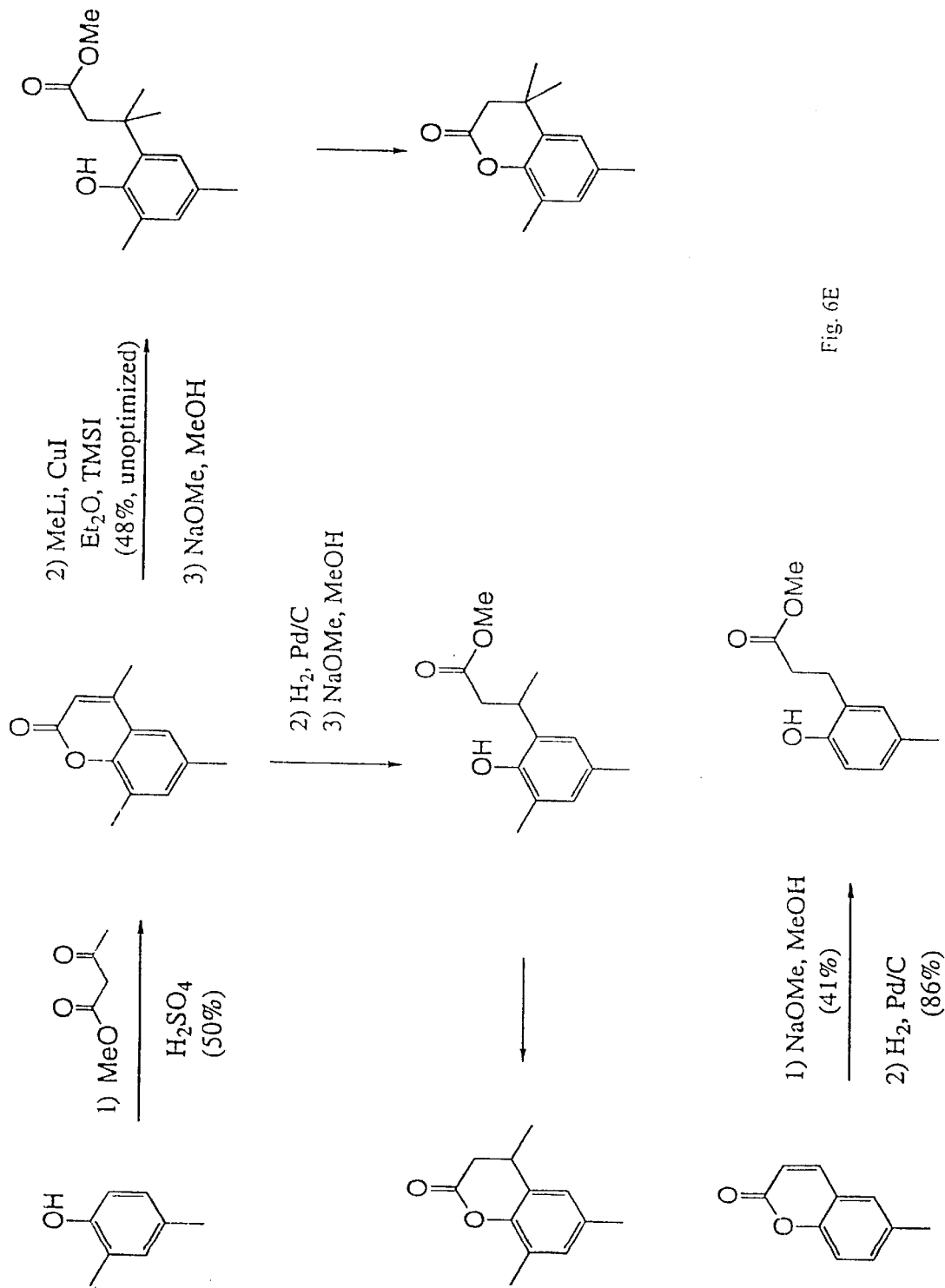

FIG. 6E is a schematic representation of a reaction process.

Figure 7:
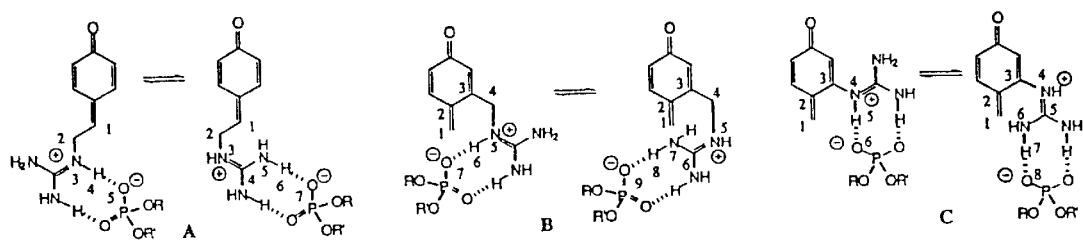
Figure 7E:
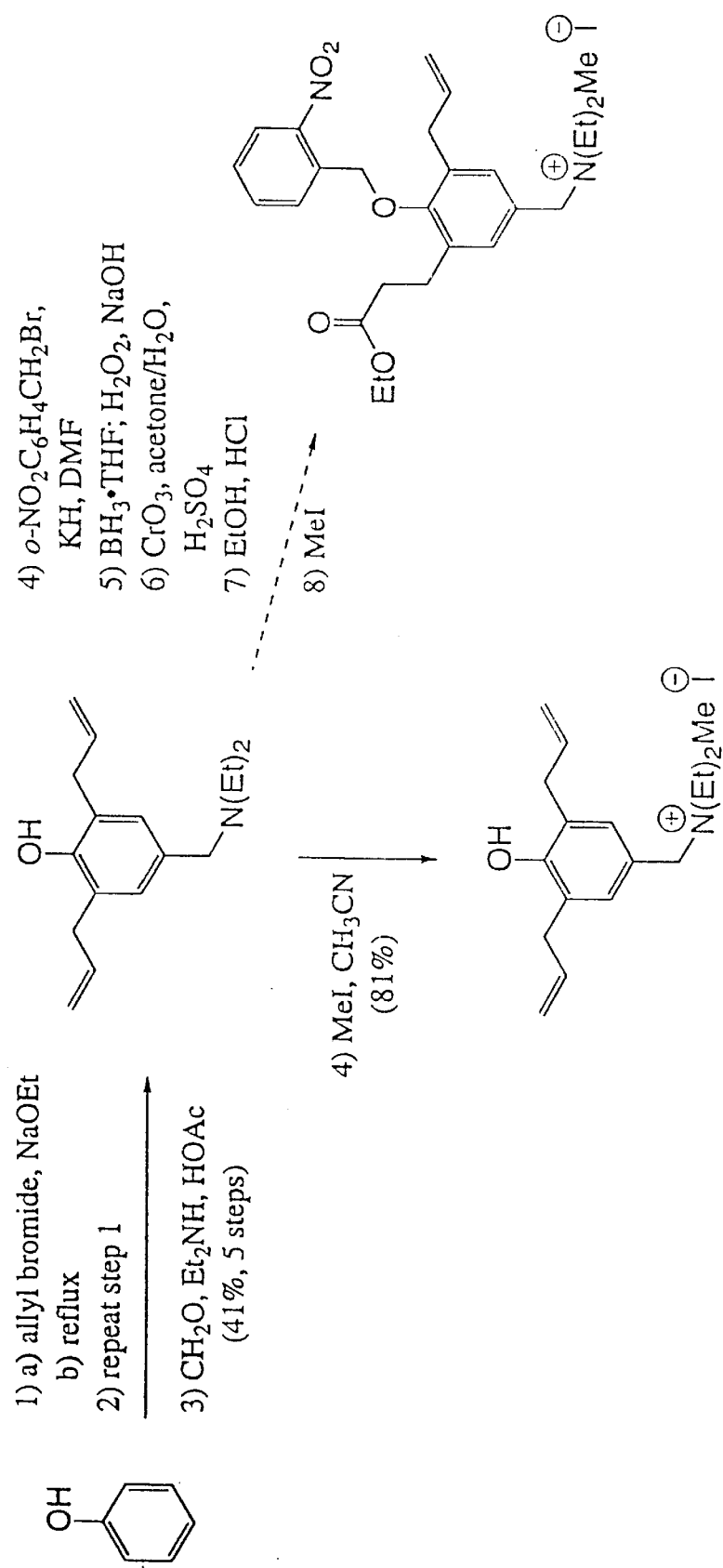

FIG. 7E is a schematic representation of a reaction process.

FIG. 8E is a schematic representation of a reaction process.

FIG. 9B is a schematic representation of a reaction process.

Figure 10E:
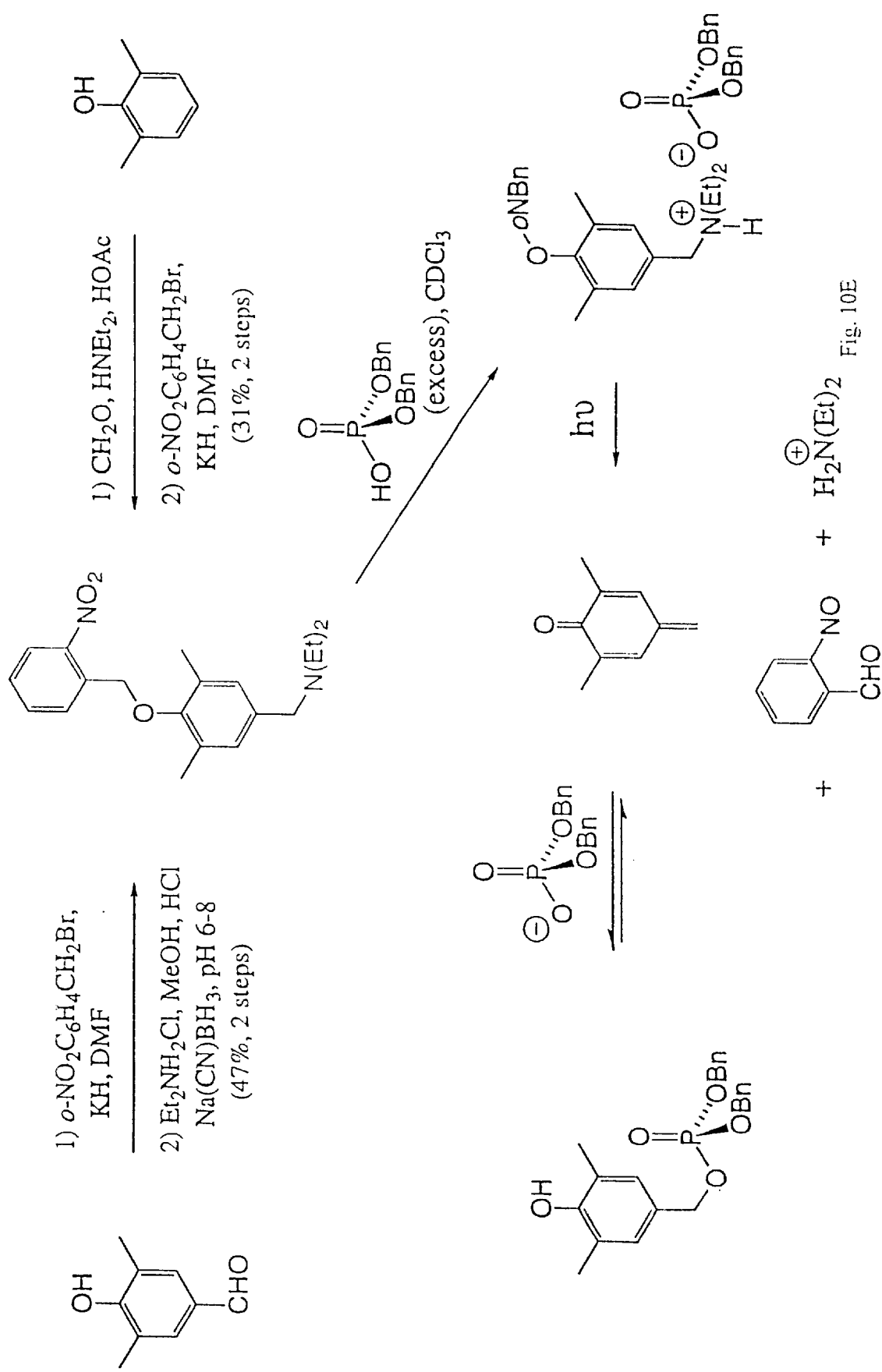

FIG. 10E is a schematic representation of a reaction process.

Figure 11E:
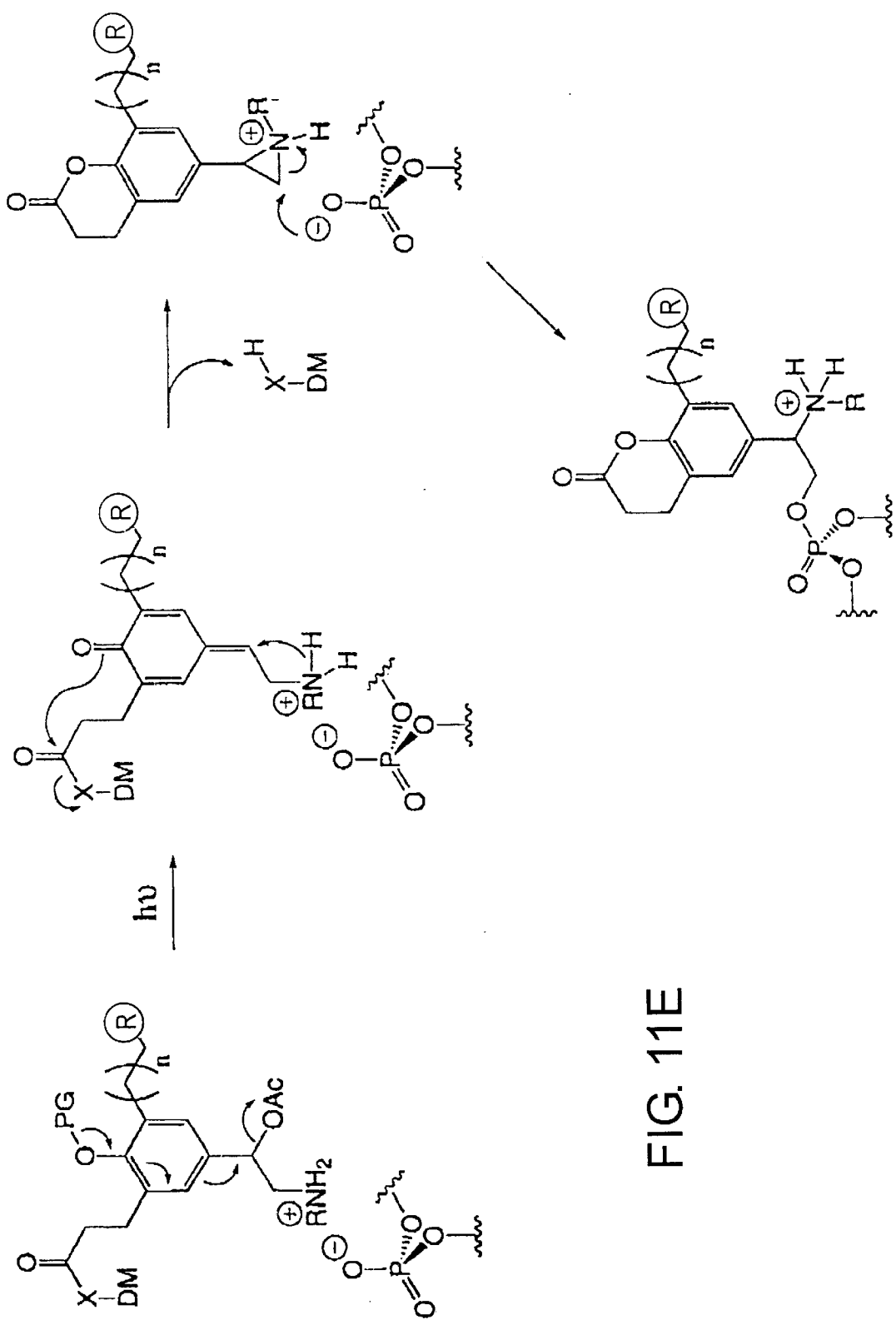

FIG. 11E is a schematic representation of a reaction process.

Figure 12E:
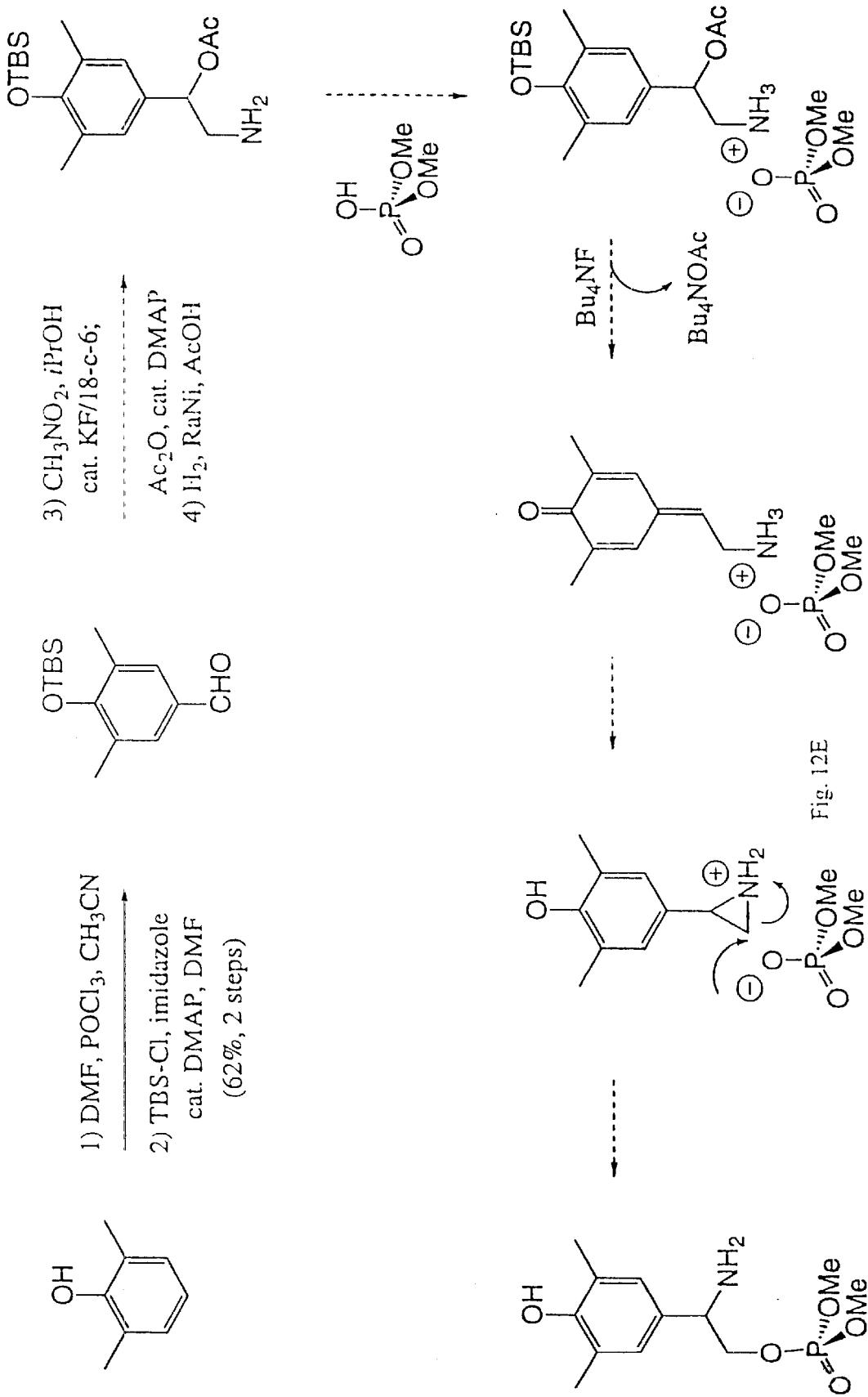

FIG. 12E is a schematic representation of a reaction process.

Figure 13E:
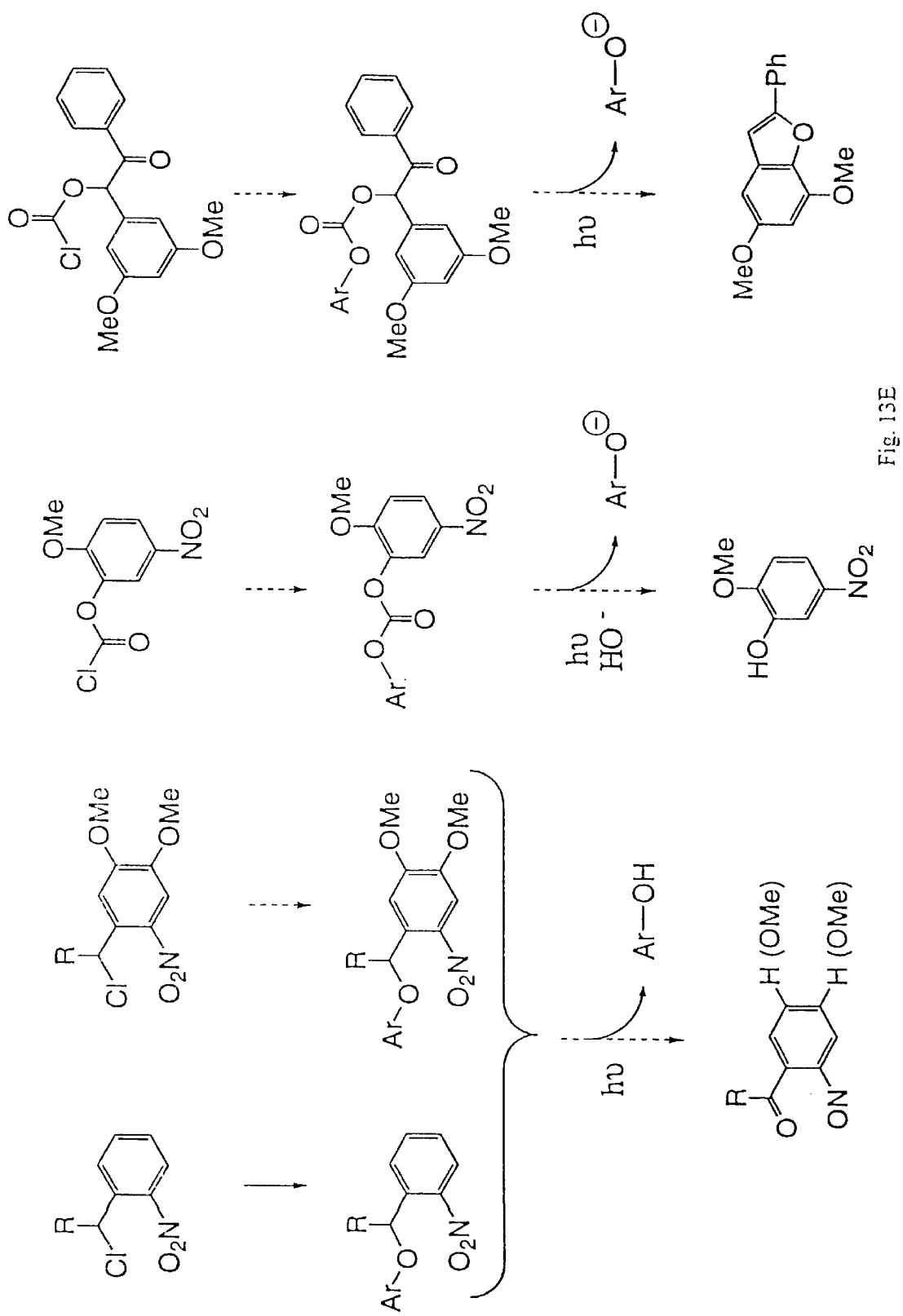

FIG. 13E is a schematic representation of a reaction process.

Figure 14E:
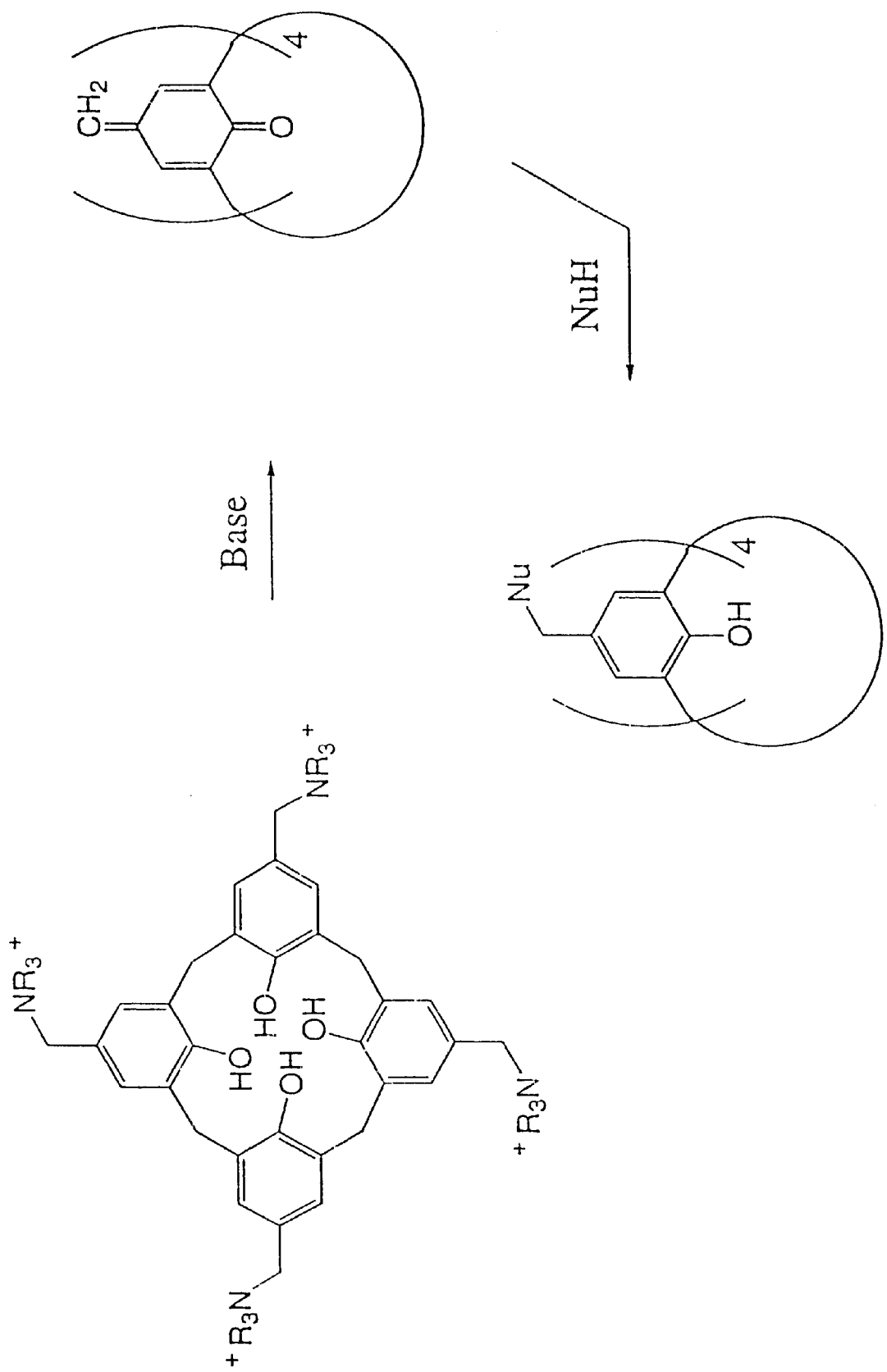
Figure 15E:
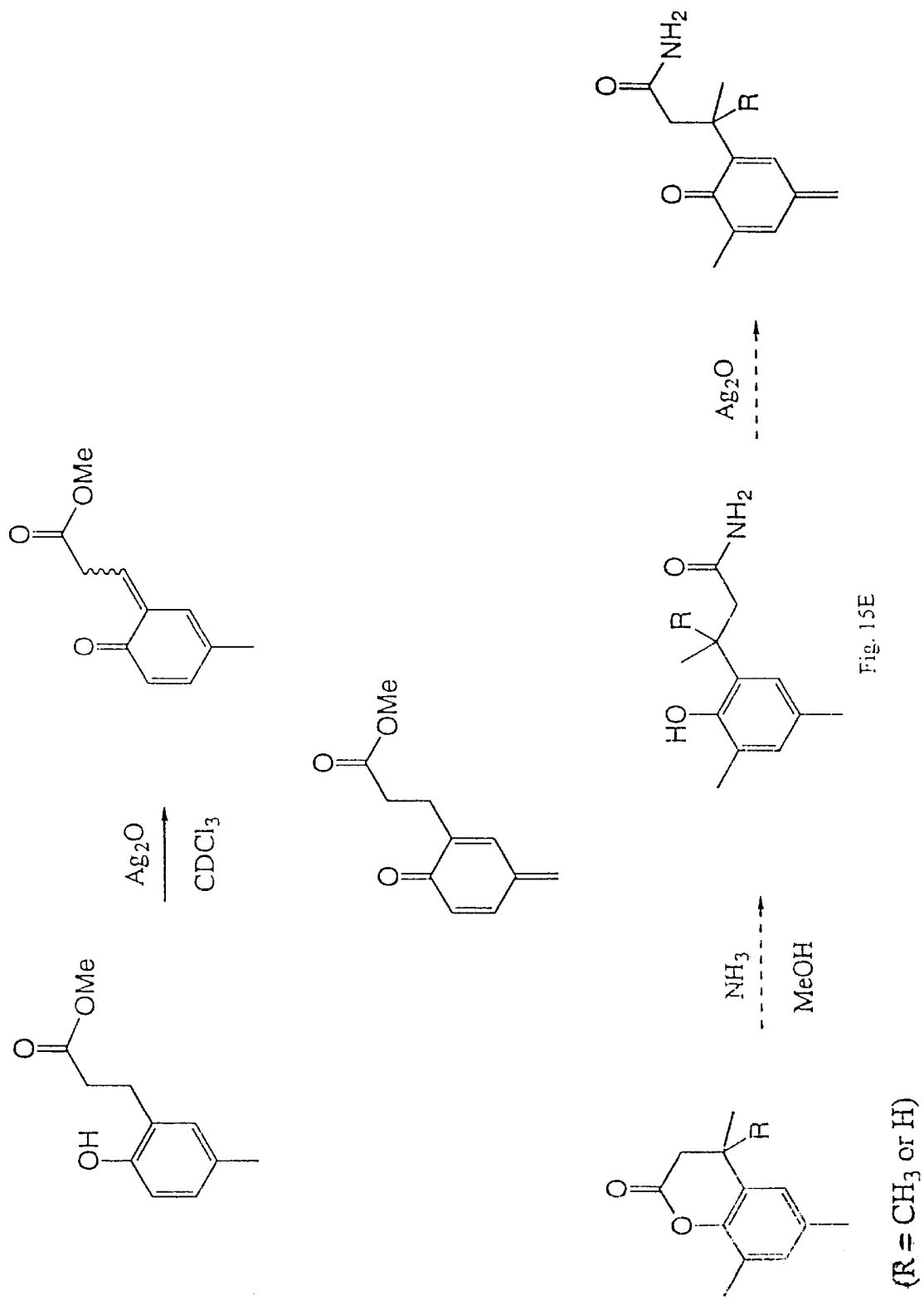

FIG. 14E is a schematic representation of a reaction process.

Figure 16E:
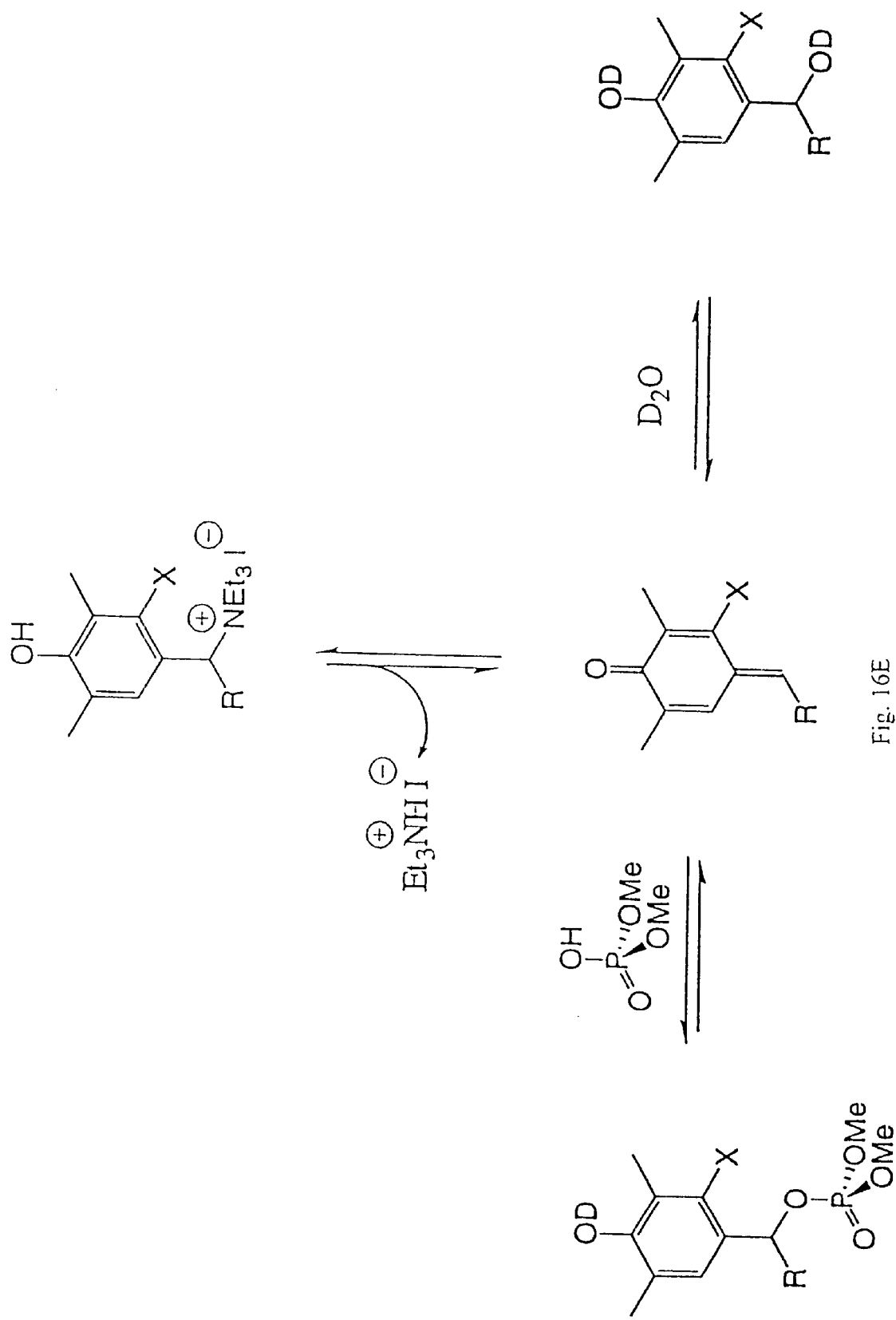

FIG. 16E is a schematic representation of a reaction process.

Figure 17E:
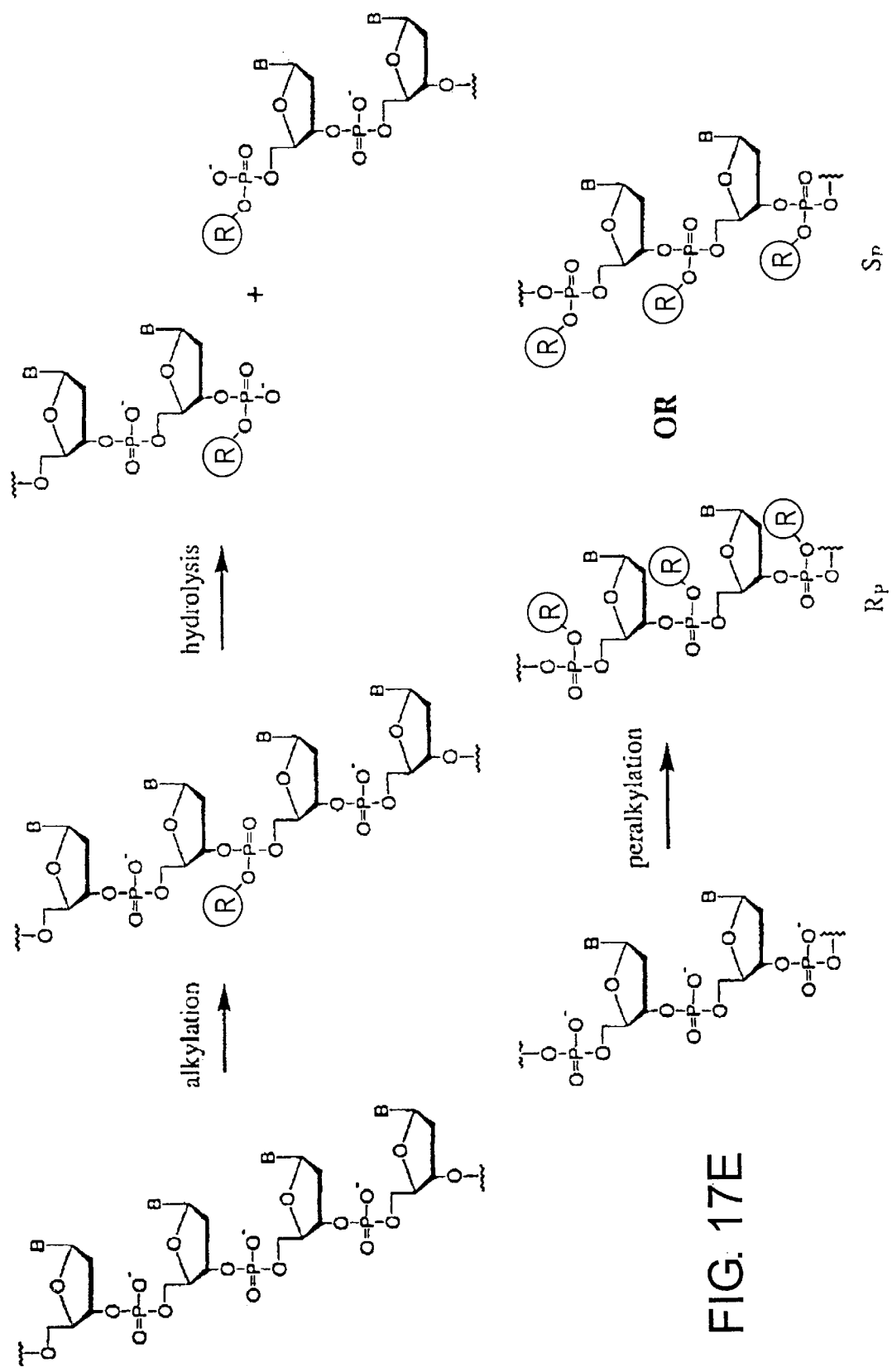

FIG. 17E is a schematic representation of a reaction process.

FIG. 18E is a schematic representation of a reaction process.

FIG. 20E is a schematic representation of a reaction process.

FIG. 21E is a schematic representation of a reaction process.

Figure 22E:
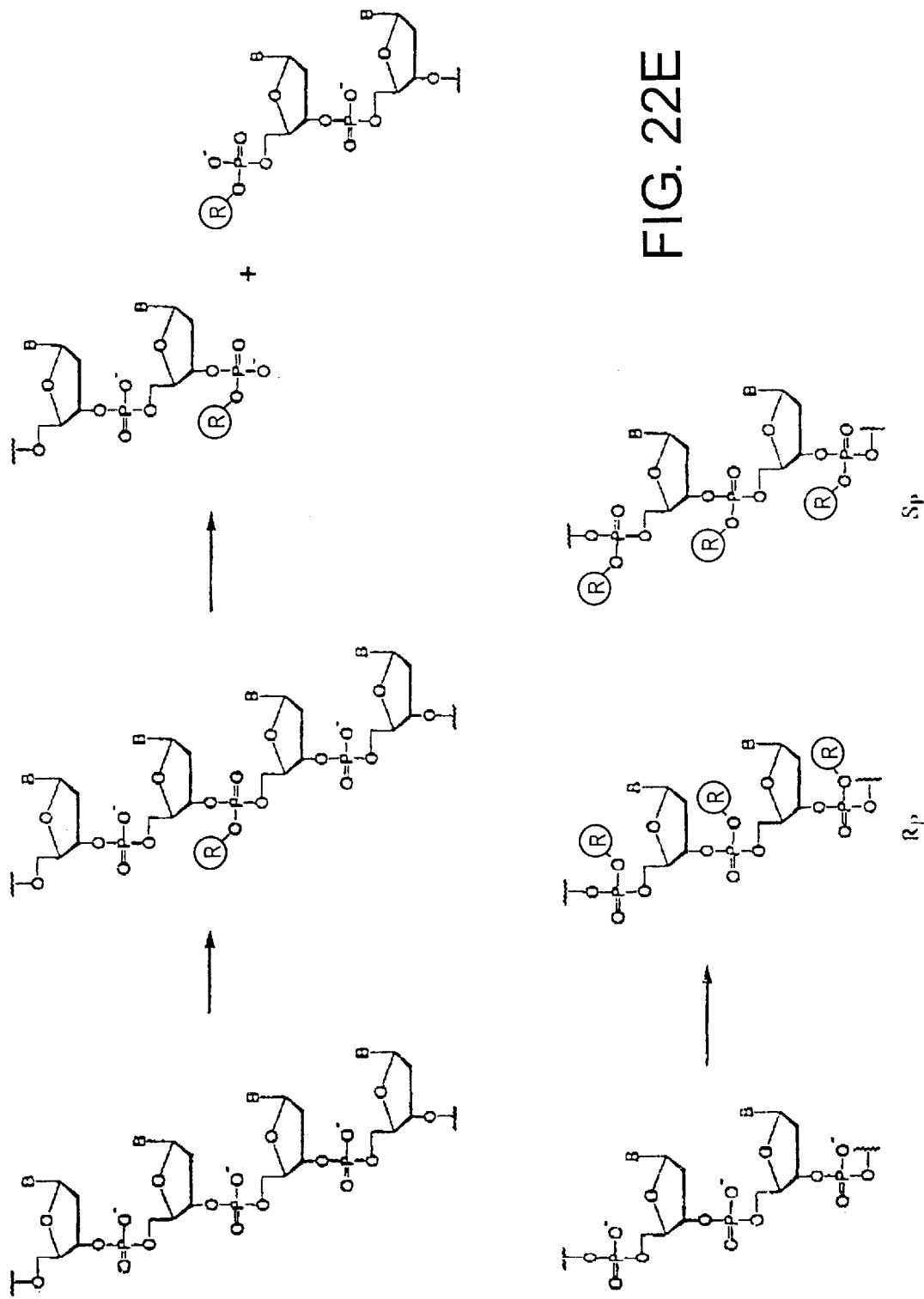

FIG. 22E is a schematic representation of a reaction process.

Figure 23E:
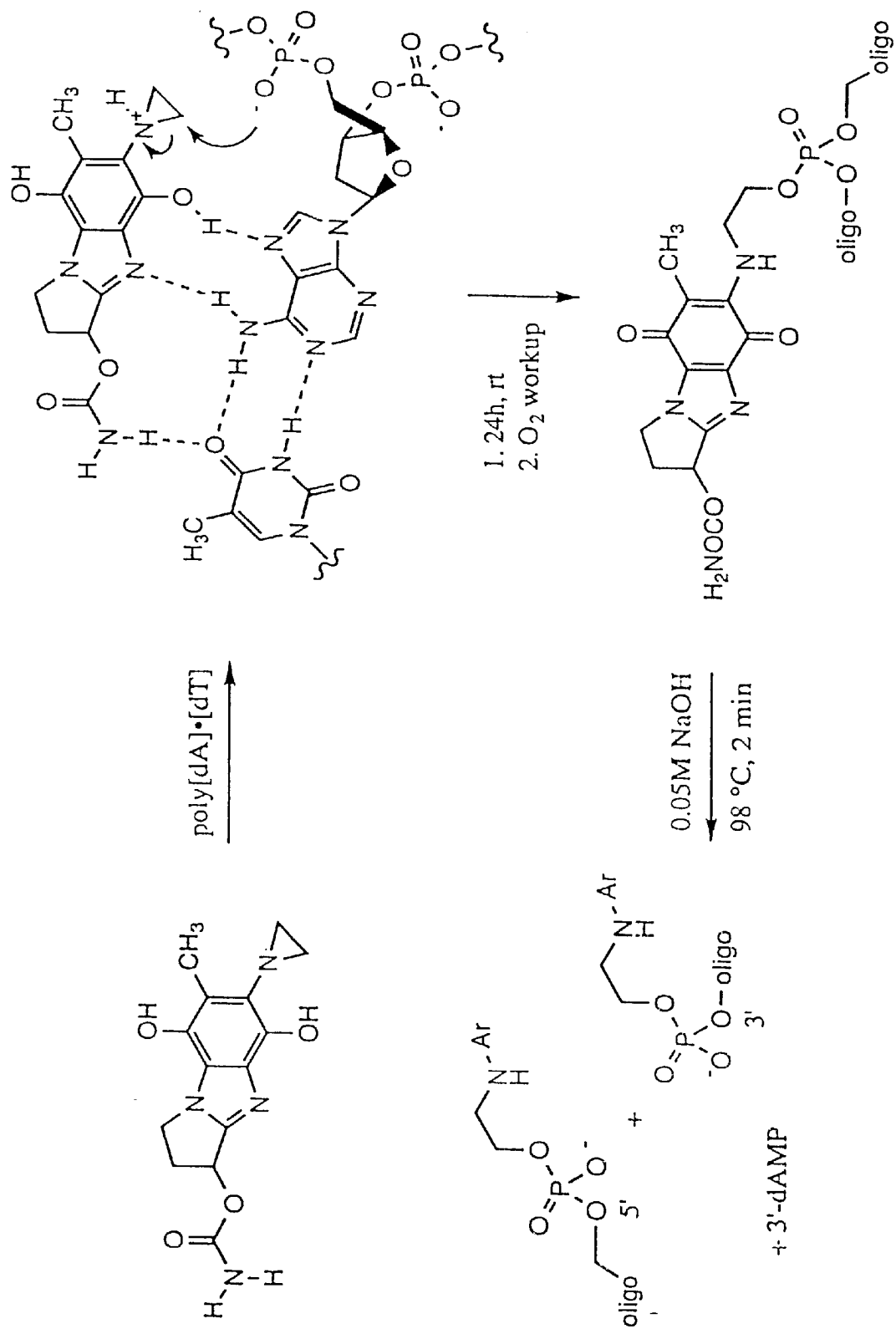

FIG. 23E is a schematic representation of a reaction process.

Figure 24E:
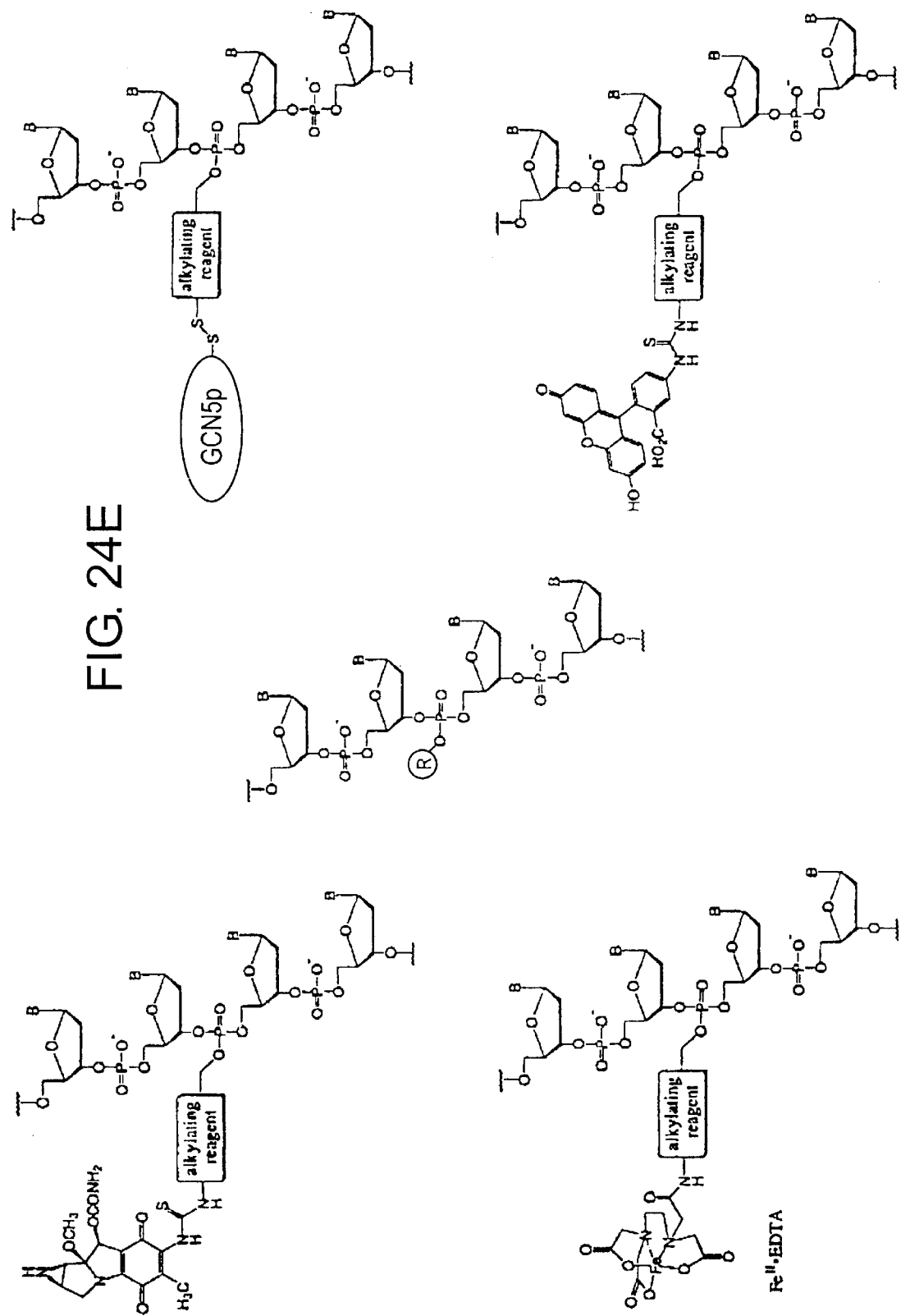

FIG. 24E is a schematic representation of a reaction process.

Figure 25E:
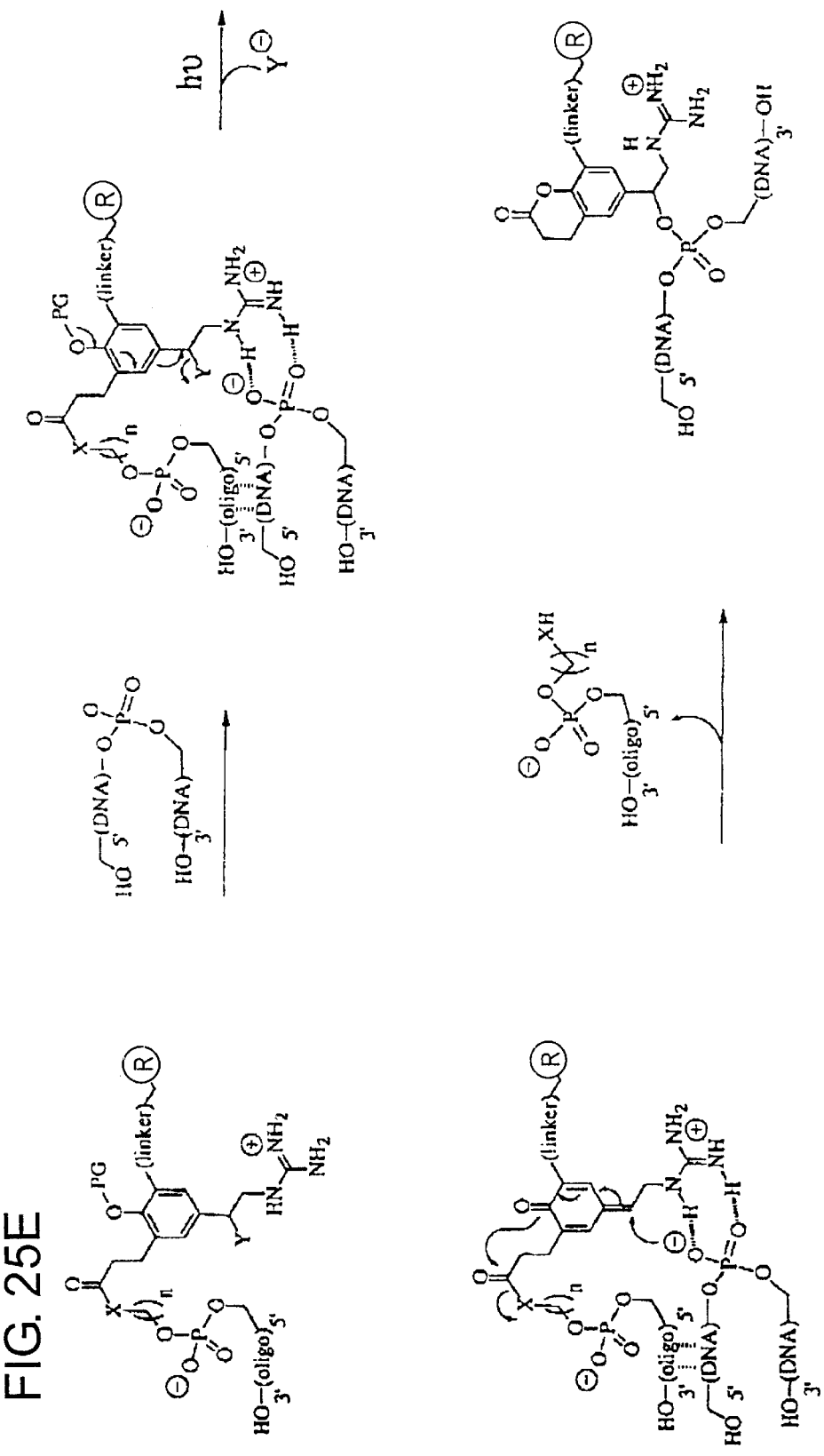

FIG. 25E is a schematic representation of a reaction process.

Figure 26E:
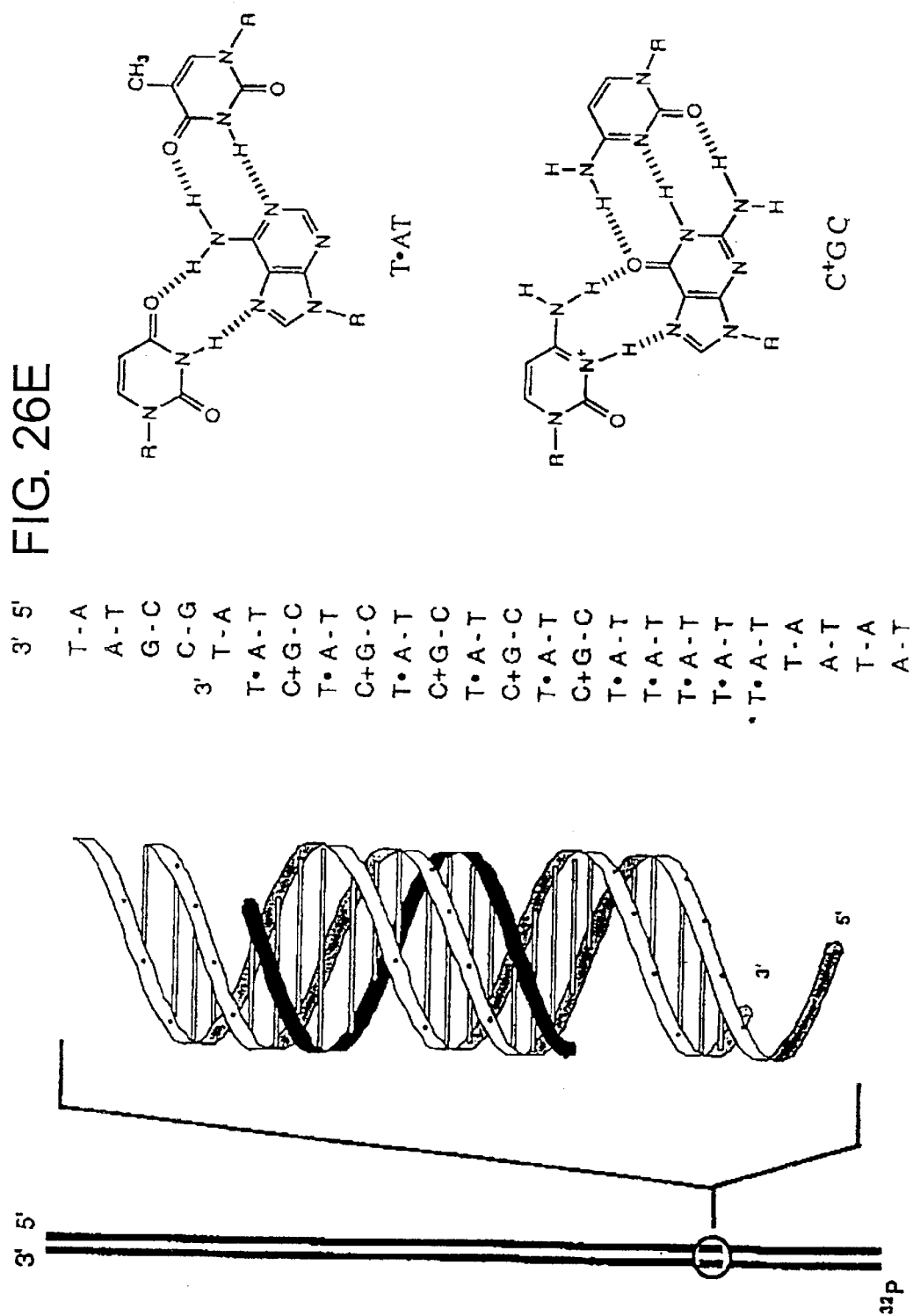

FIG. 26E is a schematic representation of a reaction process.

Figure 27E:
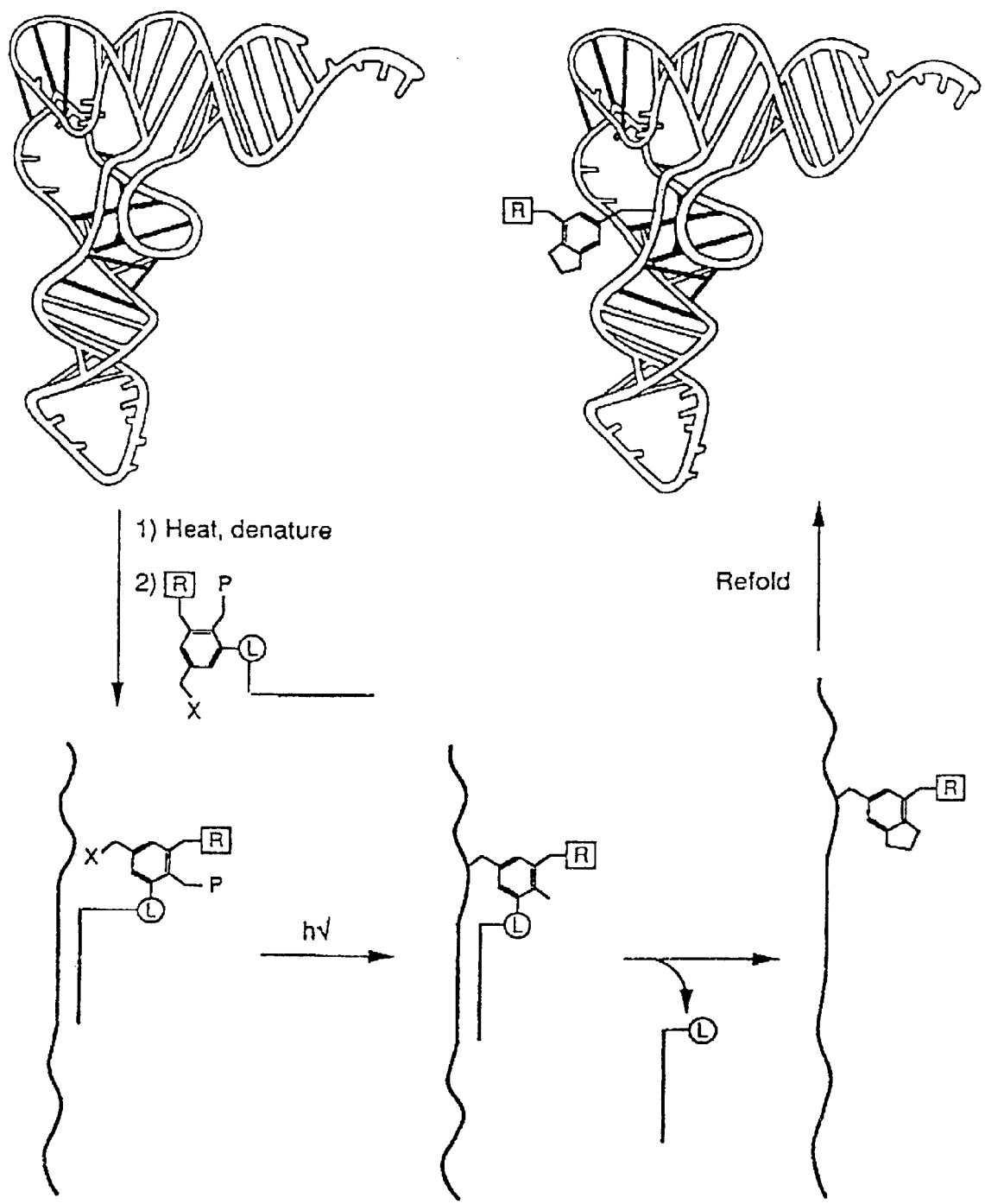

FIG. 27E is a schematic representation of a reaction process.

Figure 28E:
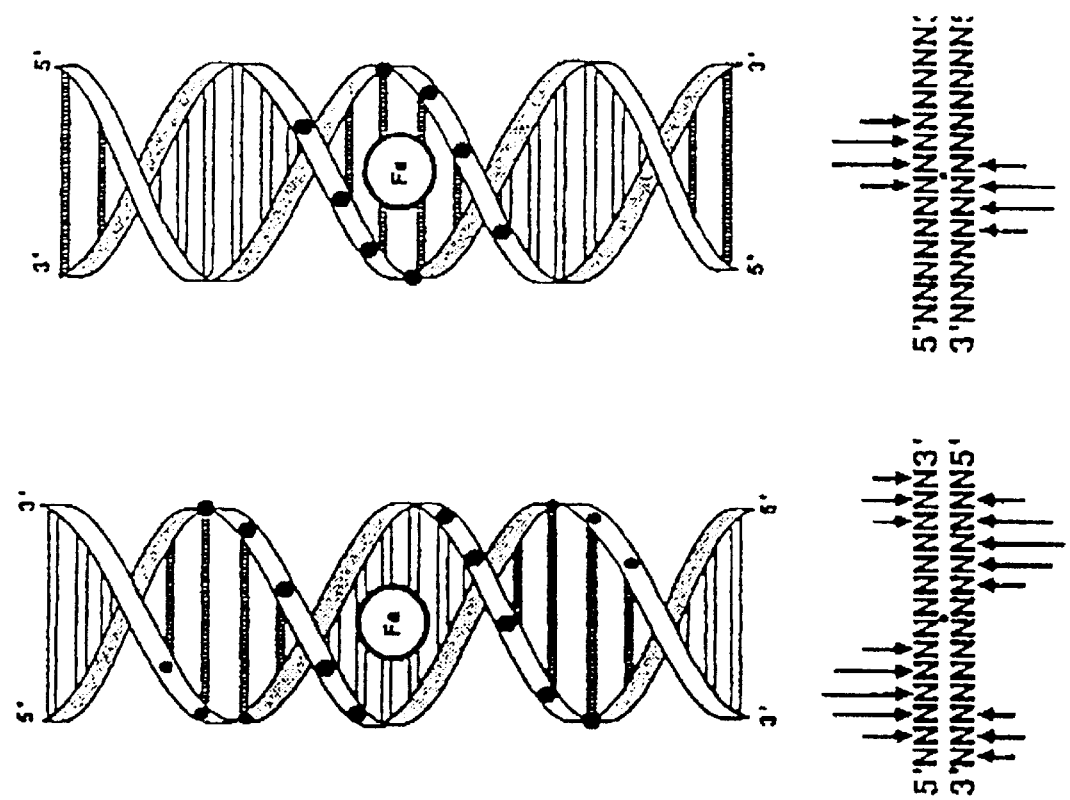

FIG. 28E is a schematic representation of a reaction process.

Figure 29E:
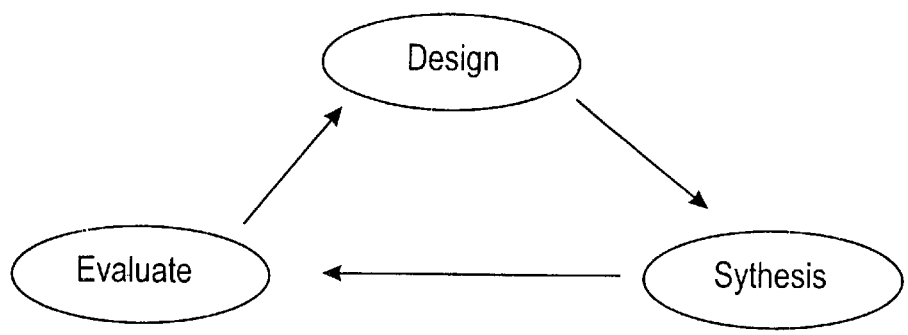

FIG. 29E is a schematic representation of a reaction process.

Figure 30E:
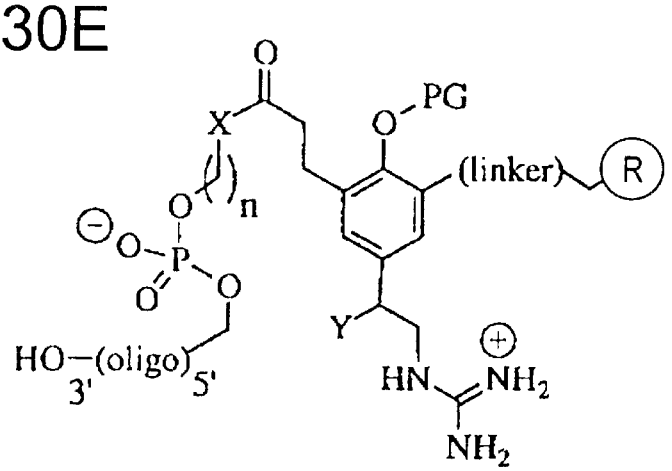

FIG. 30E is a schematic representation of a reaction process.

Figure 31E:
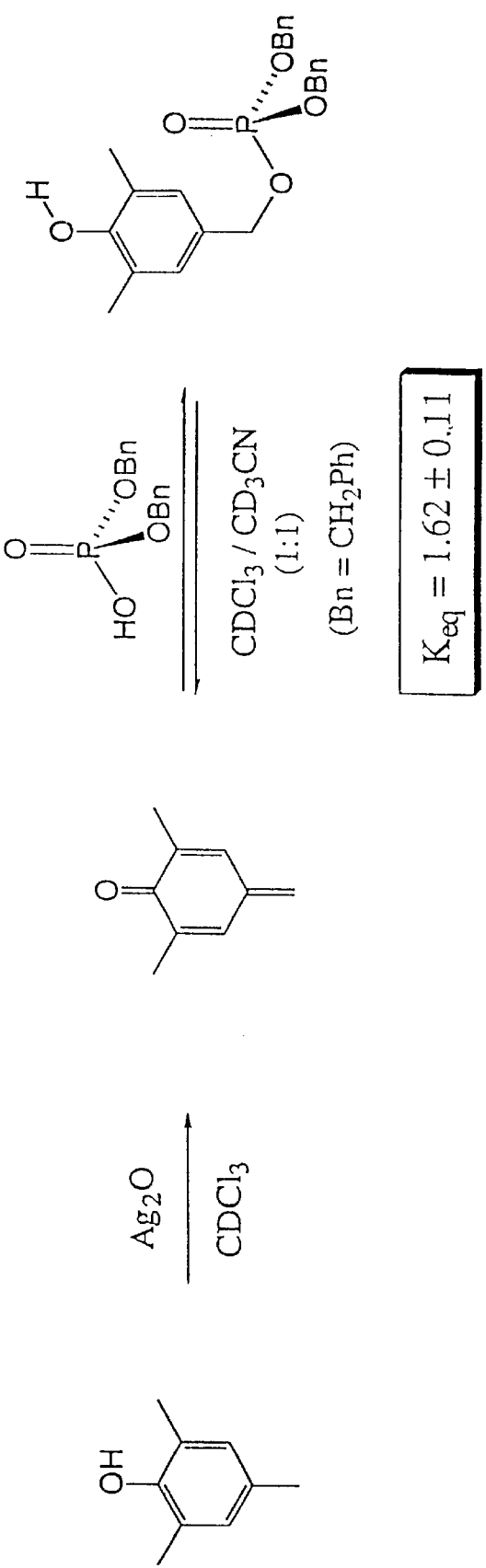

FIG. 31E is a schematic representation of a reaction process.

FIG. 32E is a schematic representation of a reaction process.

Figure 33E:
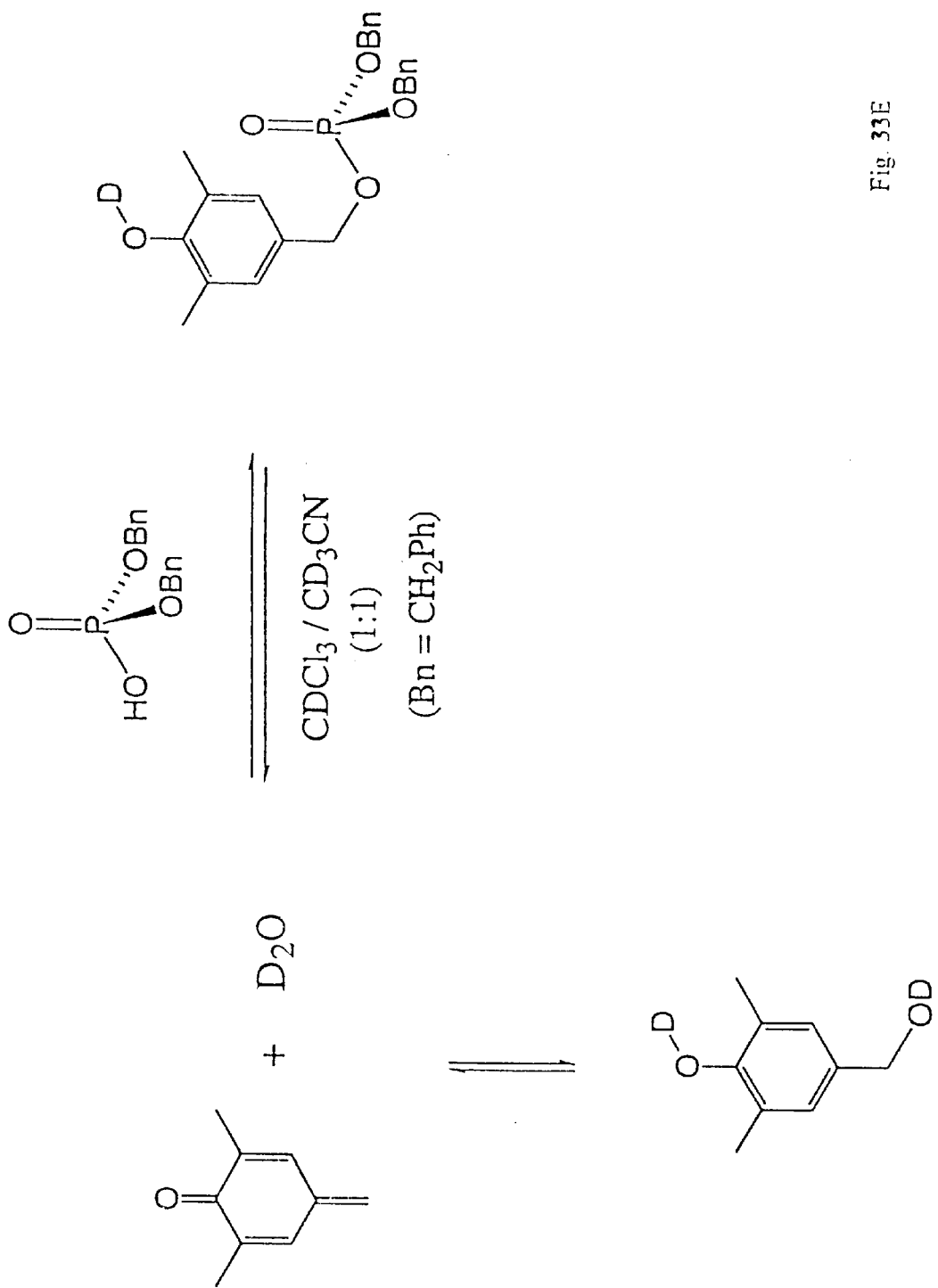

FIG. 33E is a schematic representation of a reaction process.

Figure 34E:
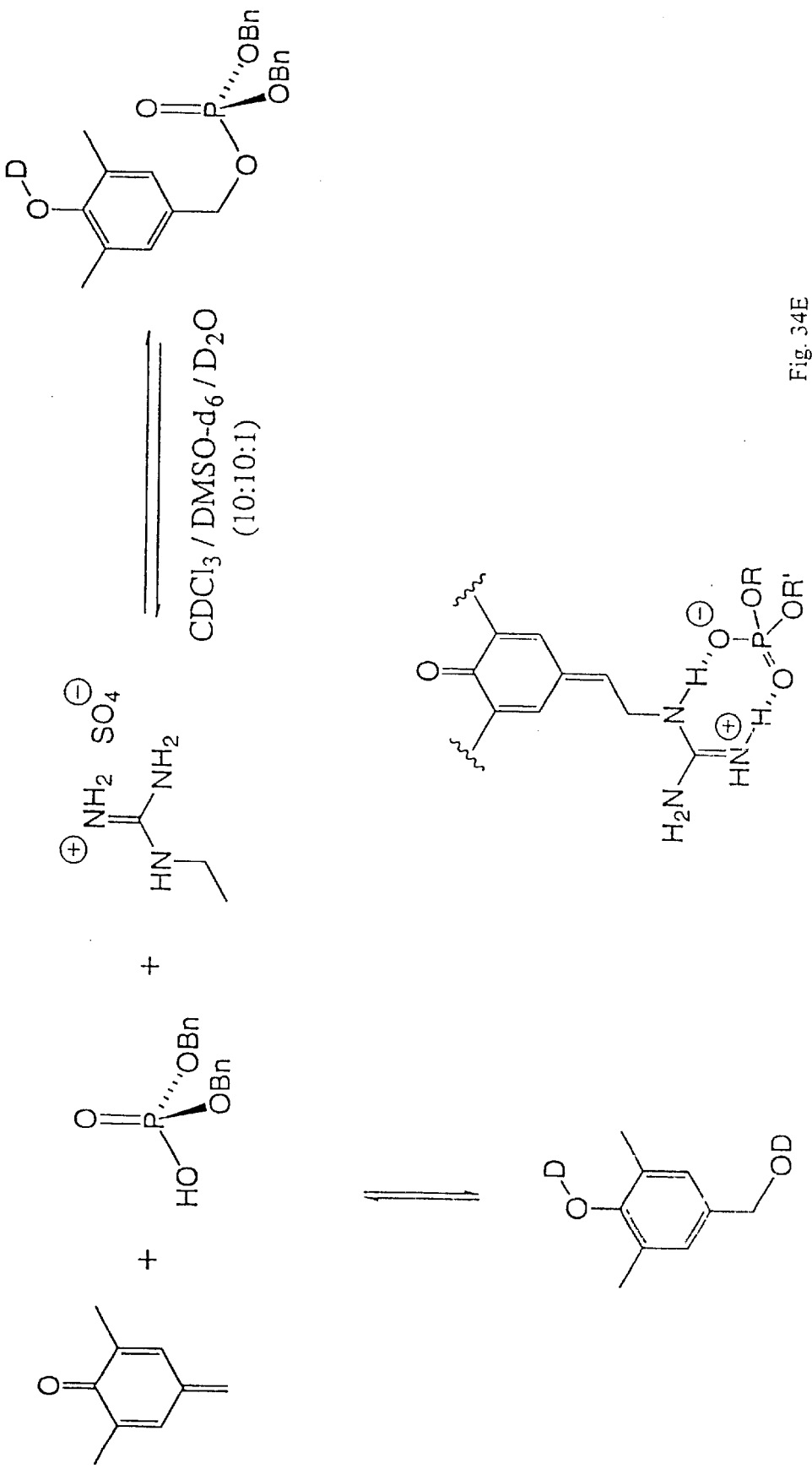

FIG. 34E is a schematic representation of a reaction process.

Figure 35E:
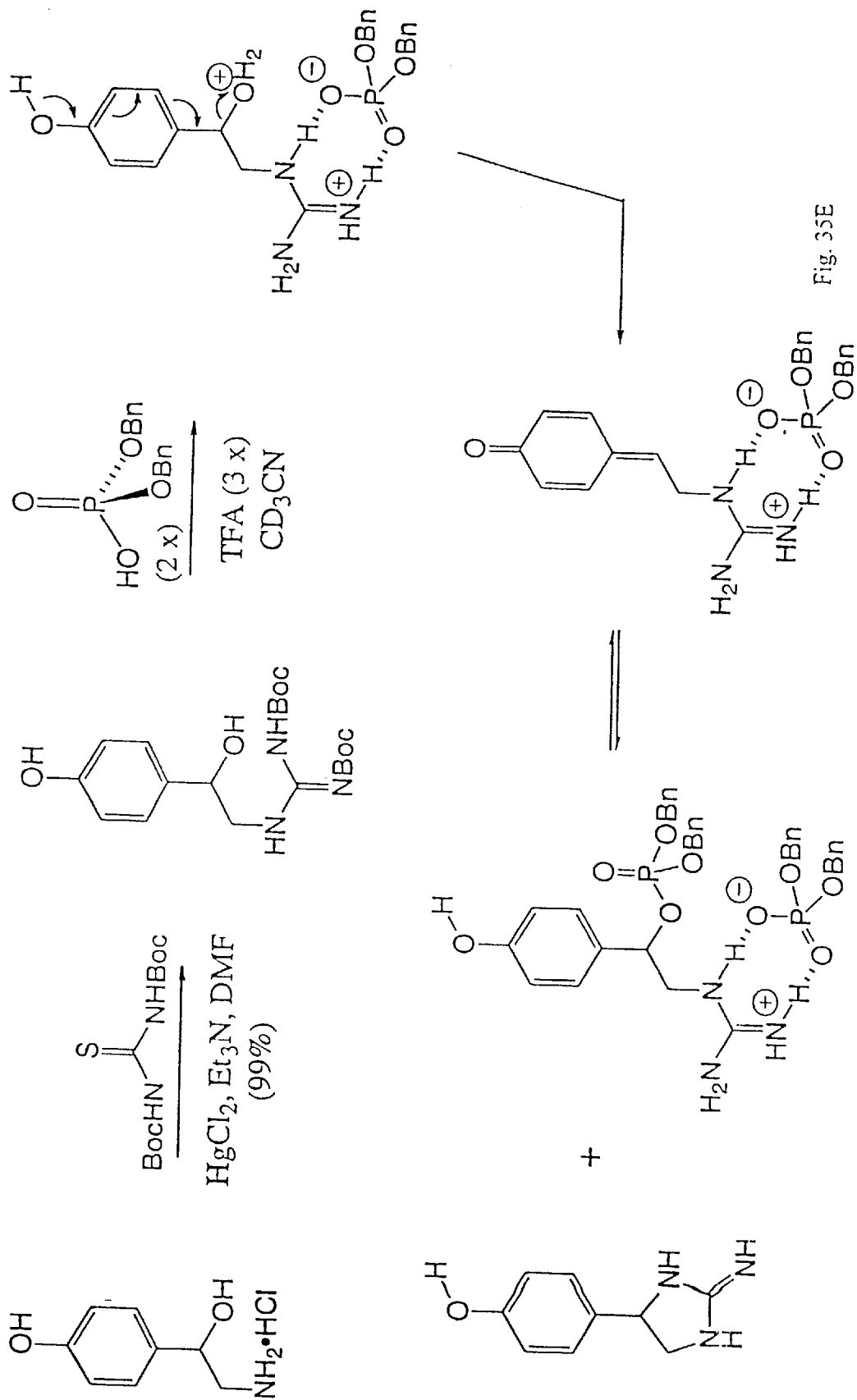

FIG. 35E is a schematic representation of a reaction process.

Figure 36E:
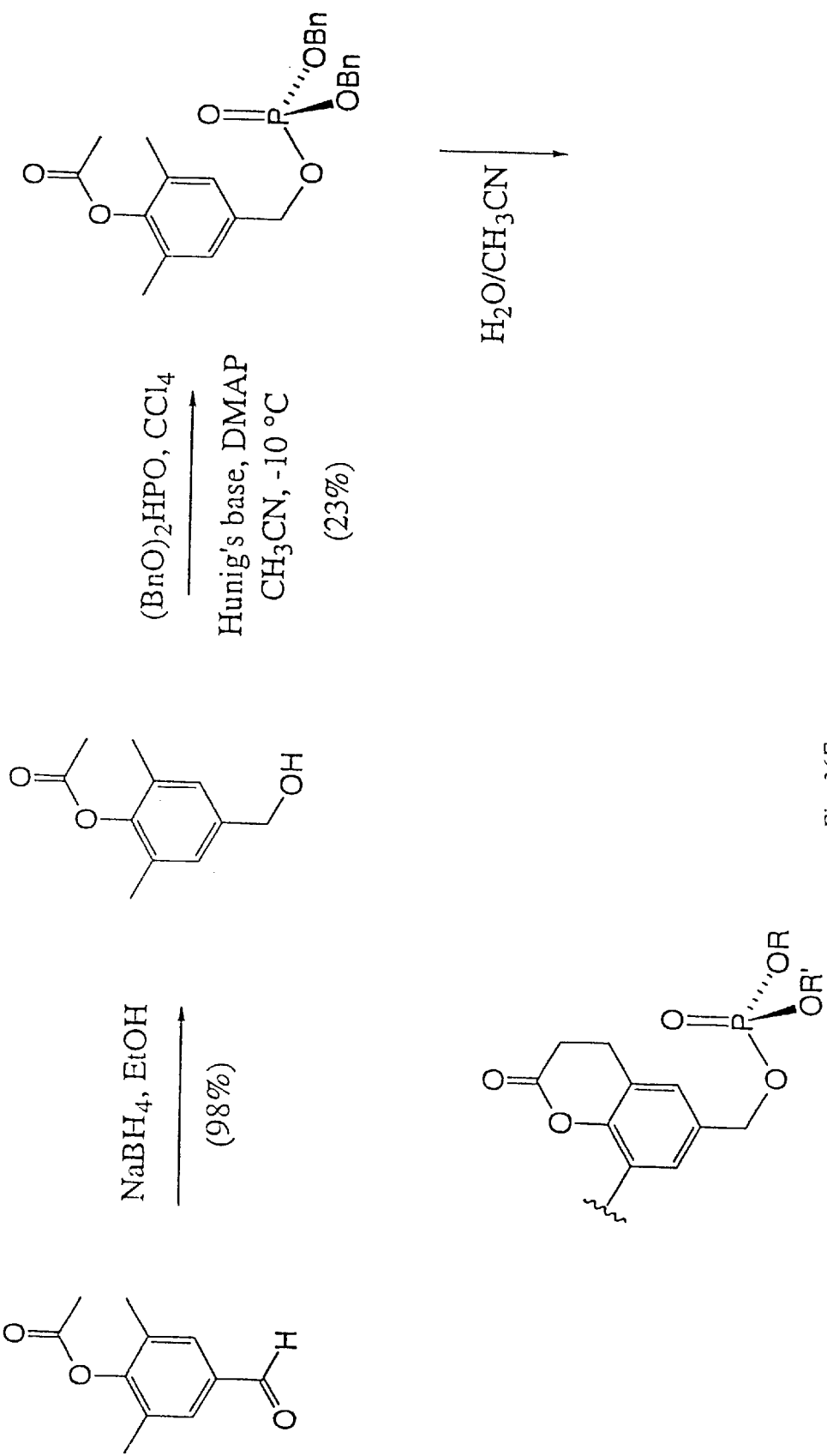

FIG. 36E is a schematic representation of a reaction process.

Figure 37E:
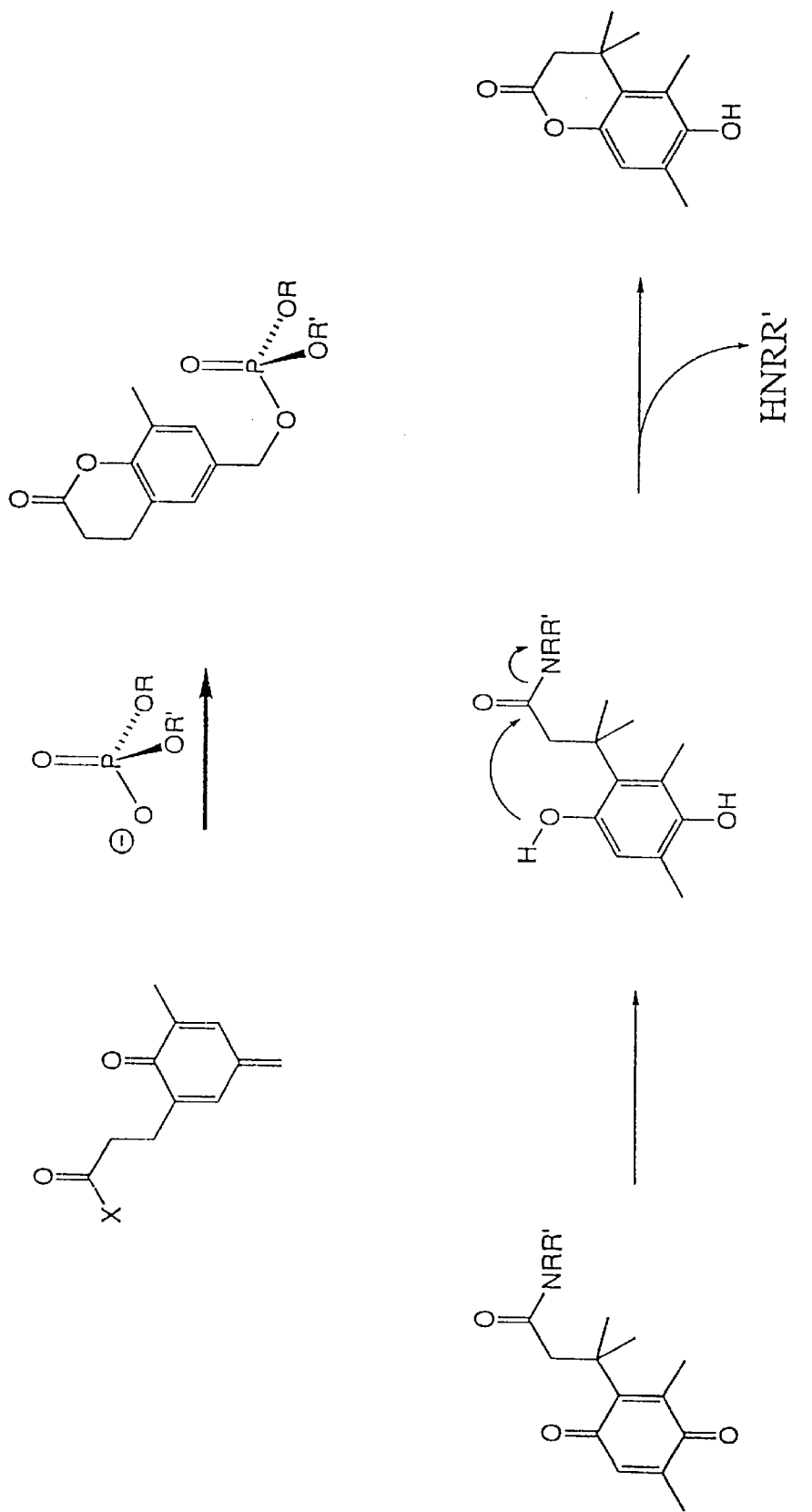

FIG. 37E is a schematic representation of a reaction process.

Figure 38E:
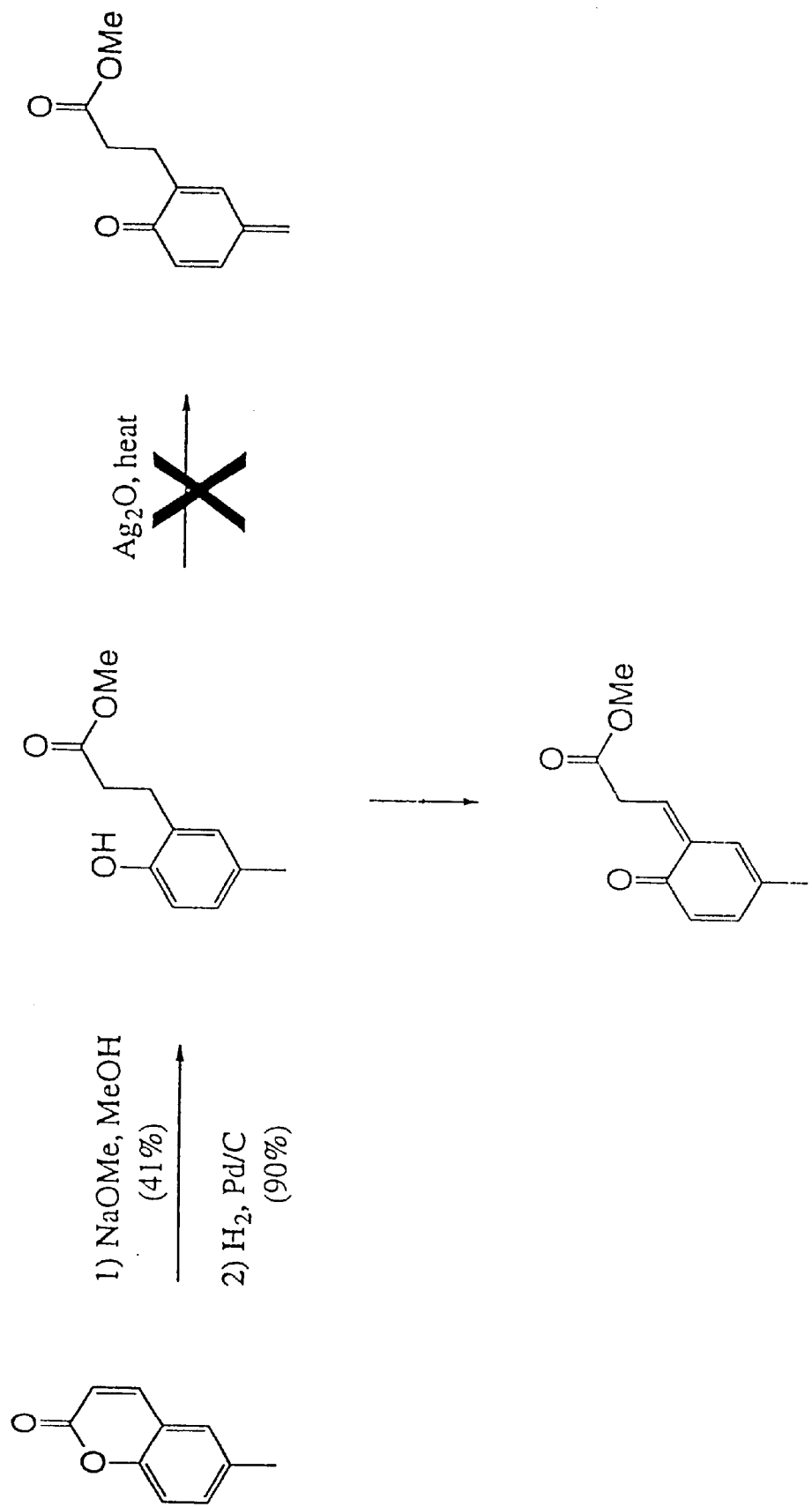

FIG. 38E is a schematic representation of a reaction process.

Figure 39E:
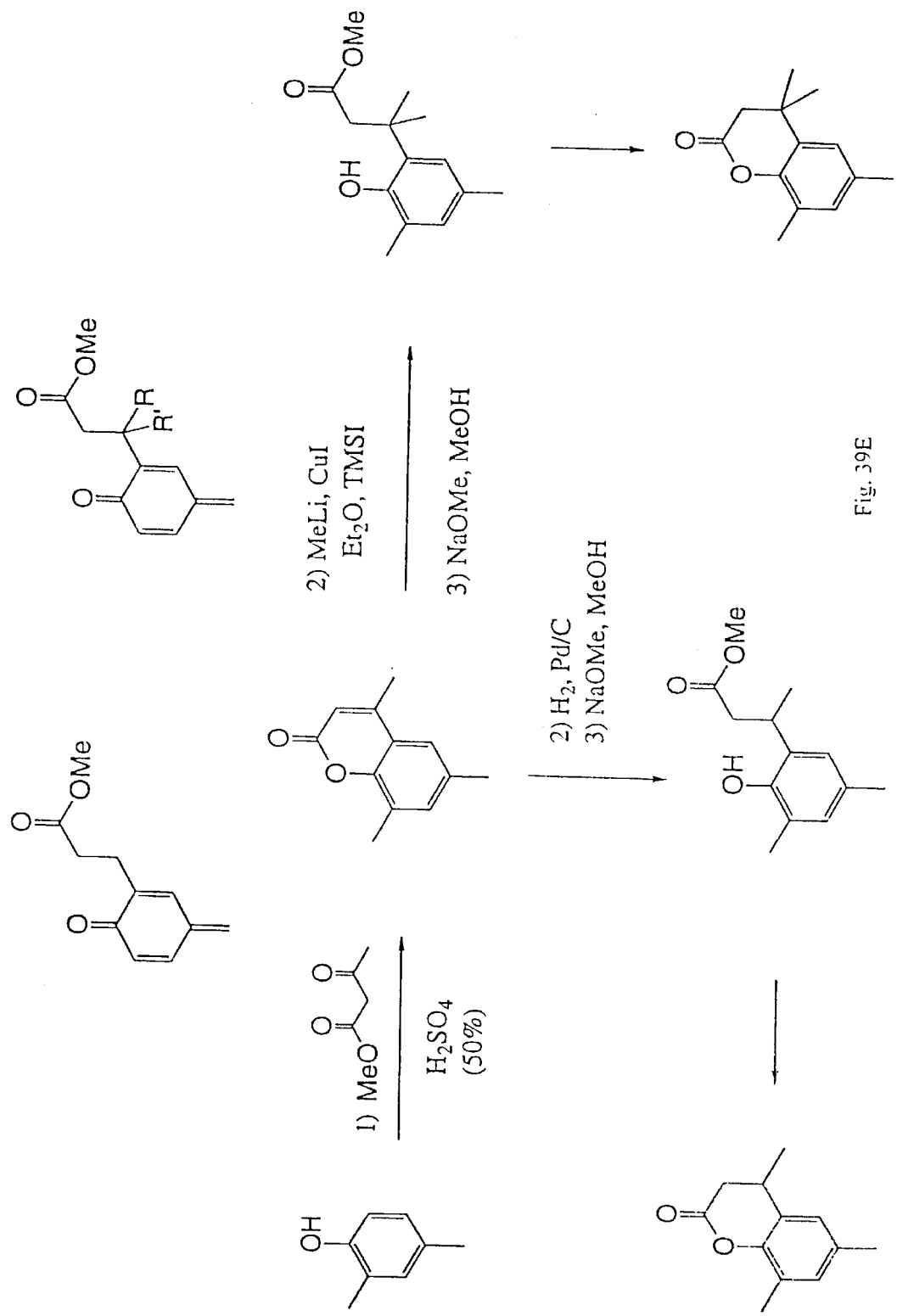

FIG. 39E is a schematic representation of a reaction process.

Figure 40E:
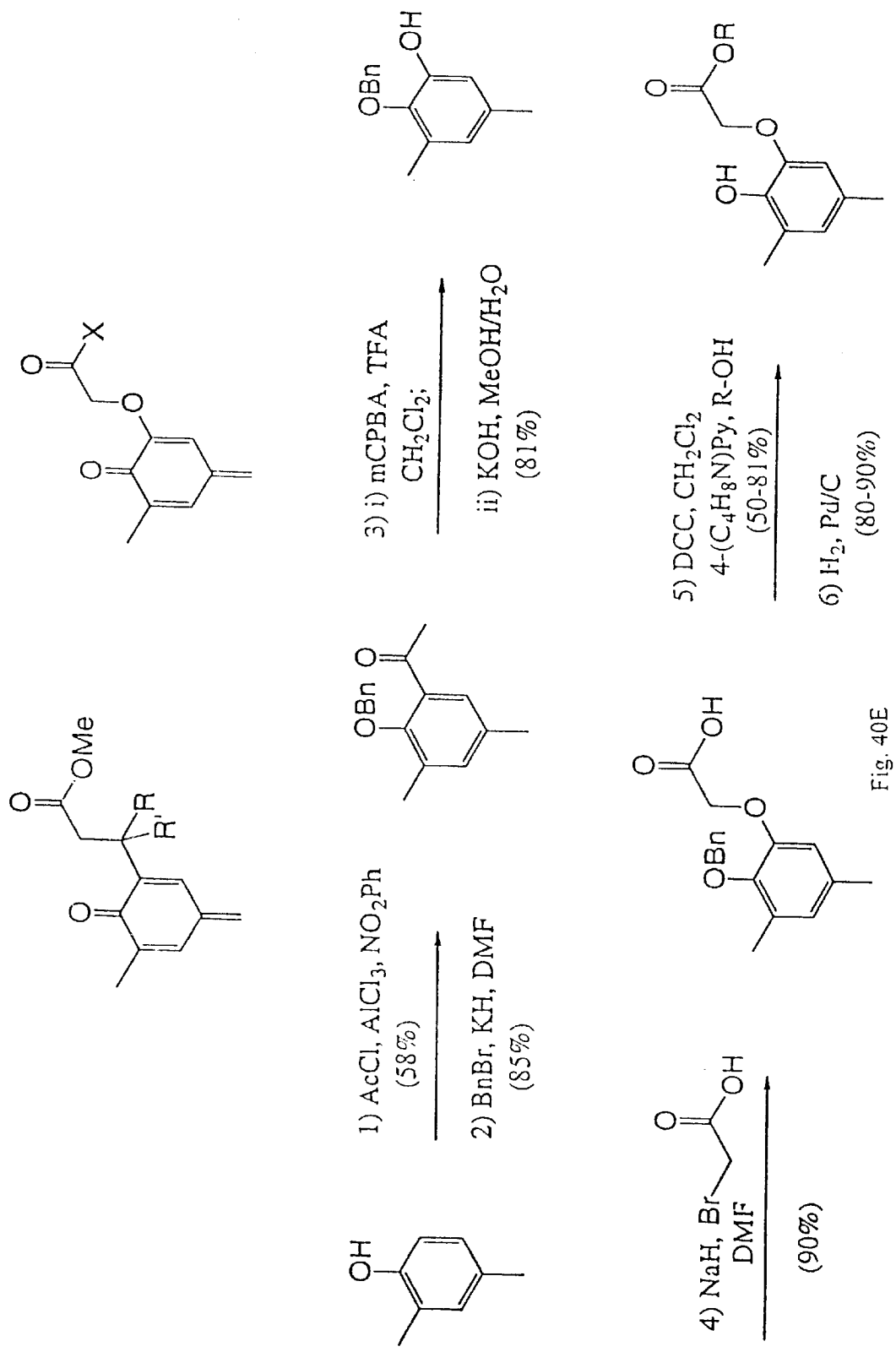

FIG. 40E is a schematic representation of a reaction process.

Figure 41E:
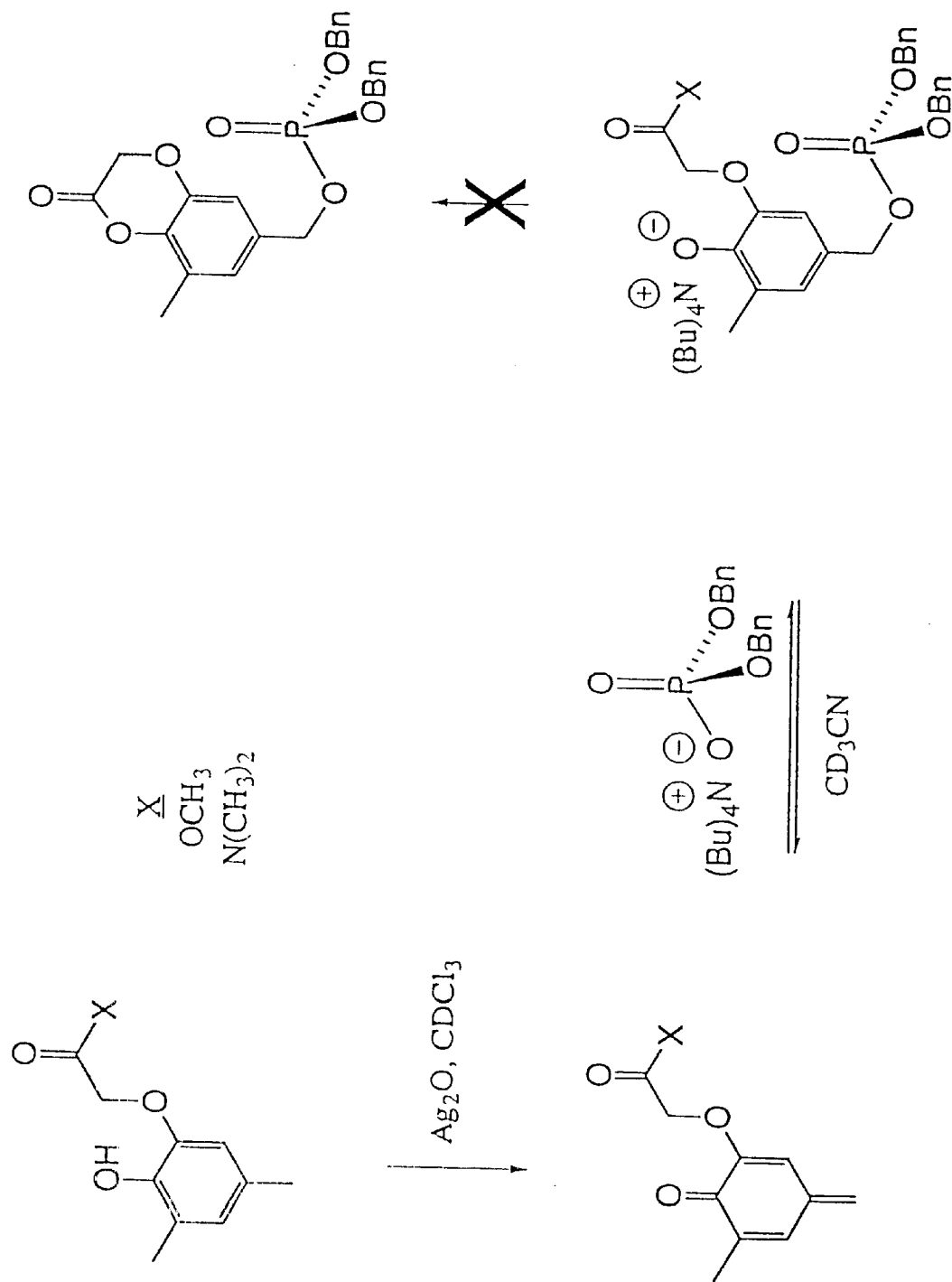

FIG. 41E is a schematic representation of a reaction process.

FIG. 42E is a schematic representation of a reaction process.

Figure 43E:
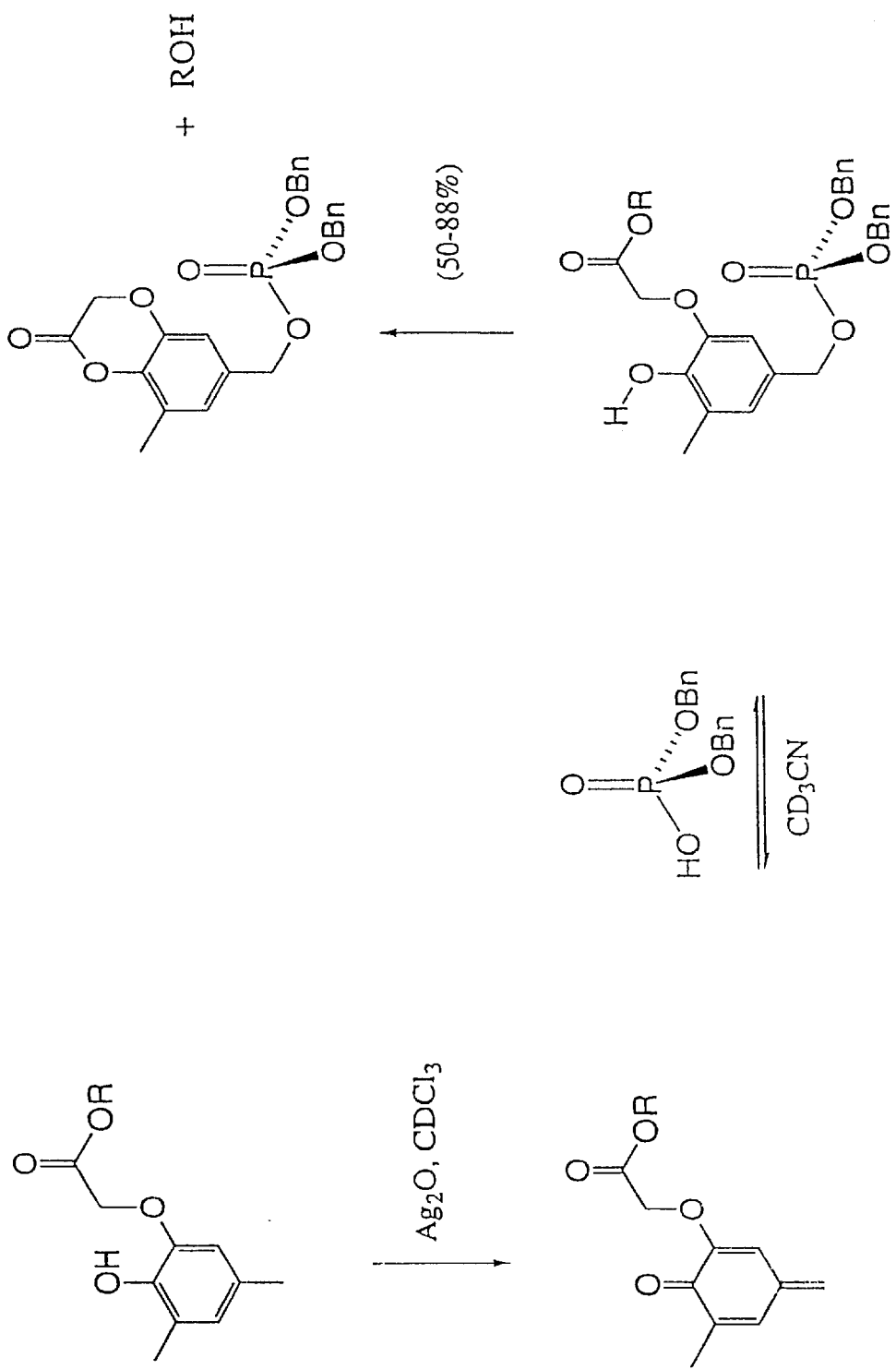

FIG. 43E is a schematic representation of a reaction process.

Figure 44E:
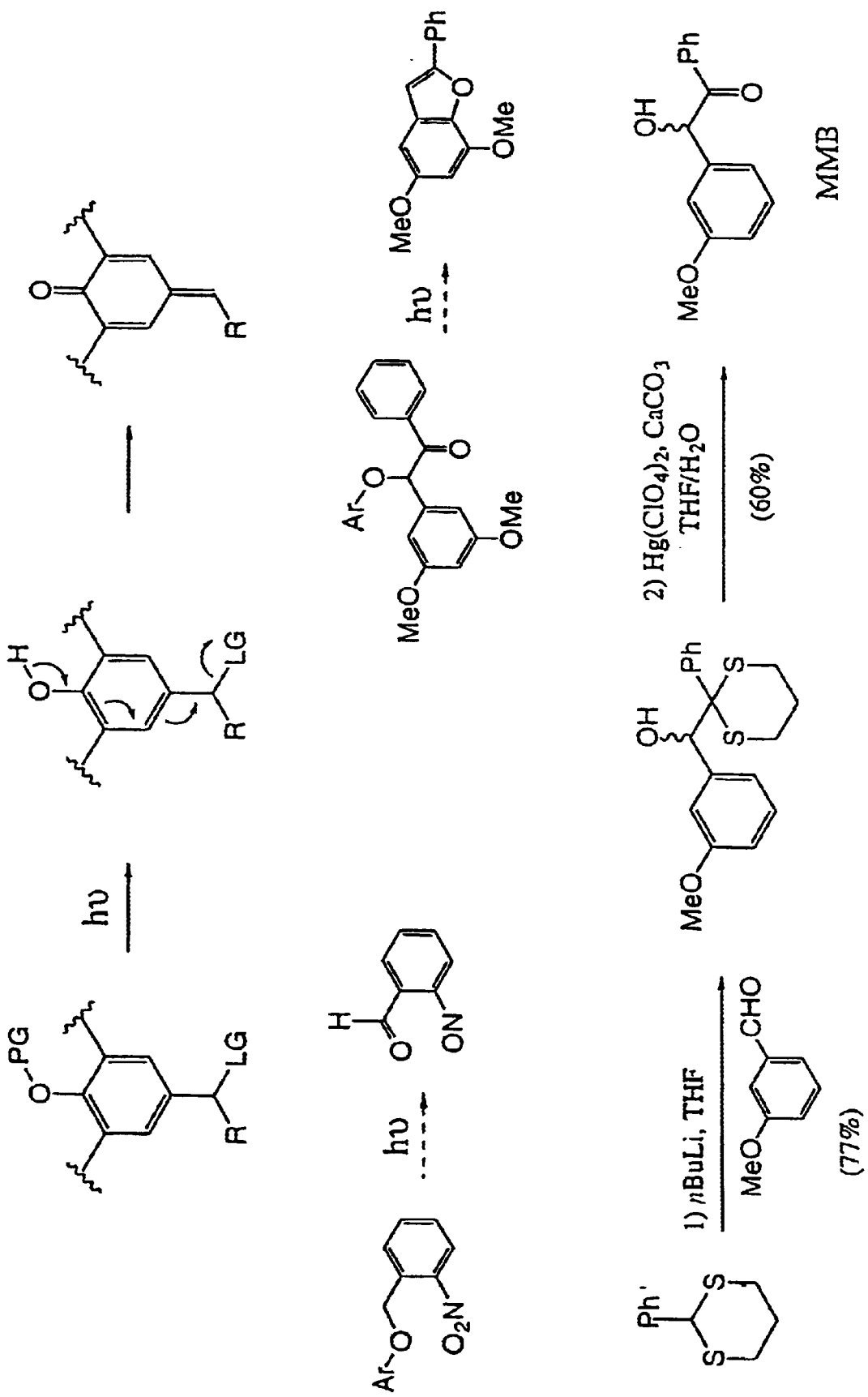

FIG. 44E is a schematic representation of a reaction process.

Figure 45E:
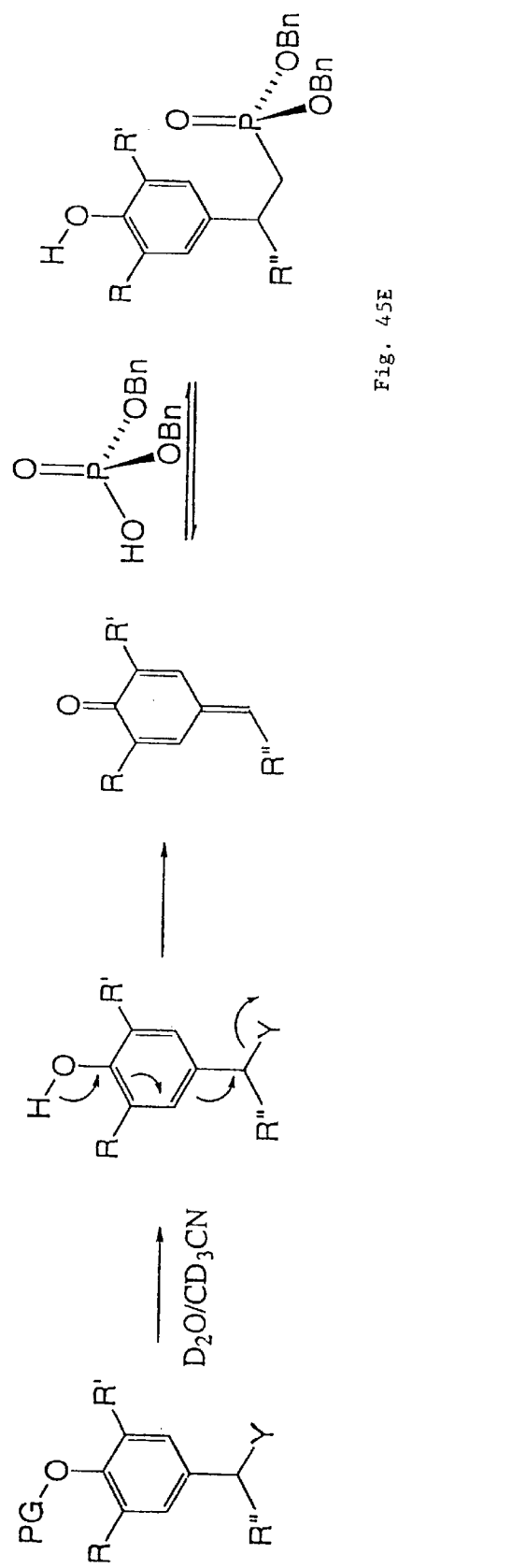

FIG. 45E is a schematic representation of a reaction process.

Figure 46E:
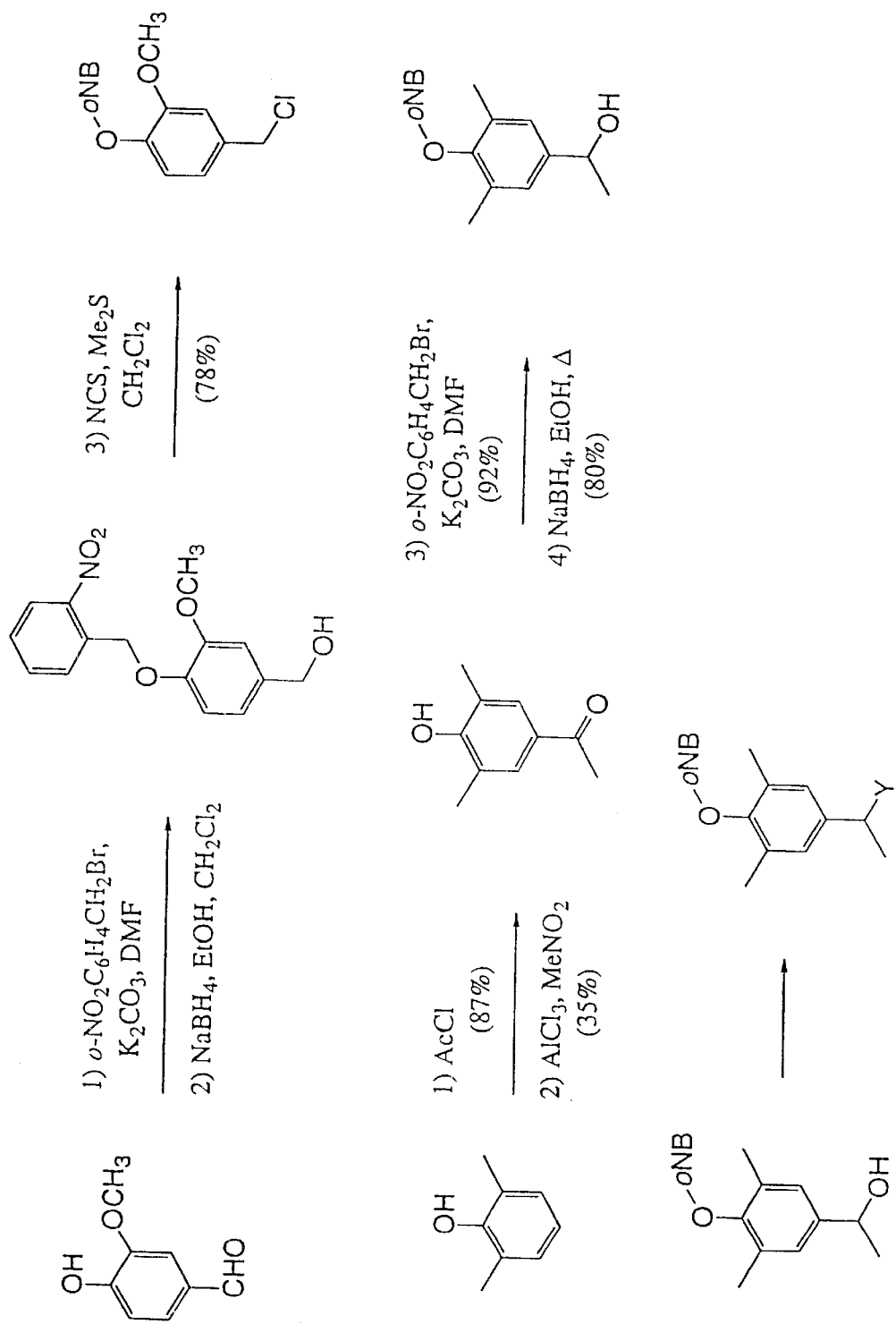

FIG. 46E is a schematic representation of a reaction process.

Figure 47E:
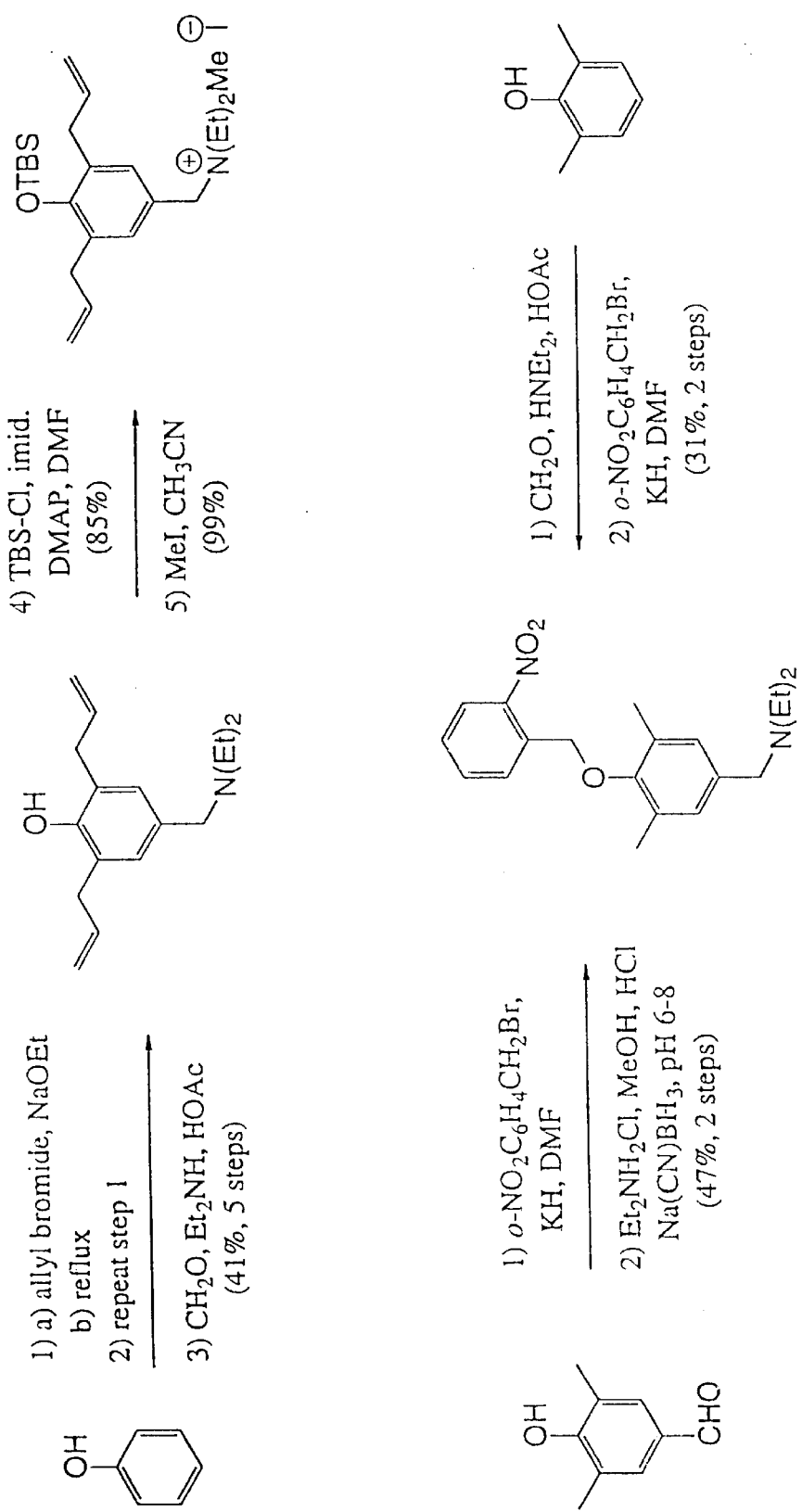

FIG. 47E is a schematic representation of a reaction process.

FIG. 48E is a schematic representation of a reaction process.

Figure 49E:
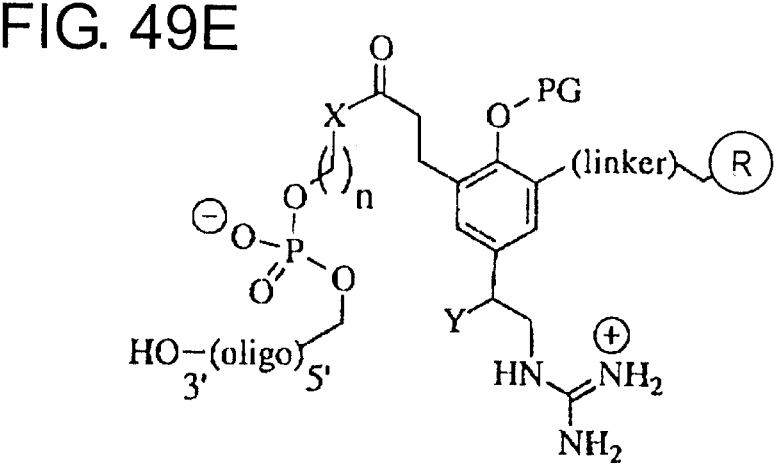

FIG. 49E is a schematic representation of a reaction process.

FIG. S1E is a schematic representation of a reaction process.

FIG. S2E is a schematic representation of a reaction process.

FIG. S3E is a schematic representation of a reaction process.

FIG. S4E is a schematic representation of a reaction process.

FIG. S5E is a schematic representation of a reaction process.

FIG. 7 is a schematic representation of a reaction process.

What is claimed is:

1. A method for chemospecifically and regiospecifically labeling DNA molecules through phosphodiester alkylation comprising the steps of:
   producing an independently tethered delivering oligonucleotide;
   appending said oligonucleotide to a DNA synthesizer, machine-ready core reagent;
   providing phosphate specficity through a guanidinium-phosphate complex;
   providing latent reactivity activated by photolysis to afford a quinone methide precursor;
   alkylating a phosphodiester with quinone methide resulting in situ release of said delivering oligonucleotide through lactonization; and
   forming a covalently stable trialkyiphosphate upon lactone formation by trapping an alkylated product thereby preventing reaction reversibility.

2. The method for chemospecifically and regiospecifically labeling DNA molecules through phosphodiester alkylation of claim 1 wherein said step for providing phosphate specificity through a guanidinium-phosphate complex comprises:
   a Rathke guanylation;
   ortho-bromination; and
   iodination.

3. The method for chemospecifically and regiospecifically labeling DNA molecules through phosphodiester alkylation of claim 1, further comprising the use of a photolabile protecting group for in situ activation of a latently reactive quinone methides.

4. The method for chemospecifically and regiospecifically labeling DNA molecules through phosphodiester alkylation of claim 1, further comprising the steps of:
   producing said trialkylphosphate as a covalent modification of said oligonucleotide.

5. A method for chemospecifically and regiospecifically labeling nucleic acid polymers comprising the steps of:
   producing an independently tethered delivering molecule for site-specific recognition of the nucleic acid polymer;
   appending said delivering molecule to a DNA synthesizer, machine-ready core reagent;

providing phosphate specificity through a phosphate-binding functional group;

providing latent reactivity through in situ activation;

alkylating a phosphodiester resulting in the in situ release of said site-specific delivering molecule through intramolecular cleavage of the attaching tether; and, forming a covalently stable trialkylphosphate upon trapping an alkylated product preventing reaction reversibility.

6. The method as recited in claim 5, wherein latent reactivity is any means to send in a non-reactive alkylating agent and activating it only after it is bound to its target site.

7. The method as recited in claim 6, wherein the non-reactive alkylating agent is activated by at least one of photolysis, enzymatic activation, pH, salt, or other activating agent.

8. The method as recited in claim 7, wherein any natural or non-natural nucleic acid polymer is the target for covalent modification.

9. The method as recited in claim 5, further comprising the steps of:

producing a quinone methide for phosphodiester alkylation; and, incorporating a group which will assist in quinione methide formation through proton removal and activate the quinone methide through electron withdrawal, prior to alkylating the phosphodiester.

10. The method as recited in claim 9, wherein the group which will assist in quinone methide formation and ensuing activation is any functional group which can accept and donate a proton or chelate with a Lewis acidic metal atom to activate the quinone methide oxygen.

* * * * *